(12) United States Patent
Wilcke et al.

(10) Patent No.: US 11,083,199 B2
(45) Date of Patent: Aug. 10, 2021

(54) HETEROCYCLE DERIVATIVES AS PESTICIDES

(71) Applicants: Bayer Aktiengesellschaft, Leverkusen (DE); BAYER CROPSCIENCE AKTIENGESELLSCHAFT, Monheim am Rhein (DE)

(72) Inventors: David Wilcke, Duesseldorf (DE); Dominik Hager, Monheim (DE); Laura Hoffmeister, Duesseldorf (DE); Nina Kausch-Busies, Bergisch Gladbach (DE); Marc Mosrin, Cologne (DE); Matthieu Willot, Duesseldorf (DE); Ruediger Fischer, Pulheim (DE); Kerstin Ilg, Cologne (DE); Ulrich Goergens, Ratingen (DE); Andreas Turberg, Haan (DE)

(73) Assignees: Bayer Aktiengesellschaft, Leverkusen (DE); Bayer CropScience Aktiengesellschaft, Monheim am Rhein (DE)

( * ) Notice: Subject to any disclaimer, the term of this patent is extended or adjusted under 35 U.S.C. 154(b) by 35 days.

(21) Appl. No.: 16/476,393

(22) PCT Filed: Jan. 3, 2018

(86) PCT No.: PCT/EP2018/050117
§ 371 (c)(1),
(2) Date: Jul. 8, 2019

(87) PCT Pub. No.: WO2018/130443
PCT Pub. Date: Jul. 19, 2018

(65) Prior Publication Data
US 2020/0045976 A1    Feb. 13, 2020

(30) Foreign Application Priority Data
Jan. 10, 2017   (EP) ..................... 17150794

(51) Int. Cl.
| C07D 487/04 | (2006.01) |
| A01N 43/90 | (2006.01) |
| A01N 43/56 | (2006.01) |
| C07D 403/04 | (2006.01) |
| C07D 471/04 | (2006.01) |

(52) U.S. Cl.
CPC ............ *A01N 43/90* (2013.01); *A01N 43/56* (2013.01); *C07D 403/04* (2013.01); *C07D 471/04* (2013.01); *C07D 487/04* (2013.01)

(58) Field of Classification Search
CPC .......................... C07D 471/04; C07D 487/04; A61K 31/5025; A61K 31/439
USPC ........... 544/236; 546/118, 119; 514/248, 300
See application file for complete search history.

(56) References Cited

U.S. PATENT DOCUMENTS

| 10,087,192 B2 | 10/2018 | Fischer et al. |
| 10,188,108 B2 | 1/2019 | Fischer et al. |
| 2017/0073342 A1 | 3/2017 | Fischer et al. |
| 2018/0002345 A1 | 1/2018 | Fischer et al. |
| 2018/0016273 A1 | 1/2018 | Fischer et al. |
| 2020/0054017 A1 | 2/2020 | Wilcke et al. |

FOREIGN PATENT DOCUMENTS

| WO | 2010125985 A1 | 11/2010 |
| WO | 2012074135 A1 | 6/2012 |
| WO | 2012086848 A1 | 6/2012 |
| WO | 2013018928 A1 | 2/2013 |
| WO | 2013180193 A1 | 12/2013 |
| WO | 2013191113 A1 | 12/2013 |
| WO | 2014142292 A1 | 9/2014 |
| WO | 2014148451 A1 | 9/2014 |
| WO | 2015000715 A1 | 1/2015 |
| WO | 2015002211 A1 | 1/2015 |
| WO | 2015071180 A1 | 5/2015 |
| WO | 2015091945 A1 | 6/2015 |
| WO | 2015121136 A1 | 8/2015 |
| WO | 2015133603 A1 | 9/2015 |
| WO | 2015198817 A1 | 12/2015 |
| WO | 2015198859 A1 | 12/2015 |
| WO | 2016005263 A1 | 1/2016 |
| WO | 2016020286 A1 | 2/2016 |
| WO | 2016023954 A2 | 2/2016 |
| WO | 2016026848 A1 | 2/2016 |
| WO | 2016039441 A1 | 3/2016 |

(Continued)

OTHER PUBLICATIONS

International Search Report for PCT/EP2018/050117 dated Mar. 22, 2018.

*Primary Examiner* — Jeffrey H Murray
(74) *Attorney, Agent, or Firm* — McBee Moore & Vanik IP, LLC

(57) ABSTRACT

The invention relates to novel compounds of the formula (I),

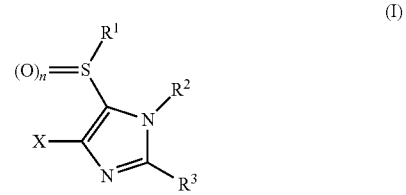

in which X, $R^1$, $R^2$, $R^3$, and n have the meanings given above,
to the use thereof as acaricides and/or insecticides for controlling animal pests and to methods and intermediates for the preparation thereof.

15 Claims, No Drawings

(56) References Cited

FOREIGN PATENT DOCUMENTS

| | | |
|---|---|---|
| WO | 2016039444 A1 | 3/2016 |
| WO | 2016041819 A1 | 3/2016 |
| WO | 2016046071 A1 | 3/2016 |
| WO | 2016058928 A1 | 4/2016 |
| WO | 2016059145 A1 | 4/2016 |
| WO | 2016071214 A1 | 5/2016 |
| WO | 2016091731 A1 | 6/2016 |
| WO | 2016096584 A1 | 6/2016 |
| WO | 2016107742 A1 | 7/2016 |
| WO | 2016107831 A1 | 7/2016 |
| WO | 2016113155 A1 | 7/2016 |
| WO | 2016116338 A1 | 7/2016 |
| WO | 2016121997 A1 | 8/2016 |
| WO | 2016124557 A1 | 8/2016 |
| WO | 2016124563 A1 | 8/2016 |
| WO | 2016125621 A1 | 8/2016 |
| WO | 2016125622 A1 | 8/2016 |
| WO | 2016129684 A1 | 8/2016 |
| WO | 2016142326 A1 | 9/2016 |
| WO | 2016142327 A1 | 9/2016 |
| WO | 2016162318 A1 | 10/2016 |
| WO | 2016169882 A1 | 10/2016 |
| WO | 2016169886 A1 | 10/2016 |
| WO | 2018/130437 A1 | 7/2018 |

HETEROCYCLE DERIVATIVES AS PESTICIDES

CROSS-REFERENCE TO RELATED APPLICATIONS

This application is the National Stage entry of International Application No. PCT/EP2018/050117, filed 03 Jan. 2018, which claims priority to European Patent Application No. 17150794.0, filed 10 Jan. 2017.

BACKGROUND

Field

The present invention relates to heterocycle derivatives of the formula (I), to their use as acaricides and/or insecticides for controlling animal pests, particularly arthropods and especially insects and arachnids, and to methods and intermediates for their preparation.

Description of Related Art

Heterocycle derivatives having insecticidal properties are already described in the literature, for example in WO 2010/125985, WO 2012/074135, WO 2012/086848, WO 2013/018928, WO 2013/180193, WO 2013/191113, WO 2014/142292, WO 2014/148451, WO 2015/000715, WO 2016/124563, WO 2016/124557, WO 2015/121136, WO 2015/133603, WO 2015/198859, WO 2015/002211, WO 2015/071180, WO 2015/091945, WO 2016/005263, WO 2016/039441, WO 2015/198817, WO 2016/041819, WO 2016/039441, WO 2016/039444, WO 2016/026848, WO 2016/023954, WO 2016/020286, WO 2016/046071, WO 2016/058928, WO 2016/059145, WO 2016/071214, WO 2016/091731, WO 2016/096584, WO 2016/107742, WO 2016/107831, WO 2016/113155, WO 2016/116338, WO 2016/121997, WO 2016/125621, WO 2016/125622, WO 2016/129684, WO 2016/142326, WO 2016/142327, WO 2016/169882 and WO 2016/169886.

Modem crop protection compositions have to meet many demands, for example in relation to extent, persistence and spectrum of their action and possible use. Questions of toxicity, sparing of beneficial species and pollinators, environmental properties, application rates, combinability with other active ingredients or formulation auxiliaries play a role, as does the question of the complexity involved in the synthesis of an active ingredient, and resistances can also occur, to mention just a few parameters. For all these reasons alone, the search for novel crop protection compositions cannot be considered complete, and there is a constant need for novel compounds having improved properties compared to the known compounds, at least in relation to individual aspects.

SUMMARY

It was an object of the present invention to provide compounds which broaden the spectrum of the pesticides in various aspects and/or improve their activity.

Novel heterocycle derivatives have now been found, these having advantages over the compounds already known, examples of which include better biological or environmental properties, a wider range of application methods, better insecticidal or acaricidal action, and good compatibility with crop plants. The heterocycle derivatives can be used in combination with further compositions for improving efficacy, especially against insects that are difficult to control.

The subject matter of the present invention is therefore novel compounds of the formula (I)

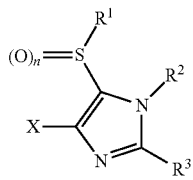

in which (configuration 1-1)

$R^1$ is $(C_1-C_6)$alkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkyl, $(C_2-C_6)$alkenyl, $(C_2-C_6)$haloalkenyl, $(C_2-C_6)$alkynyl, $(C_2-C_6)$haloalkynyl or $(C_3-C_8)$cycloalkyl, $R^2$ is hydrogen, $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$alkynyloxy-$(C_1-C_6)$alkyl, $(C_2-C_6)$haloalkynyloxy-$(C_1-C_6)$alkyl, $(C_2-C_6)$haloalkynyl, $(C_2-C_6)$cyanoalkynyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, cyano$(C_3-C_8)$cycloalkyl, $(C_1-C_6)$alkylthio-$(C_1-C_6)$alkyl, $(C_1-C_6)$haloalkylthio-$(C_1-C_6)$alkyl, $(C_1-C_6)$alkylsulfinyl-$(C_1-C_6)$alkyl, $(C_1-C_6)$haloalkylsulfinyl-$(C_1-C_6)$alkyl, $(C_1-C_6)$alkylsulfonyl-$(C_1-C_6)$alkyl, $(C_1-C_6)$haloalkylsulfonyl-$(C_1-C_6)$alkyl, $(C_1-C_6)$alkylcarbonyl-$(C_1-C_6)$alkyl, $(C_1-C_6)$haloalkylcarbonyl-$(C_1-C_6)$alkyl, $(C_1-C_6)$alkoxycarbonyl-$(C_1-C_6)$alkyl or $(C_1-C_6)$haloalkoxycarbonyl-$(C_1-C_6)$alkyl, $R^3$ is hydrogen, halogen, cyano, nitro, $(C_1-C_6)$alkyl, $(C_1-C_6)$haloalkyl, $(C_1-C_6)$alkoxy, $(C_1-C_6)$haloalkoxy, $(C_1-C_6)$alkylthio, $(C_1-C_6)$haloalkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, SCN, $(C_1-C_6)$alkylcarbonyl, $(C_1-C_6)$haloalkylcarbonyl, $(C_1-C_6)$alkoxycarbonyl, $(C_1-C_6)$haloalkoxycarbonyl, aminocarbonyl, $(C_1-C_6)$alkylaminocarbonyl, di$(C_1-C_6)$alkylaminocarbonyl, $(C_1-C_6)$haloalkylaminocarbonyl, $(C_3-C_8)$cycloalkylaminocarbonyl, aminothiocarbonyl, $(C_1-C_6)$alkylaminothiocarbonyl, di$(C_1-C_6)$alkylaminothiocarbonyl, $(C_1-C_6)$haloalkylaminothiocarbonyl, $(C_3-C_8)$cycloalkylaminothiocarbonyl, amino, $(C_1-C_6)$alkylamino, $(C_1-C_6)$haloalkylamino, di$(C_1-C_6)$alkylamino, $(C_3-C_8)$cycloalkylamino, $(C_1-C_6)$alkylsulfonylamino, $(C_1-C_6)$alkylcarbonylamino, $(C_1-C_6)$haloalkylcarbonylamino, $(C_1-C_6)$alkylcarbonyl-$(C_1-C_6)$alkylamino, $(C_1-C_6)$haloalkylcarbonyl-$(C_1-C_6)$alkylamino, $(C_3-C_8)$cycloalkylcarbonylamino, $(C_3-C_8)$cycloalkylcarbonyl-$(C_1-C_6)$alkylamino, $(C_1-C_6)$alkylthiocarbonylamino, $(C_1-C_6)$haloalkylthiocarbonylamino, $(C_1-C_6)$alkylthiocarbonyl-$(C_1-C_6)$alkylamino, $(C_1-C_6)$haloalkylthiocarbonyl-$(C_1-C_6)$alkylamino, $(C_3-C_8)$cycloalkylthiocarbonylamino, $(C_3-C_8)$cycloalkylthiocarbonyl-$(C_1-C_6)$alkylamino, $(C_2-C_6)$alkenyl, $(C_2-C_6)$haloalkenyl, $(C_2-C_6)$cyanoalkenyl, $(C_3-C_8)$cycloalkyl-$(C_2)$alkenyl, $(C_2-C_6)$alkynyl or $(C_2-C_6)$haloalkynyl, or is aryl or hetaryl, each of which is optionally mono- or polysubstituted by identical or different substituents, where (in the case of hetaryl) at least one carbonyl group may optionally be present and where possible substituents in each case are as follows: cyano, carboxyl, halogen, nitro, acetyl, hydroxyl, amino, SCN, SF$_5$, tri(C$_1$-C$_6$)alkylsilyl, (C$_3$-C$_8$)cycloalkyl, (C$_3$-C$_8$)cycloalkyl-(C$_3$-C$_8$)cycloalkyl, (C$_1$-C$_6$)alkyl-(C$_3$-C$_8$)cycloalkyl, (C$_1$-C$_6$)haloalkyl-(C$_3$-C$_8$)cycloalkyl, halo(C$_3$-C$_8$)cycloalkyl, cyano(C$_3$-C$_8$)cycloalkyl, (C$_1$-C$_6$)alkyl, (C$_1$-C$_6$)haloalkyl, (C$_1$-C$_6$)cyanoalkyl, (C$_1$-C$_6$)hydroxyalkyl, hydroxycarbonyl-(C$_1$-C$_6$)alkoxy, (C$_1$-C$_6$)alkoxycarbonyl-(C$_1$-C$_6$)alkyl, (C$_1$-C$_6$)alkoxy-(C$_1$-C$_6$)alkyl, (C$_2$-C$_6$)alkenyl, (C$_2$-C$_6$)haloalkenyl, (C$_2$-C$_6$)cyanoalkenyl, (C$_3$-C$_8$)cycloalkyl-(C$_2$)alkenyl, (C$_2$-C$_6$)alkynyl, (C$_2$-C$_6$)haloalkynyl, (C$_2$-C$_6$)cyanoalkynyl, (C$_1$-C$_6$)alkoxy, (C$_1$-C$_6$)haloalkoxy, (C$_1$-C$_6$)cyanoalkoxy, (C$_1$-C$_6$)alkoxycarbonyl-(C$_1$-C$_6$)alkoxy, (C$_1$-C$_6$)alkoxy-(C$_1$-C$_6$)alkoxy, (C$_1$-C$_6$)alkoxyimino, (C$_1$-C$_6$)haloalkoxyimino, (C$_1$-C$_6$)alkylthio, (C$_1$-C$_6$)haloalkylthio, (C$_1$-C$_6$)alkoxy-(C$_1$-C$_6$)alkylthio, (C$_1$-C$_6$)alkylthio-(C$_1$-C$_6$)alkyl, (C$_1$-C$_6$)alkylsulfinyl, (C$_1$-C$_6$)haloalkylsulfinyl, (C$_1$-C$_6$)alkoxy-(C$_1$-C$_6$)alkylsulfinyl, (C$_1$-C$_6$)alkylsulfinyl-(C$_1$-C$_6$)alkyl, (C$_1$-C$_6$)alkylsulfonyl, (C$_1$-C$_6$)haloalkylsulfonyl, (C$_1$-C$_6$)alkoxy-(C$_1$-C$_6$)alkylsulfonyl, (C$_1$-C$_6$)alkylsulfonyl-(C$_1$-C$_6$)alkyl, (C$_1$-C$_6$)alkylsulfonyloxy, (C$_1$-C$_6$)haloalkylsulfonyloxy, (C$_1$-C$_6$)alkylcarbonyl, (C$_1$-C$_6$)haloalkylcarbonyl, (C$_1$-C$_6$)alkylcarbonyloxy, (C$_1$-C$_6$)alkoxycarbonyl, (C$_1$-C$_6$)haloalkoxycarbonyl, aminocarbonyl, (C$_1$-C$_6$)alkylaminocarbonyl, di(C$_1$-C$_6$)alkylaminocarbonyl, (C$_1$-C$_6$)haloalkylaminocarbonyl, (C$_2$-C$_6$)alkenylaminocarbonyl, di(C$_2$-C$_6$)alkenylaminocarbonyl, (C$_3$-C$_8$)cycloalkylaminocarbonyl, (C$_1$-C$_6$)alkylsulfonylamino, (C$_1$-C$_6$)alkylamino, di(C$_1$-C$_6$)alkylamino, (C$_1$-C$_6$)haloalkylamino, (C$_3$-C$_8$)cycloalkylamino, aminosulfonyl, (C$_1$-C$_6$)alkylaminosulfonyl, di(C$_1$-C$_6$)alkylaminosulfonyl, (C$_1$-C$_6$)alkylsulfoximino, aminothiocarbonyl, (C$_1$-C$_6$)alkylaminothiocarbonyl, di(C$_1$-C$_6$)alkylaminothiocarbonyl, (C$_1$-C$_6$)haloalkylaminothiocarbonyl, (C$_3$-C$_8$)cycloalkylaminothiocarbonyl, (C$_1$-C$_6$)alkylcarbonylamino, (C$_1$-C$_6$)haloalkylcarbonylamino, (C$_1$-C$_6$)alkylcarbonyl-(C$_1$-C$_6$)alkylamino, (C$_1$-C$_6$)haloalkylcarbonyl-(C$_1$-C$_6$)alkylamino, (C$_3$-C$_8$)cycloalkylcarbonylamino, (C$_3$-C$_8$)cycloalkylcarbonyl-(C$_1$-C$_6$)alkylamino, (C$_1$-C$_6$)alkylthiocarbonylamino, (C$_1$-C$_6$)haloalkylthiocarbonylamino, (C$_1$-C$_6$)alkylthiocarbonyl-(C$_1$-C$_6$)alkylamino, (C$_1$-C$_6$)haloalkylthiocarbonyl-(C$_1$-C$_6$)alkylamino, (C$_3$-C$_8$)cycloalkylthiocarbonylamino, (C$_3$-C$_8$)cycloalkylthiocarbonyl-(C$_1$-C$_6$)alkylamino, hetaryl, oxohetaryl, halohetaryl, halooxohetaryl, cyanohetaryl, cyanooxohetaryl, (C$_1$-C$_6$)haloalkylhetaryl or (C$_1$-C$_6$)haloalkyloxohetaryl, X is a heteroaromatic 9-membered or 12-membered fused bicyclic or tricyclic ring system from the group of Q1 to Q12

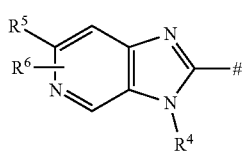
Q1

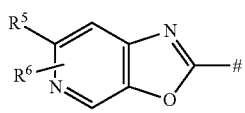
Q2

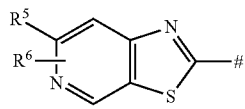
Q3

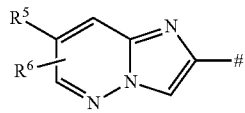
Q4

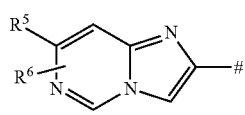
Q5

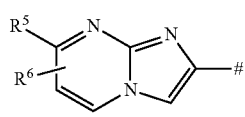
Q6

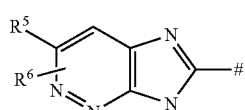
Q7

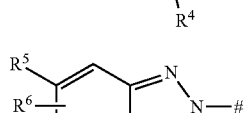
Q8

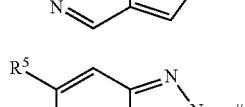
Q9

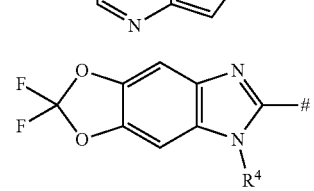
Q10

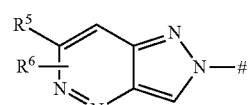
Q11

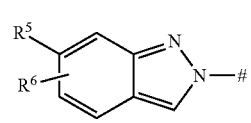
Q12

R$^4$ is hydrogen, (C$_1$-C$_6$)alkyl, (C$_1$-C$_6$)haloalkyl, (C$_1$-C$_6$)cyanoalkyl, (C$_1$-C$_6$)hydroxyalkyl, (C$_1$-C$_6$)alkoxy-(C$_1$-C$_6$)alkyl, (C$_1$-C$_6$)haloalkoxy-(C$_1$-C$_6$)alkyl, (C$_2$-C$_6$)alkenyl, (C$_2$-C$_6$)alkenyloxy-(C$_1$-C$_6$)alkyl, (C$_2$-C$_6$)haloalkenyloxy-(C$_1$-C$_6$)alkyl, (C$_2$-C$_6$)haloalkenyl, (C$_2$-C$_6$)cyanoalkenyl, (C$_2$-C$_6$)alkynyl, (C$_2$-C$_6$)haloalkynyl or (C$_3$-C$_8$)cycloalkyl, R$^5$, R$^6$ are independently hydrogen, cyano, halogen, (C$_1$-C$_6$)alkyl, (C$_1$-C$_6$)haloalkyl, (C$_2$-C$_6$)alkenyl, (C$_2$-C$_6$)haloalkenyl, (C$_2$-C$_6$)alkynyl, (C$_2$-C$_6$)haloalkynyl, (C$_3$-C$_8$)cycloalkyl, (C$_3$-C$_8$)cycloalkyl-(C$_3$-C$_8$)cycloalkyl, (C$_1$-C$_6$)alkyl-(C$_3$-C$_8$)cycloalkyl, (C$_1$-C$_6$)haloalkyl-(C$_3$-C$_8$)cycloalkyl, cyano-(C$_3$-C$_8$)cycloalkyl, halo(C$_3$-C$_8$)cycloalkyl, (C$_1$-C$_6$)alkoxy, (C$_1$-C$_6$)haloalkoxy, (C$_1$-C$_6$)

alkoxyimino, (C$_1$-C$_6$)haloalkoxyimino (C$_1$-C$_6$)alkylthio, (C$_1$-C$_6$)haloalkylthio, (C$_1$-C$_6$)alkylsulfinyl, (C$_1$-C$_6$)haloalkylsulfinyl, (C$_1$-C$_6$)alkylsulfonyl, (C$_1$-C$_6$)haloalkylsulfonyl, (C$_1$-C$_6$)alkylsulfonyloxy, (C$_1$-C$_6$)haloalkylsulfonyloxy, (C$_1$-C$_6$)alkylcarbonyl, (C$_1$-C$_6$)haloalkylcarbonyl, aminocarbonyl, (C$_1$-C$_6$)alkylaminocarbonyl, di(C$_1$-C$_6$)alkylaminocarbonyl, (C$_1$-C$_6$)alkylsulfonylamino, (C$_1$-C$_6$)alkylamino, di(C$_1$-C$_6$)alkylamino, aminosulfonyl, (C$_1$-C$_6$)alkylaminosulfonyl or di(C$_1$-C$_6$)alkylaminosulfonyl, n is 0, 1 or 2.

DETAILED DESCRIPTION OF A PREFERRED EMBODIMENT

In a further embodiment, the invention relates to compounds of the formula (I), in which X, R$^1$, R$^2$, R$^3$, R$^4$, R$^5$, R$^6$ and n have the meanings specified in configuration 1-1, where if X is Q7, then R$^3$ is not hydrogen, halogen, cyano, nitro, (C$_1$-C$_6$)alkyl, (C$_1$-C$_6$)haloalkyl, (C$_1$-C$_6$)alkoxy, (C$_1$-C$_6$)haloalkoxy, (C$_1$-C$_6$)alkylthio, (C$_1$-C$_6$)haloalkylthio, (C$_1$-C$_6$)alkylsulfinyl, (C$_1$-C$_6$)haloalkylsulfinyl, (C$_1$-C$_6$)alkylsulfonyl or (C$_1$-C$_6$)haloalkylsulfonyl.

Configuration 1-2

R$^1$ is (C$_1$-C$_6$)alkyl, (C$_1$-C$_6$)cyanoalkyl, (C$_1$-C$_6$)hydroxyalkyl, (C$_1$-C$_6$)alkoxy-(C$_1$-C$_6$)alkyl, (C$_1$-C$_6$)haloalkyl, (C$_2$-C$_6$)alkenyl, (C$_2$-C$_6$)haloalkenyl, (C$_2$-C$_6$)alkynyl, (C$_2$-C$_6$)haloalkynyl or (C$_3$-C$_8$)cycloalkyl, R$^2$ is hydrogen, (C$_1$-C$_6$)alkyl, (C$_1$-C$_6$)haloalkyl, (C$_1$-C$_6$)cyanoalkyl, (C$_1$-C$_6$)hydroxyalkyl, (C$_1$-C$_6$)alkoxy-(C$_1$-C$_6$)alkyl, (C$_1$-C$_6$)haloalkoxy-(C$_1$-C$_6$)alkyl, (C$_2$-C$_6$)alkenyl, (C$_2$-C$_6$)alkenyloxy-(C$_1$-C$_6$)alkyl, (C$_2$-C$_6$)haloalkenyloxy-(C$_1$-C$_6$)alkyl, (C$_2$-C$_6$)haloalkenyl, (C$_2$-C$_6$)cyanoalkenyl, (C$_2$-C$_6$)alkynyl, (C$_2$-C$_6$)alkynyloxy-(C$_1$-C$_6$)alkyl, (C$_2$-C$_6$)haloalkynyloxy-(C$_1$-C$_6$)alkyl, (C$_2$-C$_6$)haloalkynyl, (C$_2$-C$_6$)cyanoalkynyl, (C$_3$-C$_8$)cycloalkyl, (C$_3$-C$_8$)cycloalkyl-(C$_3$-C$_8$)cycloalkyl, (C$_1$-C$_6$)alkyl-(C$_3$-C$_8$)cycloalkyl, halo(C$_3$-C$_8$)cycloalkyl, cyano(C$_3$-C$_8$)cycloalkyl, (C$_1$-C$_6$)alkylthio-(C$_1$-C$_6$)alkyl, (C$_1$-C$_6$)haloalkylthio-(C$_1$-C$_6$)alkyl, (C$_1$-C$_6$)alkylsulfinyl-(C$_1$-C$_6$)alkyl, (C$_1$-C$_6$)haloalkylsulfinyl-(C$_1$-C$_6$)alkyl, (C$_1$-C$_6$)alkylsulfonyl-(C$_1$-C$_6$)alkyl, (C$_1$-C$_6$)haloalkylsulfonyl-(C$_1$-C$_6$)alkyl, (C$_1$-C$_6$)alkylcarbonyl-(C$_1$-C$_6$)alkyl, (C$_1$-C$_6$)haloalkylcarbonyl-(C$_1$-C$_6$)alkyl, (C$_1$-C$_6$)alkoxycarbonyl-(C$_1$-C$_6$)alkyl or (C$_1$-C$_6$)haloalkoxycarbonyl-(C$_1$-C$_6$)alkyl, R$^3$ is hydrogen, halogen, cyano, nitro, (C$_1$-C$_6$)alkyl, (C$_1$-C$_6$)haloalkyl, (C$_1$-C$_6$)alkoxy, (C$_1$-C$_6$)haloalkoxy, (C$_1$-C$_6$)alkylthio, (C$_1$-C$_6$)haloalkylthio, (C$_1$-C$_6$)alkylsulfinyl, (C$_1$-C$_6$)haloalkylsulfinyl, (C$_1$-C$_6$)alkylsulfonyl, (C$_1$-C$_6$)haloalkylsulfonyl, SCN, (C$_1$-C$_6$)alkylcarbonyl, (C$_1$-C$_6$)haloalkylcarbonyl, (C$_1$-C$_6$)alkoxycarbonyl, (C$_1$-C$_6$)haloalkoxycarbonyl, aminocarbonyl, (C$_1$-C$_6$)alkylaminocarbonyl, di(C$_1$-C$_6$)alkylaminocarbonyl, (C$_1$-C$_6$)haloalkylaminocarbonyl, (C$_3$-C$_8$)cycloalkylaminocarbonyl, aminothiocarbonyl, (C$_1$-C$_6$)alkylaminothiocarbonyl, di(C$_1$-C$_6$)alkylaminothiocarbonyl, (C$_1$-C$_6$)haloalkylaminothiocarbonyl, (C$_3$-C$_8$)cycloalkylaminothiocarbonyl, amino, (C$_1$-C$_6$)alkylamino, (C$_1$-C$_6$)haloalkylamino, di(C$_1$-C$_6$)alkylamino, (C$_3$-C$_8$)cycloalkylamino, (C$_1$-C$_6$)alkylsulfonylamino, (C$_1$-C$_6$)alkylcarbonylamino, (C$_1$-C$_6$)haloalkylcarbonylamino, (C$_1$-C$_6$)alkylcarbonyl-(C$_1$-C$_6$)alkylamino, (C$_1$-C$_6$)haloalkylcarbonyl-(C$_1$-C$_6$)alkylamino, (C$_3$-C$_8$)cycloalkylcarbonylamino, (C$_3$-C$_8$)cycloalkylcarbonyl-(C$_1$-C$_6$)alkylamino, (C$_1$-C$_6$)alkylthiocarbonylamino, (C$_1$-C$_6$)haloalkylthiocarbonylamino, (C$_1$-C$_6$)alkylthiocarbonyl-(C$_1$-C$_6$)alkylamino, (C$_1$-C$_6$)haloalkylthiocarbonyl-(C$_1$-C$_6$)alkylamino, (C$_3$-C$_8$)cycloalkylthiocarbonylamino, (C$_3$-C$_8$)cycloalkylthiocarbonyl-(C$_1$-C$_6$)alkylamino, (C$_2$-C$_6$)alkenyl, (C$_2$-C$_6$)haloalkenyl, (C$_2$-C$_6$)cyanoalkenyl, (C$_3$-C$_8$)cycloalkyl-(C$_2$)alkenyl, (C$_2$-C$_6$)alkynyl, (C$_2$-C$_6$)haloalkynyl, (C$_3$-C$_6$)cycloalkyl-(C$_2$)alkynyl, (C$_3$-C$_6$)cycloalkyl-(C$_1$-C$_6$)alkyl, (C$_1$-C$_6$)alkylaminocarbonylamino, di(C$_1$-C$_6$)alkylaminocarbonylamino, (C$_3$-C$_6$)cycloalkylaminocarbonylamino, (C$_1$-C$_6$)haloalkylaminocarbonylamino, (C$_1$-C$_6$)alkylaminocarbonyl-(C$_1$-C$_6$)alkylamino, di(C$_1$-C$_6$)alkylaminocarbonyl-(C$_1$-C$_6$)alkylamino, (C$_3$-C$_6$)cycloalkylaminocarbonyl-(C$_1$-C$_6$)alkylamino or (C$_1$-C$_6$)haloalkylaminocarbonyl-(C$_1$-C$_6$)alkylamino, or is aryl, hetaryl, cyclopentenyl or cyclohexenyl, each of which is optionally mono- or polysubstituted by identical or different substituents, where (in the case of hetaryl) at least one carbonyl group may optionally be present and where possible substituents in each case are as follows: cyano, carboxyl, halogen, nitro, acetyl, hydroxyl, amino, SCN, SF$_5$, tri(C$_1$-C$_6$)alkylsilyl, (C$_3$-C$_8$)cycloalkyl, (C$_3$-C$_8$)cycloalkyl-(C$_3$-C$_8$)cycloalkyl, (C$_1$-C$_6$)alkyl-(C$_3$-C$_8$)cycloalkyl, (C$_1$-C$_6$)haloalkyl-(C$_3$-C$_8$)cycloalkyl, halo(C$_3$-C$_8$)cycloalkyl, cyano(C$_3$-C$_8$)cycloalkyl, (C$_1$-C$_6$)alkyl, (C$_1$-C$_6$)haloalkyl, (C$_1$-C$_6$)cyanoalkyl, (C$_1$-C$_6$)hydroxyalkyl, hydroxycarbonyl-(C$_1$-C$_6$)alkoxy, (C$_1$-C$_6$)alkoxycarbonyl-(C$_1$-C$_6$)alkyl, (C$_1$-C$_6$)alkoxy-(C$_1$-C$_6$)alkyl, (C$_2$-C$_6$)alkenyl, (C$_2$-C$_6$)haloalkenyl, (C$_2$-C$_6$)cyanoalkenyl, (C$_3$-C$_8$)cycloalkyl-(C$_2$)alkenyl, (C$_2$-C$_6$)alkynyl, (C$_2$-C$_6$)haloalkynyl, (C$_2$-C$_6$)cyanoalkynyl, (C$_1$-C$_6$)alkoxy, (C$_1$-C$_6$)haloalkoxy, (C$_1$-C$_6$)cyanoalkoxy, (C$_1$-C$_6$)alkoxycarbonyl-(C$_1$-C$_6$)alkoxy, (C$_1$-C$_6$)alkoxy-(C$_1$-C$_6$)alkoxy, (C$_1$-C$_6$)alkoxyimino, (C$_1$-C$_6$)haloalkoxyimino, (C$_1$-C$_6$)alkylthio, (C$_1$-C$_6$)haloalkylthio, (C$_1$-C$_6$)alkoxy-(C$_1$-C$_6$)alkylthio, (C$_1$-C$_6$)alkylthio-(C$_1$-C$_6$)alkyl, (C$_1$-C$_6$)alkylsulfinyl, (C$_1$-C$_6$)haloalkylsulfinyl, (C$_1$-C$_6$)alkoxy-(C$_1$-C$_6$)alkylsulfinyl, (C$_1$-C$_6$)alkylsulfinyl-(C$_1$-C$_6$)alkyl, (C$_1$-C$_6$)alkylsulfonyl, (C$_1$-C$_6$)haloalkylsulfonyl, (C$_1$-C$_6$)alkoxy-(C$_1$-C$_6$)alkylsulfonyl, (C$_1$-C$_6$)alkylsulfonyl-(C$_1$-C$_6$)alkyl, (C$_1$-C$_6$)alkylsulfonyloxy, (C$_1$-C$_6$)haloalkylsulfonyloxy, (C$_1$-C$_6$)alkylcarbonyl, (C$_1$-C$_6$)haloalkylcarbonyl, (C$_1$-C$_6$)alkylcarbonyloxy, (C$_1$-C$_6$)alkoxycarbonyl, (C$_1$-C$_6$)haloalkoxycarbonyl, aminocarbonyl, (C$_1$-C$_6$)alkylaminocarbonyl, di(C$_1$-C$_6$)alkylaminocarbonyl, (C$_1$-C$_6$)haloalkylaminocarbonyl, (C$_2$-C$_6$)alkenylaminocarbonyl, di(C$_2$-C$_6$)alkenylaminocarbonyl, (C$_3$-C$_8$)cycloalkylaminocarbonyl, (C$_1$-C$_6$)alkylsulfonylamino, (C$_1$-C$_6$)alkylamino, di(C$_1$-C$_6$)alkylamino, (C$_1$-C$_6$)haloalkylamino, (C$_3$-C$_8$)cycloalkylamino, aminosulfonyl, (C$_1$-C$_6$)alkylaminosulfonyl, di(C$_1$-C$_6$)alkylaminosulfonyl, (C$_1$-C$_6$)alkylsulfoximino, aminothiocarbonyl, (C$_1$-C$_6$)alkylaminothiocarbonyl, di(C$_1$-C$_6$)alkylaminothiocarbonyl, (C$_1$-C$_6$)haloalkylaminothiocarbonyl, (C$_3$-C$_8$)cycloalkylaminothiocarbonyl, (C$_1$-C$_6$)alkylcarbonylamino, (C$_1$-C$_6$)haloalkylcarbonylamino, (C$_1$-C$_6$)alkylcarbonyl-(C$_1$-C$_6$)alkylamino, (C$_1$-C$_6$)haloalkylcarbonyl-(C$_1$-C$_6$)alkylamino, (C$_3$-C$_8$)cycloalkylcarbonylamino, (C$_3$-C$_8$)cycloalkylcarbonyl-(C$_1$-C$_6$)alkylamino, (C$_1$-C$_6$)alkylthiocarbonylamino, (C$_1$-C$_6$)haloalkylthiocarbonylamino, (C$_1$-C$_6$)alkylthiocarbonyl-(C$_1$-C$_6$)alkylamino, (C$_1$-C$_6$)haloalkylthiocarbonyl-(C$_1$-C$_6$)alkylamino, (C$_3$-C$_8$)

cycloalkylthiocarbonylamino, ($C_3$-$C_8$)cycloalkylthiocarbonyl-($C_1$-$C_6$)alkylamino, hetaryl, oxohetaryl, halohetaryl, halooxohetaryl, cyanohetaryl, cyanooxohetaryl, ($C_1$-$C_6$)haloalkylhetaryl or ($C_1$-$C_6$)haloalkyloxohetaryl, X is a heteroaromatic 9-membered or 12-membered fused bicyclic or tricyclic ring system from the group of Q1 to Q12

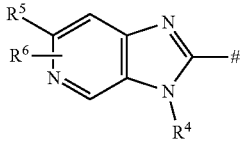

Q1

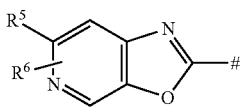

Q2

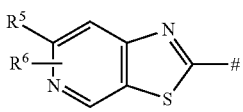

Q3

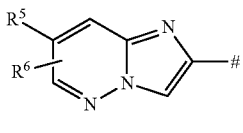

Q4

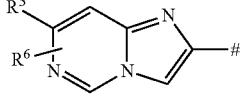

Q5

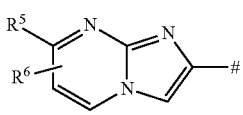

Q6

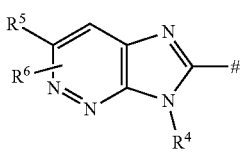

Q7

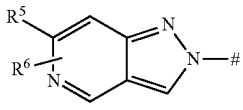

Q8

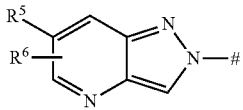

Q9

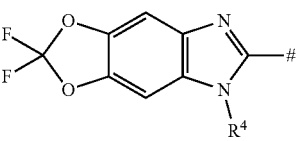

Q10

-continued

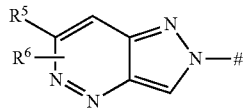

Q11

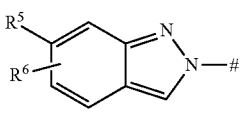

Q12

$R^4$ is hydrogen, ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_1$-$C_6$)haloalkoxy-($C_1$-$C_6$)alkyl, ($C_2$-$C_6$)alkenyl, ($C_2$-$C_6$)alkenyloxy-($C_1$-$C_6$)alkyl, ($C_2$-$C_6$)haloalkenyloxy-($C_1$-$C_6$)alkyl, ($C_2$-$C_6$)haloalkenyl, ($C_2$-$C_6$)cyanoalkenyl, ($C_2$-$C_6$)alkynyl, ($C_2$-$C_6$)haloalkynyl or ($C_3$-$C_8$)cycloalkyl, $R^5$, $R^6$ are independently hydrogen, cyano, halogen, ($C_1$-$C_6$)alkyl, ($C_1$-$C_6$)haloalkyl, ($C_2$-$C_6$)alkenyl, ($C_2$-$C_6$)haloalkenyl, ($C_2$-$C_6$)alkynyl, ($C_2$-$C_6$)haloalkynyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, ($C_1$-$C_6$)haloalkyl-($C_3$-$C_8$)cycloalkyl, cyano-($C_3$-$C_8$)cycloalkyl, halo($C_3$-$C_8$)cycloalkyl, ($C_1$-$C_6$)alkoxy, ($C_1$-$C_6$)haloalkoxy, ($C_1$-$C_6$)alkoxyimino, ($C_1$-$C_6$)haloalkoxyimino ($C_1$-$C_6$)alkylthio, ($C_1$-$C_6$)haloalkylthio, ($C_1$-$C_6$)alkylsulfinyl, ($C_1$-$C_6$)haloalkylsulfinyl, ($C_1$-$C_6$)alkylsulfonyl, ($C_1$-$C_6$)haloalkylsulfonyl, ($C_1$-$C_6$)alkylsulfonyloxy, ($C_1$-$C_6$)haloalkylsulfonyloxy, ($C_1$-$C_6$)alkylcarbonyl, ($C_1$-$C_6$)haloalkylcarbonyl, aminocarbonyl, ($C_1$-$C_6$)alkylaminocarbonyl, di($C_1$-$C_6$)alkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl or di($C_1$-$C_6$)alkylaminosulfonyl, n is 0, 1 or 2.

In a further embodiment, the invention relates to compounds of the formula (I), in which X, $R^1$, $R^2$, $R^3$, $R^4$, $R^5$, $R^6$ and n have the meanings specified in configuration 1-2, where if X is Q7, then $R^3$ is not hydrogen, halogen, cyano, nitro, ($C_1$-$C_6$)alkyl, ($C_1$-$C_6$)haloalkyl, ($C_1$-$C_6$)alkoxy, ($C_1$-$C_6$)haloalkoxy, ($C_1$-$C_6$)alkylthio, ($C_1$-$C_6$)haloalkylthio, ($C_1$-$C_6$)alkylsulfinyl, ($C_1$-$C_6$)haloalkylsulfinyl, ($C_1$-$C_6$)alkylsulfonyl or ($C_1$-$C_6$)haloalkylsulfonyl.

It has additionally been found that the compounds of the formula (I) have very good efficacy as pesticides, preferably as insecticides and/or acaricides, and additionally generally have very good plant compatibility, in particular with respect to crop plants.

The compounds according to the invention are defined in general terms by the formula (I). Preferred substituents or ranges of the radicals given in the formulae mentioned above and below are illustrated hereinafter:

Configuration 2-1

$R^1$ is preferably ($C_1$-$C_4$)alkyl, ($C_1$-$C_4$)cyanoalkyl, ($C_1$-$C_4$)alkoxy-($C_1$-$C_4$)alkyl, ($C_1$-$C_4$)haloalkyl, ($C_2$-$C_4$)alkenyl, ($C_2$-$C_4$)haloalkenyl, ($C_2$-$C_4$)alkynyl, ($C_2$-$C_4$)haloalkynyl or ($C_3$-$C_6$)cycloalkyl, $R^2$ is preferably hydrogen, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_1$-$C_4$)haloalkoxy-($C_1$-$C_4$)alkyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, cyano($C_3$-$C_6$)cycloalkyl, ($C_1$-$C_4$)alkylthio-($C_1$-$C_4$)alkyl, ($C_1$-$C_4$)haloalkylthio-($C_1$-$C_4$)alkyl, ($C_1$-$C_4$)alkylsulfinyl- $(C_1-C_4)$alkyl, $(C_1-C_4)$haloalkylsulfinyl-$(C_1-C_4)$alkyl, $(C_1-C_4)$alkylsulfonyl-$(C_1-C_4)$alkyl or $(C_1-C_4)$haloalkylsulfonyl-$(C_1-C_4)$alkyl, $R^3$ is preferably hydrogen, halogen, cyano, nitro, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, SCN, $(C_1-C_4)$alkylcarbonyl, $(C_1-C_4)$haloalkylcarbonyl, $(C_1-C_4)$alkoxycarbonyl, $(C_1-C_4)$haloalkoxycarbonyl, aminocarbonyl, $(C_1-C_4)$alkylaminocarbonyl, di$(C_1-C_4)$alkylaminocarbonyl, $(C_1-C_4)$haloalkylaminocarbonyl, $(C_3-C_6)$cycloalkylaminocarbonyl, aminothiocarbonyl, $(C_1-C_4)$alkylaminothiocarbonyl, di$(C_1-C_4)$alkylaminothiocarbonyl, $(C_1-C_4)$haloalkylaminothiocarbonyl, $(C_3-C_6)$cycloalkylaminothiocarbonyl, amino, $(C_1-C_4)$alkylamino, $(C_1-C_4)$haloalkylamino, di$(C_1-C_4)$alkylamino, $(C_3-C_6)$cycloalkylamino, $(C_1-C_4)$alkylsulfonylamino, $(C_1-C_4)$alkylcarbonylamino, $(C_1-C_4)$haloalkylcarbonylamino, $(C_1-C_4)$alkylcarbonyl-$(C_1-C_4)$alkylamino, $(C_1-C_4)$haloalkylcarbonyl-$(C_1-C_4)$alkylamino, $(C_3-C_6)$cycloalkylcarbonylamino, $(C_3-C_6)$cycloalkylcarbonyl-$(C_1-C_4)$alkylamino, $(C_1-C_4)$alkylthiocarbonylamino, $(C_1-C_4)$haloalkylthiocarbonylamino, $(C_1-C_4)$alkylthiocarbonyl-$(C_1-C_4)$alkylamino, $(C_1-C_4)$haloalkylthiocarbonyl-$(C_1-C_4)$alkylamino, $(C_3-C_6)$cycloalkylthiocarbonylamino, $(C_3-C_6)$cycloalkylthiocarbonyl-$(C_1-C_4)$alkylamino, $(C_2-C_4)$alkenyl, $(C_2-C_4)$haloalkenyl, $(C_2-C_4)$cyanoalkenyl, $(C_3-C_6)$cycloalkyl-$(C_2)$alkenyl, $(C_2-C_4)$alkynyl or $(C_2-C_4)$haloalkynyl, or is preferably aryl or hetaryl, each of which is optionally mono- or polysubstituted by identical or different substituents, where (in the case of hetaryl) at least one carbonyl group may optionally be present and where possible substituents in each case are as follows: cyano, carboxyl, halogen, nitro, acetyl, hydroxyl, amino, SCN, $SF_5$, tri$(C_1-C_4)$alkylsilyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$haloalkyl-$(C_3-C_6)$cycloalkyl, halo$(C_3-C_6)$cycloalkyl, cyano$(C_3-C_6)$cycloalkyl, $(C_1-C_4)$alkyl, $(C_1-C_4)$haloalkyl, $(C_1-C_4)$cyanoalkyl, $(C_1-C_4)$hydroxyalkyl, hydroxycarbonyl-$(C_1-C_4)$alkoxy, $(C_1-C_4)$alkoxycarbonyl-$(C_1-C_4)$alkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_3-C_6)$cycloalkyl-$(C_2)$alkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkoxycarbonyl-$(C_1-C_4)$alkoxy, $(C_1-C_4)$alkoxy-$(C_1-C_4)$alkoxy, $(C_1-C_4)$alkoxyimino, $(C_1-C_4)$haloalkoxyimino, $(C_1-C_4)$alkylthio, $(C_1-C_4)$haloalkylthio, $(C_1-C_4)$alkoxy-$(C_1-C_4)$alkylthio, $(C_1-C_4)$alkylthio-$(C_1-C_4)$alkyl, $(C_1-C_4)$alkylsulfinyl, $(C_1-C_4)$haloalkylsulfinyl, $(C_1-C_4)$alkoxy-$(C_1-C_4)$alkylsulfinyl, $(C_1-C_4)$alkylsulfinyl-$(C_1-C_4)$alkyl, $(C_1-C_4)$alkylsulfonyl, $(C_1-C_4)$haloalkylsulfonyl, $(C_1-C_4)$alkoxy-$(C_1-C_4)$alkylsulfonyl, $(C_1-C_4)$alkylsulfonyl-$(C_1-C_4)$alkyl, $(C_1-C_4)$alkylsulfonyloxy, $(C_1-C_4)$haloalkylsulfonyloxy, $(C_1-C_4)$alkylcarbonyl, $(C_1-C_4)$haloalkylcarbonyl, $(C_1-C_4)$alkylcarbonyloxy, $(C_1-C_4)$alkoxycarbonyl, $(C_1-C_4)$haloalkoxycarbonyl, aminocarbonyl, $(C_1-C_4)$alkylaminocarbonyl, $(C_1-C_4)$haloalkylaminocarbonyl, di$(C_1-C_4)$alkylaminocarbonyl, $(C_2-C_4)$alkenylaminocarbonyl, di$(C_2-C_4)$alkenylaminocarbonyl, $(C_3-C_6)$cycloalkylaminocarbonyl, $(C_1-C_4)$alkylsulfonylamino, $(C_1-C_4)$alkylamino, di$(C_1-C_4)$alkylamino, $(C_1-C_4)$haloalkylamino, $(C_3-C_6)$cycloalkylamino, aminosulfonyl, $(C_1-C_4)$alkylaminosulfonyl, di$(C_1-C_4)$alkylaminosulfonyl, $(C_1-C_4)$alkylsulfoximino, aminothiocarbonyl, $(C_1-C_4)$alkylaminothiocarbonyl, di$(C_1-C_4)$alkylaminothiocarbonyl, $(C_1-C_4)$haloalkylaminothiocarbonyl, $(C_3-C_6)$cycloalkylaminothiocarbonyl, $(C_1-C_4)$alkylcarbonylamino, $(C_1-C_4)$haloalkylcarbonylamino, $(C_1-C_4)$alkylcarbonyl-$(C_1-C_4)$alkylamino, $(C_1-C_4)$haloalkylcarbonyl-$(C_1-C_4)$alkylamino, $(C_3-C_6)$cycloalkylcarbonylamino, $(C_3-C_6)$cycloalkylcarbonyl-$(C_1-C_4)$alkylamino, $(C_1-C_4)$alkylthiocarbonylamino, $(C_1-C_4)$haloalkylthiocarbonylamino, $(C_1-C_4)$alkylthiocarbonyl-$(C_1-C_4)$alkylamino, $(C_1-C_4)$haloalkylthiocarbonyl-$(C_1-C_4)$alkylamino, $(C_3-C_6)$cycloalkylthiocarbonylamino, $(C_3-C_6)$cycloalkylthiocarbonyl-$(C_1-C_4)$alkylamino, hetaryl, oxohetaryl, halohetaryl, halooxohetaryl, cyanohetaryl, cyanooxohetaryl, $(C_1-C_4)$haloalkylhetaryl or $(C_1-C_4)$haloalkyloxohetaryl, X is preferably a heteroaromatic 9-membered or 12-membered fused bicyclic or tricyclic ring system from the series Q1 to Q12, $R^4$ is preferably hydrogen, $(C_1-C_4)$alkyl, $(C_1-C_4)$haloalkyl, $(C_1-C_4)$cyanoalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$haloalkenyl, $(C_2-C_4)$alkynyl, $(C_2-C_4)$haloalkynyl or $(C_3-C_6)$cycloalkyl, $R^5$, $R^6$ are preferably each independently hydrogen, cyano, halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$haloalkyl-$(C_3-C_6)$cycloalkyl, cyano$(C_3-C_6)$cycloalkyl, halo$(C_3-C_6)$cycloalkyl, $(C_1-C_4)$alkoxy, $(C_1-C_4)$haloalkoxy, $(C_1-C_4)$alkoxyimino, $(C_1-C_4)$haloalkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$haloalkylsulfonyloxy, $(C_1-C_4)$alkylcarbonyl or $(C_1-C_4)$haloalkylcarbonyl, n is preferably 0, 1 or 2.

In a further embodiment, the invention relates to compounds of the formula (I), in which X, $R^1$, $R^2$, $R^3$, $R^4$, $R^5$, $R^6$ and n have the meanings specified in configuration 2-1, where if X is preferably Q7, then $R^3$ is not hydrogen, halogen, cyano, nitro, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl or $(C_1-C_4)$haloalkylsulfonyl.

Configuration 2-2

$R^1$ is preferably $(C_1-C_4)$alkyl, $(C_1-C_4)$cyanoalkyl, $(C_1-C_4)$alkoxy-$(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl or $(C_3-C_6)$cycloalkyl, $R^2$ is preferably hydrogen, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, cyano$(C_3-C_6)$cycloalkyl, $(C_1-C_4)$alkylthio-$(C_1-C_4)$alkyl, $(C_1-C_4)$haloalkylthio-$(C_1-C_4)$alkyl, $(C_1-C_4)$alkylsulfinyl-$(C_1-C_4)$alkyl, $(C_1-C_4)$haloalkylsulfinyl-$(C_1-C_4)$alkyl, $(C_1-C_4)$alkylsulfonyl-$(C_1-C_4)$alkyl or $(C_1-C_4)$haloalkylsulfonyl-$(C_1-C_4)$alkyl, $R^3$ is preferably hydrogen, halogen, cyano, nitro, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, SCN, $(C_1-C_4)$alkylcarbonyl, $(C_1-C_4)$haloalkylcarbonyl, $(C_1-C_4)$alkoxycarbonyl, $(C_1-C_4)$haloalkoxycarbonyl, aminocarbonyl, $(C_1-C_4)$alkylaminocarbonyl, di$(C_1-C_4)$alkylaminocarbonyl, $(C_1-C_4)$haloalkylaminocarbonyl, $(C_3-C_6)$cycloalkylaminocarbonyl, aminothiocarbonyl, $(C_1-C_4)$alkylaminothiocarbonyl, di$(C_1-C_4)$alkylaminothiocarbonyl, $(C_1-C_4)$haloalkylaminothiocarbonyl, $(C_3-C_6)$cycloalkylaminothiocarbonyl, amino, $(C_1-C_4)$alkylamino, $(C_1-C_4)$haloalkylamino, di$(C_1-C_4)$alkylamino, $(C_3-C_6)$cycloalkylamino, $(C_1-C_4)$alkylsulfonylamino, $(C_1-C_4)$alkylcarbonylamino, $(C_1-C_4)$haloalkylcarbonylamino, $(C_1-C_4)$alkylcarbonyl-$(C_1-C_4)$alkylamino, $(C_1-C_4)$haloalkylcarbonyl-$(C_1-C_4)$alkylamino, $(C_3-C_6)$cycloalkylcarbonylamino, $(C_3-C_6)$cycloalkylcarbonyl-$(C_1-C_4)$alkylamino, $(C_1-C_4)$alkylthiocarbonylamino, $(C_1-C_4)$haloalkylthiocarbonylamino, $(C_1-C_4)$alkylthiocarbonyl-$(C_1-C_4)$alkylamino, $(C_1-C_4)$haloalkylthiocarbonyl-$(C_1-C_4)$alkylamino, $(C_3-C_6)$cycloalkylthiocarbonylamino, $(C_3-C_6)$cycloalkylthiocarbonyl-$(C_1-C_4)$alkylamino, $(C_2-C_4)$alkenyl, $(C_2-C_4)$haloalkenyl, $(C_2-C_4)$cyanoalkenyl, $(C_3-C_6)$cycloalkyl-$(C_2)$alkenyl, $(C_2-C_4)$alkynyl, $(C_2-C_4)$haloalkynyl, $(C_3-C_6)$cycloalkyl-$(C_2)$alkynyl, $(C_3-C_6)$cycloalkyl-$(C_1-C_4)$alkyl, $(C_1-C_4)$alkylaminocarbonylamino, di$(C_1-C_4)$alkylaminocarbonylamino, $(C_3-C_6)$cycloalkylaminocarbonylamino, $(C_1-C_4)$haloalkylaminocarbonylamino, $(C_1-C_4)$alkylaminocarbonyl-$(C_1-C_4)$alkylamino, di$(C_1-C_4)$alkylaminocarbonyl-$(C_1-C_4)$alkylamino, $(C_3-C_6)$cycloalkylaminocarbonyl-$(C_1-C_4)$alkylamino or $(C_1-C_4)$haloalkylaminocarbonyl-$(C_1-C_4)$alkylamino, or is preferably aryl, hetaryl, cyclopentenyl or cyclohexenyl, each of which is optionally mono- or polysubstituted by identical or different substituents, where (in the case of hetaryl) at least one carbonyl group may optionally be present and where possible substituents in each case are as follows: cyano, carboxyl, halogen, nitro, acetyl, hydroxyl, amino, SCN, $SF_5$, tri$(C_1-C_4)$alkylsilyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$haloalkyl-$(C_3-C_6)$cycloalkyl, halo$(C_3-C_6)$cycloalkyl, cyano$(C_3-C_6)$cycloalkyl, $(C_1-C_4)$alkyl, $(C_1-C_4)$haloalkyl, $(C_1-C_4)$cyanoalkyl, $(C_1-C_4)$hydroxyalkyl, hydroxycarbonyl-$(C_1-C_4)$alkoxy, $(C_1-C_4)$alkoxycarbonyl-$(C_1-C_4)$alkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_3-C_6)$cycloalkyl-$(C_2)$alkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkoxycarbonyl-$(C_1-C_4)$alkoxy, $(C_1-C_4)$alkoxy-$(C_1-C_4)$alkoxy, $(C_1-C_4)$alkoxyimino, $(C_1-C_4)$haloalkoxyimino, $(C_1-C_4)$alkylthio, $(C_1-C_4)$haloalkylthio, $(C_1-C_4)$alkoxy-$(C_1-C_4)$alkylthio, $(C_1-C_4)$alkylthio-$(C_1-C_4)$alkyl, $(C_1-C_4)$alkylsulfinyl, $(C_1-C_4)$haloalkylsulfinyl, $(C_1-C_4)$alkoxy-$(C_1-C_4)$alkylsulfinyl, $(C_1-C_4)$alkylsulfinyl-$(C_1-C_4)$alkyl, $(C_1-C_4)$alkylsulfonyl, $(C_1-C_4)$haloalkylsulfonyl, $(C_1-C_4)$alkoxy-$(C_1-C_4)$alkylsulfonyl, $(C_1-C_4)$alkylsulfonyl-$(C_1-C_4)$alkyl, $(C_1-C_4)$alkylsulfonyloxy, $(C_1-C_4)$haloalkylsulfonyloxy, $(C_1-C_4)$alkylcarbonyl, $(C_1-C_4)$haloalkylcarbonyl, $(C_1-C_4)$alkylcarbonyloxy, $(C_1-C_4)$alkoxycarbonyl, $(C_1-C_4)$haloalkoxycarbonyl, aminocarbonyl, $(C_1-C_4)$alkylaminocarbonyl, $(C_1-C_4)$haloalkylaminocarbonyl, di$(C_1-C_4)$alkylaminocarbonyl, $(C_2-C_4)$alkenylaminocarbonyl, di$(C_2-C_4)$alkenylaminocarbonyl, $(C_3-C_6)$cycloalkylaminocarbonyl, $(C_1-C_4)$alkylsulfonylamino, $(C_1-C_4)$alkylamino, di$(C_1-C_4)$alkylamino, $(C_1-C_4)$haloalkylamino, $(C_3-C_6)$cycloalkylamino, aminosulfonyl, $(C_1-C_4)$alkylaminosulfonyl, di$(C_1-C_4)$alkylaminosulfonyl, $(C_1-C_4)$alkylsulfoximino, aminothiocarbonyl, $(C_1-C_4)$alkylaminothiocarbonyl, di$(C_1-C_4)$alkylaminothiocarbonyl, $(C_1-C_4)$haloalkylaminothiocarbonyl, $(C_3-C_6)$cycloalkylaminothiocarbonyl, $(C_1-C_4)$alkylcarbonylamino, $(C_1-C_4)$haloalkylcarbonylamino, $(C_1-C_4)$alkylcarbonyl-$(C_1-C_4)$alkylamino, $(C_1-C_4)$haloalkylcarbonyl-$(C_1-C_4)$alkylamino, $(C_3-C_6)$cycloalkylcarbonylamino, $(C_3-C_6)$cycloalkylcarbonyl-$(C_1-C_4)$alkylamino, $(C_1-C_4)$alkylthiocarbonylamino, $(C_1-C_4)$haloalkylthiocarbonylamino, $(C_1-C_4)$alkylthiocarbonyl-$(C_1-C_4)$alkylamino, $(C_1-C_4)$haloalkylthiocarbonyl-$(C_1-C_4)$alkylamino, $(C_3-C_6)$cycloalkylthiocarbonylamino, $(C_3-C_6)$cycloalkylthiocarbonyl-$(C_1-C_4)$alkylamino, hetaryl, oxohetaryl, halohetaryl, halooxohetaryl, cyanohetaryl, cyanooxohetaryl, $(C_1-C_4)$haloalkylhetaryl or $(C_1-C_4)$haloalkyloxohetaryl, X is preferably a heteroaromatic 9-membered or 12-membered fused bicyclic or tricyclic ring system from the series Q1 to Q12, $R^4$ is preferably hydrogen, $(C_1-C_4)$alkyl, $(C_1-C_4)$haloalkyl, $(C_1-C_4)$cyanoalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$haloalkenyl, $(C_2-C_4)$alkynyl, $(C_2-C_4)$haloalkynyl or $(C_3-C_6)$cycloalkyl, $R^5$, $R^6$ are preferably each independently hydrogen, cyano, halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, $(C_1-C_4)$haloalkyl-$(C_3-C_6)$cycloalkyl, cyano$(C_3-C_6)$cycloalkyl, halo$(C_3-C_6)$cycloalkyl, $(C_1-C_4)$alkoxy, $(C_1-C_4)$haloalkoxy, $(C_1-C_4)$alkoxyimino, $(C_1-C_4)$haloalkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$haloalkylsulfonyloxy, $(C_1-C_4)$alkylcarbonyl or $(C_1-C_4)$haloalkylcarbonyl, n is preferably 0, 1 or 2.

In a further embodiment, the invention relates to compounds of the formula (I), in which X, $R^1$, $R^2$, $R^3$, $R^4$, $R^5$, $R^6$ and n have the meanings specified in configuration 2-2, where if X is preferably Q7, then $R^3$ is not hydrogen, halogen, cyano, nitro, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl or $(C_1-C_4)$haloalkylsulfonyl.

Configuration 3-1

$R^1$ is more preferably $(C_1-C_4)$alkyl, $(C_1-C_4)$haloalkyl, $(C_2-C_4)$alkenyl, $(C_2-C_4)$haloalkenyl or $(C_3-C_6)$cycloalkyl, $R^2$ is more preferably hydrogen, $(C_1-C_4)$alkyl, $(C_1-C_4)$haloalkyl, $(C_3-C_6)$cycloalkyl or halo$(C_3-C_6)$cycloalkyl, $R^3$ is more preferably hydrogen, halogen, cyano, $(C_1-C_4)$alkyl, $(C_1-C_4)$haloalkyl, $(C_1-C_4)$alkoxy, $(C_1-C_4)$haloalkoxy, aminocarbonyl, $(C_1-C_4)$alkylaminocarbonyl, di$(C_1-C_4)$alkylaminocarbonyl, $(C_1-C_4)$haloalkylaminocarbonyl, $(C_3-C_6)$cycloalkylaminocarbonyl, amino, $(C_1-C_4)$alkylamino, $(C_1-C_4)$haloalkylamino, di$(C_1-C_4)$alkylamino, $(C_3-C_6)$cycloalkylamino, $(C_1-C_4)$alkylsulfonylamino, $(C_1-C_4)$alkylcarbonylamino, $(C_1-C_4)$haloalkylcarbonylamino, $(C_1-C_4)$alkylcarbonyl-$(C_1-C_2)$alkylamino, $(C_1-C_4)$haloalkylcarbonyl-$(C_1-C_2)$alkylamino, $(C_3-C_6)$cycloalkylcarbonylamino, $(C_3-C_6)$cycloalkylcarbonyl-$(C_1-C_2)$alkylamino, $(C_2-C_4)$alkenyl, $(C_2-C_4)$haloalkenyl, $(C_2-C_4)$cyanoalkenyl or $(C_3-C_6)$cycloalkyl-$(C_2)$alkenyl, or is more preferably phenyl, pyridyl, pyrimidyl, pyridazinyl, thiophenyl, furanyl, pyrazolyl, thiazolyl, oxazolyl or imidazolyl, each of which is optionally mono- or polysubstituted by identical or different substituents, where (in the case of hetaryl) at least one carbonyl group may optionally be present and where possible substituents in each case are as follows: cyano, halogen, nitro, acetyl, hydroxyl, amino, $SF_5$, $(C_3-C_6)$cycloalkyl, $(C_1-C_4)$alkyl-$(C_3-C_6)$cycloalkyl, halo$(C_3-C_6)$cycloalkyl, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_2)$alkyl, $(C_2-C_4)$alkenyl, $(C_2-C_4)$haloalkenyl, $(C_2-C_4)$cyanoalkenyl, $(C_3-C_6)$cycloalkyl-$(C_2)$alkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkoxy-$(C_1-C_2)$alkoxy, $(C_1-C_4)$alkoxyimino, $(C_1-C_4)$haloalkoxyimino, $(C_1-C_4)$alkylthio, $(C_1-C_4)$haloalkylthio, $(C_1-C_4)$alkylthio-$(C_1-C_2)$alkyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$haloalkylsulfonyloxy, $(C_1-C_4)$alkylcarbonyl, $(C_1-C_4)$haloalkylcarbonyl, aminocarbonyl, $(C_1-C_4)$alkylaminocarbonyl, $(C_1-C_4)$haloalkylaminocarbonyl, di$(C_1-C_4)$alkylaminocarbonyl, $(C_3-C_6)$cycloalkylaminocarbonyl, aminothiocarbonyl, $(C_1-C_4)$alkylaminothiocarbonyl, di$(C_1-C_4)$alkylaminothiocarbonyl, $(C_1-C_4)$haloalkylaminothiocarbonyl, $(C_3-C_6)$cycloalkylaminothiocarbonyl, $(C_1-C_4)$alkylsulfonylamino, $(C_1-C_4)$alkylamino, di$(C_1-C_4)$alkylamino, $(C_1-C_4)$haloalkylamino, $(C_3-C_6)$cycloalkylamino, aminosulfonyl, $(C_1-C_4)$alkylaminosulfonyl, di$(C_1-C_4)$alkylaminosulfonyl, $(C_1-C_4)$alkylcarbonylamino, $(C_1-C_4)$haloalkylcarbonylamino, $(C_1-C_4)$alkylcarbonyl-$(C_1-C_2)$alkylamino, $(C_1-C_2)$haloalkylcarbonyl-$(C_1-C_2)$alkylamino, $(C_3-C_6)$cycloalkylcarbonylamino, $(C_3-C_6)$cycloalkylcarbonyl-$(C_1-C_2)$alkylamino, $(C_1-C_4)$alkylthiocarbonylamino, $(C_1-C_4)$haloalkylthiocarbonylamino, $(C_1-C_4)$alkylthiocarbonyl-$(C_1-C_2)$alkylamino, $(C_1-C_4)$haloalkylthiocarbonyl-$(C_1-C_2)$alkylamino, $(C_3-C_6)$cycloalkylthiocarbonylamino or $(C_3-C_6)$cycloalkylthiocarbonyl-$(C_1-C_2)$alkylamino, X is more preferably a heteroaromatic 9-membered or 12-membered fused bicyclic or tricyclic ring system from the group of Q1, Q2, Q4, Q5, Q6, Q7, Q8, Q9, Q10, Q11 or Q12, $R^4$ is more preferably hydrogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_1-C_4)$alkoxy-$(C_1-C_4)$alkyl or $(C_3-C_6)$cycloalkyl, $R^5$ is more preferably halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_1-C_4)$haloalkyl-$(C_3-C_6)$cycloalkyl, cyano-$(C_3-C_6)$cycloalkyl, halo $(C_3-C_6)$cycloalkyl, $(C_1-C_4)$alkoxy, $(C_1-C_4)$haloalkoxy, $(C_1-C_4)$alkoxyimino, $(C_1-C_4)$haloalkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$haloalkylsulfonyloxy, $(C_1-C_4)$alkylcarbonyl or $(C_1-C_4)$haloalkylcarbonyl, $R^6$ is more preferably hydrogen, cyano, halogen, $(C_1-C_4)$alkyl, $(C_1-C_4)$haloalkyl or $(C_3-C_6)$cycloalkyl, n is more preferably 0, 1 or 2.

In a further embodiment, the invention relates to compounds of the formula (I), in which X, $R^1$, $R^2$, $R^3$, $R^4$, $R^5$, $R^6$ and n have the meanings specified in configuration 3-1, where if X is preferably Q7, then $R^3$ is not hydrogen, halogen, cyano, $(C_1-C_4)$alkyl, $(C_1-C_4)$haloalkyl, $(C_1-C_4)$alkoxy or $(C_1-C_4)$haloalkoxy.

Configuration 3-2

$R^1$ is more preferably $(C_1-C_4)$alkyl, $(C_1-C_4)$haloalkyl, $(C_2-C_4)$alkenyl, $(C_2-C_4)$haloalkenyl or $(C_3-C_6)$cycloalkyl, $R^2$ is more preferably hydrogen, $(C_1-C_4)$alkyl, $(C_1-C_4)$haloalkyl, $(C_3-C_6)$cycloalkyl or halo$(C_3-C_6)$cycloalkyl, $R^3$ is more preferably hydrogen, halogen, cyano, $(C_1-C_4)$alkyl, $(C_1-C_4)$haloalkyl, $(C_1-C_4)$alkoxy, $(C_1-C_4)$haloalkoxy, aminocarbonyl, $(C_1-C_4)$alkylaminocarbonyl, di$(C_1-C_4)$alkylaminocarbonyl, $(C_1-C_4)$haloalkylaminocarbonyl, $(C_3-C_6)$cycloalkylaminocarbonyl, amino, $(C_1-C_4)$alkylamino, $(C_1-C_4)$haloalkylamino, di$(C_1-C_4)$alkylamino, $(C_3-C_6)$cycloalkylamino, $(C_1-C_4)$alkylsulfonylamino, $(C_1-C_4)$alkylcarbonylamino, $(C_1-C_4)$haloalkylcarbonylamino, $(C_1-C_4)$alkylcarbonyl-$(C_1-C_2)$alkylamino, $(C_1-C_4)$haloalkylcarbonyl-$(C_1-C_2)$alkylamino, $(C_3-C_6)$cycloalkylcarbonylamino, $(C_3-C_6)$cycloalkylcarbonyl-$(C_1-C_2)$alkylamino, $(C_2-C_4)$alkenyl, $(C_2-C_4)$haloalkenyl, $(C_2-C_4)$cyanoalkenyl, $(C_3-C_6)$cycloalkyl-$(C_2)$alkenyl, $(C_2-C_4)$alkynyl, $(C_3-C_6)$cycloalkyl-$(C_2)$alkynyl, $(C_3-C_6)$cycloalkyl-$(C_1-C_4)$alkyl, $(C_1-C_4)$alkoxycarbonyl, aminothiocarbonyl, $(C_1-C_4)$alkylaminothiocarbonyl, di$(C_1-C_4)$alkylaminothiocarbonyl, $(C_1-C_4)$haloalkylaminothiocarbonyl, or is more preferably phenyl, pyridyl, pyrimidyl, pyridazinyl, thiophenyl, furanyl, pyrazolyl, thiazolyl, oxazolyl, imidazolyl, pyrrolyl, cyclopentenyl or cyclohexenyl, each of which is optionally mono- or polysubstituted by identical or different substituents, where (in the case of hetaryl) at least one carbonyl group may optionally be present and where possible substituents in each case are as follows: cyano, halogen, nitro, acetyl, hydroxyl, amino, $SF_5$, $(C_3-C_6)$cycloalkyl, $(C_1-C_4)$alkyl-$(C_3-C_6)$cycloalkyl, halo$(C_3-C_6)$cycloalkyl, cyano$(C_3-C_6)$cycloalkyl, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_2)$alkyl, $(C_2-C_4)$alkenyl, $(C_2-C_4)$haloalkenyl, $(C_2-C_4)$cyanoalkenyl, $(C_3-C_6)$cycloalkyl-$(C_2)$alkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkoxy-$(C_1-C_2)$alkoxy, $(C_1-C_4)$alkoxyimino, $(C_1-C_4)$haloalkoxyimino, $(C_1-C_4)$alkylthio, $(C_1-C_4)$haloalkylthio, $(C_1-C_4)$alkylthio-$(C_1-C_2)$alkyl, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$haloalkylsulfonyloxy, $(C_1-C_4)$alkylcarbonyl, $(C_1-C_4)$haloalkylcarbonyl, aminocarbonyl, $(C_1-C_4)$alkylaminocarbonyl, $(C_1-C_4)$haloalkylaminocarbonyl, di$(C_1-C_4)$alkylaminocarbonyl, $(C_3-C_6)$cycloalkylaminocarbonyl, aminothiocarbonyl, $(C_1-C_4)$alkylaminothiocarbonyl, di$(C_1-C_4)$alkylaminothiocarbonyl, $(C_1-C_4)$haloalkylaminothiocarbonyl, $(C_3-C_6)$ cycloalkylaminothiocarbonyl, $(C_1-C_4)$ alkylsulfonylamino, $(C_1-C_4)$alkylamino, di$(C_1-C_4)$alkylamino, $(C_1-C_4)$haloalkylamino, $(C_3-C_6)$cycloalkylamino, aminosulfonyl, $(C_1-C_4)$alkylaminosulfonyl, di$(C_1-C_4)$alkylaminosulfonyl, $(C_1-C_4)$alkylcarbonylamino, $(C_1-C_4)$haloalkylcarbonylamino, $(C_1-C_4)$alkylcarbonyl-$(C_1-C_2)$alkylamino, $(C_1-C_2)$haloalkylcarbonyl-$(C_1-C_2)$alkylamino, $(C_3-C_6)$cycloalkylcarbonylamino, $(C_3-C_6)$cycloalkylcarbonyl-$(C_1-C_2)$alkylamino, $(C_1-C_4)$alkylthiocarbonylamino, $(C_1-C_4)$haloalkylthiocarbonylamino, $(C_1-C_4)$alkylthiocarbonyl-$(C_1-C_2)$alkylamino, $(C_1-C_4)$haloalkylthiocarbonyl-$(C_1-C_2)$alkylamino, $(C_3-C_6)$cycloalkylthiocarbonylamino or $(C_3-C_6)$cycloalkylthiocarbonyl-$(C_1-C_2)$alkylamino, X is more preferably a heteroaromatic 9-membered or 12-membered fused bicyclic or tricyclic ring system from the group of Q1, Q2, Q4, Q5, Q6, Q7, Q8, Q9, Q10, Q11 or Q12, $R^4$ is more preferably hydrogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_1-C_4)$alkoxy-$(C_1-C_4)$alkyl or $(C_3-C_6)$cycloalkyl, $R^5$ is more preferably halogen, $(C_1-C_4)$alkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_1-C_4)$haloalkyl-$(C_3-C_6)$cycloalkyl, cyano-$(C_3-C_6)$cycloalkyl, halo$(C_3-C_6)$cycloalkyl, $(C_1-C_4)$alkoxy, $(C_1-C_4)$haloalkoxy, $(C_1-C_4)$alkoxyimino, $(C_1-C_4)$haloalkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$haloalkylsulfonyloxy, $(C_1-C_4)$alkylcarbonyl or $(C_1-C_4)$haloalkylcarbonyl, $R^6$ is more preferably hydrogen, cyano, halogen, $(C_1-C_4)$alkyl, $(C_1-C_4)$haloalkyl or $(C_3-C_6)$cycloalkyl, n is more preferably 0, 1 or 2.

In a further embodiment, the invention relates to compounds of the formula (I), in which X, $R^1$, $R^2$, $R^3$, $R^4$, $R^5$, $R^6$ and n have the meanings specified in configuration 3-2, where if X is preferably Q7, then $R^3$ is not hydrogen, halogen, cyano, $(C_1-C_4)$alkyl, $(C_1-C_4)$haloalkyl, $(C_1-C_4)$alkoxy or $(C_1-C_4)$haloalkoxy.

Configuration 4-1

$R^1$ is even more preferably methyl, ethyl, n-propyl, isopropyl, cyclopropyl, fluoromethyl, difluoromethyl, trifluoromethyl, fluoroethyl, difluoroethyl, trifluoroethyl, tetrafluoroethyl or pentafluoroethyl, $R^2$ is even more preferably hydrogen, methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, $R^3$ is even more preferably hydrogen, $(C_1-C_4)$alkyl, $(C_1-C_4)$haloalkyl, $(C_2-C_4)$alkenyl, $(C_2-C_4)$haloalkenyl, $(C_2-C_4)$cyanoalkenyl or $(C_3-C_6)$cycloalkyl-$(C_2)$alkenyl, or is even more preferably phenyl, pyridyl, pyrimidyl, pyridazinyl, thiophenyl, thiazolyl, oxazolyl or imidazolyl, each of which is optionally mono- or polysubstituted by identical or different substitutents—bridged via a carbon atom to the rest of the molecule—where possible substituents in each case are as follows: cyano, halogen, nitro, acetyl, hydroxyl, amino, $(C_3-C_6)$cycloalkyl, $(C_1-C_4)$alkyl-$(C_3-C_6)$cycloalkyl, halo$(C_3-C_6)$cycloalkyl, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_2)$alkyl, $(C_1-C_4)$alkoxy, $(C_1-C_4)$haloalkoxy, $(C_1-C_4)$alkoxy-$(C_1-C_2)$alkoxy-$(C_1-C_2)$alkoxy, $(C_1-C_4)$alkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylcarbonyl, aminocarbonyl, $(C_1-C_4)$alkylaminocarbonyl, di$(C_1-C_4)$alkylaminocarbonyl, $(C_1-C_4)$haloalkylaminocarbonyl, $(C_3-C_6)$cycloalkylaminocarbonyl, $(C_1-C_4)$alkylsulfonylamino, $(C_1-C_4)$alkylamino, di$(C_1-C_4)$alkylamino, $(C_1-C_4)$haloalkylamino, $(C_3-C_6)$cycloalkylamino, $(C_1-C_4)$alkylcarbonylamino, $(C_1-C_4)$haloalkylcarbonylamino, $(C_1-C_4)$alkylcarbonyl-$(C_1-C_2)$alkylamino, $(C_1-C_4)$haloalkylcarbonyl-$(C_1-C_2)$alkylamino, $(C_3-C_6)$cycloalkylcarbonylamino, $(C_3-C_6)$cycloalkylcarbonyl-$(C_1-C_2)$alkylamino, X is even more preferably Q1, Q4, Q5, Q7, Q8, Q9 or Q11, $R^4$ is even more preferably methyl, ethyl, n-propyl, isopropyl, n-butyl, isobutyl, tert-butyl, methoxymethyl or methoxyethyl, $R^5$ is even more preferably fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulfonyl or trifluoromethylsulfinyl, $R^6$ is even more preferably hydrogen, cyano, methyl, trifluoromethyl, fluorine or chlorine, n is even more preferably 0, 1 or 2.

In a further embodiment, the invention relates to compounds of the formula (I), in which X, $R^1$, $R^2$, $R^3$, $R^4$, $R^5$, $R^6$ and n have the meanings specified in configuration 4-1, where if X is even more preferably Q7, then $R^3$ is not hydrogen, $(C_1-C_4)$alkyl or $(C_1-C_4)$haloalkyl.

Configuration 4-2

$R^1$ is even more preferably methyl, ethyl, n-propyl, isopropyl, cyclopropyl, fluoromethyl, difluoromethyl, trifluoromethyl, fluoroethyl, difluoroethyl, trifluoroethyl, tetrafluoroethyl or pentafluoroethyl, $R^2$ is even more preferably hydrogen, methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, $R^3$ is even more preferably hydrogen, $(C_1-C_4)$alkyl, $(C_1-C_4)$haloalkyl, $(C_2-C_4)$alkenyl, $(C_2-C_4)$haloalkenyl, $(C_2-C_4)$cyanoalkenyl, $(C_3-C_6)$cycloalkyl-$(C_2)$alkenyl, halogen, cyano, $(C_2-C_4)$alkynyl, $(C_3-C_6)$cycloalkyl-$(C_2)$alkynyl, $(C_3-C_6)$cycloalkyl-$(C_1-C_4)$alkyl, $(C_1-C_4)$alkoxycarbonyl, aminocarbonyl, $(C_1-C_4)$alkylaminocarbonyl, di$(C_1-C_4)$alkylaminocarbonyl, $(C_1-C_4)$haloalkylaminocarbonyl, aminothiocarbonyl, $(C_1-C_4)$alkylaminothiocarbonyl, di$(C_1-C_4)$alkylaminothiocarbonyl, $(C_1-C_4)$haloalkylaminothiocarbonyl, or is even more preferably phenyl, pyridyl, pyrimidyl, pyridazinyl, thiophenyl, thiazolyl, oxazolyl, imidazolyl, pyrazolyl, pyrrolyl, cyclopentenyl or cyclohexenyl, each of which is optionally mono- or polysubstituted by identical or different substitutents—bridged via a carbon atom to the rest of the molecule—where possible substituents in each case are as follows: cyano, halogen, nitro, acetyl, hydroxyl, amino, $(C_3-C_6)$cycloalkyl, $(C_1-C_4)$alkyl-$(C_3-C_6)$cycloalkyl, halo$(C_3-C_6)$cycloalkyl, cyano$(C_3-C_6)$cycloalkyl, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_2)$alkyl, $(C_1-C_4)$alkoxy, $(C_1-C_4)$haloalkoxy, $(C_1-C_4)$alkoxy-$(C_1-C_2)$alkoxy, $(C_1-C_4)$alkoxyimino, $(C_1-C_4)$alkylthio, $(C_1-C_4)$haloalkylthio, $(C_1-C_4)$alkylsulfinyl, $(C_1-C_4)$ haloalkylsulfinyl, $(C_1-C_4)$alkylsulfonyl, $(C_1-C_4)$haloalkylsulfonyl, $(C_1-C_4)$alkylcarbonyl, aminocarbonyl, $(C_1-C_4)$alkylaminocarbonyl, di$(C_1-C_4)$alkylaminocarbonyl, $(C_1-C_4)$haloalkylaminocarbonyl, $(C_3-C_6)$cycloalkylaminocarbonyl, $(C_1-C_4)$alkylsulfonylamino, $(C_1-C_4)$alkylamino, di$(C_1-C_4)$alkylamino, $(C_1-C_4)$haloalkylamino, $(C_3-C_6)$cycloalkylamino, $(C_1-C_4)$alkylcarbonylamino, $(C_1-C_4)$haloalkylcarbonylamino, $(C_1-C_4)$alkylcarbonyl-$(C_1-C_2)$alkylamino, $(C_1-C_4)$haloalkylcarbonyl-$(C_1-C_2)$alkylamino, $(C_3-C_6)$cycloalkylcarbonylamino, $(C_3-C_6)$cycloalkylcarbonyl-$(C_1-C_2)$alkylamino, or is even more preferably pyrazolyl or imidazolyl, each of which is optionally mono- or polysubstituted by identical or different substitutents—bridged via a nitrogen atom to the rest of the molecule—where possible substituents in each case are as follows: cyano, halogen, nitro, hydroxyl, amino, $(C_3-C_6)$cycloalkyl, $(C_1-C_4)$alkyl, $(C_1-C_4)$haloalkyl, $(C_1-C_4)$alkoxy, $(C_1-C_4)$haloalkoxy, aminocarbonyl, X is even more preferably Q1, Q4, Q5, Q7, Q8, Q9, Q11 or Q12, $R^4$ is even more preferably methyl, ethyl, n-propyl, isopropyl, n-butyl, isobutyl, tert-butyl, methoxymethyl or methoxyethyl, $R^5$ is even more preferably fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulfonyl or trifluoromethylsulfinyl, $R^6$ is even more preferably hydrogen, cyano, methyl, trifluoromethyl, fluorine or chlorine, n is even more preferably 0, 1 or 2.

In a further embodiment, the invention relates to compounds of the formula (I), in which X, $R^1$, $R^2$, $R^3$, $R^4$, $R^5$, $R^6$ and n have the meanings specified in configuration 4-2, where if X is even more preferably Q7, then $R^3$ is not hydrogen, $(C_1-C_4)$alkyl, halogen, cyano or $(C_1-C_4)$haloalkyl.

Configuration 4-3

$R^1$, $R^2$, $R^4$, $R^5$, $R^6$ and n have the meanings specified in Configuration 4-2 and X is even more preferably Q1, Q7, Q8, Q9 or Q12 and $R^3$ is especially hydrogen, fluorine, chlorine, bromine, cyano, methyl, ethyl, isopropyl, ethenyl, isopropenyl, cyclopropylmethyl, cyclopropylethyl, cyclopropylethenyl, cyclopropylethynyl, methoxycarbonyl, ethoxycarbonyl, trifluoromethylaminocarbonyl, trifluoroethylaminocarbonyl, aminocarbonyl, methylaminocarbonyl, dimethylaminocarbonyl, ethylaminocarbonyl, aminothiocarbonyl, methylaminothiocarbonyl, dimethylaminothiocarbonyl, ethylaminothiocarbonyl, or is phenyl, pyridyl, pyrimidyl, pyridazinyl, thiophenyl, thiazolyl, imidazolyl, pyrazolyl, pyrrolyl or cyclohexenyl, each of which is optionally mono-, di- or trisubstituted by identical or different substituents—bridged via a carbon atom to the rest of the molecule—where possible substituents in each case are as follows: cyano, fluorine, chlorine, methyl, ethyl, isopropyl, cyclopropyl, cyanomethyl, cyanoethyl, cyanoisopropyl, cyanocylopropyl, trifluoromethyl, trifluoroethyl, aminocarbonyl, or is pyrazolyl or imidazolyl, each of which is optionally monosubstituted by fluorine or chlorine—bridged via a nitrogen atom to the rest of the molecule.

In a further embodiment, the invention relates to compounds of the formula (I), in which X, $R^1$, $R^2$, $R^3$, $R^4$, $R^5$, $R^6$ and n have the meanings specified in configuration 4-3, where if X is even more preferably Q7, then $R^3$ is not hydrogen, fluorine, chlorine, bromine, cyano, methyl, ethyl or isopropyl.

Configuration 5-1

$R^1$ with emphasis is ethyl or isopropyl, $R^2$ with emphasis is methyl, ethyl or isopropyl, $R^3$ with emphasis is hydrogen, bromine, cyano, ethenyl, cyclopropylethenyl, isopropenyl, cyclopropylethynyl, methyl, ethyl, isopropyl, cyclopropylethyl, methoxycarbonyl, trifluoroethylaminocarbonyl, aminocarbonyl, methylaminocarbonyl, dimethylaminocarbonyl, ethylaminocarbonyl, aminothiocarbonyl, methylaminothiocarbonyl, dimethylaminothiocarbonyl, or with emphasis is phenyl, pyridyl, pyrimidyl, pyridazinyl, thiophenyl (thienyl), thiazolyl, imidazolyl, pyrazolyl, pyrrolyl or cyclohexenyl, each of which is optionally mono-, di- or trisubstituted by identical or different substituents—bridged via a carbon atom to the rest of the molecule—where possible substituents in each case are as follows: cyano, fluorine, chlorine, methyl, cyclopropyl, cyanomethyl, cyanoisopropyl, cyanocylopropyl, trifluoromethyl, trifluoroethyl, aminocarbonyl, or with emphasis is pyrazolyl or imidazolyl, each of which is optionally monosubstituted by chlorine—bridged via a nitrogen atom to the rest of the molecule, X with emphasis is Q1, Q7, Q8, Q9 or Q12, $R^4$ with emphasis is methyl, $R^5$ with emphasis is trifluoromethyl, $R^6$ with emphasis is hydrogen, n with emphasis is 0 or 2.

In a further embodiment, the invention relates to compounds of the formula (I), in which X, $R^1$, $R^2$, $R^3$, $R^4$, $R^5$, $R^6$ and n have the meanings specified in configuration 5-1, where if X is Q7, then $R^3$ is not hydrogen, bromine, cyano, methyl, ethyl or isopropyl.

Configuration 5-2

$R^1$, $R^2$, X, $R^4$, $R^5$, $R^6$, n have the meanings specified in Configuration 5-1 and $R^3$ with emphasis is hydrogen, bromine, cyano, ethenyl, cyclopropylethenyl, isopropenyl, cyclopropylethynyl, methyl, ethyl, isopropyl, cyclopropylethyl, methoxycarbonyl, trifluoroethylaminocarbonyl, aminocarbonyl, methylaminocarbonyl, dimethylaminocarbonyl, ethylaminocarbonyl, aminothiocarbonyl, methylaminothiocarbonyl, dimethylaminothiocarbonyl, or is phenyl, pyridin-2-yl, pyridin-3-yl, pyridin-4-yl, pyrimidin-5-yl, pyridazin-4-yl, thien-2-yl, thien-3-yl, 1,3-thiazol-5-yl, 1H-imidazol-1-yl, 1H-imidazol-2-yl, 1H-imidazol-5-yl, 1H-pyrazol-1-yl, 1H-pyrazol-3-yl, 1H-pyrazol-4-yl, 1H-pyrazol-5-yl, 1H-pyrrol-2-yl or 1-cyclohexenyl, each of which is optionally mono-, di- or trisubstituted by identical or different substituents, where possible substituents in each case are as follows: cyano, fluorine, chlorine, methyl, cyclopropyl, cyanomethyl, cyanoisopropyl, cyanocylopropyl, trifluoromethyl, trifluoroethyl, aminocarbonyl.

In a further embodiment, the invention relates to compounds of the formula (I), in which X, $R^1$, $R^2$, $R^3$, $R^4$, $R^5$, $R^6$ and n have the meanings specified in configuration 5-2, where if X is Q7, then $R^3$ is not hydrogen, bromine, cyano, methyl, ethyl or isopropyl.

Configuration 5-3

$R^1$, $R^2$, X, $R^4$, $R^5$, $R^6$, n have the meanings specified in Configuration 5-1 and $R^3$ with emphasis is hydrogen, bromine, cyano, ethenyl, cyclopropylethenyl, isopropenyl, cyclopropylethynyl, methyl, ethyl, isopropyl, cyclopropylethyl, methoxycarbonyl, trifluoroethylaminocarbonyl, aminocarbonyl, methylaminocarbonyl, dimethylaminocarbonyl, ethylaminocarbonyl, aminothiocarbonyl, methylaminothiocarbonyl, dimethylaminothiocarbonyl,
- phenyl, in each case optionally mono-, di- or trisubstituted identically or differently by cyano, fluorine, chlorine, methyl, cyanomethyl, cyanoisopropyl, cyanocylopropyl, trifluoromethyl or aminocarbonyl,
- pyridin-2-yl, pyridin-3-yl or pyridin-4-yl, each of which is optionally monosubstituted by fluorine or chlorine,
- pyrimidin-5-yl,
- pyridazin-4-yl,
- thien-2-yl or thien-3-yl, each of which is optionally mono- or disubstituted by chlorine,
- 1,3-thiazol-5-yl, optionally monosubstituted by methyl,
- 1H-imidazol-1-yl, 1H-imidazol-2-yl or 1H-imidazol-5-yl, each of which is optionally mono- or disubstituted by chlorine or methyl,
- 1H-pyrazol-1-yl, 1H-pyrazol-3-yl, 1H-pyrazol-4-yl or 1H-pyrazol-5-yl, each of which is optionally mono-, di- or trisubstituted identically or differently by chlorine, methyl, cyclopropyl, trifluoromethyl or trifluoroethyl,
- 1H-pyrrol-2-yl, in each case optionally mono- or disubstituted identically or differently by methyl or cyano,
- 1-cyclohexenyl, in each case optionally mono- or disubstituted identically or differently by methyl or trifluoromethyl.

In a further embodiment, the invention relates to compounds of the formula (I), in which X, $R^1$, $R^2$, $R^3$, $R^4$, $R^5$, $R^6$ and n have the meanings specified in configuration 5-3, where if X is Q7, then $R^3$ is not hydrogen, bromine, cyano, methyl, ethyl or isopropyl.

If $R^3$ is a substituted hetaryl, then the substitution on the hetaryl group may be by substitution of hydrogen on a carbon atom and/or on a nitrogen atom.

In a preferred embodiment, the invention relates to compounds of the formula (I), where X is Q1 and $R^1$, $R^2$, $R^3$, $R^4$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3).

In a preferred embodiment, the invention relates to compounds of the formula (I), where X is Q1, $R^4$ is methyl, $R^5$ is trifluoromethyl, $R^6$ is hydrogen and $R^1$, $R^2$, $R^3$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3).

In a preferred embodiment, the invention relates to compounds of the formula (I), where X is Q7 and $R^1$, $R^2$, $R^3$, $R^4$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3).

In a preferred embodiment, the invention relates to compounds of the formula (I), where X is Q7, $R^4$ is methyl, $R^5$ is trifluoromethyl, $R^6$ is hydrogen and $R^1$, $R^2$, $R^3$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3).

In a preferred embodiment, the invention relates to compounds of the formula (I), where X is Q8 and $R^1$, $R^2$, $R^3$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3).

In a preferred embodiment, the invention relates to compounds of the formula (I), where X is Q8, $R^5$ is trifluoromethyl, $R^6$ is hydrogen and $R^1$, $R^2$, $R^3$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3).

In a preferred embodiment, the invention relates to compounds of the formula (I), where X is Q9 and $R^1$, $R^2$, $R^3$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3).

In a preferred embodiment, the invention relates to compounds of the formula (I), where X is Q9, $R^5$ is trifluoromethyl, $R^6$ is hydrogen and $R^1$, $R^2$, $R^3$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3).

In a preferred embodiment, the invention relates to compounds of the formula (I), where X is Q12 and $R^1$, $R^2$, $R^3$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3).

In a preferred embodiment, the invention relates to compounds of the formula (I), where X is Q12, $R^5$ is trifluoromethyl, $R^6$ is hydrogen and $R^1$, $R^2$, $R^3$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3).

In a preferred embodiment, the invention relates to compounds of the formula (I), where X is Q1, Q7, Q8, Q9 or Q12 and $R^1$, $R^2$, $R^3$, $R^4$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3).

In a preferred embodiment, the invention relates to compounds of the formula (I), where X is Q1, Q8, Q9 or Q12 and $R^1$, $R^2$, $R^3$, $R^4$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3).

In a preferred embodiment, the invention relates to compounds of the formula (I), where $R^1$, $R^2$, X, $R^4$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3) and $R^3$ has the meanings specified in configuration (5-1).

In a preferred embodiment, the invention relates to compounds of the formula (I), where $R^1$, $R^2$, X, $R^4$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3) and $R^3$ has the meanings specified in configuration (5-2).

In a preferred embodiment, the invention relates to compounds of the formula (I), where $R^1$, $R^2$, X, $R^4$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3) and $R^3$ has the meanings specified in configuration (5-3).

In a preferred embodiment, the invention relates to compounds of the formula (I), where $R^1$, $R^2$, X, $R^4$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3) and $R^3$ is hydrogen, bromine, cyano, ethenyl, cyclopropylethenyl, isopropenyl, cyclopropylethynyl, methyl, ethyl, isopropyl, cyclopropylethyl, methoxycarbonyl, trifluoroethylaminocarbonyl, aminocarbonyl, methylaminocarbonyl, dimethylaminocarbonyl, ethylaminocarbonyl, aminothiocarbonyl, methylaminothiocarbonyl or dimethylaminothiocarbonyl.

In a preferred embodiment, the invention relates to compounds of the formula (I), where $R^1$, $R^2$, X, $R^4$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3) and $R^3$ is phenyl, pyridyl, pyrimidyl, pyridazinyl, thiophenyl (thienyl), thiazolyl, imidazolyl, pyrazolyl, pyrrolyl or cyclohexenyl, each of which is optionally mono-, di- or trisubstituted by identical or different substituents— bridged via a carbon atom to the rest of the molecule— where possible substituents in each case are as follows: cyano, fluorine, chlorine, methyl, cyclopropyl, cyanomethyl, cyanoisopropyl, cyanocylopropyl, trifluoromethyl, trifluoroethyl, aminocarbonyl.

In a preferred embodiment, the invention relates to compounds of the formula (I), where $R^1$, $R^2$, X, $R^4$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3) and $R^3$ is pyrazolyl or imidazolyl, each of which is optionally monosubstituted by chlorine—bridged via a nitrogen atom to the rest of the molecule.

In a preferred embodiment, the invention relates to compounds of the formula (I), where $R^2$, $R^3$, X, $R^4$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3) and $R^1$ is ethyl.

In a preferred embodiment, the invention relates to compounds of the formula (I), where $R^2$, $R^3$, X, $R^4$, $R^5$, $R^6$ and n have the meanings specified in configuration (1-1) or configuration (1-2) or configuration (2-1) or configuration (2-2) or configuration (3-1) or configuration (3-2) or configuration (4-1) or configuration (4-2) or configuration (4-3) or configuration (5-1) or configuration (5-2) or configuration (5-3) and $R^1$ is isopropyl.

In the definitions listed in general or within areas of preference, unless stated otherwise, halogen is selected from the group of fluorine, chlorine, bromine and iodine, preferably in turn from the group of fluorine, chlorine and bromine.

Aryl (including as part of a larger unit, for example arylalkyl), unless defined differently elsewhere, is selected from the series phenyl, naphthyl, anthryl, phenanthrenyl, and is preferably in turn phenyl.

In the context of the present invention, unless defined differently elsewhere, the term "alkyl", either on its own or else in combination with further terms, for example haloalkyl, is understood to mean a radical of a saturated, aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, particular preference is given to $C_1$-$C_6$-alkyl radicals. Special preference is given to $C_1$-$C_4$-alkyl radicals.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. Among these, preference is given to $C_3$-$C_6$-alkynyl radicals and particular preference to $C_3$-$C_4$-alkynyl radicals. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

The term "alkoxy", either on its own or else in combination with further terms, for example haloalkoxy, is understood in the present case to mean an O-alkyl radical, where the term "alkyl" is as defined above.

Halogen-substituted radicals, for example haloalkyl, are mono- or polyhalogenated, up to the maximum number of possible substituents. In the case of polyhalogenation, the halogen atoms may be identical or different. Halogen here is fluorine, chlorine, bromine or iodine, especially fluorine, chlorine or bromine.

Unless stated otherwise, optionally substituted radicals may be mono- or polysubstituted, where the substituents in the case of polysubstitutions may be the same or different.

The radical definitions or illustrations given above in general terms or listed within ranges of preference apply correspondingly to the end products and to the starting materials and intermediates. These radical definitions can be combined with one another as desired, i.e. including combinations between the respective preferred ranges.

Preference according to the invention is given to using compounds of the formula (I) which contain a combination of the meanings listed above as being preferred.

Particular preference according to the invention is given to using compounds of the formula (I) which contain a combination of the meanings listed above as being particularly preferred.

Very particular preference according to the invention is given to using compounds of the formula (I) which contain a combination of the definitions listed above as being very particularly preferred.

Most preference according to the invention is given to using compounds of the formula (I) which contain a combination of the meanings listed above as being most preferable.

Depending on the nature of the substituents, the compounds of the formula (I) may take the form of geometric and/or optically active isomers or corresponding isomer mixtures in different compositions. These stereoisomers are, for example, enantiomers, diastereomers, atropisomers or geometric isomers. The invention therefore encompasses both pure stereoisomers and any desired mixtures of these isomers.

The inventive compounds of the formula (I) can be obtained by the processes shown in the following schemes:

Method A

The general method for preparing compounds of the formula (I), in which $R^3$ is aryl, hetaryl, cyclopentenyl or cyclohexenyl—optionally substituted as described above—and X is Q1, Q2, Q3, Q7 or Q10, is described below by way of example by means of compounds of the formula (I), in which X is Q1, Q2 or Q3.

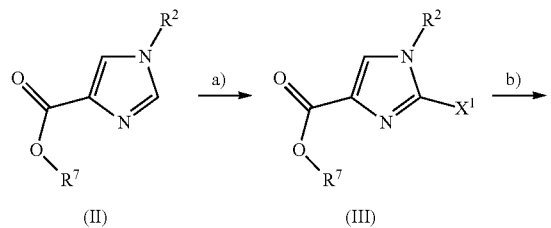

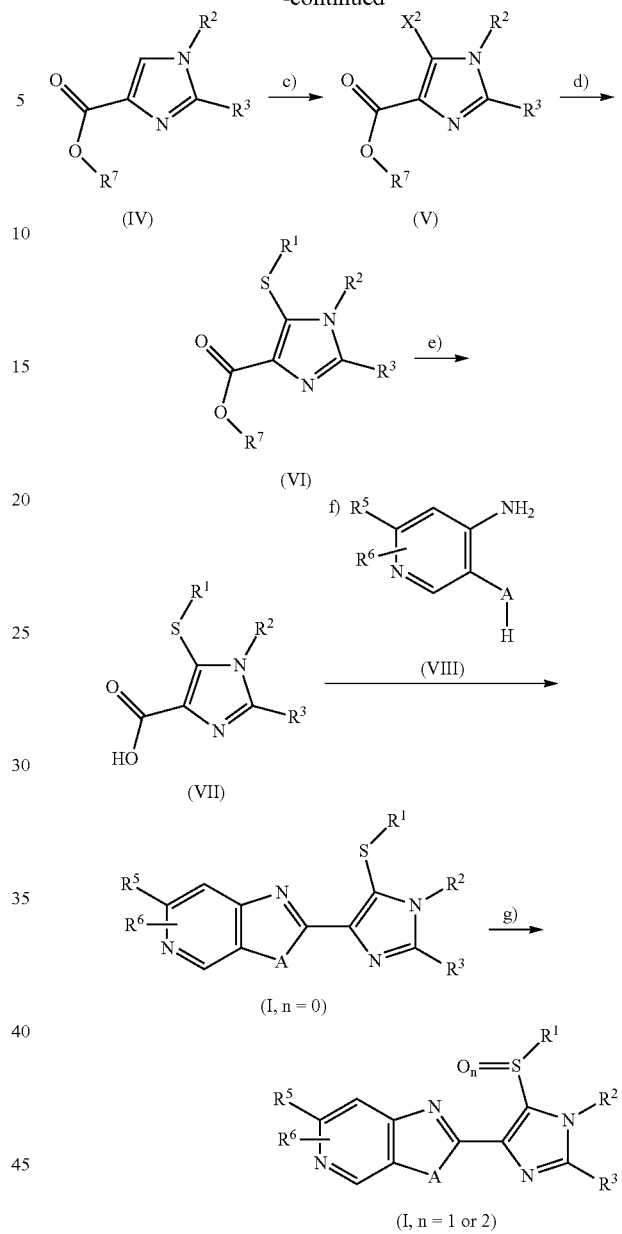

The radicals $R^1$, $R^2$, $R^3$, $R^5$ and $R^6$ have the meanings described above. A is —N—$R^4$, O or S, where $R^4$ has the meaning described above. $X^1$ and $X^2$ are halogen. $R^7$ is ($C_1$-$C_4$)alkyl.

Step a)

Compounds of the formula (III) may be prepared from imidazole derivatives of the formula (II), for example by reaction with a halogenating reagent such as N-bromosuccinimide (NBS) in a solvent such as for example tetrahydrofuran or by reaction of compounds of the formula (II) with NBS in combination with azobis(isobutyronitrile) (AIBN) in tetrachloromethane or chloroform, analogously to the methods described, for example, in WO2013/149997, WO2014/115077 or WO2011/123609.

Imidazole derivatives of the formula (II) are either commercially available or can be prepared by known methods, for example analogously to the methods described in WO2014/191894, US2003/229079 or WO2013/156608.

Step b)

Compounds of the formula (III), in which $X^1$ is preferably halogen from the series chlorine or bromine, may be converted to compounds of the formula (IV), for example by transition metal-mediated cross-couplings [cf. *Chem. Rev.* 1995, 95, 2457-2483; *Tetrahedron* 2002, 58, 9633-9695; *Metal-Catalyzed Cross-Coupling Reactions* (Eds.: A. de Meijere, F. Diederich), 2nd ed., Wiley-VCH, Weinheim, 2004] or by nucleophilic aromatic substitution (cf. the methods described in *Bioorganic and Medicinal Chemistry Letters* 2007, 17, 5825-5830 or U.S. Pat. No. 4,125,726).

For example, compounds of the formula (III), in which $X^1$ is preferably chlorine or bromine, may be reacted with suitable boronic acids $[R^3—B(OH)_2]$ or boronic esters according to known methods (cf. WO2012/143599, US2014/94474, US2014/243316, US2015/284358 or *Journal of Organic Chemistry* 2004, 69, 8829-8835) in the presence of suitable catalysts from the series of transition metal salts to give compounds of the formula (IV). Examples of preferred coupling catalysts include palladium catalysts such as [1,1'-bis(diphenylphosphino)ferrocene]dichloropalladium(II), bis(triphenylphosphine)palladium(II) dichloride or tetrakis(triphenylphosphine)palladium. Suitable basic reaction auxiliaries used to conduct the methods are preferably carbonates of sodium, potassium or caesium. Some of the required boronic acid derivatives $[R^3—B(OH)_2]$ or boronic ester derivatives are known and/or commercially available, or they can be prepared by generally known methods (cf. Boronic Acids (eds.: D. G. Hall), 2nd ed., Wiley-VCH, Weinheim, 2011). In this case, the reaction is preferably conducted in a mixture of water and an organic solvent selected from customary organic solvents that are inert under the prevailing reaction conditions. Ethers such as tetrahydrofuran, dioxane or 1,2-dimethoxyethane are frequently used.

Alternatively, it is possible to use stannane derivatives $[R^3—Sn(Et)_4]$ as coupling partners (cf. US2013/281433, WO2004/99177 or WO2016/71214). Some of the required stannane derivatives $[R^3—Sn(Et)_4]$ are known and/or commercially available, or they can be prepared by generally known methods (cf. WO2016/71214 or WO2007/148093).

Coupling of the halogenated imidazole derivative of the formula (III) with NH-containing heteroaromatics such as imidazoles or pyrazoles, optionally substituted as described above, to give compounds of the formula (IV) can be conducted by reaction under basic conditions (e.g. with sodium hydride in dimethylformamide (cf e.g. WO2005/58898). Alternatively, the reaction can be carried out under an inert gas atmosphere by catalysis with copper(I) salts, copper(I) iodide for example, in the presence of a suitable ligand, e.g. (trans)-N,N'-dimethylcyclohexane-1,2-diamine or R-(+)-proline, and a suitable base, e.g. potassium carbonate or potassium phosphate, in a suitable solvent such as 1,4-dioxane or toluene (cf. e.g. WO2016/109559). Under these reaction conditions, compounds of the formula (IV) where $R^3$=H may also be formed.

Step c)

Imidazole derivatives of the formula (V), in which $X^2$ is preferably halogen from the series of bromine or iodine, may be prepared using standard methods from compounds of the formula (IV) by reaction with, for example, bromine or N-bromosuccinimide (NBS), (cf. WO2009/115572 or WO2010/91411) or N-iodosuccinimide (NIS), optionally in the presence of acetic acid or trifluoroacetic acid (cf. WO2008/63287, WO2007/87548 or WO2009/152025).

Step d)

Compounds of the formula (V), in which $X^2$ is preferably halogen from the series of bromine or iodine, may be converted to compounds of the formula (VI), for example by reaction under basic conditions with mercaptan derivatives $(R^1—SH)$ and copper(I) salts (cf. EP257918 or WO2009/152025) or by nucleophilic aromatic substitution (cf. *Australian Journal of Chemistry* 1987, 40, 1415-1425).

Alternatively, the reaction of compounds of the formula (V), in which $X^2$ is preferably halogen from the series of bromine or iodine, with mercaptan derivatives $(R^1—SH)$ can be carried out in the presence of palladium catalysts such as tris(dibenzylideneacetone)dipalladium $[Pd_2(dba)_3]$. In this case, frequently used are amine bases such as triethylamine or N,N-diisopropylethylamine (DIPEA) and also phosphine ligands such as Xantphos (cf. WO2013/25958, WO2013/66869, US2009/27039, WO2011/58149, WO2011/143466 or *Bioorganic and Medicinal Chemistry Letters* 2016, 26, 2984-2987). In this case, the reaction is preferably conducted in a solvent selected from customary organic solvents that are inert under the prevailing reaction conditions. Preference is given to ethers, for example dioxane or 1,2-dimethoxyethane.

Mercaptan derivatives, for example methyl mercaptan, ethyl mercaptan or isopropyl mercaptan, are either commercially available or can be prepared by known methods, for example analogously to the methods described in US2006/25633, US2006/111591, U.S. Pat. No. 2,820,062, *Chemical Communications*, 13 (2000), 1163-1164 or *Journal of the American Chemical Society*, 44 (1922), pp. 1323-1333.

Step e)

Esters of the formula (VI) can be converted to carboxylic acids of the formula (VII) using standard methods (cf., for example, WO2014/191894, US2006/194779, WO2014/86663 or *European Journal of Organic Chemistry*, 2009, 213-222), for example with an alkali metal hydroxide as base, such as sodium hydroxide or lithium hydroxide, in an alcohol as solvent, for example methanol or ethanol.

Step f)

Compounds of the formula (I, n=0) can be prepared from compounds of the formulae (VII) with compounds of the formula (VIII) in the presence of a condensing composition.

Compounds of the formula (VIII) are either commercially available or can be prepared by known methods, for example analogously to the methods described in WO 2010/125985, WO 2012/074135, WO 2012/086848, WO 2013/018928, WO 2015/000715, WO 2015/121136, WO2016/039441, WO2016/059145, WO2016/071214, WO 2016/169882, WO 2016/169886 or WO2016/124557.

The conversion to compounds of the formula (I, n=0) can be effected neat or in a solvent, preference being given to conducting the reaction in a solvent selected from the customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; alcohols such as methanol, ethanol or isopropanol; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Examples of suitable condensing compositions are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

The reaction can be conducted in the presence of a suitable catalyst, for example 1-hydroxybenzotriazole.

The reaction can be carried out in the presence of an acid or a base.

Examples of an acid which can be used in the reaction described are sulfonic acids such as methanesulfonic acid or para-toluenesulfonic acid; carboxylic acids such as acetic acid, or polyphosphoric acids.

Examples of suitable bases are nitrogenous heterocycles such as pyridine, picoline, 2,6-lutidine, 1,8-diazabicyclo [5.4.0]-7-undecene (DBU); tertiary amines such as triethylamine and N,N-diisopropylethylamine; inorganic bases such as potassium phosphate, potassium carbonate and sodium hydride.

Step g)

The compounds of the formula (I, n=1 or 2) can be prepared by oxidation of compounds of the formula (I, n=0), for example analogously to the methods described in 2016/169882 or WO 2016/124557. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing compositions is hydrogen peroxide and meta-chloroperbenzoic acid.

Method B

The general method for the preparation of compounds of the formula (I) in which X is Q4, Q5 or Q6 is described hereinafter by way of example with reference to compounds of the formula (I) in which X is Q5.

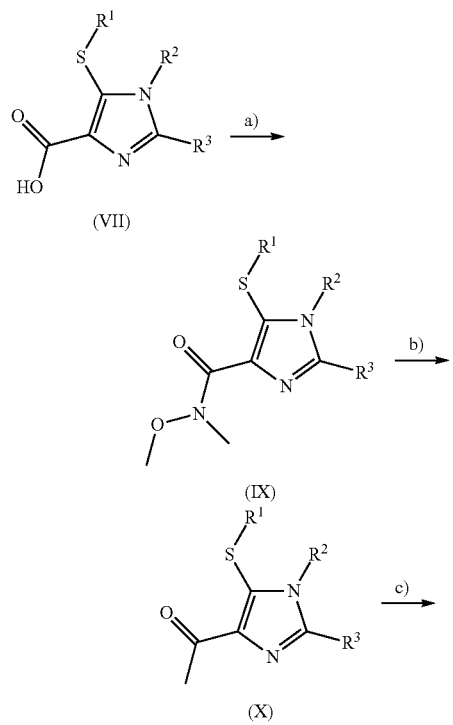

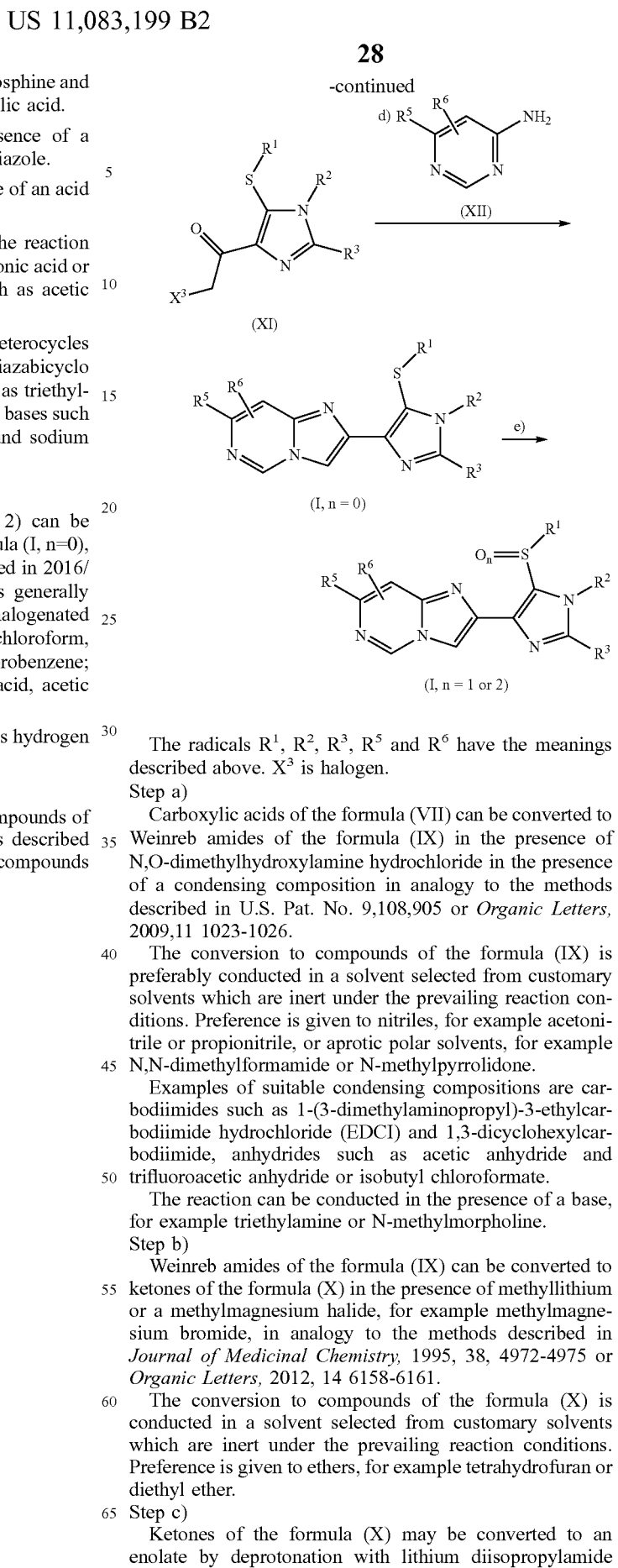

The radicals $R^1$, $R^2$, $R^3$, $R^5$ and $R^6$ have the meanings described above. $X^3$ is halogen.

Step a)

Carboxylic acids of the formula (VII) can be converted to Weinreb amides of the formula (IX) in the presence of N,O-dimethylhydroxylamine hydrochloride in the presence of a condensing composition in analogy to the methods described in U.S. Pat. No. 9,108,905 or *Organic Letters*, 2009,11 1023-1026.

The conversion to compounds of the formula (IX) is preferably conducted in a solvent selected from customary solvents which are inert under the prevailing reaction conditions. Preference is given to nitriles, for example acetonitrile or propionitrile, or aprotic polar solvents, for example N,N-dimethylformamide or N-methylpyrrolidone.

Examples of suitable condensing compositions are carbodiimides such as 1-(3-dimethylaminopropyl)-3-ethylcarbodiimide hydrochloride (EDCI) and 1,3-dicyclohexylcarbodiimide, anhydrides such as acetic anhydride and trifluoroacetic anhydride or isobutyl chloroformate.

The reaction can be conducted in the presence of a base, for example triethylamine or N-methylmorpholine.

Step b)

Weinreb amides of the formula (IX) can be converted to ketones of the formula (X) in the presence of methyllithium or a methylmagnesium halide, for example methylmagnesium bromide, in analogy to the methods described in *Journal of Medicinal Chemistry*, 1995, 38, 4972-4975 or *Organic Letters*, 2012, 14 6158-6161.

The conversion to compounds of the formula (X) is conducted in a solvent selected from customary solvents which are inert under the prevailing reaction conditions. Preference is given to ethers, for example tetrahydrofuran or diethyl ether.

Step c)

Ketones of the formula (X) may be converted to an enolate by deprotonation with lithium diisopropylamide (LDA) in tetrahydrofuran in analogy to the methods described in *Chemistry—A European Journal* 2011, 17, 4839-4848. The enolate formed can then be converted to silyl enol ethers, for example with trimethylsilyl chloride (TMSCl), which are subsequently converted to compounds of the formula (XI) by alpha-halogenation, for example with N-bromosuccinimide (NBS). Alternatively, proceeding from ketones of the formula (X), it is also possible to use other methods known from the literature for alpha-halogenation, for example analogously to the methods described in US2006/52378, WO2005/7631, US2012/214791 or U.S. Pat. No. 4,544,664.

Step d)

Compounds of the formula (I, n=0) can be prepared by cyclizing the compounds of the formula (XI) with amines of the formula (XII). The cyclization is effected, for example, in ethanol, acetonitrile or N,N-dimethylformamide by known methods in analogy to the processes described, for example, in WO2005/66177, WO2012/88411, WO2013/3298, US2009/203705, US2012/258951, WO2012/168733, WO2014/187762 or *J. Med. Chem.* 1988 31 1590-1595.

The compounds of the formula (XII) are commercially available or can be prepared by known methods, for example analogously to the processes described in US2009/170849, WO2016/51193, WO2016/107742 or WO2016/71214.

Step e)

The compounds of the formula (I, n=0) are converted to compounds of the formula (I, n=1 or 2) analogously to method A, step g).

Method C

The general method for the preparation of compounds of the formula (I) in which X is Q8, Q9, Q11 or Q12 is described hereinafter by way of example with reference to compounds of the formula (I) in which X is Q8.

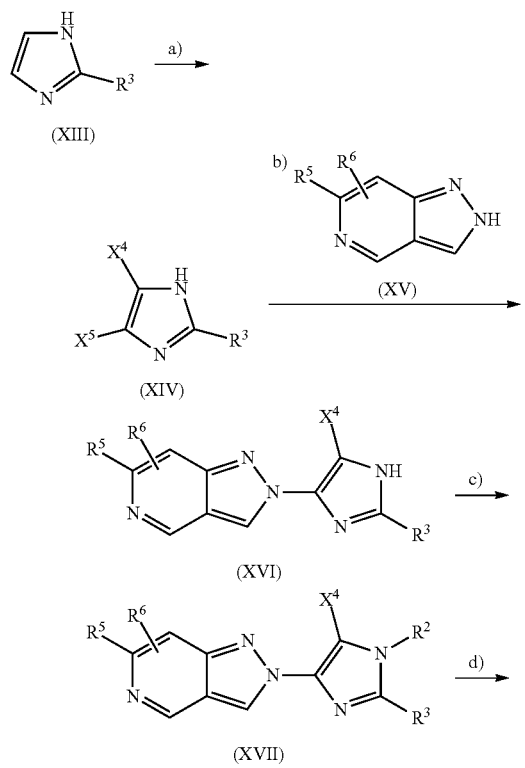

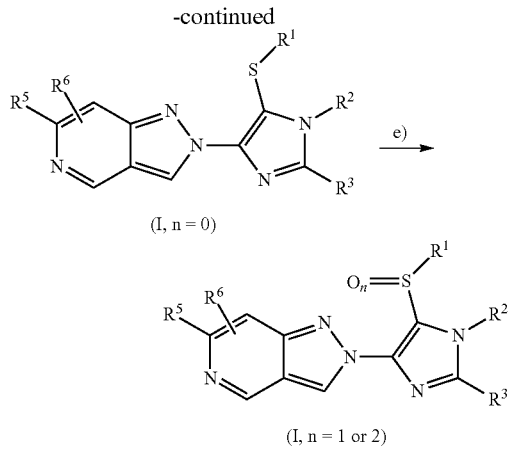

The radicals $R^1$, $R^2$, $R^3$, $R^5$ and $R^6$ have the meanings described above. $X^4$ and $X^5$ are halogen.

The sequence of steps b) to e) may be varied with one another.

Step a)

Imidazole derivatives of the formula (XIII), in analogy to method A, step a) and step c), may be reacted with a halogenating reagent such as NBS, bromine or iodine to give compounds of the formula (XIV)—in which $X^4$ and $X^5$ are preferably halogen from the series of bromine or iodine (cf. WO2011/85269, WO2004/80998 or WO2016/87487).

Compounds of the formula (XIII) are commercially available or may be prepared by known methods, for example in analogy to the methods described in *Advanced Synthesis and Catalysis* 2009, 351, 2912-2920; *Synthetic Communications* 1989, 19, 2551-2566 or WO2009/27746.

Step b)

Compounds of the formula (XVI) may be synthesized from compounds of the formula (XIV) by reaction with compounds of the formula (XV), for example by reaction under basic conditions—for example by using carbonate bases such as sodium carbonate or lithium carbonate—in an aprotic polar solvent such as N,N-dimethylformamide, in analogy to the methods described in *Bioorganic and Medicinal Chemistry* 2008, 16, 9524-9535; *Bioorganic and Medicinal Chemistry Letters* 1997, 7, 2723-2728 or WO2016/20286.

Alternatively, the reaction may be carried out in the presence of copper or copper(I) iodide and basic reaction auxiliaries, such as trans-N,N'-dimethylcyclohexane-1,2-diamine, potassium carbonate or potassium phosphate, in a suitable solvent or diluent, for example in analogy to the methods described in WO2016/20286 or KR2015/66012. Useful solvents or diluents include all inert organic solvents, for example aliphatic or aromatic hydrocarbons. Preference is given to using toluene.

Compounds of the formula (XV) are commercially available or may be prepared by known methods, for example in analogy to the method described in *Organic Letters* 2011, 13, 3542-3545.

Step c)

Imidazole derivatives of the formula (XVI) may be converted to N-substituted imidazole derivatives of the formula (XVII) using standard methods (cf. e.g. *Heterocycles* 1999, 50, 1081-1090; WO2009/70045 or *Bioorganic and Medicinal Chemistry Letters* 2007, 17, 1369-1375) by reaction with electrophiles, compounds comprising a leaving group ($R^2$-LG; LG=chlorine, bromine, iodine, O-triflate, O-mesyl), for example using an alkali metal hydroxide such as sodium hydroxide or potassium hydroxide as base, in an alcohol such as ethanol as solvent.

Step d)

The compounds of the formula (XVII) are converted to compounds of the formula (I, n=0) analogously to method A, step d).

Step e)

The compounds of the formula (I, n=0) are converted to compounds of the formula (I, n=1 or 2) analogously to method A, step g).

Method D

The general method for the preparation of compounds of the formula (I) in which X is Q8, Q9, Q11 or Q12 is described hereinafter by way of example with reference to compounds of the formula (I) in which X is Q8.

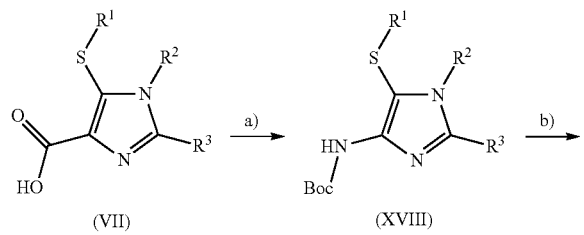

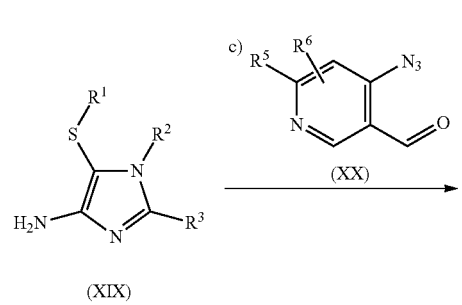

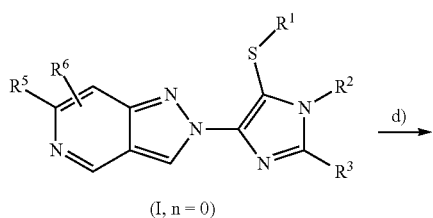

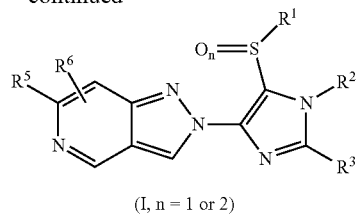

The radicals $R^1$, $R^2$, $R^3$, $R^5$ and $R^6$ have the meanings described above. [Boc=tert-butyloxycarbonyl Step a)

Imidazole derivatives of the formula (XVIII) may be prepared by known methods from compounds of the formula (VII) by reaction with diphenyl azidophosphate (DPPA) in tert-butanol in the presence of an amine base such as triethylamine, for example in analogy to the methods described in US2012/149699, WO2011/112766 or WO2009/23179.

Step b)

N-Boc-protected imidazole derivatives of the formula (XVIII) may be converted to imidazole derivatives of the formula (XIX) using standard methods (cf. e.g. WO2015/166289, US2008/9497 or WO2006/77424) by using an acid such as hydrochloric acid or trifluoroacetic acid in a solvent, for example 1,4-dioxane or methanol.

Step c)

Imidazole derivatives of the formula (XIX) may be converted to compounds of the formula (I, n=0) by reaction with compounds of the formula (XX) via imine formation (e.g. in toluene or dichloromethane) and subsequent cyclization with optional use of an acid such as titanium tetrachloride or titanium isopropoxide, for example in analogy to the methods described in WO2012/66061 or *Bioorganic and Medicinal Chemistry Letters* 2017, 27, 1593-1597.

Compounds of the formula (XX) may be prepared in analogy to methods known in the literature (see e.g. WO2015/116882, WO2017/75694, *Angewandte Chemie International Edition* 2011, 50, 1702-1706 or *Organic Letters* 2010, 12, 2884-2887).

Step d)

The compounds of the formula (I, n=0) are converted to compounds of the formula (I, n=1 or 2) analogously to method A, step g).

Method E

The general method for the preparation of compounds of the formula (I) in which X is Q1, Q2, Q3, Q7 or Q10 is described hereinafter by way of example with reference to compounds of the formula (I) in which X is Q1, Q2 or Q3.

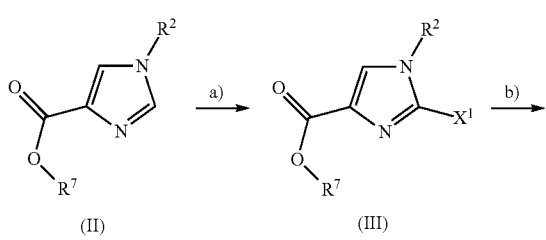

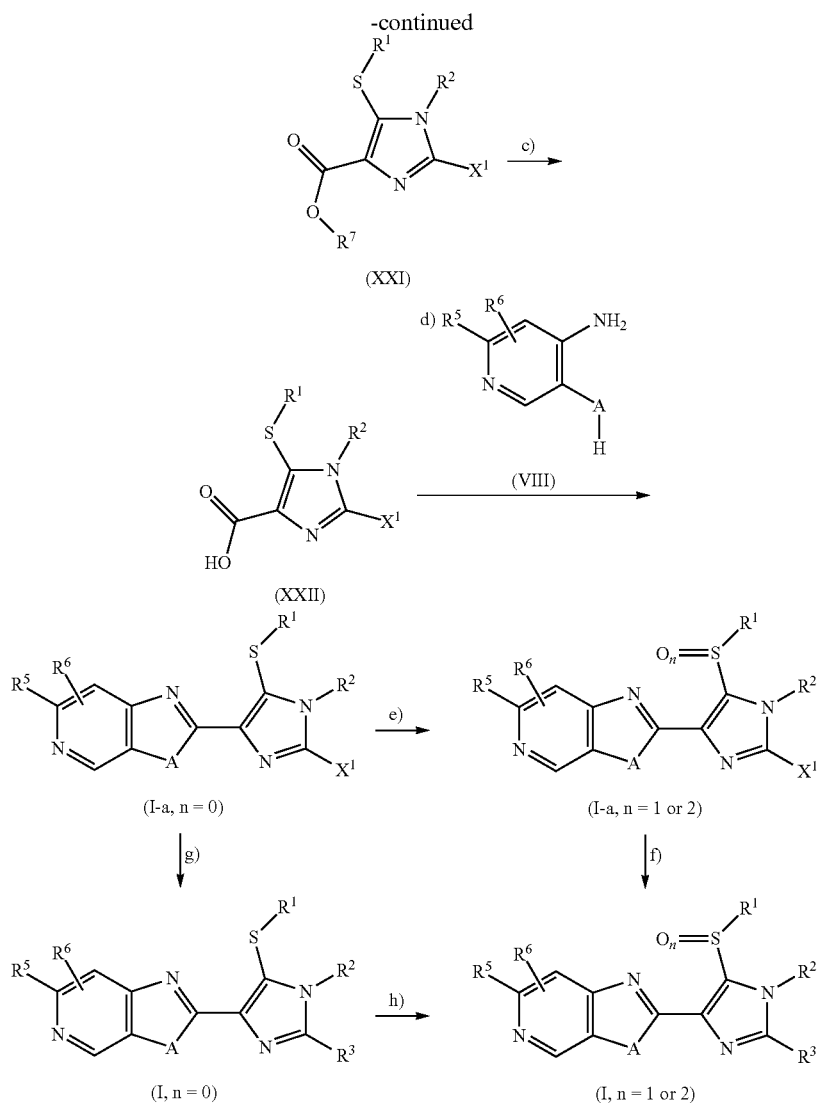

The radicals $R^1$, $R^2$, $R^3$, $R^5$ and $R^6$ have the meanings described above. A is —N—$R^4$, O or S, where $R^4$ has the meaning described above. $X^1$ is halogen. $R^7$ is ($C_1$-$C_4$)alkyl.

Step a)

Compounds of the formula (III) may be prepared from imidazole derivatives of the formula (II), for example by reaction with a halogenating reagent such as for example N-bromosuccinimide (NBS) in a solvent such as tetrahydrofuran or by reaction of compounds of the formula (II) with NBS in combination with azobis(isobutyronitrile) (AIBN) in tetrachloromethane or chloroform, for example analogously to the methods described in WO2013/149997, WO2014/115077 or WO2011/123609.

Imidazole derivatives of the formula (II) are either commercially available or can be prepared by known methods, for example analogously to the methods described in WO2014/191894, US2003/229079 or WO2013/156608.

Step b)

Imidazole derivatives of the formula (XXI) may be prepared using standard methods from compounds of the formula (III) by reaction with a disulfide ($R^1$—S—S—$R^1$) and, for example, a strong base, preferably lithium diisopropylamide (LDA) in tetrahydrofuran (cf. Bioorganic and Medicinal Chemistry Letters 2010, 20, 1084-108) or, for example, hydrogen peroxide and iodine in ethanol (cf. Synthesis 2015, 47, 659-671).

Step c)

The compounds of the formula (XXI) are converted to compounds of the formula (XXII) analogously to method A, step e).

Step d)

The compounds of the formula (XXII) are reacted with compounds of the formula (VIII) to give compounds of the formula (Ia, $X^1$=$R^3$=halogen, n=0) in analogy to method A, step f).

Step e, h)

The conversion of compounds of the formula (I-a, n=0) to compounds of the formula (I-a, n=1 or 2) and also the conversion of compounds of the formula (I, n=0) to compounds of the formula (I, n=1 or 2) are effected in analogy to method A, step g).

Step f, g)

The conversion of compounds of the formula (I-a, n=0) to compounds of the formula (I, n=0) and also the conversion of compounds of the formula (I-a, n=1 or 2) to compounds of the formula (I, n=1 or 2) are effected in analogy to method A, step b).

Starting from compounds of the formula (XXII), compounds of the formula (I) can also be prepared, in analogy to method B and subsequently carrying out steps e)->f) or g)->h) of method E, in which X is Q4, Q5 or Q6.

Method F

The general method for the preparation of compounds of the formula (I) in which R³ is, by way of illustration, functional groups described above, is described hereinafter by way of example with reference to compounds of the formula (I) in which X is Q1, Q2 or Q3.

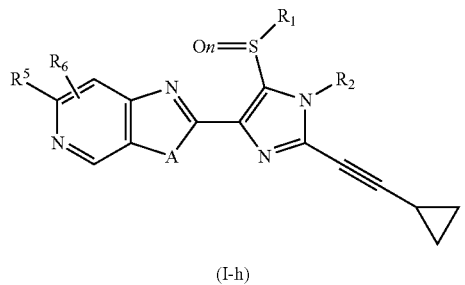

(I-h)

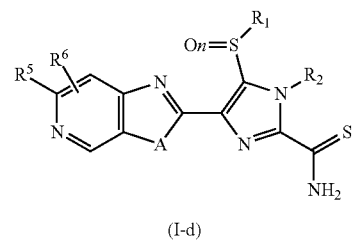

(I-d)

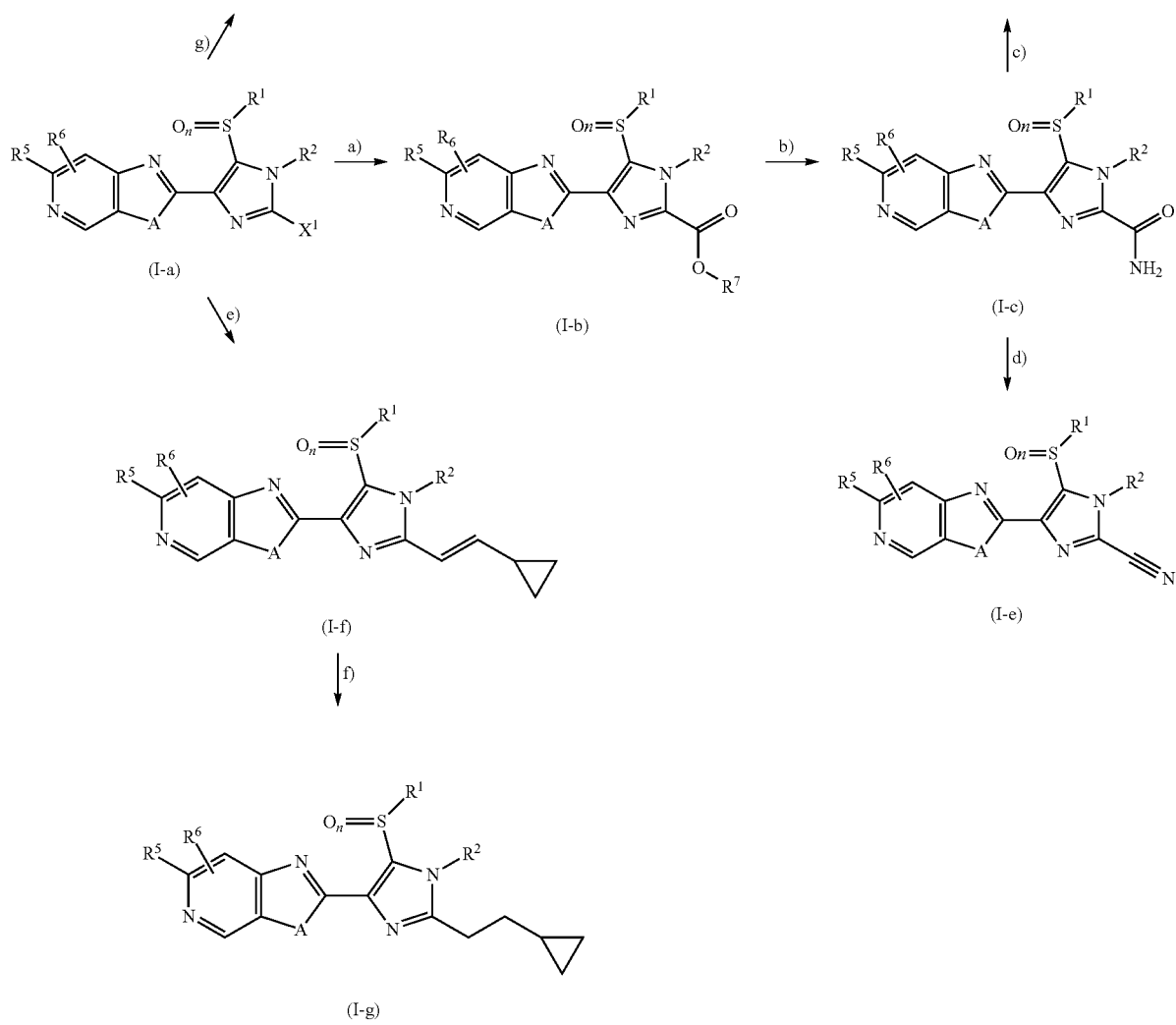

The radicals $R^1$, $R^2$, $R^5$ and $R^6$ have the meanings described above. A is —N—$R^4$, O or S, where $R^4$ has the meaning described above. $X^1$ is halogen. $R^7$ is ($C_1$-$C_4$)alkyl. n is 0, 1 or 2.

Step a)

Compounds of the formula (I-b) may be prepared from compounds of the formula (I-a) by reaction with carbon monoxide according to methods known from the literature, for example by reaction in a suitable alcohol (e.g. methanol or ethanol) and catalysis using a palladium catalyst such as palladium(II) dichloride, tetrakis(triphenylphosphine)palladium or bis(acetonitrile)palladium(II) dichloride, in the presence of a phosphine ligand, e.g. triphenylphosphine, Xantphos [(4,5-bis(diphenylphosphino)-9,9-dimethylxanthene)] or BINAP [2,2'-bis(diphenylphosphino)-1,1'-binaphthalene] and optionally in the presence of a suitable base, triethylamine for example [cf. e.g. US2014/46072, WO2004/106293 or *Journal of Medicinal Chemistry* 2009, 52, 2880-2898].

Step b)

The resulting esters of the formula (I-b) can be converted to the corresponding amides of the formula (I-c), for example by saponification in analogy to method A, step e) and subsequent activation of the carboxylic acid by coupling reagents such as 1-(3-dimethylaminopropyl)-3-ethylcarbodiimide hydrochloride (EDCI) [see also method A, step f)] or by conversion to the acyl chloride and reaction with an amine [cf e.g. WO2012/146666, US2014/315924 or WO2005/4863].

The amide formation can be effected directly from esters of the formula (I-b) by reaction with an amine, for example in methanol [cf. e.g. WO2014/72261 or US2013/338137], optionally in the presence of a base such as lithium bis(trimethylsilyl)amide (LHMDS) [cf. e.g. WO2016/87487].

Step c)

Thioamides of the formula (I-d) can be prepared from amides of the formula (I-c) by reaction with a suitable thionating reagent, for example Lawesson's reagent (cf., in analogy, for example, WO2005/9435) or $P_4S_{10}$ (cf., in analogy, for example, European Journal of Medicinal Chemistry 1995 30, 915-924), in suitable solvents, for example toluene or xylene.

Step d)

Compounds of the formula (I-e) can be prepared from primary amides of the formula [I-c, $R^3$=—C(O)$NH_2$] by reaction with a suitable condensing composition, for example phosphorus oxychloride ($POCl_3$) or phosphorus pentachloride ($PCl_5$), optionally in a suitable solvent such as dimethylformamide or toluene (cf in analogy to, e.g. US2013/338137, WO2005/77950, WO2007/123516), or alternatively by trifluoroacetic anhydride in a suitable solvent such as, e.g. dichloromethane, tetrahydrofuran or pyridine and optionally in the presence of a base such as triethylamine (cf. in analogy to, e.g. WO2014/198853 or *Bioorganic and Medicinal Chemistry Letters* 2011, 21, 6515-6518).

Step e)

The compounds of the formula (I-a) are converted to compounds of the formula (I-f) analogously to method A, step b).

Step f)

Compounds of the formula (I-g) may be prepared using standard methods from compounds of the formula (I-f) in a solvent (e.g. ethyl acetate or methanol) by using a hydrogenation catalyst (e.g. palladium on carbon or platinum dioxide) and reaction with hydrogen (cf. US2008/318935, US2011/275801 or WO2015/91584).

Step g)

The compounds of the formula (I-a) can be converted to compounds of the formula (I-f) analogously to method A, step b).

Alternatively, the reaction can also be carried out by using terminal alkyne derivatives, palladium catalysts such as bis(triphenylphosphine)palladium(II) dichloride or tetrakis (triphenylphosphine)palladium, copper iodide and an amine base such as triethylamine in a suitable solvent such as dimethylformamide (cf. by analogy e.g. WO 2002046166 or *Organic & Biomolecular Chemistry* 2011, 9, 450-462).

Methods and Uses

The invention also relates to methods for controlling animal pests, in which compounds of the formula (I) are allowed to act on animal pests and/or their habitat. The control of the animal pests is preferably carried out in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection compositions.

In the context of the present application, the term "pesticide" in each case also always encompasses the term "crop protection composition".

The compounds of the formula (I), given good plant tolerance, favourable endotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, especially nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" should be understood to mean any and all measures, provisions and procedures which have the aim of preventing diseases, especially infection diseases, and which serve to protect the health of humans and animals and/or protect the environment and/or maintain cleanliness. According to the invention, this especially includes measures for cleaning, disinfection and sterilization, for example of textiles or hard surfaces, especially surfaces made of glass, wood, cement, porcelain, ceramic, plastic or else metal(s), in order to ensure that these are free of hygiene pests and/or their secretions. The scope of protection of the invention in this regard preferably excludes surgical or therapeutic treatment procedures to be applied to the human body or the bodies of animals, and diagnostic procedures which are carried out on the human body or the bodies of animals.

The term "hygiene sector" covers all areas, technical fields and industrial applications in which these hygiene measures, provisions and procedures are important, for example with regard to hygiene in kitchens, bakeries, airports, bathrooms, swimming pools, department stores, hotels, hospitals, stables, animal keeping, etc.

The term "hygiene pest" should therefore be understood to mean one or more animal pests whose presence in the hygiene sector is problematic, especially for reasons of health. A main aim is therefore that of avoiding, or limiting to a minimum degree, the presence of hygiene pests and/or the exposure to these in the hygiene sector. This can especially be achieved through the use of a pesticide which can be used both for prevention of infestation and for prevention of an existing infestation. It is also possible to use formulations which prevent or reduce exposure to pests. Hygiene pests include, for example, the organisms mentioned below.

The term "hygiene protection" thus covers all acts by which these hygiene measures, provisions and procedures are maintained and/or improved.

The compounds of the formula (I) can preferably be used as pesticides. They are active against normally sensitive and resistant species and also against all or specific stages of development. The abovementioned pests include:

pests from the phylum of the Arthropoda, in particular from the class of the Arachnida, for example *Acarus* spp., for example *Acarus siro, Aceria kuko, Aceria sheldoni, Aculops* spp., *Aculus* spp., e.g. *Aculus fockeui, Aculus schlechtendali, Amblyomma* spp., *Amphitetranychus viennensis, Argas* spp., *Boophilus* spp., *Brevipalpus* spp., e.g. *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., e.g. *Eotetranychus hicoriae, Epitrimerus pyri, Eutetranychus* spp., e.g. *Eutetranychus banksi, Eriophyes* spp., e.g. *Eriophyes pyri, Glycyphagus domesticus, Halotydeus destructor, Hemitarsonemus* spp., e.g. *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., e.g. *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., e.g. *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., e.g. *Tarsonemus confusus, Tarsonemus pallidus, Tetranychus* spp., e.g. *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea e.g. *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., e.g. *Periplaneta americana, Periplaneta australasiae, Pycnoscelus surinamensis, Supella longipalpa;* from the order of the Coleoptera, for example, *Acalymma vittatum, Acanthoscelides obtectus, Adoretus* spp., *Aethina tumida, Agelastica alni, Agrilus* spp., e.g. *Agrilus planipennis, Agrilus coxalis, Agrilus bilineatus, Agrilus anxius, Agriotes* spp., e.g. *Agriotes linneatus, Agriotes mancus, Alphitobius diaperinus, Amphimallon solstitialis, Anobium punctatum, Anoplophora* spp., e.g. *Anoplophora glabripennis, Anthonomus* spp., e.g. *Anthonomus grandis, Anthrenus* spp., *Apion* spp., *Apogonia* spp., *Atomaria* spp., e.g. *Atomaria linearis, Attagenus* spp., *Baris caerulescens, Bruchidius obtectus, Bruchus* spp., e.g. *Bruchus pisorum, Bruchus rufimanus, Cassida* spp., *Cerotoma trifurcata, Ceutorrhynchus* spp., e.g. *Ceutorrhynchus assimilis, Ceutorrhynchus quadridens, Ceutorrhynchus rapae, Chaetocnema* spp., e.g. *Chaetocnema confinis, Chaetocnema denticulata, Chaetocnema ectypa, Cleonus mendicus, Conoderus* spp., *Cosmopolites* spp., e.g. *Cosmopolites sordidus, Costelytra zealandica, Ctenicera* spp., *Curculio* spp., e.g. *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus fumissi, Dendroctonus* spp., e.g. *Dendroctonus ponderosae, Dermestes* spp., *Diabrotica* spp., e.g. *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., e.g. *Epilachna borealis, Epilachna varivestis, Epitrix* spp., e.g. *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., e.g. *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., e.g. *Leucoptera coffeella, Limonius ectypus, Lissorhoptrus oryzophilus, Listronotus* (=*Hyperodes*) *spp., Lixus* spp., *Luperodes* spp., *Luperomorpha xanthodera, Lyctus* spp., *Megacyllene* spp., e.g. *Megacyllene robiniae, Megascelis* spp., *Melanotus* spp., e.g. *Melanotus longulus oregonensis, Meligethes aeneus, Melolontha* spp., e.g. *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., e.g. *Otiorhynchus cribricollis, Otiorhynchus ligustici, Otiorhynchus ovatus, Otiorhynchus rugosostriarus, Otiorhynchus sulcatus, Oulema* spp., e.g. *Oulema melanopus, Oulema oryzae, Oxycetonia jucunda, Phaedon cochleariae, Phyllophaga* spp., *Phyllophaga helleri, Phyllotreta* spp., e.g. *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., e.g. *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Scolytus* spp., e.g. *Scolytus multistriatus, Sinoxylon perforans, Sitophilus* spp., e.g. *Sitophilus granarius, Sitophilus linearis, Sitophilus oryzae, Sitophilus zeamais, Sphenophorus* spp., *Stegobium paniceum, Sternechus* spp., e.g. *Sternechus paludatus, Symphyletes* spp., *Tanymecus* spp., e.g. *Tanymecus dilaticollis, Tanymecus indicus, Tanymecus palliatus, Tenebrio molitor, Tenebrioides mauretanicus, Tribolium* spp., e.g. *Tribolium audax, Tribolium castaneum, Tribolium confusum, Trogoderma* spp., *Tychius* spp., *Xylotrechus* spp., *Zabrus* spp., e.g. *Zabrus tenebrioides;* from the order of the Dermaptera, for example *Anisolabis maritime, Forficula auricularia, Labidura riparia;* from the order of the Diptera, for example *Aedes* spp., e.g. *Aedes aegypti, Aedes albopictus, Aedes sticticus, Aedes vexans, Agromyza* spp., e.g. *Agromyza frontella, Agromyza parvicornis, Anastrepha* spp., *Anopheles* spp., e.g. *Anopheles quadrimaculatus, Anopheles gambiae, Asphondylia* spp., *Bactrocera* spp., e.g. *Bactrocera cucurbitae, Bactro-* cera dorsalis, Bactrocera oleae, Bibio hortulanus, Calliphora erythrocephala, Calliphora vicina, Ceratitis capitata, Chironomus spp., Chrysomya spp., Chrysops spp., Chrysozona pluvialis, Cochliomya spp., Contarinia spp., e.g. Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex spp., e.g. Culex pipiens, Culex quinquefasciatus, Culicoides spp., Culiseta spp., Cuterebra spp., Dacus oleae, Dasineura spp., e.g. Dasineura brassicae, Delia spp., e.g. Delia antiqua, Delia coarctata, Delia florilega, Delia platura, Delia radicum, Dermatobia hominis, Drosophila spp., e.g. Drosphila melanogaster, Drosophila suzukii, Echinocnemus spp., Euleia heraclei, Fannia spp., Gasterophilus spp., Glossina spp., Haematopota spp., Hydrellia spp., Hydrellia griseola, Hylemya spp., Hippobosca spp., Hypoderma spp., Liriomyza spp., e.g. Liriomyza brassicae, Liriomyza huidobrensis, Liriomyza sativae, Lucilia spp., e.g. Lucilia cuprina, Lutzomyia spp., Mansonia spp., Musca spp., e.g. Musca domestica, Musca domestica vicina, Oestrus spp., Oscinella frit, Paratanytarsus spp., Paralauterborniella subcincta, Pegomya oder Pegomyia spp., e.g. Pegomya betae, Pegomya hyoscyami, Pegomya rubivora, Phlebotomus spp., Phorbia spp., Phormia spp., Piophila casei, Platyparea poeciloptera, Prodiplosis spp., Psila rosae, Rhagoletis spp., e.g. Rhagoletis cingulata, Rhagoletis completa, Rhagoletis fausta, Rhagoletis indifferens, Rhagoletis mendax, Rhagoletis pomonella, Sarcophaga spp., Simulium spp., e.g. Simulium meridionale, Stomoxys spp., Tabanus spp., Tetanops spp., Tipula spp., e.g. Tipula paludosa, Tipula simplex, Toxotrypana curvicauda;

from the order of the Hemiptera, for example Acizzia acaciaebaileyanae, Acizzia dodonaeae, Acizzia uncatoides, Acrida turrita, Acyrthosipon spp., e.g. Acyrthosiphon pisum, Acrogonia spp., Aeneolamia spp., Agonoscena spp., Aleurocanthus spp., Aleyrodes proletella, Aleurolobus barodensis, Aleurothrixus floccosus, Allocaridara malayensis, Amrasca spp., e.g. Amrasca bigutulla, Amrasca devastans, Anuraphis cardui, Aonidiella spp., e.g. Zygina spp.; Aonidiella aurantii, Aonidiella citrina, Aonidiella inornata, Aphanostigma piri, Aphis spp., e.g. Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis vibumiphila, Arboridia apicalis, Arytainilla spp., Aspidiella spp., Aspidiotus spp., e.g. Aspidiotus nerii, Atanus spp., Aulacorthum solani, Bemisia tabaci, Blastopsylla occidentalis, Boreioglycaspis melaleucae, Brachycaudus helichrysi, Brachycolus spp., Brevicoryne brassicae, Cacopsylla spp., e.g. Cacopsylla pyricola, Calligypona marginata, Capulinia spp., Carneocephala fulgida, Ceratovacuna lanigera, Cercopidae, Ceroplastes spp., Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus spp., e.g. Coccus hesperidum, Coccus longulus, Coccus pseudomagnoliarum, Coccus viridis, Cryptomyzus ribis, Cryptoneossa spp., Ctenarytaina spp., Dalbulus spp., Dialeurodes chittendeni, Dialeurodes citri, Diaphorina citri, Diaspis spp., Diuraphis spp., Doralis spp., Drosicha spp., Dysaphis spp., e.g. Dysaphis apiifolia, Dysaphis plantaginea, Dysaphis tulipae, Dysmicoccus spp., Empoasca spp., e.g. Empoasca abrupta, Empoasca fabae, Empoasca maligna, Empoasca solana, Empoasca stevensi, Eriosoma spp., e.g. Eriosoma americanum, Eriosoma lanigerum, Eriosoma pyricola, Erythroneura spp., Eucalyptolyma spp., Euphyllura spp., Euscelis bilobatus, Ferrisia spp., Fiorinia spp., Furcaspis oceanica, Geococcus coffeae, Glycaspis spp., Heteropsylla cubana, Heteropsylla spinulosa, Homalodisca coagulata, Hyalopterus arundinis, Hyalopterus pruni, Icerya spp., e.g. Icerya purchasi, Idiocerus spp., Idioscopus spp., Laodelphax striatellus, Lecanium spp., e.g. Lecanium comi (=Parthenolecanium corni), Lepidosaphes spp., e.g. Lepidosaphes ulmi, Lipaphis erysimi, Lopholeucaspis japonica, Lycorma delicatula, Macrosiphum spp., e.g. Macrosiphum euphorbiae, Macrosiphum lilii, Macrosiphum rosae, Macrosteles facifrons, Mahanarva spp., Melanaphis sacchari, Metcalfiella spp., Metcalfa pruinosa, Metopolophium dirhodum, Monellia costalis, Monelliopsis pecanis, Myzus spp., e.g. Myzus ascalonicus, Myzus cerasi, Myzus ligustri, Myzus ornatus, Myzus persicae, Myzus nicotianae, Nasonovia ribisnigri, Neomaskellia spp., Nephotettix spp., e.g. Nephotettix cincticeps, Nephotettix nigropictus, Nettigoniclla spectra, Nilaparvata lugens, Oncometopia spp., Orthezia praelonga, Oxya chinensis, Pachypsylla spp., Parabemisia myricae, Paratrioza spp., e.g. Paratrioza cockerelli, Parlatoria spp., Pemphigus spp., e.g. Pemphigus bursarius, Pemphigus populivenae, Peregrinus maidis, Perkinsiella spp., Phenacoccus spp., e.g. Phenacoccus madeirensis, Phloeomyzus passerinii, Phorodon humuli, Phylloxera spp., e.g. Phylloxera devastatrix, Phylloxera notabilis, Pinnaspis aspidistrae, Planococcus spp., e.g. Planococcus citri, Prosopidopsylla flava, Protopulvinaria pyriformis, Pseudaulacaspis pentagona, Pseudococcus spp., e.g. Pseudococcus calceolariae, Pseudococcus comstocki, Pseudococcus longispinus, Pseudococcus maritimus, Pseudococcus viburni, Psyllopsis spp., Psylla spp., e.g. Psylla buxi, Psylla mali, Psylla pyri, Pteromalus spp., Pulvinaria spp., Pyrilla spp., Quadraspidiotus spp., e.g. Quadraspidiotus juglansregiae, Quadraspidiotus ostreaeformis, Quadraspidiotus perniciosus, Quesada gigas, Rastrococcus spp., Rhopalosiphum spp., e.g. Rhopalosiphum maidis, Rhopalosiphum oxyacanthae, Rhopalosiphum padi, Rhopalosiphum rufiabdominale, Saissetia spp., e.g. Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata spp., Sogatella furcifera, Sogatodes spp., Stictocephala festina, Siphoninus phillyreae, Tenalaphara malayensis, Tetragonocephela spp., Tinocallis caryaefoliae, Tomaspis spp., Toxoptera spp., e.g. Toxoptera aurantii, Toxoptera citricidus, Trialeurodes vaporariorum, Trioza spp., e.g. Trioza diospyri, Typhlocyba spp., Unaspis spp., Viteus vitifolii, Zygina spp.;

from the suborder of the Heteroptera, for example, Aelia spp., Anasa tristis, Antestiopsis spp., Boisea spp., Blissus spp., Calocoris spp., Campylomma livida, Cavelerius spp., Cimex spp., e.g. Cimex adjunctus, Cimex hemipterus, Cimex lectularius, Cimex pilosellus, Collaria spp., Creontiades dilutus, Dasynus piperis, Dichelops furcatus, Diconocoris hewetti, Dysdercus spp., Euschistus spp., e.g. Euschistus heros, Euschistus servus, Euschistus tristigmus, Euschistus variolarius, Eurydema spp., Eurygaster spp., Halyomorpha halys, Heliopeltis spp., Horcias nobilellus, Leptocorisa spp., Leptocorisa varicornis, Leptoglossus occidentalis, Leptoglossus phyllopus, Lygocoris spp., e.g. Lygocoris pabulinus, Lygus spp., e.g. Lygus elisus, Lygus hesperus, Lygus lineolaris, Macropes excavatus, Megacopta cribraria, Miridae, Monalonion atratum, Nezara spp., e.g. Nezara viridula, Nysius spp., Oebalus spp., Pentomidae, Piesma quadrata, Piezodorus spp., e.g. Piezodorus guildinii, Psallus spp., Pseudacysta persea, Rhodnius spp., Sahlbergella singularis, Scaptocoris castanea, Scotinophora spp., Stephanitis nashi, Tibraca spp., Triatoma spp.;

from the order of the Hymenoptera, for example, *Acromyrmex* spp., *Athalia* spp., e.g. *Athalia rosae*, *Atta* spp., *Camponotus* spp., *Dolichovespula* spp., *Diprion* spp., e.g. *Diprion similis*, *Hoplocampa* spp., e.g. *Hoplocampa cookei*, *Hoplocampa testudinea*, *Lasius* spp., *Linepithema* (*Iridiomyrmex*) *humile*, *Monomorium pharaonis*, *Paratrechina* spp., *Paravespula* spp., *Plagiolepis* spp., *Sirex* spp., e.g. *Sirex noctilio*, *Solenopsis invicta*, *Tapinoma* spp., *Technomyrmex albipes*, *Urocerus* spp., *Vespa* spp., e.g. *Vespa crabro*, *Wasmannia auropunctata*, *Xeris* spp.;

from the order of the Isopoda, for example *Armadillidium vulgare*, *Oniscus asellus*, *Porcellio scaber;* from the order of the Isoptera, for example, *Reticulitermes flavipes*, *Reticulitermes hesperus;* from the order of the Lepidoptera, for example, *Achroia grisella*, *Acronicta major*, *Adoxophyes* spp., e.g. *Adoxophyes orana*, *Aedia leucomelas*, *Agrotis* spp., e.g. *Agrotis segetum*, *Agrotis ipsilon*, *Alabama* spp., e.g. *Alabama argillacea*, *Amyelois transitella*, *Anarsia* spp., *Anticarsia* spp., e.g. *Anticarsia gemmatalis*, *Argyroploce* spp., *Autographa* spp., *Barathra brassicae*, *Blastodacna atra*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., e.g. *Chilo plejadellus*, *Chilo suppressalis*, *Choreutis pariana*, *Choristoneura* spp., *Chrysodeixis chalcites*, *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., e.g. *Cydia nigricana*, *Cydia pomonella*, *Dalaca noctuides*, *Diaphania* spp., *Diparopsis* spp., *Diatraea saccharalis*, *Dioryctria* spp., e.g. *Dioryctria zimmermani*, *Earias* spp., *Ecdytolopha aurantium*, *Elasmopalpus lignosellus*, *Eldana saccharina*, *Ephestia* spp., e.g. *Ephestia elutella*, *Ephestia kuehniella*, *Epinotia* spp., *Epiphyas postvittana*, *Erannis* spp., *Erschoviella musculana*, *Etiella* spp., *Eudocima* spp., *Eulia* spp., *Eupoecilia ambiguella*, *Euproctis* spp., e.g. *Euproctis chrysorrhoea*, *Euxoa* spp., *Feltia* spp., *Galleria mellonella*, *Gracillaria* spp., *Grapholitha* spp., e.g. *Grapholita molesta*, *Grapholita prunivora*, *Hedylepta* spp., *Helicoverpa* spp., e.g. *Helicoverpa armigera*, *Helicoverpa zea*, *Heliothis* spp., e.g. *Heliothis virescens*, *Hofmannophila pseudospretella*, *Homoeosoma* spp., *Homona* spp., *Hyponomeuta padella*, *Kakivoria flavofasciata*, *Lampides* spp., *Laphygma* spp., *Laspeyresia molesta*, *Leucinodes orbonalis*, *Leucoptera* spp., e.g. *Leucoptera coffeella*, *Lithocolletis* spp., e.g. *Lithocolletis blancardella*, *Lithophane antennata*, *Lobesia* spp., e.g. *Lobesia botrana*, *Loxagrotis albicosta*, *Lymantria* spp., e.g. *Lymantria dispar*, *Lyonetia* spp., e.g. *Lyonetia clerkella*, *Malacosoma neustria*, *Maruca testulalis*, *Mamestra brassicae*, *Melanitis leda*, *Mocis* spp., *Monopis obviella*, *Mythimna separata*, *Nemapogon cloacellus*, *Nymphula* spp., *Oiketicus* spp., *Omphisa* spp., *Operophtera* spp., *Oria* spp., *Orthaga* spp., *Ostrinia* spp., e.g. *Ostrinia nubilalis*, *Panolis flammea*, *Parnara* spp., *Pectinophora* spp., e.g. *Pectinophora gossypiella*, *Perileucoptera* spp., *Phthorimaea* spp., e.g. *Phthorimaea operculella*, *Phyllocnistis citrella*, *Phyllonorycter* spp., e.g. *Phyllonorycter blancardella*, *Phyllonorycter crataegella*, *Pieris* spp., e.g. *Pieris rapae*, *Platynota stultana*, *Plodia interpunctella*, *Plusia* spp., *Plutella xylostella* (=*Plutella maculipennis*), *Podesia* spp., e.g. *Podesia syringae*, *Prays* spp., *Prodenia* spp., *Protoparce* spp., *Pseudaletia* spp., e.g. *Pseudaletia unipuncta*, *Pseudoplusia includens*, *Pyrausta nubilalis*, *Rachiplusia nu*, *Schoenobius* spp., e.g. *Schoenobius bipunctifer*, *Scirpophaga* spp., e.g. *Scirpophaga innotata*, *Scotia segetum*, *Sesamia* spp., e.g. *Sesamia inferens*, *Sparganothis* spp., *Spodoptera* spp., e.g. *Spodoptera eradiana*, *Spodoptera exigua*, *Spodoptera frugiperda*, *Spodoptera praefica*, *Stathmopoda* spp., *Stenoma* spp., *Stomopteryx subsecivella*, *Synanthedon* spp., *Tecia solanivora*, *Thaumetopoea* spp., *Thermesia gemmatalis*, *Tinea cloacella*, *Tinea pellionella*, *Tineola bisselliella*, *Tortrix* spp., *Trichophaga tapetzella*, *Trichoplusia* spp., e.g. *Trichoplusia ni*, *Tryporyza incertulas*, *Tuta absoluta*, *Virachola* spp.;

from the order of the Orthoptera or Saltatoria, for example *Acheta domesticus*, *Dichroplus* spp., *Gryllotalpa* spp., e.g. *Gryllotalpa gryllotalpa*, *Hieroglyphus* spp., *Locusta* spp., e.g. *Locusta migratoria*, *Melanoplus* spp., e.g. *Melanoplus devastator*, *Paratlanticus ussuriensis*, *Schistocerca gregaria;* from the order of the Phthiraptera, for example *Damalinia* spp., *Haematopinus* spp., *Linognathus* spp., *Pediculus* spp., *Phylloxera vastatrix*, *Phthirus pubis*, *Trichodectes* spp.; *Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., for example *Ctenocephalides canis*, *Ctenocephalides felis*, *Pulex irritans*, *Tunga penetrans*, *Xenopsylla cheopis;* from the order of the Thysanoptera, for example *Anaphothrips obscurus*, *Baliothrips biformis*, *Chaetanaphothrips leeuweni*, *Drepanothrips reuteri*, *Enneothrips flavens*, *Frankliniella* spp., e.g. *Frankliniella fusca*, *Frankliniella occidentalis*, *Frankliniella schultzei*, *Frankliniella tritici*, *Frankliniella vaccinii*, *Frankliniella williamsi*, *Haplothrips* spp., *Heliothrips* spp., *Hercinothrips femoralis*, *Kakothrips* spp., *Rhipiphorothrips cruentatus*, *Scirtothrips* spp., *Taeniothrips cardamomi*, *Thrips* spp., e.g. *Thrips palmi*, *Thrips tabaci;* from the order of the Zygentoma (=Thysanura), for example *Ctenolepisma* spp., *Lepisma saccharina*, *Lepismodes inquilinus*, *Thermobia domestica;* from the class of the Symphyla, for example *Scutigerella* spp., e.g. *Scutigerella immaculata;* pests from the phylum of the Mollusca, for example from the class of the Bivalvia, e.g. *Dreissena* spp.;

and also from the class of the Gastropoda, for example *Arion* spp., e.g. *Arion ater rufus*, *Biomphalaria* spp., *Bulinus* spp., *Deroceras* spp., e.g. *Deroceras laeve*, *Galba* spp., *Lymnaea* spp., *Oncomelania* spp., *Pomacea* spp., *Succinea* spp.;

plant pests from the phylum of the Nematoda, i.e. phytoparasitic nematodes, especially *Aglenchus* spp., e.g. *Aglenchus agricola*, *Anguina* spp., e.g. *Anguina tritici*, *Aphelenchoides* spp., e.g. *Aphelenchoides arachidis*, *Aphelenchoides fragariae*, *Belonolaimus* spp., e.g. *Belonolaimus gracilis*, *Belonolaimus longicaudatus*, *Belonolaimus nortoni*, *Bursaphelenchus* spp., e.g. *Bursaphelenchus cocophilus*, *Bursaphelenchus eremus*, *Bursaphelenchus xylophilus*, *Cacopaurus* spp., e.g. *Cacopaurus pestis*, *Criconemella* spp., e.g. *Criconemella curvata*, *Criconemella onoensis*, *Criconemella ornata*, *Criconemella rusium*, *Criconemella xenoplax* (=*Mesocriconema xenoplax*), *Criconemoides* spp., e.g. *Criconemoides femiae*, *Criconemoides onoense*, *Criconemoides ornatum*, *Ditylenchus* spp., e.g. *Ditylenchus dipsaci*, *Dolichodorus* spp., *Globodera* spp., e.g. *Globodera pallida*, *Globodera rostochiensis*, *Helicotylenchus* spp., e.g. *Helicotylenchus dihystera*, *Hemicriconemoides* spp., *Hemicycliophora* spp., *Heterodera* spp., e.g. *Heterodera avenae*, *Heterodera glycines*, *Heterodera schachtii*, *Hirschmaniella* spp., *Hoplolaimus* spp., *Longidorus* spp., e.g. *Longidorus africanus*, *Meloidogyne* spp., e.g. *Meloidogyne chitwoodi*, *Meloidogyne fallax*, *Meloidogyne hapla*, *Meloidogyne*

*incognita, Meloinema* spp., *Nacobbus* spp., *Neotylenchus* spp., *Paralongidorus* spp., *Paraphelenchus* spp., *Paratrichodorus* spp., e.g. *Paratrichodorus minor, Paratylenchus* spp., e.g. *Pratylenchus penetrans, Pseudohalenchus* spp., *Psilenchus* spp., *Punctodera* spp., *Quinisulcius* spp., *Radopholus* spp., e.g. *Radopholus citrophilus, Radopholus similis, Rotylenchulus* spp., *Rotylenchus* spp., *Scutellonema* spp., *Subanguina* spp., *Trichodorus* spp., e.g. *Trichodorus obtusus, Trichodorus primitivus, Tylenchorhynchus* spp., e.g. *Tylenchorhynchus annulatus, Tylenchulus* spp., e.g. *Tylenchulus semipenetrans, Xiphinema* spp., e.g. *Xiphinema index.*

The compounds of the formula (I) can, as the case may be, at certain concentrations or application rates, also be used as herbicides, safeners, growth regulators or compositions to improve plant properties, as microbicides or gametocides, for example as fungicides, antimycotics, bactericides, virucides (including compositions against viroids) or as compositions against MLO (mycoplasma-like organisms) and RLO (rickettsia-like organisms). They can, as the case may be, also be used as intermediates or precursors for the synthesis of other active ingredients.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemical active ingredients.

Preference is given to formulations or use forms comprising auxiliaries, for example extenders, solvents, spontaneity promoters, carriers, emulsifiers, dispersants, frost protection compositions, biocides, thickeners and/or further auxiliaries, for example adjuvants. An adjuvant in this context is a component which enhances the biological effect of the formulation, without the component itself having any biological effect. Examples of adjuvants are compositions which promote retention, spreading, attachment to the leaf surface or penetration.

These formulations are produced in a known manner, for example by mixing the compounds of the formula (I) with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and their ethers and esters, ketones, for example acetone, methyl ethyl ketone, methyl isobutyl ketone or cyclohexanone, strongly polar solvents, for example dimethyl sulfoxide, and water.

In principle, it is possible to use all suitable carriers. Suitable carriers include more particularly the following: e.g. ammonium salts and natural, finely ground rocks, such as kaolins, aluminas, talc, chalk, quartz, attapulgite, montmorillonite or diatomaceous earth, and synthetic, finely ground rocks, such as highly disperse silica, aluminium oxide and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable extenders or carriers are those which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting compositions having ionic or nonionic properties or mixtures of these surface-active substances are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste liquors and methylcellulose. The presence of a surfactant is advantageous if one of the compounds of the formula (I) and/or one of the inert carriers is insoluble in water and if the application takes place in water.

Further auxiliaries which may be present in the formulations and the use forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other compositions which improve chemical and/or physical stability. Foam generators or antifoams may also be present.

In addition, the formulations and use forms derived therefrom may also comprise, as additional auxiliaries, stickers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing compositions, humectants, spreaders. In general, the compounds of the formula (I) can be combined with any solid or liquid additive commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of agrochemical active ingredients into plants. Penetrants are defined in this context by their ability to penetrate from the (generally aqueous) application liquor and/or from the spray coating into the cuticle of the plant and hence to increase the mobility of the active ingredients in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active ingredient combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processibility of the harvested products.

In addition, the compounds of the formula (I) may be present in a mixture with other active ingredients or semiochemicals such as attractants and/or bird repellents and/or plant activators and/or growth regulators and/or fertilizers. Likewise, the compounds of the formula (I) can be used to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case. All the mixing components mentioned, as the case may be, may also form salts with suitable bases or acids if they are capable of doing so on the basis of their functional groups.

Insecticides/Acaricides/Nematicides

The active ingredients specified here with their common names are known and are described for example in "The Pesticide Manual", 16th ed., British Crop Protection Council 2012, or can be searched for on the Internet (e.g. http://www.alanwood.net/pesticides). The classification is based on the IRAC Mode of Action Classification Scheme applicable at the time of filing of this patent application.

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel blockers, for example cyclodiene-organochlorines, e.g. chlordane and endosulfan or phenylpyrazoles (fiproles), e.g. ethiprole and fipronil.

(3) Sodium channel modulators, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer], tralomethrin and transfluthrin or DDT or methoxychlor.

(4) Nicotinic acetylcholine receptor (nAChR) competitive modulators, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, for example spinosyns, e.g. spinetoram and spinosad.

(6) Glutamate-gated chloride channel (GluCl) allosteric modulators, for example avermectins/milbemycins, e.g. abamectin, emamectin benzoate, lepimectin and milbemectin.

(7) Juvenile hormone mimetics, for example juvenile hormone analogues, e.g. hydroprene, kinoprene and methoprene or fenoxycarb or pyriproxyfen.

(8) Miscellaneous non-specific (multisite) inhibitors, for example alkyl halides, e.g. methyl bromide and other alkyl halides; or chloropicrin or sulfuryl fluoride or borax or tartar emetic or methyl isocyanate generator, e.g. diazomet and metam.

(9) Chordotonal organ modulators, e.g. pymetrozine or flonicamide.

(10) Mite growth inhibitors, for example clofentezine, hexythiazox and diflovidazin or etoxazole.

(11) Microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis* and B.t. plant proteins: Cry1Ab, Cry1Ac, Cry1Fa, Cry1A.105, Cry2Ab, VIP3A, mCry3A, Cry3Ab, Cry3Bb, Cry34Ab1/35Ab1.

(12) Inhibitors of mitochondrial ATP synthase, such as ATP disruptors, for example diafenthiuron or organotin compounds, e.g. azocyclotin, cyhexatin and fenbutatin oxide or propargite or tetradifon.

(13) Uncouplers of oxidative phosphorylation via disruption of the proton gradient, for example chlorfenapyr, DNOC and sulfluramid.

(14) Nicotinic acetylcholine receptor channel blockers, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptors (especially in the case of Diptera), for example cyromazine.

(18) Ecdysone receptor agonists, for example chromafenozide, halofenozide, methoxyfenozide and tebufenozide.

(19) Octopamine receptor agonists, for example amitraz.

(20) Mitochondrial complex III electron transport inhibitors, for example hydramethylnon or acequinocyl or fluacrypyrim.

(21) Mitochondrial complex I electron transport inhibitors, for example METI acaricides, e.g. fenazaquin, fenpyroximate, pyrimidifen, pyridaben, tebufenpyrad and tolfenpyrad or rotenone (Derris).

(22) Voltage-dependent sodium channel blockers, for example indoxacarb or metaflumizone.

(23) Inhibitors of acetyl CoA carboxylase, for example tetronic and tetramic acid derivatives, e.g. spirodiclofen, spiromesifen and spirotetramat.

(24) Mitochondrial complex IV electron transport inhibitors, for example phosphines, e.g. aluminium phosphide, calcium phosphide, phosphine and zinc phosphide, or cyanides, calcium cyanide, potassium cyanide and sodium cyanide.

(25) Mitochondrial complex II electron transport inhibitors, for example beta-keto nitrile derivatives, e.g. cyenopyrafen and cyflumetofen and carboxanilides, for example pyflubumide.

(28) Ryanodine receptor modulators, for example diamides, e.g. chlorantraniliprole, cyantraniliprole and flubendiamide, further active ingredients, for example afidopyropen, afoxolaner, azadirachtin, benclothiaz, benzoximate, bifenazate, broflanilide, bromopropylate, chinomethionat, chloroprallethrin, cryolite, cyclaniliprole, cycloxaprid, cyhalodiamide, dicloromezotiaz, dicofol, epsilon metofluthrin, epsilon momfluthrin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, kappa bifenthrin, kappa tefluthrin, lotilaner, meperfluthrin, paichongding, pyridalyl, pyrifluquinazon, pyriminostrobin, spirobudiclofen, tetramethylfluthrin, tetraniliprole, tetrachlorantraniliprole, tioxazafen, thiofluoximate, triflumezopyrim and iodomethane; additionally preparations based on *Bacillus firmus* (I-1582, BioNeem, Votivo), and the following compounds: 1-{2-fluoro-4-methyl-5-[(2,2,2-trifluoroethyl)sulfinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indole-3,4'-piperidine]-1(2H)-yl}(2-chloropyridin-4-yl)methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethylcarbonate (known from EP 2647626) (CAS-1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS Reg. No. 1204776-60-2), N-[(2E)-1-[(6-chloropyridin-3-yl) methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoropropan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)benzamide, 4-[5-(3,5-dichlorophenyl)-4,5-dihydro-5-(trifluoromethyl)-3-isoxazolyl]-2-methyl-N-(trans-1-oxido-3-thietanyl)benzamide and 4-[(5S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]propanamide, (+)-N-[3-chloro-1-(3-pyridinyl)-1H-pyrazol-4-yl]-N-ethyl-3-[(3,3,3-trifluoropropyl)sulfinyl]propanamide and (−)-N-[3-chloro-1-(3-pyridinyl)-1H-pyrazol-4-yl]-N-ethyl-3-[(3,3,3-trifluoropropyl)sulfinyl]propanamide (known from WO 2013/162715 A2, WO 2013/162716 A2, US 2014/0213448 A1) (CAS 1477923-37-7), 5-[[(2E)-3-chloro-2-propen-1-yl] amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide (Liudaibenjiaxuanan, known from CN 103109816 A) (CAS 1232543-85-9); N-[4-chloro-2-[[(1,1-dimethylethyl)amino] carbonyl]-6-methylphenyl]-1-(3-chloro-2-pyridinyl)-3-(fluoromethoxy)-1H-pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy] phenoxy]propoxy]-2-methoxy-6-(trifluoromethyl) pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]hydrazinecarboxamide (known from CN 101715774 A) (CAS 1232543-85-9); cyclopropanecarboxylic acid 3-(2,2-dichloroethenyl)-2,2-dimethyl-4-(1H-benzimidazol-2-yl)phenyl ester (known from CN 103524422 A) (CAS 1542271-46-4); (4aS)-7-chloro-2,5-dihydro-2-[[(methoxycarbonyl) [4-[(trifluoromethyl)thio] phenyl]amino]carbonyl]indeno[1,2-e][1,3,4]oxadiazine-4a (3H)-carboxylic acid methyl ester (known from CN 102391261 A) (CAS 1370358-69-2); 6-deoxy-3-O-ethyl-2,4-di-O-methyl-1-[N-[4-[1-[4-(1,1,2,2,2-pentafluoroethoxy) phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethylphenoxy)-3-(6-trifluoromethylpyridazin-3-yl)-3-azabicyclo[3.2.1]octane (CAS 1253850-56-4), (8-anti)-8-(2-cyclopropylmethoxy-4-trifluoromethylphenoxy)-3-(6-trifluoromethylpyridazin-3-yl)-3-azabicyclo[3.2.1]octane (CAS 933798-27-7), (8-syn)-8-(2-cyclopropylmethoxy-4-trifluoromethylphenoxy)-3-(6-trifluoromethylpyridazin-3-yl)-3-azabicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7).

Fungicides

The active ingredients specified herein by their common name are known and described, for example, in "Pesticide Manual" (16th Ed. British Crop Protection Council) or searchable on the internet (for example: http://www.alanwood.net/pesticides).

All the mixing components mentioned in classes (1) to (15), as the case may be, may form salts with suitable bases or acids if they are capable of doing so on the basis of their functional groups. All the fungicidal mixing components mentioned in classes (1) to (15), as the case may be, may include tautomeric forms.

1) Inhibitors of ergosterol biosynthesis, for example (1.001) cyproconazole, (1.002) difenoconazole, (1.003) epoxiconazole, (1.004) fenhexamide, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazole, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(H-1,2,4-triazol-1-yl)propan-2-ol, (1.034) (R)-[3-(4-chloro-2-fluorophenyl)-5-(2,4-difluorophenyl)-1,2-oxazol-4-yl] (pyridin-3-yl)methanol, (1.035) (S)-[3-(4-chloro-2-fluorophenyl)-5-(2,4-difluorophenyl)-1,2-oxazol-4-yl] (pyridin-3-yl)methanol, (1.036) [3-(4-chloro-2-fluorophenyl)-5-(2,4-difluorophenyl)-1,2-oxazol-4-yl] (pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)-2-(2,4-difluorophenyl)oxiran-2-yl] methyl}-1H-1,2,4-triazol-5-yl thiocyanate, (1.041) 1-{[rel (2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3- thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)phenyl]-1-(1H-1,2,4-triazol-1-yl)propan-2-ol, (1.056) 2-{[3-(2-chlorophenyl)-2-(2,4-difluoropheny)xiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3 S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-1H-1,2,4-triazole, (1.062) 5-(allylsulfanyl)-1-{[rel(2R,3S)-3-(2-chlorophenyl)-2-(2,4-difluorophenyl)oxiran-2-yl]methyl}-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl})-N-ethyl-N-methylimidoformamide, (1.077) N'-{5-bromo-6-[(1 S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) mefentrifluconazole, (1.082) ipfentrifluconazole.

2) Inhibitors of the respiratory chain in complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of the syn-epimeric racemate 1RS,4SR,9RS and the anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034)N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-1H-pyrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1S,4R)-9-(dichloromethylene)-1,2,3,4-tetrahydro-1,4-methanonaphthalen-5-yl]-

3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain in complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadon, (3.010) fenamidon, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3 S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate.

4) Mitosis and cell division inhibitors, for example (4.001) carbendazim, (4.002) diethofencarb, (4.003) ethaboxam, (4.004) fluopicolid, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having capacity for multisite activity, for example (5.001) Bordeaux mixture, (5.002) captafol, (5.003) captan, (5.004) chlorthalonil, (5.005) copper hydroxide, (5.006) copper naphthenate, (5.007) copper oxide, (5.008) copper oxychloride, (5.009) copper(2+) sulfate, (5.010) dithianon, (5.011) dodin, (5.012) folpet, (5.013) mancozeb, (5.014) maneb, (5.015) metiram, (5.016) zinc metiram, (5.017) copper oxine, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable of triggering host defence, for example (6.001) acibenzolar-S-methyl, (6.002) isotianil, (6.003) probenazole, (6.004) tiadinil.

7) Amino acid and/or protein biosynthesis inhibitors, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

(8) ATP production inhibitors, for example (8.001) silthiofam.

9) Cell wall synthesis inhibitors, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.001) propamocarb, (10.002) propamocarb hydrochloride, (10.003) tolclofos-methyl.

11) Melanin biosynthesis inhibitors, for example (11.001) tricyclazole, (11.002) 2,2,2-trifluoroethyl {3-methyl-1-[(4-methylbenzoyl)amino]butan-2-yl}carbamate.

12) Nucleic acid synthesis inhibitors, for example (12.001) benalaxyl, (12.002) benalaxyl-M (kiralaxyl), (12.003) metalaxyl, (12.004) metalaxyl-M (mefenoxam).

13) Signal transduction inhibitors, for example (13.001) fludioxonil, (13.002) iprodione, (13.003) procymidone, (13.004) proquinazid, (13.005) quinoxyfen, (13.006) vinclozolin.

14) Compounds that can act as uncouplers, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenon, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphonic acid and salts thereof, (15.026) propamocarb-fosetylate, (15.027) pyriofenone (chlazafenone) (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl) quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy] phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts thereof, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butyric acid, (15.050) 5-amino-1,3,4-thiadiazole-2-thiol, (15.051) 5-chloro-N'-phenyl-N'-(prop-2-yn-1-yl)thiophene 2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene] amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl] pyridin-2-yl}carbamate, (15.062) 5-fluoro-4-imino-3-methyl-1-[(4-methylphenyl)sulfonyl]-3,4-dihydropyrimidin-2(1H)-one.

Biological Pesticides as Mixing Components

The compounds of the formula (I) can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM I-1562, or *Bacillus firmus*, strain I-1582 (Accession number CNCM I-1582), or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421), *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii* (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (accession number CNCM I-952).

Examples of viruses which are used or can be used as biological pesticides are:

*Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:
*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are: *Allium sativum, Artemisia absinthium*, azadirachtin, Bio-keeper WP, *Cassia nigricans, Celastrus angulatus, Chenopodium anthelminticum*, chitin, Armour-Zen, *Dryopteris filix-mas, Equisetum arvense*, Fortune Aza, Fungastop, Heads Up (*Chenopodium quinoa* saponin extract), pyrethrum/pyrethrins, Quassia amara, Quercus, Quillaja, Regalia, "Requiem™ Insecticide", rotenone, ryania/ryanodine, *Symphytum officinale, Tanacetum vulgare*, thymol, Triact 70, TriCon, *Tropaeulum majus, Urtica dioica, Veratrin, Viscum album*, Brassicaceae extract, especially oilseed rape powder or mustard powder.

Safener as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, bell peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (the fruits being apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all development stages such as seed, seedlings, young (immature) plants, up to and including mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested plants or harvested plant parts and vegetative and generative propagation material, for example cuttings, tubers, rhizomes, slips and seeds.

The inventive treatment of the plants and parts of plants with the compounds of the formula (I) is effected directly or by allowing the compounds to act on the surroundings, the habitat or the storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having novel properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants to animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants to phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidal active ingredients, for example imidazolinones, sulfonylureas, glyphosate or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (the fruits being apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, meaning that the compounds of the formula (I) are applied to the foliage, in which case the treatment frequency and the application rate should be adjusted according to the level of infestation with the pest in question.

In the case of systemically active ingredients, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) according to the invention are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and also the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention also relates to the use of the compounds of the formula (I) for the treatment of seed for protecting the seed and the resulting plant from animal pests.

The invention further relates to seed which has been treated with a compound of the formula (I) according to the invention for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and mixing components may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occur when a compound of the formula (I) acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Compounds of the formula (I) can also be used in combination with signalling technology compositions, leading to better colonization by symbionts, for example rhizobia, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this is the seed of cereals (for example wheat, barley, rye, millet and oats), maize, cotton, soya beans, rice, potatoes, sunflowers, coffee, tobacco, canola, oilseed rape, beets (for example sugar beets and fodder beets), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water, until it reaches a certain stage of the rice embryo ("pigeon breast stage") which results in stimulation of germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active ingredients which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing the compounds of the formula (I) with customary additives, for example customary extenders and solvents or diluents, dyes, wetting compositions, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting compositions which may be present in the seed-dressing formulations usable in accordance with the invention are all substances which promote wetting and which are customary for the formulation of agrochemical active ingredients. Usable with preference are alkyl naphthalenesulfonates, such as diisopropyl or diisobutyl naphthalenesulfonates.

Suitable dispersants and/or emulsifiers which may be present in the seed-dressing formulations usable in accordance with the invention are all nonionic, anionic and cationic dispersants customary for the formulation of agrochemical active ingredients. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemical active ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or the use forms prepared therefrom through the addition of water, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasite" includes especially helminths and protozoa, such as coccidia. Ectoparasites are typically and preferably arthropods, especially insects or acarids.

In the field of veterinary medicine, the compounds of the formula (I) having favourable endotherm toxicity are suitable for controlling parasites which occur in animal husbandry and animal keeping in livestock, breeding animals, zoo animals, laboratory animals, experimental animals and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets, and particularly dogs, cats, caged birds; reptiles, amphibians or aquarium fish.

In a specific embodiment, the compounds of the formula (I) are administered to mammals.

In another specific embodiment, the compounds of the formula (I) are administered to birds, namely caged birds or particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal keeping is enabled and better animal well-being is achievable.

In relation to the field of animal health, the term "control" or "controlling" in the present context means that the compounds of the formula (I) are effective in reducing the incidence of the particular parasite in an animal infected with such parasites to an innocuous degree. More specifically, "controlling" in the present context means that the compounds of the formula (I) kill the respective parasite, inhibit its growth, or inhibit its proliferation.

The arthropods include, for example, but are not limited to, from the order of Anoplurida, for example, *Haematopinus* spp., *Linognathus* spp., *Pediculus* spp., *Phtirus* spp. and *Solenopotes* spp.;

from the order Mallophagida and the suborders Amblycerina and Ischnocerina, for example *Bovicola* spp., *Damalina* spp., *Felicola* spp.; *Lepikentron* spp., *Menopon* spp., *Trichodectes* spp., *Trimenopon* spp., *Trinoton* spp., *Werneckiella* spp; *Werneckiella* spp;

from the order of Diptera and the suborders Nematocerina and Brachycerina, for example, *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.;

from the order of Siphonapterida, for example *Ceratophyllus* spp., *Ctenocephalides* spp., *Pulex* spp., *Tunga* spp., *Xenopsylla* spp.;

from the order of heteropterida, for example, *Cimex* spp., *Panstrongylus* spp., *Rhodnius* spp., *Triatoma* spp.; and also nuisance and hygiene pests from the order Blattarida.

In addition, in the case of the arthropods, mention should be made by way of example, without limitation, of the following Acari:

from the subclass Acari (Acarina) and the order Metastigmata, for example from the family Argasidae like *Argas* spp., *Ornithodorus* spp., *Otobius* spp., from the family Ixodidae like *Amblyomma* spp., *Dermacentor* spp., *Haemaphysalis* spp., *Hyalomma* spp., *Ixodes* spp., *Rhipicephalus* (*Boophilus*) *spp.*, *Rhipicephalus* spp. (the original genus of multi-host ticks); from the order Mesostigmata like *Dermanyssus* spp., *Ornithonyssus* spp., *Pneumonyssus* spp., *Raillietia* spp., *Sternostoma* spp., *Tropilaelaps* spp., *Varroa* spp.; *from the order Actinedida (Prostigmata), for example Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and *from the order Acaridida (Astigmata), for example Acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Examples of parasitic protozoa include, but are not limited to:

Mastigophora (Flagellata), such as:

Metamonada: from the order of Diplomonadida, for example, *Giardia* spp., *Spironucleus* spp.

Parabasala: from the order of Trichomonadida, for example, *Histomonas* spp., *Pentatrichomonas* spp., *Tetratrichomonas* spp., *Trichomonas* spp., *Tritrichomonas* spp.

Euglenozoa: from the order of Trypanosomatida, for example, *Leishmania* spp., *Trypanosoma* spp.

Sarcomastigophora (Rhizopoda) such as Entamoebidae, for example, *Entamoeba* spp., Centramoebidae, for example *Acanthamoeba* sp., Euamoebidae, e.g. *Hartmanella* sp.

Alveolata such as Apicomplexa (Sporozoa): e.g. *Cryptosporidium* spp.; from the order of Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; from the order of Adeleida, for example, *Hepatozoon* spp., *Klossiella* spp.; from the order of Haemosporida, for example, *Leucocytozoon* spp., *Plasmodium* spp.; *from the order of Piroplasmida, for example, Babesia* spp., *Ciliophora* spp., *Echinozoon* spp., *Theileria* spp.; from the order of Vesibuliferida, for example, *Balantidium* spp., *Buxtonella* spp.

Microspora such as *Encephalitozoon* spp., *Enterocytozoon* spp., *Globidium* spp., *Nosema* spp., and also, for example, *Myxozoa* spp.

The helminths that are pathogenic to humans or animals include, for example, Acanthocephala, nematodes, Pentastoma and Platyhelminthes (e.g. Monogenea, cestodes and trematodes).

Illustrative helminths include, but are not limited to:

Monogenea: e.g. *Dactylogyrus* spp., *Gyrodactylus* spp., *Microbothrium* spp., *Polystoma* spp., *Troglecephalus* spp.;

Cestodes: from the order of Pseudophyllidea, for example: *Bothridium* spp., *Diphyllobothrium* spp., *Diplogonoporus* spp. *Ichthyobothrium* spp., *Ligula* spp., *Schistocephalus* spp., *Spirometra* spp.

From the order of cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of Trichinellida, for example: *Capillaria* spp., *Trichinella* spp., *Trichomosoides* spp., *Trichuris* spp.

From the order of Tylenchida, for example: *Micronema* spp., *Parastrangyloides* spp., *Strongyloides* spp.

From the order of Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Crenosoma* spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

From the order of Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acanthocephala: from the order of Oligacanthorhynchida, for example: *Macracanthorhynchus* spp., *Prosthenorchis* spp.; from the order of Moniliformida, for example: *Moniliformis* spp.

From the order of Polymorphida, for example: *Filicollis* spp.; from the order of Echinorhynchida, for example *Acanthocephalus* spp., *Echinorhynchus* spp., *Leptorhynchoides* spp.

Pentastoma: from the order of Porocephalida, for example, *Linguatula* spp.

In the veterinary field and in animal keeping, the compounds of the formula (I) are administered by methods generally known in the art, such as via the enteral, parenteral, dermal or nasal route in the form of suitable preparations. Administration may be prophylactic, metaphylactic or therapeutic.

Thus, one embodiment of the present invention relates to the compounds of the formula (I) for use as a medicament.

A further aspect relates to the compounds of the formula (I) for use as an antiendoparasitic agent.

A further specific aspect of the invention relates to the compounds of the formula (I) for use as an antithelminthic agent, especially for use as a nematicide, platyhelminthicide, acanthocephalicide or pentastomicide.

A further specific aspect of the invention relates to the compounds of the formula (I) for use as an antiprotozoic agent.

A further aspect relates to the compounds of the formula (I) for use as an antiectoparasitic agent, especially an arthropodicide, very particularly an insecticide or an acaricide.

Further aspects of the invention are veterinary medicine formulations comprising an effective amount of at least one compound of the formula (I) and at least one of the following: a pharmaceutically acceptable excipient (e.g. solid or liquid diluents), a pharmaceutically acceptable auxiliary (e.g. surfactants), especially a pharmaceutically acceptable excipient used conventionally in veterinary medicine formulations and/or a pharmaceutically acceptable auxiliary conventionally used in veterinary medicine formulations.

A related aspect of the invention is a method for production of a veterinary medicine formulation as described here, which comprises the step of mixing at least one compound of the formula (I) with pharmaceutically acceptable excipients and/or auxiliaries, especially with pharmaceutically acceptable excipients used conventionally in veterinary medicine formulations and/or auxiliaries used conventionally in veterinary medicine formulations.

Another specific aspect of the invention is veterinary medicine formulations selected from the group of ectoparasiticidal and endoparasiticidal formulations, especially selected from the group of anthelmintic, antiprotozoic and arthropodicidal formulations, very particularly selected from the group of nematicidal, platyhelminthicidal, acanthocephalicidal, pentastomicidal, insecticidal and acaricidal formulations, according to the aspects mentioned, and methods for production thereof.

Another aspect relates to a method for treatment of a parasitic infection, especially an infection caused by a parasite selected from the group of the ectoparasites and endoparasites mentioned here, by use of an effective amount of a compound of the formula (I) in an animal, especially a nonhuman animal, having a need therefor.

Another aspect relates to a method for treatment of a parasitic infection, especially an infection caused by a parasite selected from the group of the ectoparasites and endoparasites mentioned here, by use of a veterinary medicine formulation as defined here in an animal, especially a nonhuman animal, having a need therefor.

Another aspect relates to the use of the compounds of the formula (I) in the treatment of a parasite infection, especially an infection caused by a parasite selected from the group of the ectoparasites and endoparasites mentioned here, in an animal, especially a nonhuman animal.

In the present context of animal health or veterinary medicine, the term "treatment" includes prophylactic, metaphylactic and therapeutic treatment.

In a particular embodiment, in this way, mixtures of at least one compound of the formula (I) with other active ingredients, especially with endo- and ectoparasiticides, are provided for the field of veterinary medicine.

In the field of animal health, "mixture" means not just that two (or more) different active ingredients are formulated in a common formulation and are correspondingly employed together, but also relates to products comprising formulations separated for each active ingredient. Accordingly, when more than two active ingredients are to be employed, all active ingredients can be formulated in a common formulation or all active ingredients can be formulated in separate formulations; likewise conceivable are mixed forms in which some of the active ingredients are formulated together and some of the active ingredients are formulated separately. Separate formulations allow the separate or successive application of the active ingredients in question.

The active ingredients specified here by their "common names" are known and are described, for example, in the "Pesticide Manual" (see above) or can be searched for on the Internet (e.g.: http://www.alanwood.net/pesticides).

Illustrative active ingredients from the group of the ectoparasiticides as mixing components include, without any intention that this should constitute a restriction, the insecticides and acaricides listed in detail above. Further usable active ingredients are listed below in accordance with the abovementioned classification based on the current IRAC Mode of Action Classification Scheme: (1) acetylcholinesterase (AChE) inhibitors; (2) GABA-gated chloride channel blockers; (3) sodium channel modulators; (4) nicotinic acetylcholine receptor (nAChR) competitive modulators; (5) nicotinic acetylcholine receptor (nAChR) allosteric modulators; (6) glutamate-gated chloride channel (GluCl) allosteric modulators; (7) juvenile hormone mimetics; (8) miscellaneous non-specific (multi-site) inhibitors; (9) chordotonal organ modulators; (10) mite growth inhibitors; (12) inhibitors of mitochondrial ATP synthase, such as ATP disruptors; (13) uncouplers of oxidative phosphorylation via disruption of the proton gradient; (14) nicotinic acetylcholine receptor channel blockers; (15) inhibitors of chitin biosynthesis, type 0; (16) inhibitors of chitin biosynthesis, type 1; (17) moulting disruptors (especially in Diptera); (18) ecdysone receptor agonists; (19) octopamine receptor agonists; (21) mitochondrial complex I electron transport inhibitors; (25) mitochondrial complex II electron transport inhibitors; (20) mitochondrial complex III electron transport inhibitors; (22) voltage-dependent sodium channel blockers; (23) inhibitors of acetyl CoA carboxylase; (28) ryanodine receptor modulators;

active ingredients having unknown or non-specific mechanisms of action, e.g. fentrifanil, fenoxacrim, cycloprene, chlorobenzilate, chlordimeform, flubenzimin, dicyclanil, amidoflumet, quinomethionat, triarathene, clothiazoben, tetrasul, potassium oleate, petroleum, metoxadiazone, gossyplur, flutenzine, brompropylate, cryolite;

compounds from other classes, for example butacarb, dimetilan, cloethocarb, phosphocarb, pirimiphos(-ethyl), parathion(-ethyl), methacrifos, isopropyl o-salicylate, trichlorfon, sulprofos, propaphos, sebufos, pyridathion, prothoate, dichlofenthion, demeton-S-methyl sulfone, isazofos, cyanofenphos, dialifos, carbophenothion, autathiofos, aromfenvinfos(-methyl), azinphos(-ethyl), chlorpyrifos(-ethyl), fosmethilan, iodofenphos, dioxabenzofos, formothion, fonofos, flupyrazofos, fensulfothion, etrimfos;

organochlorine compounds, for example camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-)metofluthrin, profluthrin, flufenprox, flubrocythrinate, fubfenprox, fenfluthrin, protrifenbut, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated hydrocarbon compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron, amidine derivatives, e.g. chlormebuform, cymiazole, demiditraz beehive varroa acaricides, for example organic acids, e.g. formic acid, oxalic acid.

Illustrative active ingredients from the group of the endoparasiticides, as mixing components, include, but are not limited to, anthelmintic active ingredients and antiprotozoic active ingredients.

The anthelmintic active ingredients include but are not limited to the following nematicidal, trematicidal and/or cestocidal active ingredients:

from the class of the macrocyclic lactones, for example: eprinomectin, abamectin, nemadectin, moxidectin, doramectin, selamectin, lepimectin, latidectin, milbemectin, ivermectin, emamectin, milbemycin;

from the class of the benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole sulfoxide, albendazole, flubendazole;

from the class of the depsipeptides, preferably cyclic depsipeptides, especially 24-membered cyclic depsipeptides, for example: emodepside, PF1022A;

from the class of the tetrahydropyrimidines, for example: morantel, pyrantel, oxantel;

from the class of the imidazothiazoles, for example: butamisole, levamisole, tetramisole;

from the class of the aminophenylamidines, for example: amidantel, deacylated amidantel (dAMD), tribendimidine;

from the class of the aminoacetonitriles, for example: monepantel;

from the class of the paraherquamides, for example: paraherquamide, derquantel;

from the class of the salicylanilides, for example: tribromsalan, bromoxanide, brotianide, clioxanide, closantel, niclosamide, oxyclozanide, rafoxanide;

from the class of the substituted phenols, for example: nitroxynil, bithionol, disophenol, hexachlorophene, niclofolan, meniclopholan;

from the class of the organophosphates, for example: trichlorfon, naphthalofos, dichlorvos/DDVP, crufomate, coumaphos, haloxon;

from the class of the piperazinones/quinolines, for example: praziquantel, epsiprantel;

from the class of the piperazines, for example: piperazine, hydroxyzine;

from the class of the tetracyclines, for example: tetracycline, chlorotetracycline, doxycycline, oxytetracycline, rolitetracycline;

from various other classes, for example: bunamidine, niridazole, resorantel, omphalotin, oltipraz, nitroscanate, nitroxynil, oxamniquin, mirasan, miracil, lucanthon, hycanthon, hetolin, emetin, diethylcarbamazine, dichlorophen, diamfenetide, clonazepam, bephenium, amoscanate, clorsulon.

Antiprotozoic active ingredients include, but are not limited to, the following active ingredients:

from the class of the triazines, for example: diclazuril, ponazuril, letrazuril, toltrazuril;

from the class of polyether ionophores, for example: monensin, salinomycin, maduramicin, narasin;

from the class of the macrocyclic lactones, for example: milbemycin, erythromycin;

from the class of the quinolones, for example: enrofloxacin, pradofloxacin;

from the class of the quinines, for example: chloroquine;

from the class of the pyrimidines, for example: pyrimethamine;

from the class of the sulfonamides, for example: sulfaquinoxaline, trimethoprim, sulfaclozin;

from the class of the thiamines, for example: amprolium;

from the class of the lincosamides, for example: clindamycin;

from the class of the carbanilides, for example: imidocarb;

from the class of the nitrofurans, for example: nifurtimox;

from the class of the quinazolinone alkaloids, for example: halofuginone;

from various other classes, for example: oxamniquin, paromomycin;

from the class of the vaccines or antigens from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All the mixing components mentioned, as the case may be, may also form salts with suitable bases or acids if they are capable of doing so on the basis of their functional groups.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) onto a host or after injection into a host (for example malaria parasites by mosquitoes).

Examples of vectors and the diseases or pathogens they transmit are:

1) Mosquitoes

*Anopheles*: malaria, filariasis;

*Culex*: Japanese encephalitis, filariasis, other viral diseases, transmission of other worms;

*Aedes*: yellow fever, dengue fever, other viral diseases, filariasis;

Simuliidae: transmission of worms, especially *Onchocerca volvulus;*

Psychodidae: transmission of leishmaniasis

2) Lice: skin infections, epidemic typhus;

3) Fleas: plague, endemic typhus, tapeworms;

4) Flies: sleeping sickness (trypanosomiasis); cholera, other bacterial diseases;

5) Mites: acariosis, epidemic typhus, rickettsialpox, tularaemia, Saint Louis encephalitis, tick-borne encephalitis (TBE), Crimean-Congo haemorrhagic fever, borreliosis;

6) Ticks: borelliosis such as *Borrelia bungdorferi* sensu lato., *Borrelia duttoni*, tick-borne encephalitis, Q fever (*Coxiella burnetii*), babesia (*Babesia canis canis*), ehrlichiosis.

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, Psychodidae such as *Phlebotomus*, Lutzomyia, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, glues, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) take the form of a ready-to-use pesticide, meaning that they can be applied to the material in question without further modifications. Useful further insecticides or fungicides especially include those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active ingredients, as antifouling compositions.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids, ticks and mites encountered in enclosed spaces, for example dwellings, factory halls, offices, vehicle cabins, animal breeding facilities. For controlling animal pests, the compounds of the formula (I) are used alone or in combination with other active ingredients and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES

Ethyl 2-bromo-1-methyl-1H-imidazole-4-carboxylate

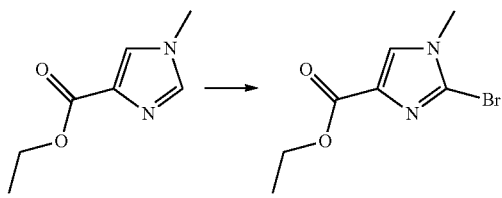

30 g (193.5 mmol) of ethyl 1-methyl-1H-imidazole-4-carboxylate were dissolved in 500 mL of tetrahydrofuran and cooled to 0° C. To this solution 34.5 g (193.5 mmol) of NBS were added a little at a time, and the reaction mixture was stirred at room temperature overnight. The reaction was terminated by the addition of saturated sodium thiosulfate solution (Na$_2$S$_2$O$_3$) and 800 ml of ethyl acetate were added. The phases were separated and the aqueous phase was extracted three times with 800 ml of ethyl acetate each time. The organic phases were combined, dried over sodium sulphate and filtered. The solvent was distilled off under reduced pressure and the residue was purified by column chromatography purification using a petroleum ether/ethyl acetate gradient as mobile phase.

$^1$H-NMR (300 MHz, D$_6$-DMSO) δ ppm: 1.26 (t, 3H), 3.64 (s, 3H), 4.22 (q, 2H), 8.07 (s, 1H).

Ethyl 1-methyl-2-[4-(trifluoromethyl)phenyl]-1H-imidazole-4-carboxylate

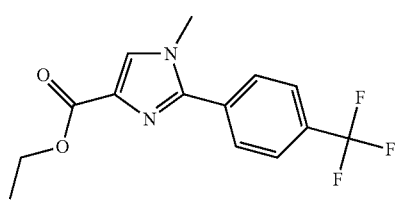 [SMILES: CCOC(=O)c1cn(C)c(-c2ccc(C(F)(F)F)cc2)n1]

To a solution of 10 g (43.1 mmol) of ethyl 2-bromo-1-methyl-1H-imidazole-4-carboxylate in 1,2-dimethoxyethane (30 mL) and water (10 mL) were added under a nitrogen atmosphere 3.2 g (4.4 mmol) of tetrakis(triphenylphosphine)palladium, 9.1 g (85.8 mmol) of sodium carbonate and 16.4 g (86.3 mmol) of (4-trifluoromethyl)phenylboronic acid. The reaction mixture was stirred at 80° C. overnight. The mixture was then cooled to room temperature and extracted twice with 100 ml of ethyl acetate each time. The organic phases were combined, dried over sodium sulfate and filtered. The solvent was distilled off under reduced pressure and the residue was purified by column chromatography purification using a petroleum ether/ethyl acetate gradient as mobile phase.

$^1$H-NMR (300 MHz, D$_6$-DMSO) δ ppm: 1.28 (t, 3H), 3.85 (s, 3H), 4.25 (q, 2H), 7.86-7.89 (m, 2H), 7.97-8.00 (m, 2H), 8.09 (s, 1H).

Ethyl 5-iodo-1-methyl-2-[4-(trifluoromethyl)phenyl]-1H-imidazole-4-carboxylate

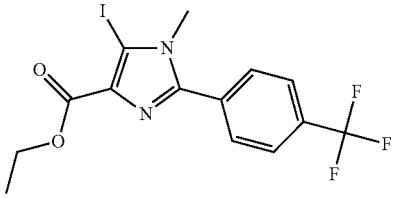 [SMILES: CCOC(=O)c1nc(-c2ccc(C(F)(F)F)cc2)n(C)c1I]

To a solution of 5.2 g (17.4 mmol) of ethyl 1-methyl-2-[4-(trifluoromethyl)phenyl]-1H-imidazole-4-carboxylate in acetic acid (20 mL) were added 7.9 g (35.1 mmol) of N-iodosuccinimide (NIS). The reaction mixture was stirred at room temperature overnight. The mixture was then concentrated under reduced pressure and diluted by adding saturated sodium thiosulfate solution. The pH was adjusted to pH=7-8 by adding saturated sodium carbonate solution. The mixture was then extracted with ethyl acetate. The organic phases were combined, dried over sodium sulfate and filtered. The solvent was distilled off under reduced pressure and the residue was purified by column chromatography purification using a petroleum ether/ethyl acetate gradient as mobile phase.

$^1$H-NMR (300 MHz, D$_6$-DMSO) δ ppm: 1.31 (t, 3H), 3.74 (s, 3H), 4.27 (q, 2H), 7.85-7.95 (m, 4H).

Ethyl 5-(ethylsulfanyl)-1-methyl-2-[4-(trifluoromethyl)phenyl]-1H-imidazole-4-carboxylate

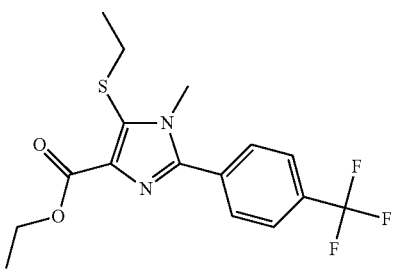 [SMILES: CCOC(=O)c1nc(-c2ccc(C(F)(F)F)cc2)n(C)c1SCC]

To a solution of 4.1 g (9.7 mmol) of ethyl 5-iodo-1-methyl-2-[4-(trifluoromethyl)phenyl]-1H-imidazole-4-carboxylate in 1,4-dioxane (150 mL) were added 6.0 g (96.7 mmol) of ethanethiol, 2.9 g (29.0 mmol) of N,N-diisopropylethylamine (DIPEA), 1.5 g (1.5 mmol) of tris(dibenzylideneacetone)dipalladium(0)-chloroform adduct [Pd$_2$ (dba)₃. CHCl₃] and 1.7 g (2.9 mmol) of Xantphos. The mixture was stirred at 80° C. overnight. Subsequently, the reaction mixture was cooled to room temperature and water was added to the mixture. The mixture was then extracted twice with ethyl acetate. The organic phases were combined, dried over sodium sulfate and filtered. The solvent was distilled off under reduced pressure and the residue was purified by column chromatography purification using a petroleum ether/ethyl acetate gradient as mobile phase.

¹H-NMR (300 MHz, D₆-DMSO) δ ppm: 1.15 (t, 3H), 1.31 (t, 3H), 2.92 (q, 2H), 3.80 (s, 3H), 4.28 (q, 2H), 7.88-7.99 (m, 4H).

5-(Ethylsulfanyl)-1-methyl-2-[4-(trifluoromethyl) phenyl]-1H-imidazole-4-carboxylic acid

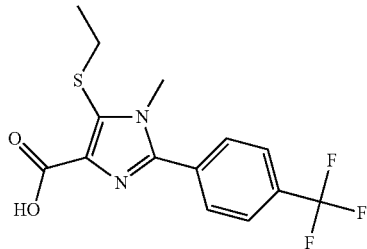 [SMILES: CCSc1c(C(=O)O)nc(-c2ccc(C(F)(F)F)cc2)n1C]

To a solution of 3.1 g (8.7 mmol) of ethyl 5-(ethylsulfanyl)-1-methyl-2-[4-(trifluoromethyl)phenyl]-1H-imidazole-4-carboxylate in methanol (60 mL) and water (60 ml) was added 0.69 g (17.3 mmol) of sodium hydroxide. The mixture was stirred at room temperature overnight. The solution was adjusted to pH=3-4 by adding concentrated aqueous hydrochloric acid. The reaction mixture was then extracted with a mixture of chloroform/i-propanol (3:1). The organic phases were combined, dried over sodium sulfate and filtered. The solvent was distilled off under reduced pressure and the residue was used for the next synthesis step without further purification.

Tert-butyl {5-(ethylsulfanyl)-1-methyl-2-[4-(trifluoromethyl)phenyl]-1H-imidazol-4-yl}carbamate

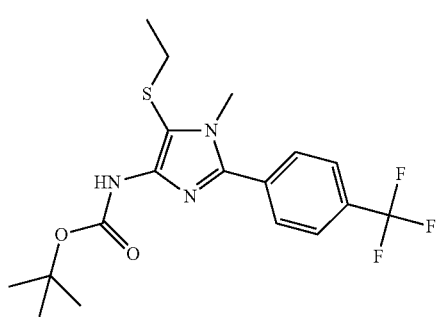 [SMILES: CCSc1c(NC(=O)OC(C)(C)C)nc(-c2ccc(C(F)(F)F)cc2)n1C]

To a solution of 3.6 g (10.9 mmol) of 5-(ethylsulfanyl)-1-methyl-2-[4-(trifluoromethyl)phenyl]-1H-imidazole-4-carboxylic acid in tert-butanol (60 mL) were added 4.5 g (16.4 mmol) of diphenyl azidophosphate (DPPA) and 3.9 g (38.2 mmol) of triethylamine. The mixture was stirred at 80° C. overnight, cooled and concentrated under reduced pressure. 100 ml of water were then added and the mixture was extracted with ethyl acetate. The combined organic phases were washed with saturated sodium chloride solution, dried over sodium sulfate, filtered and the solvent was removed under reduced pressure. The crude product was purified by column chromatography purification using an ethyl acetate/ petroleum ether gradient as eluent.

¹H-NMR (300 MHz, D₆-DMSO) δ ppm: 1.15 (t, 3H), 1.44 (s, 9H), 2.72 (q, 2H), 3.79 (s, 3H), 7.85-7.96 (m, 4H), 8.65 (s, 1H).

5-(Ethylsulfanyl)-1-methyl-2-[4-(trifluoromethyl) phenyl]-1H-imidazol-4-amine

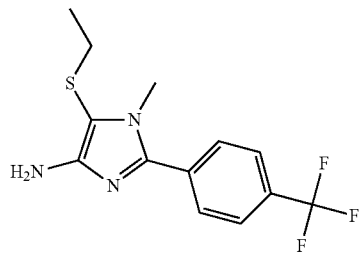 [SMILES: CCSc1c(N)nc(-c2ccc(C(F)(F)F)cc2)n1C]

To a solution of 2.4 g (6.0 mmol) of tert-butyl {5-(ethylsulfanyl)-1-methyl-2-[4-(trifluoromethyl)phenyl]-1H-imidazol-4-yl}carbamate in dioxane (40 mL) were added 40 mL of conc. hydrochloric acid. The mixture was stirred at room temperature overnight and then concentrated to dryness under reduced pressure. The crude product was used without further purification.

¹H-NMR (300 MHz, D₆-DMSO) δ ppm: 1.15 (t, 3H), 2.58 (q, 2H), 3.68 (s, 3H), 4.81 (s, breit, 2H), 7.80-7.92 (m, 4H).

3-Azido-5-(trifluoromethyl)pyridine-2-carbaldehyde

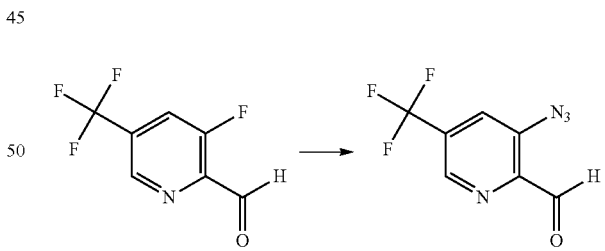

1 g (5.2 mmol) of 3-fluoro-5-(trifluoromethyl)pyridine-2-carbaldehyde was initially charged in 10 ml of dimethylformamide (DMF) and cooled to 0° C. Then, 0.34 g (5.2 mmol, dissolved in 10 mL of DMF) of sodium azide was added and the mixture was stirred at room temperature for 4 h. The reaction was terminated by adding 100 mL of water. The mixture was extracted twice with 100 ml of ethyl acetate each time. The combined organic phases were washed with saturated sodium chloride solution, dried over sodium sulfate, filtered and the solvent was removed under reduced pressure. The crude product was used without further purification.

2-{5-(Ethylsulfanyl)-1-methyl-2-[4-(trifluoromethyl)phenyl]-1H-imidazol-4-yl}-6-(trifluoromethyl)-2H-pyrazolo[4,3-b]pyridine

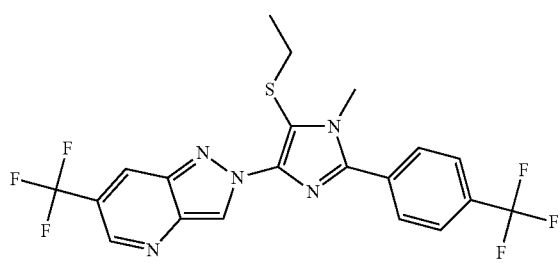 [SMILES: CCSc1c(-n2cc3ncc(C(F)(F)F)cc3n2)nc(-c2ccc(C(F)(F)F)cc2)n1C]

To a solution of 200 mg (0.66 mmol) of 5-(ethylsulfanyl)-1-methyl-2-[4-(trifluoromethyl)phenyl]-1H-imidazol-4-amine in toluene (15 mL) were added 290 mg (1.3 mmol) of 3-azido-5-(trifluoromethyl)pyridine-2-carbaldehyde and 850 mg (2.99 mmol) of titanium isopropoxide. The mixture was stirred first at 50° C. for 4 h and then at 100° C. for 1 h. After cooling to room temperature, 100 ml of water were added and the mixture was extracted with ethyl acetate. The combined organic phases were washed with saturated sodium chloride solution, dried over sodium sulfate, filtered and the solvent was removed under reduced pressure. The crude product was purified by column chromatography purification using an ethyl acetate/petroleum ether gradient as eluent.

$^1$H-NMR (300 MHz, D$_6$-DMSO) δ ppm: 1.10 (t, 3H), 2.90 (q, 2H), 3.93 (s, 3H), 7.94-7.96 (m, 2H), 8.08-8.11 (m, 2H), 8.82 (s, 1H), 8.91 (s, 1H), 9.34 (s, 1H).

2-{5-(Ethylsulfonyl)-1-methyl-2-[4-(trifluoromethyl)phenyl]-1H-imidazol-4-yl}-6-(trifluoromethyl)-2H-pyrazolo[4,3-b]pyridine (I-098)

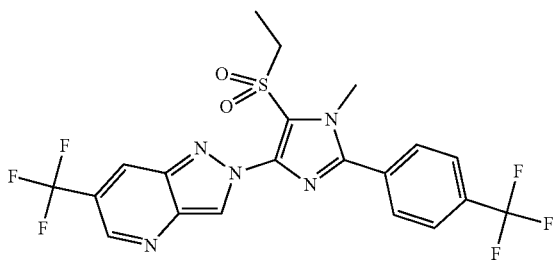 [SMILES: CCS(=O)(=O)c1c(-n2cc3ncc(C(F)(F)F)cc3n2)nc(-c2ccc(C(F)(F)F)cc2)n1C]

A solution of 130 mg (0.28 mmol) of 2-{5-(ethylsulfanyl)-1-methyl-2-[4-(trifluoromethyl)phenyl]-1H-imidazol-4-yl}-6-(trifluoromethyl)-2H-pyrazolo[4,3-b]pyridine in dichloromethane (20 mL) was cooled to 0° C. and 100 mg (1.2 mmol, 35% in water) of hydrogen peroxide and 100 mg (2.9 mmol) of formic acid were added. The mixture was stirred at room temperature for 5 h, diluted by adding 50 mL of dichloromethane and then washed with saturated sodium thiosulfate solution and saturated sodium hydrogencarbonate solution. The organic phase was separated, dried over sodium sulfate, filtered, and the solvent was removed under reduced pressure. The crude product was purified by preparative HPLC using a water/acetonitrile gradient as eluent.

$^1$H-NMR (300 MHz, D$_6$-DMSO) δ ppm: 1.33 (t, 3H), 3.79 (q, 2H), 4.00 (s, 3H), 7.98-8.00 (m, 2H), 8.06-8.09 (m, 2H), 8.84 (s, 1H), 8.93 (s, 1H), 9.36 (s, 1H).

2-Bromo-5-(ethylsulfanyl)-1-methyl-1H-imidazole-4-carboxylic acid

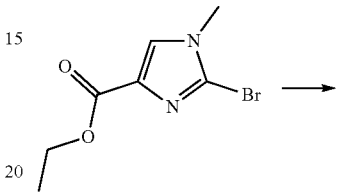

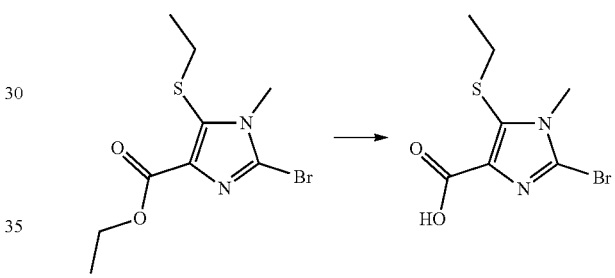

31 g (134 mmol) of ethyl 2-bromo-1-methyl-1H-imidazole-4-carboxylate and 24.4 g (200 mmol) of diethyl disulfide were dissolved in 620 mL of tetrahydrofuran and cooled to −78° C. To this solution were added dropwise 100 mL (2M in THF, 200 mmol) of lithium diisopropylamide (LDA) and the reaction mixture was stirred at −78° C. for 30 minutes. The reaction was terminated by adding saturated ammonium chloride solution. The phases were separated and the aqueous phase was extracted three times with 300 ml of ethyl acetate each time. The organic phases were combined, dried over magnesium sulphate and filtered. The solvent was distilled off under reduced pressure and the residue was purified by column chromatography purification using a petroleum ether/ethyl acetate gradient as mobile phase. This gave 28.5 g (97.3 mmol) of ethyl 2-bromo-5-(ethylsulfanyl)-1-methyl-1H-imidazole-4-carboxylate. This was dissolved in 300 mL of methanol and the solution was cooled to 0° C. 300 mL (2N in water, 600 mmol) of sodium hydroxide were then added and the mixture was stirred at room temperature for 1 h. The mixture was concentrated on a rotary evaporator and neutralized by adding 1N HCl. The mixture was extracted with ethyl acetate. The solvent was distilled off under reduced pressure and the target compound was obtained.

$^1$H-NMR (300 MHz, D$_6$-DMSO) δ ppm: 1.09 (t, 3H), 2.86 (q, 2H), 3.64 (s, 3H), 12.60 (s, 1H).

2-[2-Bromo-5-(ethylsulfanyl)-1-methyl-1H-imidazol-4-yl]-3-methyl-6-(trifluoromethyl)-3H-imidazo[4,5-c]pyridine (I-010)

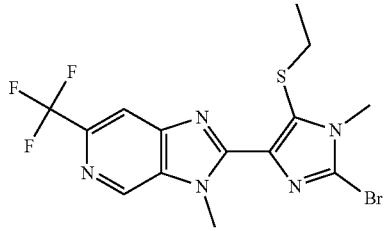 [SMILES: CCSc1c(-c2nc3cc(C(F)(F)F)ncc3n2C)nc(Br)n1C]

To a solution of 9.02 g (34.0 mmol) of 2-bromo-5-(ethylsulfanyl)-1-methyl-1H-imidazole-4-carboxylic acid in pyridine (50 mL) were added 5.00 g (26.1 mmol) of $N^3$-methyl-6-(trifluoromethyl)pyridine-3,4-diamine and 5.01 g (26.1 mmol) of 1-(3-dimethylaminopropyl)-3-ethylcarbodiimide hydrochloride (EDCI). The mixture was stirred at room temperature for three days. Subsequently, the solvent was distilled off under reduced pressure and the residue was taken up in ethyl acetate (50 ml). The mixture was stirred at 100° C. for 6 h, cooled to room temperature, slurried with water, then filtered over a Nutsche filter, dried and the target compound thus obtained.

$^1$H-NMR (400 MHz, $D_6$-DMSO) δ ppm: 1.11 (t, 3H), 3.00 (q, 2H), 3.76 (s, 3H), 4.15 (s, 3H), 8.19 (s, 1H), 9.15 (s, 1H).

2-[2-Bromo-5-(ethylsulfonyl)-1-methyl-1H-imidazol-4-yl]-3-methyl-6-(trifluoromethyl)-3H-imidazo[4,5-c]pyridine (I-004)

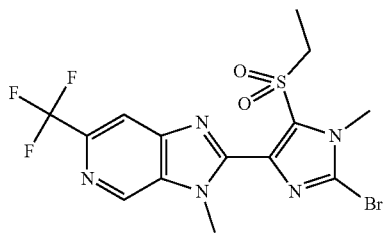 [SMILES: CCS(=O)(=O)c1c(-c2nc3cc(C(F)(F)F)ncc3n2C)nc(Br)n1C]

To a solution of 10.3 g (24.5 mmol) of 2-[2-bromo-5-(ethylsulfanyl)-1-methyl-1H-imidazol-4-yl]-3-methyl-6-(trifluoromethyl)-3H-imidazo[4,5-c]pyridine in dichloromethane (100 mL) were added 4.64 mL (122 mmol) of formic acid and 15.1 mL (172 mmol, 35% in water) of hydrogen peroxide. The mixture was stirred at room temperature overnight and the reaction was terminated by adding saturated sodium thiosulfate solution. The organic phase was separated off, dried over sodium sulfate, filtered, and the target compound thus obtained.

$^1$H-NMR (400 MHz, $D_6$-DMSO) δ ppm: 1.27 (t, 3H), 3.74 (q, 2H), 3.92 (s, 3H), 3.96 (s, 3H), 8.24 (s, 1H), 9.22 (s, 1H).

2-{2-[(E)-2-Cyclopropylvinyl]-5-(ethylsulfonyl)-1-methyl-1H-imidazol-4-yl}-3-methyl-6-(trifluoromethyl)-3H-imidazo[4,5-c]pyridine (I-007)

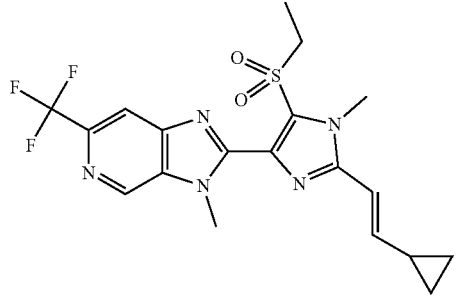 [SMILES: CCS(=O)(=O)c1c(-c2nc3cc(C(F)(F)F)ncc3n2C)nc(/C=C/C2CC2)n1C]

150 mg (0.33 mmol) of 2-[2-bromo-5-(ethylsulfonyl)-1-methyl-1H-imidazol-4-yl]-3-methyl-6-(trifluoromethyl)-3H-imidazo[4,5-c]pyridine (I-004), 64.4 mg (0.33 mmol) of 2-[(E)-2-cyclopropylvinyl]-4,4,5,5-tetramethyl-1,3,2-dioxaborolane and 11.5 mg (0.01 mmol) of tetrakis(triphenylphosphine)palladium were initially charged under a protective gas atmosphere. 2.6 mL of degassed dioxane and 1.3 mL of degassed aqueous sodium carbonate solution (1M) were then added. The mixture was stirred at 92° C. overnight. After cooling, the solvent was distilled off under reduced pressure. The residue was taken up in dichloromethane and washed with water. The organic phase was separated, dried over magnesium sulfate, filtered, and the solvent was distilled off under reduced pressure. The crude product was purified by column chromatography purification using a cyclohexane/acetone gradient as eluent.

$^1$H-NMR (400 MHz, $D_6$-DMSO) δ ppm: 0.64-0.68 (m, 2H), 0.90-0.95 (m, 2H), 1.24 (t, 3H), 1.73-1.77 (m, 1H), 3.65 (q, 2H), 3.92 (s, 3H), 3.93 (s, 3H), 6.38-6.44 (m, 1H), 6.75 (d, 1H), 8.22 (s, 1H), 9.20 (s, 1H).

2-[2-(2-Cyclopropylethyl)-5-(ethylsulfonyl)-1-methyl-1H-imidazol-4-yl]-3-methyl-6-(trifluoromethyl)-3H-imidazo[4,5-c]pyridine (I-085)

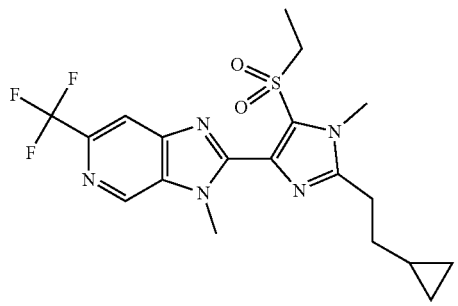 [SMILES: CCS(=O)(=O)c1c(-c2nc3cc(C(F)(F)F)ncc3n2C)nc(CCC2CC2)n1C]

179 mg (0.40 mmol) of 2-{2-[(E)-2-cyclopropylvinyl]-5-(ethylsulfonyl)-1-methyl-1H-imidazol-4-yl}-3-methyl-6-(trifluoromethyl)-3H-imidazo[4,5-c]pyridine (I-007) in 10 mL of methanol were initially charged in an autoclave. 50 mg (0.04 mmol, 10%) of palladium on carbon were then added and the mixture stirred under a hydrogen atmosphere at 5 bar for 16 h. After pressure equalization and removal of the hydrogen atmosphere, the mixture was filtered over celite and the solvent distilled off under reduced pressure. The crude product was purified by column chromatography purification using a cyclohexane/acetone gradient as eluent.

$^1$H-NMR (400 MHz, D$_6$-DMSO) δ ppm: 0.04-0.08 (m, 2H), 0.40-0.44 (m, 2H), 0.80-0.85 (m, 1H), 1.26 (t, 3H), 1.64-1.70 (m, 2H), 2.94 (t, 2H), 3.69 (q, 2H), 3.89 (s, 3H), 3.95 (s, 3H), 8.21 (s, 1H), 9.19 (s, 1H).

2-[2-(6-Chloropyridin-2-yl)-5-(ethylsulfonyl)-1-methyl-1H-imidazol-4-yl]-3-methyl-6-(trifluoromethyl)-3H-imidazo[4,5-c]pyridine (I-014)

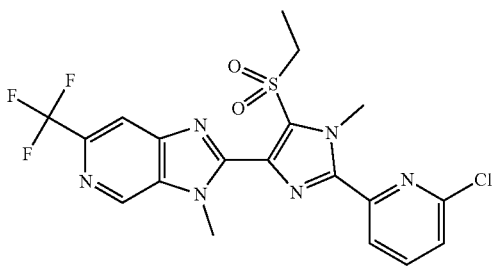 [SMILES: CCS(=O)(=O)c1c(-c2nc3cc(C(F)(F)F)ncc3n2C)nc(-c2cccc(Cl)n2)n1C]

Under a protective gas atmosphere, 200 mg (0.44 mmol) of 2-[2-bromo-5-(ethylsulfonyl)-1-methyl-1H-imidazol-4-yl]-3-methyl-6-(trifluoromethyl)-3H-imidazo[4,5-c]pyridine (I-004), 267 mg (0.66 mmol) of 2-chloro-6-(tributylstannyl)pyridine, 56 mg (1.32 mmol) of lithium chloride, 8 mg (0.04 mmol) of copper(I) iodide and 102 mg (0.08 mmol) of tetrakis(triphenylphosphine)palladium were initially charged in degassed dioxane (4 mL). The mixture was stirred at 96° C. overnight. After cooling, the mixture was diluted with dichloromethane and washed with water. The organic phase was dried over magnesium sulfate, filtered, and the solvent was distilled off under reduced pressure. The crude product was purified by column chromatography purification using a water/acetonitrile gradient as eluent.

$^1$H-NMR (400 MHz, D$_6$-DMSO) δ ppm: 1.30 (t, 3H), 3.78 (q, 2H), 4.00 (s, 3H), 4.32 (s, 3H), 7.74 (d, 1H), 8.09-8.13 (m, 1H), 8.18 (d, 1H), 8.26 (s, 1H), 9.23 (s, 1H).

2-[5-(Ethylsulfonyl)-2-(6-fluoropyridin-3-yl)-1-methyl-1H-imidazol-4-yl]-3-methyl-6-(trifluoromethyl)-3H-imidazo[4,5-c]pyridine (I-019)

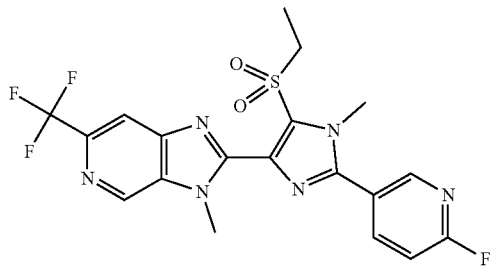 [SMILES: CCS(=O)(=O)c1c(-c2nc3cc(C(F)(F)F)ncc3n2C)nc(-c2ccc(F)nc2)n1C]

Under a protective gas atmosphere, 200 mg (0.44 mmol) of 2-[2-bromo-5-(ethylsulfonyl)-1-methyl-1H-imidazol-4-yl]-3-methyl-6-(trifluoromethyl)-3H-imidazo[4,5-c]pyridine (I-004), 62 mg (0.44 mmol) of (6-fluoropyridin-3-yl)boronic acid and 15 mg (0.01 mmol) of tetrakis(triphenylphosphine)palladium were initially charged in a mixture of degassed dioxane (4 mL) and degassed aqueous sodium carbonate solution (1M, 1.8 mL). The mixture was stirred at 96° C. overnight. After cooling, the mixture was diluted with dichloromethane and washed with water. The organic phase was dried over magnesium sulfate, filtered, and the solvent was distilled off under reduced pressure. The crude product was purified by column chromatography purification using a cyclohexane/acetone gradient as eluent.

$^1$H-NMR (400 MHz, D$_6$-DMSO) δ ppm: 1.33 (t, 3H), 3.82 (q, 2H), 3.98 (s, 3H), 4.02 (s, 3H), 7.45-7.48 (m, 1H), 8.26 (s, 1H), 8.44-8.48 (m, 1H), 8.71-8.72 (m, 1H), 9.23 (s, 1H).

2-[5-(Ethylsulfonyl)-1-methyl-1H-imidazol-4-yl]-3-methyl-6-(trifluoromethyl)-3H-imidazo[4,5-c]pyridine (I-029) and 2-[2-(4-chloro-1H-pyrazol-1-yl)-5-(ethylsulfonyl)-1-methyl-1H-imidazol-4-yl]-3-methyl-6-(trifluoromethyl)-3H-imidazo[4,5-c]pyridine (I-027)

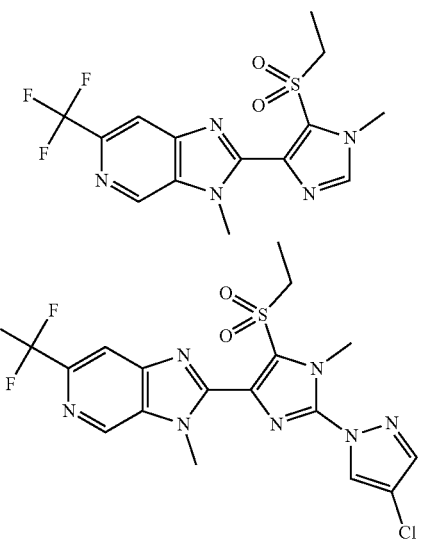

Under a protective gas atmosphere, 200 mg (0.44 mmol) of 2-[2-bromo-5-(ethylsulfonyl)-1-methyl-1H-imidazol-4-yl]-3-methyl-6-(trifluoromethyl)-3H-imidazo[4,5-c]pyridine (I-004), 45 mg (0.44 mmol) of 4-chloro-1H-pyrazole, 4 mg (0.02 mmol) of copper(I) iodide, 128 mg (0.92 mmol) of potassium carbonate and 13 mg (0.08 mmol) of trans-N,N'-dimethylcyclohexane-1,2-diamine (racemic) were initially charged in degassed dioxane (2 mL). The mixture was stirred at 96° C. overnight. After cooling, the mixture was diluted with dichloromethane and washed with water. The organic phase was dried over magnesium sulfate, filtered, and the solvent was distilled off under reduced pressure. The crude products were separated and purified by column chromatography purification using a water/acetonitrile gradient as eluent.

I-029: $^1$H-NMR (400 MHz, D$_6$-DMSO) δ ppm: 1.27 (t, 3H), 3.80 (q, 2H), 3.97 (s, 3H), 3.99 (s, 3H), 8.23 (s, 1H), 8.32 (s, 1H), 9.21 (s, 1H).

I-027: $^1$H-NMR (400 MHz, D$_6$-DMSO) δ ppm: 1.32 (t, 3H), 3.83 (q, 2H), 3.99 (s, 3H), 4.01 (s, 3H), 8.17 (s, 1H), 8.27 (s, 1H), 8.72 (s, 1H), 9.24 (s, 1H).

Methyl 5-(ethylsulfanyl)-1-methyl-4-[3-methyl-6-(trifluoromethyl)-3H-imidazo[4,5-c]pyridin-2-yl]-1H-imidazole-2-carboxylate (I-035)

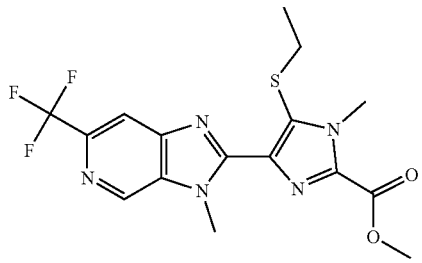 [SMILES: CCSc1c(-c2nc3cc(C(F)(F)F)ncc3n2C)nc(C(=O)OC)n1C]

4.58 g (10.8 mmol) of 2-[2-bromo-5-(ethylsulfanyl)-1-methyl-1H-imidazol-4-yl]-3-methyl-6-(trifluoromethyl)-3H-imidazo[4,5-c]pyridine (I-010) in methanol (458 ml) were initially charged in a 600 ml autoclave vessel. 1.67 g (20.3 mmol) of sodium acetate and 861 mg (1.09 mmol) of dichloro[(bisdiphenylphosphino)ferrocenyl]palladium(II)-acetone complex were then added. The reaction mixture was carbonylated under a carbon monoxide atmosphere at 5 bar and 50° C. for 24 hours. After cooling to room temperature, pressure equalization and removal of the carbon monoxide atmosphere, the mixture was filtered over celite and the solvent was removed under reduced pressure. The crude product was purified by column chromatography purification using a cyclohexane/acetone gradient as eluent.

$^1$H-NMR (400 MHz, D$_6$-DMSO) δ ppm: 1.10 (t, 3H), 3.04 (q, 2H), 3.92 (s, 3H), 4.08 (s, 3H), 4.18 (s, 3H), 8.22 (s, 1H), 9.17 (s, 1H).

Methyl 5-(ethylsulfonyl)-1-methyl-4-[3-methyl-6-(trifluoromethyl)-3H-imidazo[4,5-c]pyridin-2-yl]-1H-imidazole-2-carboxylate (I-036)

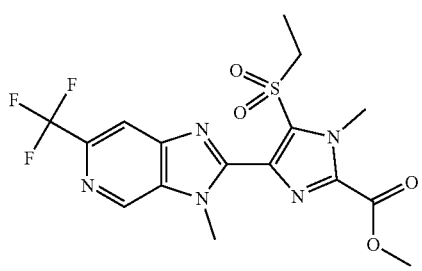 [SMILES: CCS(=O)(=O)c1c(-c2nc3cc(C(F)(F)F)ncc3n2C)nc(C(=O)OC)n1C]

To a solution of 1.60 g (3.44 mmol) of methyl 5-(ethylsulfanyl)-1-methyl-4-[3-methyl-6-(trifluoromethyl)-3H-imidazo[4,5-c]pyridin-2-yl]-1H-imidazole-2-carboxylate (I-035) in dichloromethane (80 mL) were added 0.7 mL (17.2 mmol) of formic acid and 2.1 mL (24.1 mmol, 35% in water) of hydrogen peroxide. The mixture was stirred at room temperature overnight and the reaction was terminated by adding saturated sodium thiosulfate solution. The organic phase was separated, dried over sodium sulfate, filtered and the solvent was removed under reduced pressure. The crude product was purified by column chromatography purification using a cyclohexane/acetone gradient as eluent.

$^1$H-NMR (400 MHz, D$_6$-DMSO) δ ppm: 1.27 (t, 3H), 3.76 (q, 2H), 3.93 (s, 3H), 3.94 (s, 3H), 4.24 (s, 3H), 8.26 (s, 1H), 9.23 (s, 1H).

5-(Ethylsulfonyl)-1-methyl-4-[3-methyl-6-(trifluoromethyl)-3H-imidazo[4,5-c]pyridin-2-yl]-1H-imidazole-2-carboxamide (I-038)

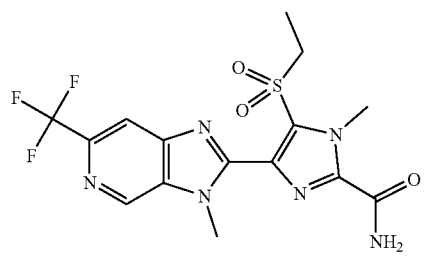 [SMILES: CCS(=O)(=O)c1c(-c2nc3cc(C(F)(F)F)ncc3n2C)nc(C(N)=O)n1C]

To a solution of 300 mg (0.69 mmol) of methyl 5-(ethylsulfonyl)-1-methyl-4-[3-methyl-6-(trifluoromethyl)-3H-imidazo[4,5-c]pyridin-2-yl]-1H-imidazole-2-carboxylate (I-036) in methanol (15 mL) and tetrahydrofuran (15 mL) were added 474 mg (6.95 mmol, 25%) of ammonia. The mixture was stirred at room temperature overnight and the product obtained by concentrating the mixture to dryness under reduced pressure.

$^1$H-NMR (400 MHz, D$_6$-DMSO) δ ppm: 1.27 (t, 3H), 3.75 (q, 2H), 3.98 (s, 3H), 4.28 (s, 3H), 8.02 (s, 1H), 8.25 (s, 1H), 8.33 (s, 1H), 9.24 (s, 1H).

5-(Ethylsulfonyl)-1-methyl-4-[3-methyl-6-(trifluoromethyl)-3H-imidazo[4,5-c]pyridin-2-yl]-1H-imidazole-2-carbonitrile (I-045)

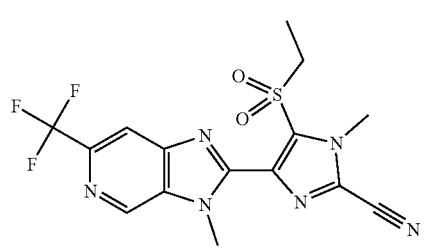 [SMILES: CCS(=O)(=O)c1c(-c2nc3cc(C(F)(F)F)ncc3n2C)nc(C#N)n1C]

A solution of 100 mg (0.24 mmol) of 5-(ethylsulfonyl)-1-methyl-4-[3-methyl-6-(trifluoromethyl)-3H-imidazo[4,5-c]pyridin-2-yl]-1H-imidazole-2-carboxamide (I-038) in phosphoryl chloride (2 mL) was stirred at room temperature for three days and then concentrated to dryness. The crude product was purified by column chromatography purification using a water/acetonitrile gradient as eluent.

$^1$H-NMR (400 MHz, D$_6$-DMSO) δ ppm: 1.30 (t, 3H), 3.86 (q, 2H), 4.00 (s, 3H), 4.09 (s, 3H), 8.28 (s, 1H), 9.25 (s, 1H).

5-(Ethylsulfonyl)-1-methyl-4-[3-methyl-6-(trifluoromethyl)-3H-imidazo[4,5-c]pyridin-2-yl]-1H-imidazole-2-carbothioamide (I-046)

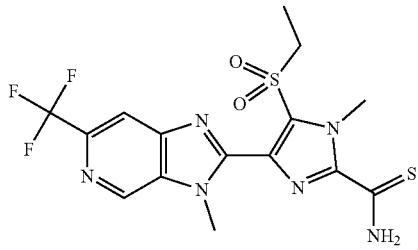

Under a protective gas atmosphere, 107 mg (0.26 mmol) of 2,4-bis(4-methoxyphenyl)-1,3,2,4-dithiadiphosphetane 2,4-disulfide (Lawessons reagent) were added to a solution of 100 mg (0.24 mmol) of 5-(ethylsulfonyl)-1-methyl-4-[3-methyl-6-(trifluoromethyl)-3H-imidazo[4,5-c]pyridin-2-yl]-1H-imidazole-2-carboxamide (I-038) in toluene (1 mL). The mixture was heated to boiling for 4 h, cooled to room temperature and concentrated under reduced pressure. The residue was taken up in dichloromethane and washed with water. The organic phase was separated, dried over magnesium sulfate, filtered, and the solvent was distilled off under reduced pressure. The crude product was purified by column chromatography purification using a water/acetonitrile gradient as eluent.

$^1$H-NMR (400 MHz, D$_6$-DMSO) δ ppm: 1.29 (t, 3H), 3.81 (q, 2H), 3.99 (s, 3H), 4.14 (s, 3H), 8.25 (s, 1H), 9.23 (s, 1H), 10.10 (s, 1H), 10.60 (s, 1H).

In analogy to the examples and according to the above described preparation processes, the following compounds of the formula (I) can be obtained:

| Example | Structure | NMR data |
|---|---|---|
| I-001 | 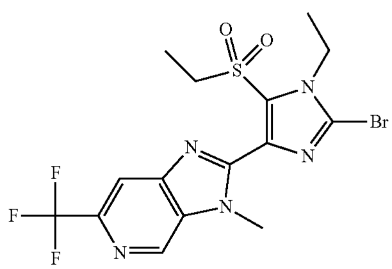 [SMILES: CCn1c(Br)nc(-c2nc3cc(C(F)(F)F)ncc3n2C)c1S(=O)(=O)CC] | I-001: $^1$H-NMR(400.0 MHz, d$_6$-DMSO): δ = 9.2252 (4.0); 8.2462 (4.2); 4.3983 (0.7); 4.3809 (2.5); 4.3630 (2.5); 4.3454 (0.7); 3.9902 (1.0); 3.9806 (16.0); 3.8342 (1.0); 3.8155 (3.4); 3.7971 (3.5); 3.7785 (1.0); 3.3207 (58.6); 2.6751 (0.6); 2.6710 (0.8); 2.6666 (0.6); 2.5239 (1.8); 2.5062 (103.1); 2.5018 (132.5); 2.4974 (94.1); 2.3328 (0.6); 2.3285 (0.8); 2.3241 (0.6); 2.0859 (1.6); 1.4434 (2.8); 1.4256 (6.4); 1.4079 (2.8); 1.3981 (0.6); 1.2976 (3.6); 1.2791 (8.0); 1.2606 (3.6); −0.0002 (2.5) |
| I-002 | 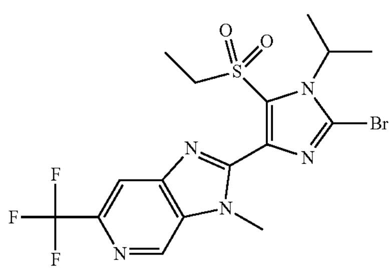 [SMILES: CCS(=O)(=O)c1c(-c2nc3cc(C(F)(F)F)ncc3n2C)nc(Br)n1C(C)C] | I-002: $^1$H-NMR(400.0 MHz, d$_6$-DMSO): δ = 9.2149 (4.0); 8.2339 (4.1); 5.7577 (3.7); 5.3553 (0.4); 5.3391 (0.5); 5.3230 (0.4); 3.9373 (0.8); 3.9233 (16.0); 3.7686 (0.9); 3.7018 (0.9); 3.6835 (3.1); 3.6650 (3.1); 3.6466 (1.0); 3.3216 (11.2); 2.6711 (0.4); 2.5241 (0.8); 2.5105 (21.8); 2.5064 (45.3); 2.5019 (60.5); 2.4975 (43.6); 2.4932 (21.0); 2.3284 (0.3); 1.7121 (13.2); 1.6946 (13.1); 1.6838 (1.2); 1.6768 (0.8); 1.6592 (0.7); 1.3113 (0.4); 1.3014 (3.7); 1.2926 (0.8); 1.2831 (8.2); 1.2645 (3.6); 0.0080 (0.4); −0.0002 (10.9): −0.0082 (0.4) |
| I-003 | 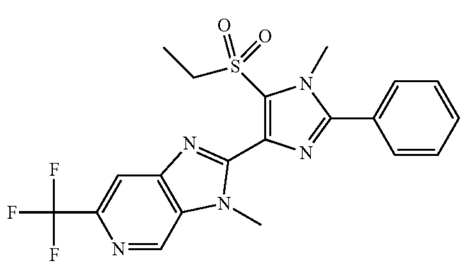 [SMILES: CCS(=O)(=O)c1c(-c2nc3cc(C(F)(F)F)ncc3n2C)nc(-c2ccccc2)n1C] | I-003: $^1$H-NMR(400.0 MHz, d$_6$-DMSO): δ = 9.2238 (3.8); 8.2524 (4.0); 7.8336 (1.9); 7.8272 (2.0); 7.8222 (1.8); 7.8185 (2.4); 7.8096 (2.2); 7.6269 (0.6); 7.6176 (4.8); 7.6103 (4.4); 7.6015 (3.5); 4.0147 (16.0); 3.9689 (14.7); 3.8366 (1.0); 3.8183 (3.3); 3.7998 (3.3); 3.7813 (1.0); 3.3211 (76.3); 2.6747 (0.7); 2.6704 (1.0); 2.6660 (0.7); 2.5237 (2.5); 2.5102 (65.5); 2.5059 (131.9); 2.5014 (170.7); 2.4969 (121.6); 2.4926 (57.9); 2.3327 (0.7); 2.3280 (1.0); 2.3239 (0.7); 2.0857 (2.3); 1.3976 (1.1); 1.3433 (3.6); 1.3248 (8.1); 1.3063 (3.5); 0.0079 (0.7); −0.0001 (19.4); −0.0083 (0.7) |
| I-004 | 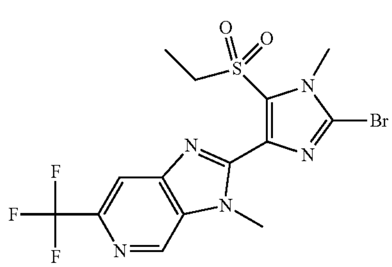 [SMILES: CCS(=O)(=O)c1c(-c2nc3cc(C(F)(F)F)ncc3n2C)nc(Br)n1C] | I-004: $^1$H-NMR(400.0 MHz, d$_6$-DMSO): δ = 9.2198 (3.9); 8.2438 (4.2); 5.7557 (3.7); 3.9590 (16.0); 3.9230 (15.3); 3.9115 (0.9); 3.8423 (0.7); 3.8249 (0.8); 3.8058 (0.6); 3.7669 (1.1); 3.7484 (3.5); 3.7299 (3.5); 3.7115 (1.1); 3.3226 (12.4); 2.6711 (0.3); 2.5067 (48.0); 2.5023 (61.6); 2.4979 (43.8); 2.3290 (0.4); 1.2911 (3.7); 1.2727 (8.2); 1.2542 (3.7); 1.2065 (0.5); 1.1829 (0.5); 0.0077 (1.0); −0.0002 (22.7); −0.0084 (0.9) |

| Example | Structure | NMR data |
|---|---|---|
| I-005 | 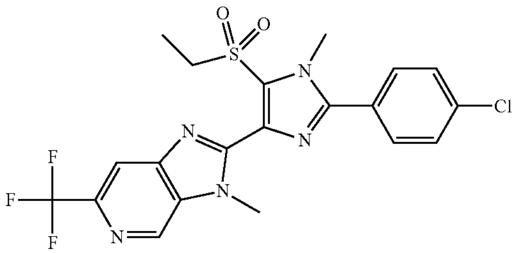 [SMILES: CCS(=O)(=O)c1c(-c2nc3cc(C(F)(F)F)ncc3n2C)nc(-c2ccc(Cl)cc2)n1C] | I-005: ¹H-NMR(400.0 MHz, d₆-DMSO): δ = 9.2227 (3.5); 8.2512 (3.8); 7.9251 (1.1); 7.8688 (3.3); 7.8476 (4.1); 7.8155 (0.4); 7.6925 (4.2); 7.6712 (3.3); 7.5936 (0.4); 7.5718 (0.4); 4.0299 (1.6); 4.0200 (1.6); 4.0087 (12.7); 3.9628 (11.9); 3.8289 (1.0); 3.8194 (0.4); 3.8090 (2.9); 3.7904 (2.9); 3.7717 (0.9); 3.3197 (71.6); 2.6748 (1.6); 2.6701 (2.0); 2.5233 (5.1); 2.5056 (272.2); 2.5013 (357.5); 2.4970 (260.8); 2.3281 (2.0); 2.3238 (1.5); 1.3976 (16.0); 1.3557 (0.5); 1.3406 (3.2); 1.3223 (6.7); 1.3039 (2.9); −0.0003 (11.3) |
| I-006 | 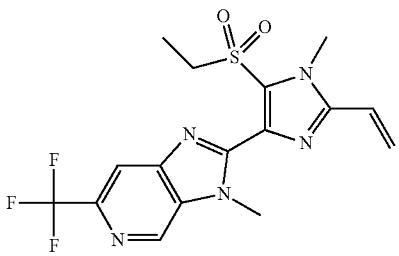 [SMILES: C=Cc1nc(-c2nc3cc(C(F)(F)F)ncc3n2C)c(S(=O)(=O)CC)n1C] | I-006: ¹H-NMR(400.0 MHz, d₆-DMSO): δ = 9.2126 (3.7); 8.2339 (4.0); 7.0471 (1.1); 7.0195 (1.2); 7.0048 (1.4); 6.9770 (1.4); 6.3732 (1.5); 6.3692 (1.5); 6.3309 (1.3); 6.3267 (1.2); 5.7904 (1.5); 5.7862 (1.4); 5.7629 (1.3); 5.7589 (1.4); 3.9705 (14.8); 3.9597 (16.0); 3.7234 (0.9); 3.7047 (3.3); 3.6862 (3.4); 3.6676 (1.0); 3.3193 (83.1); 2.6742 (1.8); 2.6698 (2.4); 2.6652 (1.8); 2.5233 (5.8); 2.5096 (158.0); 2.5054 (323.4); 2.5010 (427.3); 2.4965 (302.6); 2.4921 (142.4); 2.4433 (0.4); 2.4394 (0.4); 2.3323 (1.8); 2.3278 (2.4); 2.3232 (1.8); 2.0855 (0.8); 1.3976 (1.2); 1.2718 (3.6); 1.2535 (7.9); 1.2349 (3.6); 0.0082 (0.5); −0.0002 (15.4) |
| I-007 | 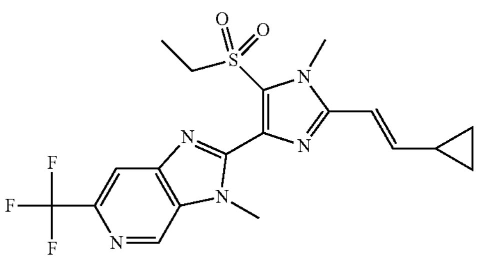 [SMILES: CCS(=O)(=O)c1c(-c2nc3cc(C(F)(F)F)ncc3n2C)nc(/C=C/C2CC2)n1C] | I-007: ¹H-NMR(400.0 MHz, d₆-DMSO): δ = 9.1990 (4.0); 8.2199 (4.2); 6.7627 (2.2); 6.7246 (2.8); 6.4410 (1.4); 6.4163 (1.4); 6.4029 (1.1); 6.3782 (1.1); 3.9323 (16.0); 3.9230 (14.4); 3.6798 (1.0); 3.6613 (3.2); 3.6429 (3.3); 3.6246 (1.0); 3.3239 (13.2); 2.5249 (0.4); 2.5111 (12.1); 2.5070 (25.0); 2.5026 (32.9); 2.4982 (23.6); 2.0864 (9.5); 1.7726 (0.4); 1.7628 (0.6); 1.7505 (0.6); 1.7383 (0.6); 1.7285 (0.4); 1.2560 (3.6); 1.2375 (7.9); 1.2191 (3.4); 0.9453 (0.5); 0.9344 (1.7); 0.9284 (1.9); 0.9146 (1.7); 0.9087 (1.8); 0.8988 (0.6); 0.6748 (0.7); 0.6645 (2.2); 0.6594 (2.0); 0.6537 (2.0); 0.6482 (2.2); 0.6375 (0.6); −0.0002 (1.3) |
| I-008 | 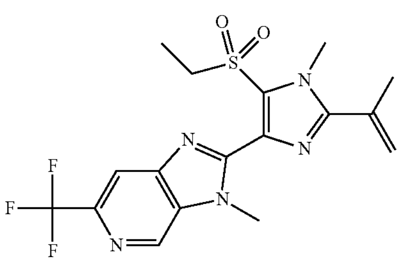 [SMILES: C=C(C)c1nc(-c2nc3cc(C(F)(F)F)ncc3n2C)c(S(=O)(=O)CC)n1C] | I-008: ¹H-NMR(400.0 MHz, d₆-DMSO): δ = 9.2074 (3.2); 8.2281 (3.4); 5.7620 (2.0); 5.5708 (2.6); 3.9590 (15.7); 3.9559 (16.0); 3.7603 (0.8); 3.7418 (2.8); 3.7233 (2.9); 3.7048 (0.8); 3.3249 (18.0); 2.5069 (34.0); 2.5025 (44.1); 2.4980 (31.3); 2.1750 (8.0); 1.3973 (2.1); 1.2955 (3.1); 1.2771 (6.8); 1.2586 (3.0); −0.0002 (1.2) |
| I-009 | 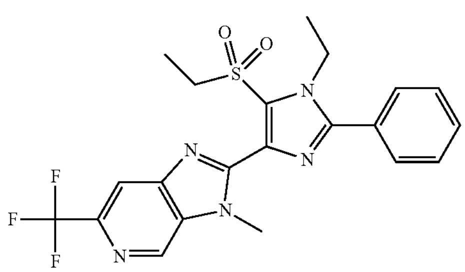 [SMILES: CCn1c(-c2ccccc2)nc(-c2nc3cc(C(F)(F)F)ncc3n2C)c1S(=O)(=O)CC] | I-009: ¹H-NMR(400.0 MHz, d₆-DMSO): δ = 9.3130 (0.4); 9.2253 (4.0); 8.3170 (0.4); 8.2511 (4.3); 7.8079 (0.4); 7.7986 (1.8); 7.7934 (2.4); 7.7839 (2.4); 7.7743 (2.5); 7.6264 (5.2); 7.6212 (4.8); 7.6128 (2.8); 7.6099 (2.7); 7.6001 (0.8); 7.5848 (0.4); 6.7556 (0.4); 4.4391 (0.8); 4.4217 (2.4); 4.4034 (2.4); 4.3849 (0.8); 4.0574 (0.4); 4.0416 (16.0); 3.9029 (0.9); 3.8841 (3.3); 3.8654 (3.4); 3.8476 (1.1); 3.3224 (556.8); 3.2801 (0.5); 3.2713 (0.3); 2.7960 (0.4); 2.6748 (2.7); 2.6702 (3.6); 2.6662 (2.7); 2.6014 (0.4); 2.5908 (0.4); 2.5234 (9.8); 2.5098 (242.5); 2.5056 (497.9); 2.5012 (660.9); 2.4967 (472.9); 2.4925 (226.2); 2.4320 (0.5); 2.3324 (2.7); 2.3276 (3.7); 2.3232 (2.9); 2.0855 (0.4); 1.3975 (7.6); 1.3462 (3.7); 1.3357 (3.2); 1.3279 (8.6); 1.3183 (6.8); 1.3094 (4.2); 1.3001 (2.8); −0.0003 (9.1) |
| I-010 | 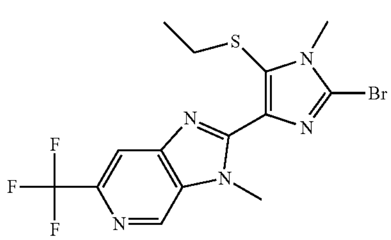 [SMILES: CCSc1c(-c2nc3cc(C(F)(F)F)ncc3n2C)nc(Br)n1C] | I-010: ¹H-NMR(400.0 MHz, d₆-DMSO): δ = 9.1511 (3.2); 8.1914 (3.5); 7.4806 (2.7); 7.4604 (3.0); 7.1198 (2.4); 7.1003 (2.1); 4.1488 (16.0); 4.0780 (2.0); 4.0728 (2.0); 4.0610 (2.0); 3.9789 (0.4); 3.9691 (0.3); 3.7605 (14.4); 3.6389 (1.2); 3.5999 (0.9); 3.0286 (1.2); 3.0102 (3.8); 2.9918 (3.9); 2.9734 (1.2); 2.6757 (0.4); 2.6711 (0.6); 2.6665 (0.5); 2.6620 (0.4); 2.5243 (1.3); 2.5195 (2.1); 2.5108 (40.7); 2.5064 (85.7); 2.5019 (114.5); 2.4973 (81.2); 2.4929 (38.0); 2.3332 (0.5); 2.3286 (0.7); 2.3240 (0.5); 2.2875 (9.0); 1.2350 (0.3); 1.1230 (4.1); 1.1144 (0.6); 1.1046 (8.9); 1.0862 (4.1); 1.0701 (0.4); 0.0080 (0.9); −0.0002 (29.8); −0.0084 (1.0) |

| Example | Structure | NMR data |
|---|---|---|
| I-011 | 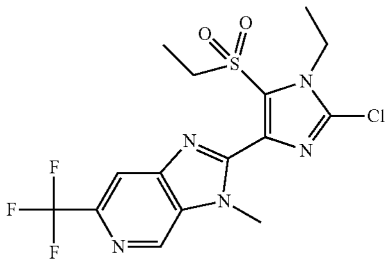 [SMILES: CCn1c(Cl)nc(-c2nc3cc(C(F)(F)F)ncc3n2C)c1S(=O)(=O)CC] | I-011: ¹H-NMR(400.0 MHz, d₆-DMSO): δ = 9.6529 (0.3); 9.2242 (3.9); 8.2496 (4.4); 7.8575 (0.3); 7.8422 (3.5); 7.8211 (4.7); 7.7000 (4.7); 7.6785 (3.5); 7.1755 (0.3); 4.4313 (0.8); 4.4132 (2.3); 4.3953 (2.2); 4.3791 (0.7); 4.0585 (0.5); 4.0366 (14.0); 3.8951 (1.1); 3.8775 (3.1); 3.8591 (3.1); 3.8419 (1.0); 3.3660 (0.4); 3.3210 (247.6); 2.6704 (3.5); 2.5054 (493.7); 2.5013 (632.5); 2.4970 (457.0); 2.4121 (0.5); 2.3279 (3.7); 1.3977 (16.0); 1.3447 (3.8); 1.3380 (3.1); 1.3266 (8.3); 1.3199 (6.5); 1.3080 (4.1); 1.3026 (3.0); 1.2381 (0.4); 1.1623 (0.4); −0.0002 (7.9); −3.5554 (0.4) |
| I-012 | 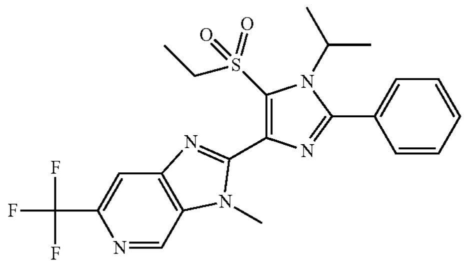 [SMILES: CCS(=O)(=O)c1c(-c2nc3cc(C(F)(F)F)ncc3n2C)nc(-c2ccccc2)n1C(C)C] | I-012: ¹H-NMR(400.0 MHz, d₆-DMSO): δ = 9.2102 (4.5); 8.2355 (5.0); 7.6806 (2.7); 7.6643 (3.6); 7.6604 (3.3); 7.6397 (0.5); 7.6202 (1.7); 7.5980 (4.5); 7.5792 (3.0); 7.5619 (0.8); 5.1080 (0.4); 5.0899 (0.8); 5.0727 (1.1); 5.0541 (0.8); 5.0380 (0.4); 3.9696 (16.0); 3.9373 (0.8); 3.8274 (1.1); 3.8093 (3.5); 3.7906 (3.5); 3.7717 (1.1); 3.3205 (82.5); 2.6707 (2.0); 2.5057 (290.3); 2.5018 (356.2); 2.4980 (261.7); 2.3285 (2.1); 1.6768 (0.6); 1.6599 (0.6); 1.4621 (11.6); 1.4446 (11.3); 1.3984 (2.4); 1.3464 (3.9); 1.3279 (8.0): 1.3093 (3.8): 1.2935 (0.5); 1.2745 (0.4); 0.0001 (3.3) |
| I-013 | 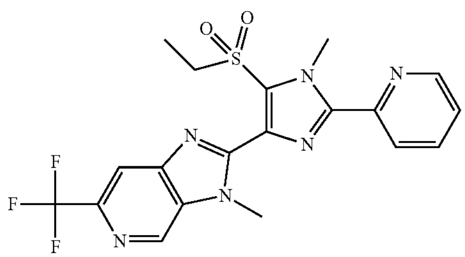 [SMILES: CCS(=O)(=O)c1c(-c2nc3cc(C(F)(F)F)ncc3n2C)nc(-c2ccccn2)n1C] | I-013: ¹H-NMR(400.0 MHz, d₆-DMSO): δ = 9.2380 (5.1); 8.7929 (0.9); 8.2597 (5.5); 8.1737 (0.9); 8.0673 (1.1); 8.0484 (1.9); 8.0295 (0.9); 7.5984 (1.2); 5.7570 (3.6); 4.3529 (16.0); 4.0056 (13.1); 3.8065 (1.3); 3.7881 (4.0); 3.7696 (4.1); 3.7512 (1.3); 3.3210 (15.0); 2.6707 (0.9); 2.5060 (132.9); 2.5022 (163.4); 2.4984 (125.2); 2.3289 (0.9); 1.3200 (4.4); 1.3016 (9.3); 1.2833 (4.3); −0.0002 (32.2) |
| I-014 | 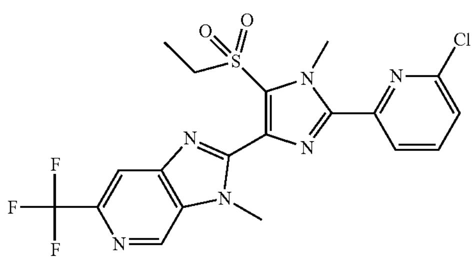 [SMILES: CCS(=O)(=O)c1c(-c2nc3cc(C(F)(F)F)ncc3n2C)nc(-c2cccc(Cl)n2)n1C] | I-014: ¹H-NMR(400.0 MHz, d₆-DMSO): δ = 9.2382 (3.6); 8.2618 (3.9); 8.1909 (1.6); 8.1716 (2.7); 8.1252 (1.6); 8.1056 (2.6); 8.0860 (1.1); 7.7476 (2.2); 7.7280 (2.0); 4.3197 (12.7); 3.9948 (13.4); 3.8026 (0.9); 3.7843 (2.9); 3.7658 (2.9); 3.7474 (0.9); 3.3218 (11.0); 2.6715 (0.3); 2.5066 (46.0); 2.5024 (59.6); 2.4982 (42.9); 2.3289 (0.3); 2.0862 (16.0); 1.3162 (3.1); 1.2978 (6.9); 1.2794 (3.1); 0.0079 (0.8); −0.0002 (23.2) |
| I-015 | 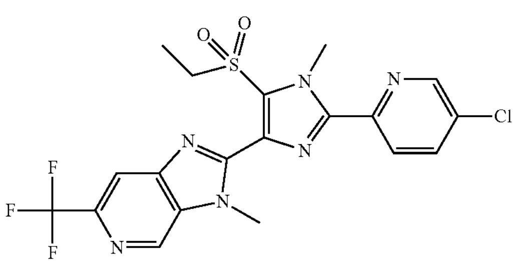 [SMILES: CCS(=O)(=O)c1c(-c2nc3cc(C(F)(F)F)ncc3n2C)nc(-c2ccc(Cl)cn2)n1C] | I-015: ¹H-NMR(400.0 MHz, d₆-DMSO): δ = 9.2391 (4.5); 8.8599 (2.2); 8.2600 (4.7); 8.2207 (0.7); 8.1987 (3.4); 8.1908 (3.6); 8.1857 (2.9); 8.1695 (0.8); 8.1637 (0.7); 5.7572 (2.4); 4.3271 (15.7); 4.0021 (16.0); 3.8083 (1.2); 3.7895 (3.7); 3.7710 (3.7); 3.7527 (1.3); 3.3214 (12.0); 2.6712 (0.6); 2.5063 (99.7); 2.5021 (115.7); 2.3289 (0.6); 1.3177 (4.1); 1.2992 (8.8); 1.2809 (4.2); 1.2330 (0.3); 0.8787 (0.5); 0.8599 (0.9); 0.8418 (0.4); −0.0002 (22.9) |
| I-016 | 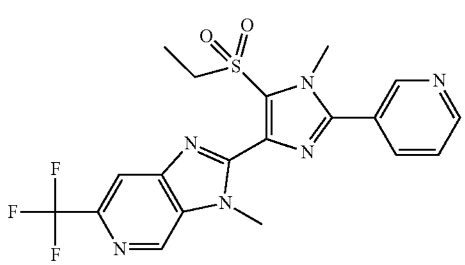 [SMILES: CCS(=O)(=O)c1c(-c2nc3cc(C(F)(F)F)ncc3n2C)nc(-c2cccnc2)n1C] | I-016: ¹H-NMR(400.0 MHz, d₆-DMSO): δ = 9.2298 (3.8); 9.0179 (2.0); 9.0139 (2.0); 8.7983 (1.3); 8.7946 (1.4); 8.7862 (1.4); 8.7825 (1.4); 8.2796 (0.9); 8.2749 (1.3); 8.2700 (0.9); 8.2560 (5.1); 8.2504 (1.1); 7.6634 (1.1); 7.6511 (1.2); 7.6449 (1.2); 7.6313 (1.2); 4.0238 (16.0); 3.9926 (14.6); 3.8476 (1.0); 3.8292 (3.2); 3.8107 (3.4); 3.7922 (1.0); 3.3393 (38.5); 3.3353 (35.9); 2.5256 (0.6); 2.5121 (14.0); 2.5079 (28.5); 2.5034 (37.6); 2.4989 (26.9); 2.4946 (12.8); 2.0868 (2.1); 1.3539 (3.6); 1.3354 (8.1); 1.3169 (3.5); 0.0079 (0.7); −0.0002 (18.4); −0.0085 (0.6) |

-continued

| Example | Structure | NMR data |
|---|---|---|
| I-017 | 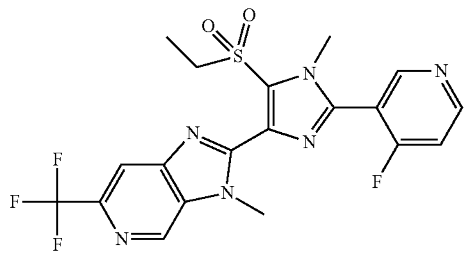 [SMILES: CCS(=O)(=O)c1c(-c2nc3cc(C(F)(F)F)ncc3n2C)nc(-c2cnccc2F)n1C] | I-017: $^1$H-NMR(400.0 MHz, d$_6$-DMSO): δ = 9.2312 (3.7); 9.2143 (0.8); 8.9740 (2.3); 8.9490 (2.2); 8.8890 (1.3); 8.8745 (1.3); 8.8688 (1.3); 8.8547 (1.1); 8.2605 (4.0); 8.2407 (0.8); 8.1279 (0.4); 7.6866 (1.2); 7.6722 (1.2); 7.6614 (1.2); 7.6468 (1.2); 4.0277 (14.2); 4.0130 (2.9); 3.9003 (1.0); 3.8760 (8.3); 3.8732 (8.0); 3.8633 (3.4); 3.8444 (1.0); 3.8117 (0.6); 3.7930 (0.6); 3.7738 (2.8); 3.5678 (0.7); 3.3197 (31.4); 2.6708 (1.2); 2.5538 (0.4); 2.5058 (164.9); 2.5014 (213.3); 2.4971 (152.7); 2.3327 (0.9); 2.3282 (1.2); 2.1171 (0.5); 2.0857 (16.0); 1.3516 (3.4); 1.3332 (7.2); 1.3147 (3.3); 1.3022 (1.5); 1.2838 (0.7); 1.2325 (0.4); 1.1401 (1.1); −0.0002 (6.1) |
| I-018 | 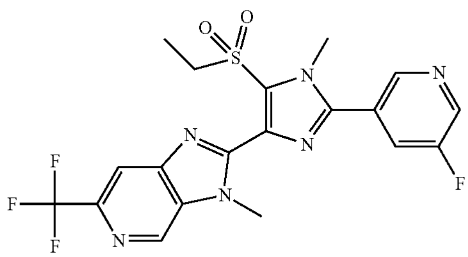 [SMILES: CCS(=O)(=O)c1c(-c2nc3cc(C(F)(F)F)ncc3n2C)nc(-c2cncc(F)c2)n1C] | I-018: $^1$H-NMR(400.0 MHz, d$_6$-DMSO): δ = 9.2336 (3.4); 8.9027 (1.6); 8.8989 (2.7); 8.8954 (1.5); 8.8352 (2.4); 8.8283 (2.5); 8.2784 (0.8); 8.2739 (1.0); 8.2715 (1.0); 8.2671 (0.9); 8.2594 (3.7); 8.2502 (1.1); 8.2477 (1.0); 8.2434 (0.8); 4.0247 (14.1); 4.0095 (13.0); 3.8553 (0.8); 3.8368 (2.8); 3.8183 (2.9); 3.7998 (0.9); 3.3232 (43.6); 2.6709 (0.4); 2.5244 (0.9); 2.5108 (24.0); 2.5064 (49.4); 2.5020 (65.1); 2.4974 (46.3); 2.4931 (22.0); 2.3287 (0.4); 2.0861 (16.0); 1.3563 (3.1); 1.3379 (7.0); 1.3194 (3.0); 0.0080 (1.0); −0.0002 (31.4); −0.0085 (1.2) |
| I-019 | 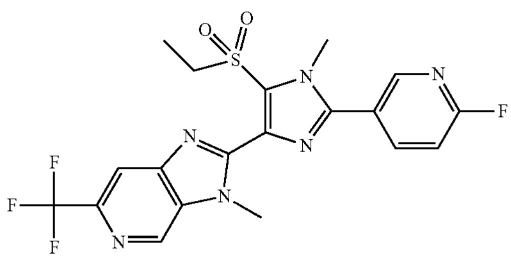 [SMILES: CCS(=O)(=O)c1c(-c2nc3cc(C(F)(F)F)ncc3n2C)nc(-c2ccc(F)nc2)n1C] | I-019: $^1$H-NMR(400.0 MHz, d$_6$-DMSO): δ = 9.2287 (3.9); 8.7155 (2.2); 8.4838 (0.8); 8.4775 (0.8); 8.4630 (1.3); 8.4567 (1.2); 8.4430 (0.8); 8.4367 (0.8); 8.2555 (4.2); 7.4791 (1.3); 7.4727 (1.3); 7.4576 (1.4); 7.4509 (1.3); 5.7571 (7.6); 4.0202 (16.0); 3.9776 (15.0); 3.9666 (0.8); 3.8441 (1.1); 3.8257 (3.4); 3.8072 (3.4); 3.7887 (1.0); 3.5682 (0.5); 3.3238 (28.0); 2.5248 (0.8); 2.5112 (19.0); 2.5069 (38.3); 2.5024 (50.1); 2.4979 (35.2); 2.4936 (16.4); 2.0863 (12.6); 1.3970 (4.4); 1.3527 (3.7); 1.3343 (8.3); 1.3158 (3.6); 0.0078 (1.9); −0.0002 (52.1); −0.0085 (1.9) |
| I-020 | 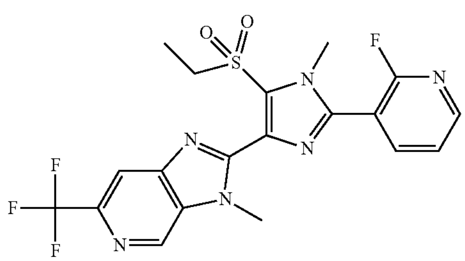 [SMILES: CCS(=O)(=O)c1c(-c2nc3cc(C(F)(F)F)ncc3n2C)nc(-c2cccnc2F)n1C] | I-020: $^1$H-NMR(400.0 MHz, d$_6$-DMSO): δ = 9.2286 (4.4); 8.5346 (1.5); 8.5239 (1.5); 8.4136 (0.8); 8.4093 (0.7); 8.3946 (1.0); 8.3901 (1.5); 8.3712 (0.8); 8.3663 (0.7); 8.2586 (4.8); 7.6637 (0.9); 7.6597 (0.9); 7.6464 (1.4); 7.6411 (0.9); 7.6327 (0.9); 7.6287 (0.8); 5.7576 (3.8); 4.0216 (16.0); 3.8934 (1.1); 3.8711 (11.1); 3.8568 (3.8); 3.8383 (1.2); 3.3211 (8.1); 2.6712 (0.3); 2.5063 (46.0); 2.5023 (57.6); 2.4982 (41.5); 1: 1.3500 (3.8); 1.3316 (8.1); 1.3131 (3.6); −0.0002 (3.7) |
| I-021 | 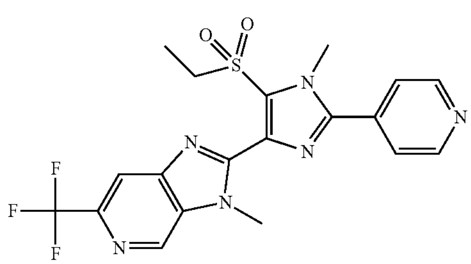 [SMILES: CCS(=O)(=O)c1c(-c2nc3cc(C(F)(F)F)ncc3n2C)nc(-c2ccncc2)n1C] | I-021: $^1$H-NMR(400.0 MHz, d$_6$-DMSO): δ = 9.2324 (3.7); 8.8336 (3.3); 8.8188 (3.2); 8.7363 (0.3); 8.2594 (4.0); 7.8561 (3.7); 7.8525 (2.3); 7.8411 (3.8); 7.8317 (0.3); 7.8269 (0.4); 4.0294 (13.0); 4.0145 (13.8); 3.8476 (1.0); 3.8292 (3.0); 3.8107 (3.0); 3.7922 (0.9); 3.3240 (9.0); 2.5070 (30.7); 2.5027 (39.5); 2.4983 (28.0); 2.0864 (16.0); 1.3492 (3.2); 1.3308 (7.1); 1.3123 (3.2); 0.0077 (0.6); −0.0002 (17.3); −0.0085 (0.6) |
| I-022 | 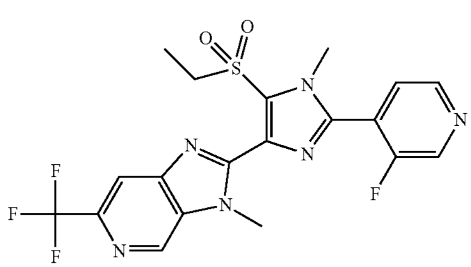 [SMILES: CCS(=O)(=O)c1c(-c2nc3cc(C(F)(F)F)ncc3n2C)nc(-c2ccncc2F)n1C] | I-022: $^1$H-NMR(400.0 MHz, d$_6$-DMSO): δ = 9.2357 (4.0); 8.5035 (2.4); 8.4906 (2.5); 8.2620 (4.3); 7.8315 (1.6); 7.8224 (1.1); 7.8187 (1.5); 7.8149 (1.0); 7.6839 (2.9); 4.0455 (14.9); 4.0151 (16.0); 3.8530 (1.0); 3.8345 (3.4); 3.8159 (3.4); 3.7973 (1.2); 3.3245 (76.2); 2.6755 (0.4); 2.6709 (0.5); 2.6666 (0.4); 2.5241 (1.5); 2.5106 (36.4); 2.5064 (73.1); 2.5020 (95.8); 2.4975 (68.1); 2.4933 (32.4); 2.3331 (0.4); 2.3289 (0.6); 1.3511 (3.6); 1.3327 (8.2); 1.3142 (3.6); −0.0002 (9.6); −0.0083 (0.4) |

-continued

| Example | Structure | NMR data |
| --- | --- | --- |
| I-023 | 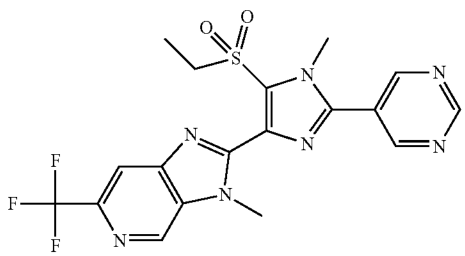 [SMILES: CCS(=O)(=O)c1c(-c2nc3cc(C(F)(F)F)ncc3n2C)nc(-c2cncnc2)n1C] | I-023: $^1$H-NMR(400.0 MHz, $d_6$-DMSO): δ = 9.4033 (5.5); 9.2790 (12.1); 9.2360 (3.8); 8.2618 (4.1); 4.0338 (15.2); 4.0290 (16.0); 3.9942 (0.7); 3.9648 (0.4); 3.8588 (0.9); 3.8404 (3.1); 3.8218 (3.1); 3.8035 (1.0); 3.3225 (17.3); 2.5245 (0.8); 2.5066 (43.2); 2.5022 (56.3); 2.4979 (40.0); 2.0861 (12.2); 1.3593 (3.3); 1.3409 (7.4); 1.3225 (3.2); 0.0079 (0.8); −0.0002 (23.5); −0.0083 (0.8) |
| I-024 | 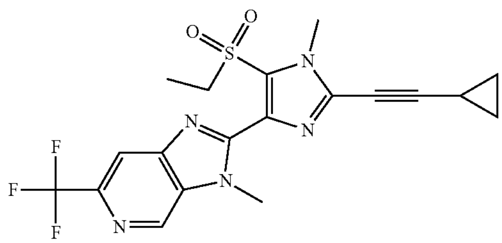 [SMILES: CCS(=O)(=O)c1c(-c2nc3cc(C(F)(F)F)ncc3n2C)nc(C#CC2CC2)n1C] | I-024: $^1$H-NMR(400.0 MHz, $d_6$-DMSO): δ = 9.2120 (4.6); 8.2319 (4.9); 3.9600 (16.0); 3.9415 (15.1); 3.8008 (1.2); 3.7824 (3.8); 3.7639 (3.8); 3.7456 (1.2); 3.3197 (31.4); 2.6706 (0.4); 2.5019 (65.6); 2.3287 (0.4); 2.0859 (1.6); 1.7846 (0.4); 1.7717 (0.7); 1.7637 (0.8); 1.7513 (1.5); 1.7389 (0.9); 1.7309 (0.8); 1.7181 (0.4); 1.2784 (3.9); 1.2600 (8.2); 1.2416 (3.9); 1.0626 (0.8); 1.0514 (2.1); 1.0443 (3.0); 1.0311 (2.3); 1.0240 (2.6); 1.0151 (1.1); 0.9799 (0.3); 0.9445 (1.1); 0.9352 (3.0); 0.9293 (3.0); 0.9237 (3.2); 0.9168 (2.7); 0.9057 (0.8); −0.0002 (37.9) |
| I-025 | 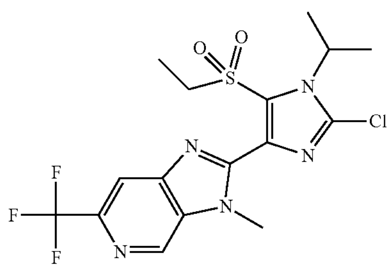 [SMILES: CCS(=O)(=O)c1c(-c2nc3cc(C(F)(F)F)ncc3n2C)nc(Cl)n1C(C)C] | I-025: $^1$H-NMR(400.0 MHz, $d_6$-DMSO): δ = 9.2070 (4.2); 8.2330 (4.4); 7.7295 (2.8); 7.7082 (5.9); 7.6702 (5.9); 7.6488 (2.8); 5.0806 (0.6); 5.0634 (0.9); 5.0463 (0.6); 3.9660 (16.0); 3.8228 (1.0); 3.8044 (3.2); 3.7859 (3.4); 3.7679 (1.0); 3.3202 (18.7); 2.6745 (0.5); 2.6705 (0.7); 2.6662 (0.5); 2.5236 (1.7); 2.5057 (91.3); 2.5014 (120.6); 2.4970 (87.3); 2.3323 (0.5); 2.3282 (0.7); 1.4632 (10.5); 1.4458 (10.4); 1.3443 (3.6); 1.3258 (8.0); 1.3073 (3.5); 0.0078 (0.4); −0.0003 (11.2) |
| I-026 | 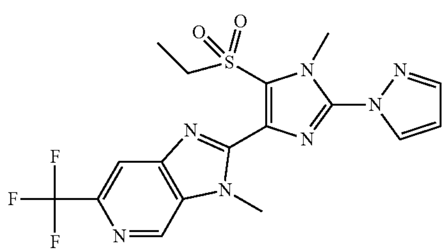 [SMILES: CCS(=O)(=O)c1c(-c2nc3cc(C(F)(F)F)ncc3n2C)nc(-n2cccn2)n1C] | I-026: $^1$H-NMR(400.0 MHz, $d_6$-DMSO): δ = 9.2363 (4.1); 8.4377 (2.8); 8.4312 (2.9); 8.3161 (0.4); 8.2655 (4.3); 8.0148 (3.1); 8.0112 (3.1); 6.6939 (1.9); 6.6888 (2.6); 6.6834 (1.9); 4.2368 (0.5); 4.0875 (0.7); 4.0182 (15.2); 4.0085 (16.0); 3.9949 (1.2); 3.9721 (0.8); 3.9664 (1.0); 3.9127 (0.8); 3.8297 (1.1); 3.8112 (3.4); 3.7929 (3.4); 3.7742 (1.1); 3.7595 (0.4); 3.7406 (0.4); 3.3200 (16.8); 2.6706 (2.3); 2.5428 (0.4); 2.5236 (5.7); 2.5058 (324.6); 2.5016 (416.9); 2.4972 (303.3); 2.4249 (0.5); 2.3934 (0.4); 2.3284 (2.5); 2.1167 (0.5); 2.0857 (10.0); 1.3505 (0.6); 1.3349 (3.8); 1.3163 (8.0); 1.2979 (4.1); 1.2800 (0.8); 1.2653 (0.6); 1.2487 (0.6); 1.2351 (1.2); 1.1916 (0.3); 1.1403 (0.9); 0.1461 (0.5); 0.0078 (3.7); −0.0002 (98.3); −0.1499 (0.5) |
| I-027 | 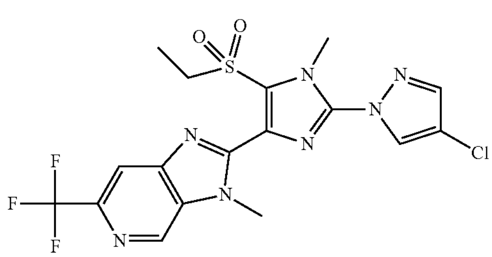 [SMILES: CCS(=O)(=O)c1c(-c2nc3cc(C(F)(F)F)ncc3n2C)nc(-n2cc(Cl)cn2)n1C] | I-027: $^1$H-NMR(400.0 MHz, $d_6$-DMSO): δ = 20.0019 (0.4); 9.2395 (3.8); 8.7231 (5.0); 8.3154 (0.7); 8.2673 (3.9); 8.1817 (0.5); 8.1731 (5.0); 4.0701 (0.4); 4.0120 (15.3); 3.9865 (14.6); 3.9196 (0.5); 3.8513 (1.0); 3.8339 (3.2); 3.8152 (3.2); 3.7968 (1.0); 3.5229 (0.8); 3.3980 (0.5); 3.3770 (0.7); 3.3210 (242.0); 3.2523 (0.6); 3.2310 (0.5); 2.7964 (0.4); 2.6748 (3.9); 2.6703 (5.4); 2.6662 (4.0); 2.6312 (0.5); 2.5949 (0.4); 2.5238 (14.0); 2.5102 (351.9); 2.5060 (728.1); 2.5015 (968.4); 2.4970 (699.6); 2.4928 (339.6); 2.4342 (0.9); 2.3847 (0.6); 2.3328 (4.0); 2.3282 (5.5); 2.3236 (4.0); 2.1174 (0.4); 2.0856 (16.0); 1.7529 (0.5); 1.6998 (0.4); 1.4624 (0.4); 1.4049 (0.5); 1.3513 (0.8); 1.3381 (3.5); 1.3195 (7.8); 1.3004 (3.6); 1.2750 (0.7); 1.2342 (1.9); 1.1921 (0.6); 1.1397 (0.9); 0.1454 (1.1); 0.0079 (9.1); −0.0002 (265.4); −0.0085 (9.6); −0.1498 (1.4) |

| Example | Structure | NMR data |
|---|---|---|
| I-028 | 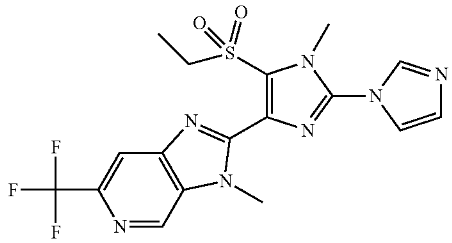 [SMILES: CCS(=O)(=O)c1c(-c2nc3cc(C(F)(F)F)ncc3n2C)nc(-n2ccnc2)n1C] | I-028: ¹H-NMR(400.0 MHz, d₆-DMSO): δ = 9.2314 (3.8); 8.2621 (4.4); 8.2403 (3.1); 8.2380 (3.6); 7.7810 (3.0); 7.7777 (3.7); 7.7744 (2.0); 7.2371 (3.0); 7.2349 (3.2); 5.7629 (1.7); 5.7554 (6.8); 4.0234 (16.0); 3.9943 (0.4); 3.8640 (1.2); 3.8456 (3.5); 3.8270 (3.8); 3.8063 (5.8); 3.7990 (15.0); 3.3238 (15.2); 2.5068 (39.7); 2.5023 (43.4); 2.4978 (28.1); 2.4933 (12.1); 1.3683 (3.9); 1.3554 (3.0); 1.3498 (8.2); 1.3313 (3.5); 0.0074 (7.2); 0.0052 (6.3); −0.0002 (28.0); −0.0085 (1.0) |
| I-029 | 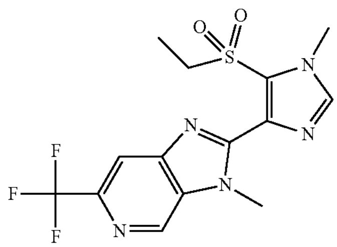 [SMILES: CCS(=O)(=O)c1c(-c2nc3cc(C(F)(F)F)ncc3n2C)ncn1C] | I-029: ¹H-NMR(400.0 MHz, d₆-DMSO): δ = 9.2122 (3.9); 8.3152 (3.0); 8.2308 (3.8); 3.9933 (15.9); 3.9653 (14.1); 3.8275 (1.0); 3.8090 (3.5); 3.7905 (3.5); 3.7721 (1.1); 3.3248 (12.4); 2.5077 (36.0); 2.5034 (47.2); 2.4990 (34.2); 2.0865 (16.0); 1.2847 (3.7); 1.2663 (8.2); 1.2478 (3.7); −0.0002 (7.7) |
| I-030 | 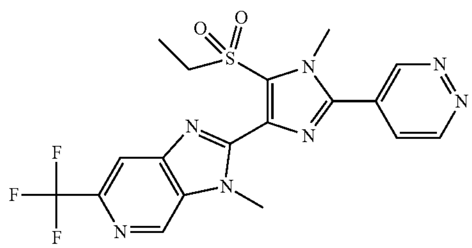 [SMILES: CCS(=O)(=O)c1c(-c2nc3cc(C(F)(F)F)ncc3n2C)nc(-c2ccnnc2)n1C] | I-030: ¹H-NMR(400.0 MHz, d₆-DMSO): δ = 9.6875 (0.7); 9.5184 (0.6); 9.2413 (4.2); 9.2199 (0.6); 9.2109 (1.7); 9.0759 (0.4); 8.3127 (1.4); 8.2655 (4.3); 8.2452 (0.6); 8.2283 (1.8); 8.1870 (1.0); 8.1777 (1.0); 7.3929 (0.5); 5.7573 (8.2); 4.0768 (14.4); 4.0251 (16.0); 3.9938 (6.8); 3.9648 (6.0); 3.9589 (2.7); 3.9226 (2.0); 3.8593 (1.0); 3.8408 (3.4); 3.8223 (3.6); 3.8101 (1.8); 3.8041 (1.3); 3.7917 (1.6); 3.7732 (0.5); 3.7483 (0.5); 3.7299 (0.5); 3.3231 (11.2); 2.6716 (0.5); 2.6669 (0.4); 2.5244 (1.2); 2.5067 (66.2); 2.5024 (88.1); 2.4981 (64.6); 2.3335 (0.4); 2.3293 (0.5); 2.3248 (0.4); 1.3563 (3.6); 1.3380 (8.0); 1.3195 (3.6); 1.2849 (1.7); 1.2717 (1.4); 1.2665 (3.6); 1.2480 (1.6); 0.1459 (0.4); 0.0078 (2.9); −0.0002 (89.1); −0.0083 (3.9); −0.1499 (0.4) |
| I-031 | 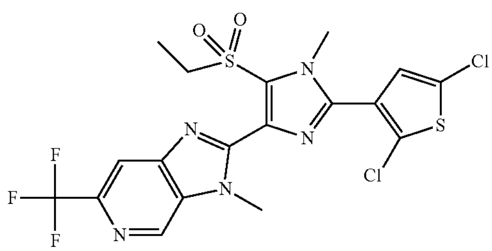 [SMILES: CCS(=O)(=O)c1c(-c2nc3cc(C(F)(F)F)ncc3n2C)nc(-c2cc(Cl)sc2Cl)n1C] | I-031: ¹H-NMR(400.0 MHz, d₆-DMSO): δ = 9.2281 (4.1); 8.2491 (4.3); 7.5783 (7.1); 7.5421 (0.4); 7.5276 (0.5); 7.5098 (0.4); 7.4641 (0.4); 7.4443 (0.4); 5.7573 (12.5); 4.0204 (16.0); 3.8913 (15.4); 3.8747 (3.5); 3.8562 (3.5); 3.8378 (1.1); 3.3223 (4.5); 2.5247 (0.6); 2.5068 (34.4); 2.5024 (45.8); 2.4980 (33.3); 2.0863 (1.3); 2.0752 (2.1); 1.3424 (3.6); 1.3240 (8.1); 1.3055 (3.6); 0.0079 (1.8); −0.0002 (54.3); −0.0084 (2.3) |
| I-032 | 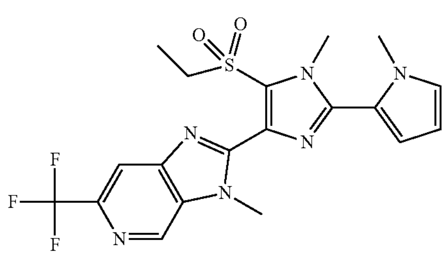 [SMILES: CCS(=O)(=O)c1c(-c2nc3cc(C(F)(F)F)ncc3n2C)nc(-c2cccn2C)n1C] | I-032: ¹H-NMR(400.0 MHz, d₆-DMSO): δ = 9.2254 (3.6); 8.2406 (3.8); 7.0932 (1.5); 7.0883 (2.2); 7.0830 (1.6); 6.6896 (1.7); 6.6855 (1.8); 6.6801 (1.9); 6.6759 (1.8); 6.2483 (1.8); 6.2416 (1.9); 6.2389 (2.0); 6.2321 (1.7); 4.0167 (15.2); 3.9799 (14.2); 3.8292 (1.0); 3.8106 (3.4); 3.8001 (16.0); 3.7924 (3.8); 3.7738 (1.0); 3.3230 (5.2); 2.5245 (0.5); 2.5108 (13.1); 2.5067 (27.3); 2.5023 (36.5); 2.4978 (26.3); 2.4936 (12.6); 1.3348 (3.4); 1.3164 (7.7); 1.2980 (3.4); 0.0079 (1.4); −0.0002 (42.2); −0.0085 (1.5) |
| I-033 | 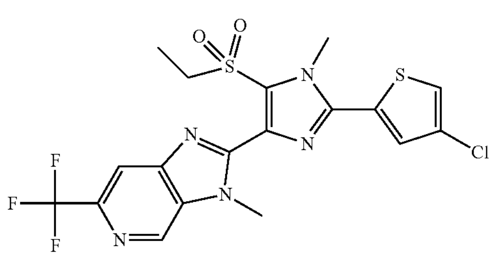 [SMILES: CCS(=O)(=O)c1c(-c2nc3cc(C(F)(F)F)ncc3n2C)nc(-c2cc(Cl)cs2)n1C] | I-033: ¹H-NMR(400.0 MHz, d₆-DMSO): δ = 9.2227 (4.0); 8.6379 (0.3); 8.2503 (4.3); 7.9218 (3.6); 7.9184 (3.7); 7.8107 (4.0); 7.8072 (3.8); 7.6455 (0.6); 7.6271 (1.3); 7.6148 (1.0); 7.5972 (1.3); 7.5743 (1.0); 7.5665 (1.2); 7.5568 (0.9); 7.5484 (1.1); 7.5216 (0.9); 7.5068 (0.8); 7.4854 (0.4); 7.4671 (0.5); 7.4488 (0.5); 7.3670 (0.4); 7.3529 (0.8); 7.3446 (0.8); 7.3352 (0.6); 7.1911 (0.4); 5.7567 (0.6); 4.2455 (0.5); 4.1139 (14.7); 4.0577 (0.6); 3.9927 (0.8); 3.9742 (16.0); 3.9221 (0.9); 3.7733 (1.0); 3.7549 (3.4); 3.7364 (3.4); 3.7180 (1.1); 3.5505 (0.8); 3.4237 (0.4); 3.3924 (0.5); 3.3233 (104.7); 2.6751 (0.7); 2.6707 (0.9); 2.6664 (0.6); 2.5240 (2.0); 2.5061 (108.3); 2.5017 (141.4); 2.4973 (100.9); 2.3286 (0.9); 2.3239 (0.7); 1.3258 (0.4); 1.3126 (3.8); 1.2942 (8.3); 1.2757 (3.6); 1.2658 (0.5); 0.8556 (0.5); 0.1461 (0.7); 0.0079 (5.8); −0.0002 (161.5); −0.0085 (6.3); −0.1497 (0.7) |

| Example | Structure | NMR data |
|---|---|---|
| I-034 | 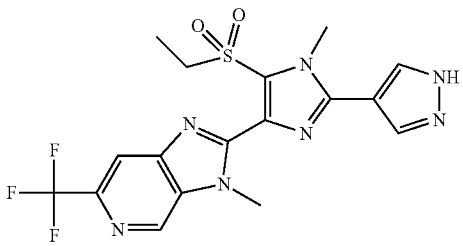 [SMILES: CCS(=O)(=O)c1c(-c2nc3cc(C(F)(F)F)ncc3n2C)nc(-c2cn[nH]c2)n1C] | I-034: ¹H-NMR(400.0 MHz, d₆-DMSO): δ = 13.4858 (0.5); 9.2179 (3.6); 8.2390 (3.8); 4.0307 (12.5); 3.9799 (13.2); 3.7469 (0.8); 3.7284 (2.8); 3.7099 (2.8); 3.6914 (0.9); 3.3235 (8.0); 2.5064 (37.4); 2.5021 (48.4); 2.4978 (35.0); 2.0860 (16.0); 1.3008 (3.1); 1.2824 (6.8); 1.2639 (3.0); 0.0077 (1.8); −0.0002 (48.2); −0.0084 (1.9) |
| I-035 | 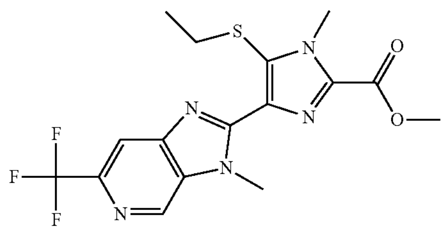 [SMILES: CCSc1c(-c2nc3cc(C(F)(F)F)ncc3n2C)nc(C(=O)OC)n1C] | I-035: ¹H-NMR(400.0 MHz, d₆-DMSO): δ = 9.1664 (3.9); 8.2168 (4.1); 4.1840 (16.0); 4.0749 (14.9); 3.9201 (15.5); 3.7166 (0.3); 3.3536 (0.7); 3.3199 (84.5); 3.2819 (0.4); 3.0673 (1.3); 3.0487 (3.9); 3.0303 (4.0); 3.0118 (1.3); 2.8035 (0.3); 2.6748 (1.5); 2.6704 (2.1); 2.5057 (285.4); 2.5014 (371.4); 2.4971 (270.5); 2.4591 (1.3); 2.4557 (1.3); 2.3282 (2.1); 1.3976 (0.9); 1.3713 (0.6); 1.1151 (4.3); 1.0967 (9.0); 1.0783 (4.1); 0.1463 (1.6); 0.0345 (2.4); 0.0077 (16.0); −0.0003 (351.8); −0.0371 (1.0); −0.1495 (1.7) |
| I-036 | 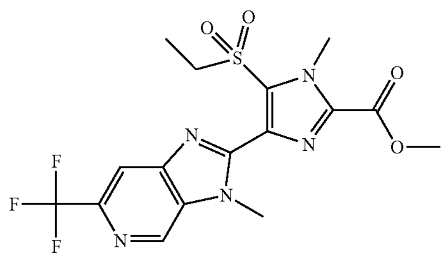 [SMILES: CCS(=O)(=O)c1c(-c2nc3cc(C(F)(F)F)ncc3n2C)nc(C(=O)OC)n1C] | I-036: ¹H-NMR(400.0 MHz, d₆-DMSO): δ = 9.2249 (4.0); 8.2560 (4.2); 4.2425 (13.6); 4.1919 (0.7); 4.1422 (0.4); 3.9939 (0.7); 3.9394 (15.9); 3.9336 (16.0); 3.8943 (0.5); 3.8390 (0.3); 3.7836 (1.0); 3.7656 (3.2); 3.7470 (3.3); 3.7270 (1.4); 3.3194 (47.5); 2.6702 (1.4); 2.5012 (244.8); 2.4971 (186.1); 2.3273 (1.4); 2.0857 (1.7); 1.3976 (2.7); 1.3041 (0.5); 1.2883 (3.4); 1.2702 (7.3); 1.2516 (3.4); 0.1459 (0.5); −0.0001 (118.8); −0.1504 (0.5) |
| I-037 | 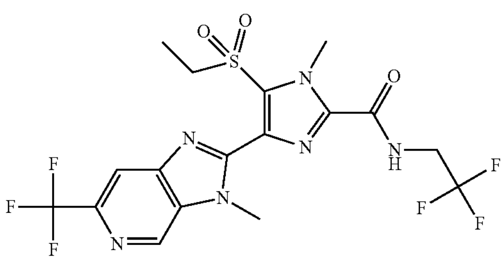 [SMILES: CCS(=O)(=O)c1c(-c2nc3cc(C(F)(F)F)ncc3n2C)nc(C(=O)NCC(F)(F)F)n1C] | I-037: ¹H-NMR(400.0 MHz, d₆-DMSO): δ = 9.5733 (0.5); 9.5569 (1.1); 9.5409 (0.6); 9.2497 (4.0); 8.2645 (4.2); 5.7564 (10.5); 4.2847 (15.0); 4.1156 (0.3); 4.0934 (1.1); 4.0765 (1.2); 4.0699 (1.2); 4.0533 (1.1); 4.0298 (0.4); 3.9776 (16.0); 3.7524 (1.0); 3.7339 (3.4); 3.7154 (3.4); 3.6971 (1.0); 3.3254 (4.2); 2.5249 (0.4); 2.5111 (10.7); 2.5068 (22.5); 2.5024 (30.2); 2.4979 (21.7); 2.4936 (10.4); 1.2805 (3.7); 1.2621 (8.3); 1.2437 (3.7); 0.0076 (1.2); −0.0002 (35.2); −0.0084 (1.3) |
| I-038 | 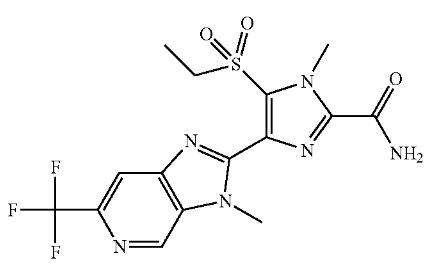 [SMILES: CCS(=O)(=O)c1c(-c2nc3cc(C(F)(F)F)ncc3n2C)nc(C(N)=O)n1C] | I-038: ¹H-NMR(400.0 MHz, d₆-DMSO): δ = 9.2407 (4.1); 8.3256 (1.6); 8.2524 (4.5); 8.0175 (1.6); 4.2789 (14.8); 4.1913 (0.3); 4.1155 (0.4); 3.9779 (16.0); 3.9413 (0.6); 3.7748 (1.1); 3.7564 (3.4); 3.7380 (3.5); 3.7194 (1.1); 3.3211 (261.3); 2.6748 (1.8); 2.6707 (2.5); 2.6662 (1.8); 2.5236 (5.8); 2.5059 (331.0); 2.5016 (435.6); 2.4972 (312.5); 2.4367 (0.4); 2.3323 (1.8); 2.3280 (2.4); 1.2831 (3.8); 1.2646 (8.3); 1.2463 (3.8); 0.1464 (1.0); 0.0078 (7.8); −0.0001 (217.9); −0.0078 (8.1); −0.1494 (1.0) |
| I-039 | 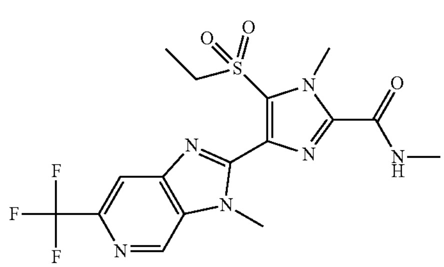 [SMILES: CCS(=O)(=O)c1c(-c2nc3cc(C(F)(F)F)ncc3n2C)nc(C(=O)NC)n1C] | I-039: ¹H-NMR(400.0 MHz, d₆-DMSO): δ = 9.2441 (4.2); 8.9444 (1.0); 8.9323 (1.0); 8.2560 (4.4); 5.7571 (7.8); 4.2855 (15.1); 4.2116 (0.4); 3.9729 (16.0); 3.7629 (1.0); 3.7445 (3.5); 3.7260 (3.6); 3.7076 (1.1); 3.6176 (0.5); 3.6013 (1.1); 3.5851 (0.5); 3.5093 (0.4); 3.3222 (7.5); 2.8314 (0.4); 2.8227 (0.4); 2.8063 (7.2); 2.7944 (7.1); 2.5936 (0.4); 2.5817 (0.3); 2.5509 (0.5); 2.5393 (0.6); 2.5064 (37.6); 2.5021 (49.7); 2.4978 (36.4); 2.3288 (0.3); 2.1838 (0.4); 2.1488 (0.4); 1.7760 (0.5); 1.7679 (0.5); 1.7597 (1.3); 1.7514 (0.5); 1.7435 (0.4); 1.3560 (2.2); 1.2788 (3.8); 1.2604 (8.4); 1.2419 (4.0); 0.0078 (1.1); −0.0002 (28.4); −0.0080 (1.2) |

-continued

| Example | Structure | NMR data |
|---|---|---|
| I-040 | 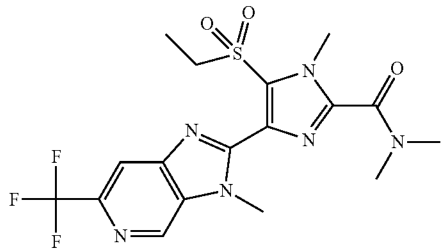 [SMILES: CCS(=O)(=O)c1c(-c2nc3cc(C(F)(F)F)ncc3n2C)nc(C(=O)N(C)C)n1C] | I-040: ¹H-NMR(400.0 MHz, d₆-DMSO): δ = 9.2261 (4.2); 8.2465 (4.4); 5.7569 (10.2); 4.1935 (0.3); 4.0142 (0.4); 3.9843 (16.0); 3.9720 (15.3); 3.8568 (1.2); 3.8492 (0.9); 3.8385 (3.5); 3.8200 (3.5); 3.8018 (1.2); 3.7273 (0.4); 3.6015 (0.8); 3.5850 (0.3); 3.3209 (6.8); 3.1305 (15.8); 3.0751 (14.6); 3.0327 (0.6); 3.0178 (0.4); 2.6709 (0.5); 2.5365 (1.9); 2.5061 (63.2); 2.5019 (78.1); 2.4977 (59.4); 2.3289 (0.4); 1.7687 (0.4); 1.7600 (0.8); 1.3557 (1.4); 1.3112 (3.8); 1.2928 (8.0); 1.2743 (3.8); 1.2367 (0.5); −0.0002 (45.9) |
| I-041 | 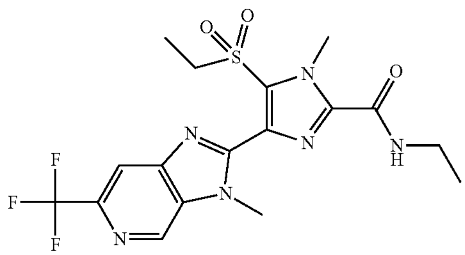 [SMILES: CCNC(=O)c1nc(-c2nc3cc(C(F)(F)F)ncc3n2C)c(S(=O)(=O)CC)n1C] | I-041: ¹H-NMR(400.0 MHz, d₆-DMSO): δ = 9.2428 (4.4); 9.0191 (0.7); 9.0050 (1.4); 8.9904 (0.7); 8.2570 (4.7); 5.7576 (5.8); 4.2823 (15.2); 4.2189 (0.4); 4.1661 (0.3); 4.0776 (0.3); 3.9645 (16.0); 3.7411 (1.1); 3.7225 (3.6); 3.7040 (3.6); 3.6857 (1.2); 3.6175 (0.7); 3.6013 (1.6); 3.5859 (0.7); 3.3331 (0.8); 3.3212 (9.0); 3.2990 (2.7); 3.2822 (2.1); 3.2648 (0.7); 2.6711 (0.4); 2.5062 (48.1); 2.5021 (62.8); 2.4980 (46.6); 2.3288 (0.4); 1.7761 (0.7); 1.7682 (0.8); 1.7600 (1.8); 1.7517 (0.8); 1.7441 (0.6); 1.3559 (0.6); 1.2718 (3.9); 1.2534 (8.3); 1.2350 (3.9); 1.1410 (4.1); 1.1231 (8.7); 1.1052 (4.1); 0.0075 (1.3); −0.0001 (35.0) |
| I-042 | 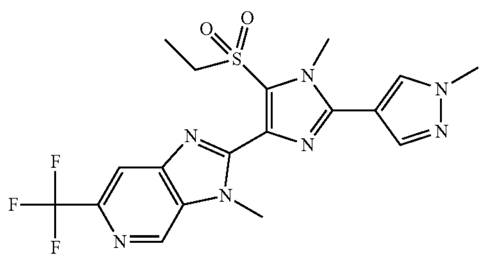 [SMILES: CCS(=O)(=O)c1c(-c2nc3cc(C(F)(F)F)ncc3n2C)nc(-c2cnn(C)c2)n1C] | I-042: ¹H-NMR(400.0 MHz, d₆-DMSO): δ = 9.2163 (3.9); 8.4144 (4.4); 8.0115 (4.9); 5.7565 (5.5); 4.0199 (14.6); 3.9770 (16.0); 3.9556 (15.4); 3.7510 (0.9); 3.7326 (3.3); 3.7141 (3.3); 3.6957 (1.0); 3.3228 (38.5); 2.6709 (0.4); 2.5242 (1.0); 2.5107 (27.7); 2.5064 (57.6); 2.5019 (76.7); 2.4974 (54.2); 2.4931 (25.3); 2.3286 (0.4); 1.3004 (3.7); 1.2820 (8.2); 1.2635 (3.5); 0.1461 (0.3); 0.0078 (2.6); −0.0002 (75.8); −0.0086 (2.7); −0.1497 (0.3) |
| I-043 | 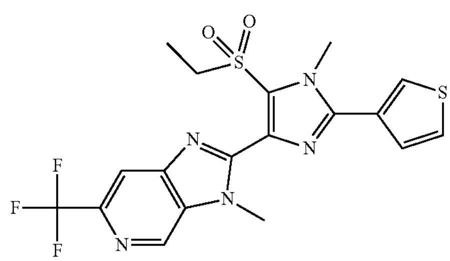 [SMILES: CCS(=O)(=O)c1c(-c2nc3cc(C(F)(F)F)ncc3n2C)nc(-c2ccsc2)n1C] | I-043: ¹H-NMR(400.0 MHz, d₆-DMSO): δ = 9.2235 (4.2); 8.2469 (4.4); 8.2292 (2.1); 8.2261 (2.3); 8.2221 (2.4); 8.2190 (2.2); 7.8163 (1.8); 7.8090 (1.8); 7.8037 (2.1); 7.7964 (2.0); 7.6257 (2.5); 7.6228 (2.4); 7.6132 (2.2); 7.6101 (2.1); 5.7569 (6.0); 4.0469 (15.1); 3.9943 (16.0); 3.9811 (0.5); 3.7964 (1.0); 3.7779 (3.4); 3.7594 (3.5); 3.7411 (1.1); 3.3241 (17.8); 2.5245 (0.6); 2.5067 (35.8); 2.5024 (46.5); 2.4980 (33.6); 1.3232 (3.7); 1.3047 (8.2); 1.2863 (3.6); 0.0080 (1.5); 0.0000 (41.4); −0.0083 (1.7) |
| I-044 | 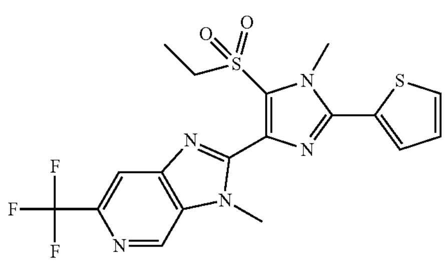 [SMILES: CCS(=O)(=O)c1c(-c2nc3cc(C(F)(F)F)ncc3n2C)nc(-c2cccs2)n1C] | I-044: ¹H-NMR(400.0 MHz, d₆-DMSO): δ = 9.2224 (4.1); 8.2491 (4.3); 7.8941 (2.1); 7.8830 (2.2); 7.7993 (2.0); 7.7975 (2.0); 7.7900 (2.2); 7.3258 (1.8); 7.3163 (1.9); 7.3133 (1.9); 7.3038 (1.7); 5.7568 (14.3); 4.1123 (14.8); 3.9812 (16.0); 3.7713 (1.0); 3.7529 (3.4); 3.7344 (3.5); 3.7160 (1.0); 3.3249 (7.3); 2.5248 (0.6); 2.5071 (28.6); 2.5027 (38.1); 2.4983 (27.5); 1.3148 (3.7); 1.2964 (8.2); 1.2779 (3.6); 0.0077 (1.5); −0.0002 (39.0); −0.0084 (1.5) |
| I-045 | 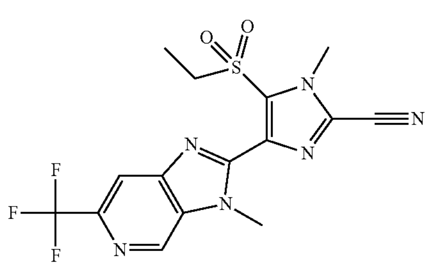 [SMILES: CCS(=O)(=O)c1c(-c2nc3cc(C(F)(F)F)ncc3n2C)nc(C#N)n1C] | I-045: ¹H-NMR(400.0 MHz, d₆-DMSO): δ = 10.1998 (0.5); 9.2474 (3.8); 8.2746 (4.0); 5.7566 (1.2); 4.3215 (0.6); 4.2387 (0.6); 4.1254 (0.6); 4.0878 (14.5); 3.9946 (16.0); 3.9634 (0.4); 3.9277 (0.5); 3.8915 (1.0); 3.8728 (3.4); 3.8543 (3.4); 3.8358 (1.0); 3.3196 (32.3); 2.6750 (0.6); 2.6705 (0.8); 2.6659 (0.6); 2.5238 (1.8); 2.5101 (49.3); 2.5059 (104.6); 2.5015 (141.8); 2.4970 (102.3); 2.4927 (49.2); 2.3327 (0.6); 2.3283 (0.8); 2.3238 (0.6); 1.3511 (1.0); 1.3425 (0.4); 1.3228 (3.9); 1.3043 (8.0); 1.2858 (3.6); 1.2652 (0.4); 1.2601 (0.5); 1.2332 (1.4); 0.1457 (0.5); 0.0079 (3.3); −0.0002 (111.7); −0.0084 (4.4); −0.1497 (0.5) |

-continued

| Example | Structure | NMR data |
|---|---|---|
| I-046 | 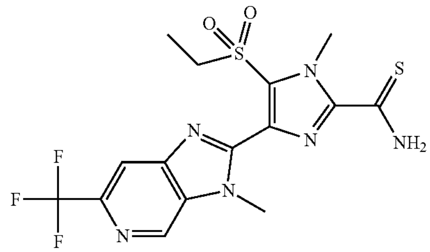 [SMILES: CCS(=O)(=O)c1c(-c2nc3cc(C(F)(F)F)ncc3n2C)nc(C(N)=S)n1C] | I-046: ¹H-NMR(400.0 MHz, d₆-DMSO): δ = 10.6016 (0.9); 10.1030 (0.9); 9.2297 (4.0); 8.3154 (0.4); 8.2500 (4.3); 4.1417 (15.0); 3.9941 (16.0); 3.8340 (1.0); 3.8154 (3.4); 3.7969 (3.5); 3.7780 (1.1); 3.3630 (0.5); 3.3229 (172.6); 2.6750 (2.3); 2.6705 (3.0); 2.6663 (2.2); 2.5235 (7.5); 2.5101 (197.8); 2.5058 (410.0); 2.5014 (548.3); 2.4970 (393.8); 2.4928 (189.2); 2.3326 (2.3); 2.3282 (3.0); 2.3237 (2.2); 1.3047 (3.6); 1.2864 (8.1); 1.2679 (3.5); 0.1464 (1.0); 0.0078 (8.2); −0.0002 (231.4); −0.0083 (9.0); −0.1497 (1.1) |
| I-047 | 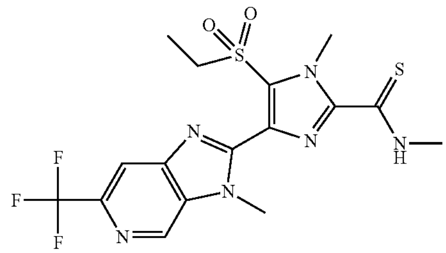 [SMILES: CCS(=O)(=O)c1c(-c2nc3cc(C(F)(F)F)ncc3n2C)nc(C(=S)NC)n1C] | I-047: ¹H-NMR(400.0 MHz, d₆-DMSO): δ = 11.0260 (0.9); 11.0143 (0.8); 9.2316 (4.0); 8.3158 (0.5); 8.2542 (4.4); 4.1062 (14.9); 3.9927 (16.0); 3.8284 (1.0); 3.8099 (3.6); 3.7911 (4.0); 3.7733 (2.0); 3.4128 (0.3); 3.3308 (102.0); 3.2859 (0.6); 3.1744 (7.0); 3.1624 (6.9); 2.6749 (2.7); 2.6704 (3.6); 2.6656 (2.8); 2.5407 (1.4); 2.5363 (1.2); 2.5235 (8.9); 2.5057 (490.1); 2.5013 (643.6); 2.4969 (460.1); 2.4525 (1.0); 2.4437 (0.8); 2.3285 (3.6); 2.3235 (2.7); 1.3032 (3.5); 1.2847 (8.1); 1.2662 (3.6); 0.1459 (1.3); 0.0078 (9.9); −0.0003 (266.2); −0.0081 (11.0); −0.0379 (0.4); −0.1494 (1.3) |
| I-048 | 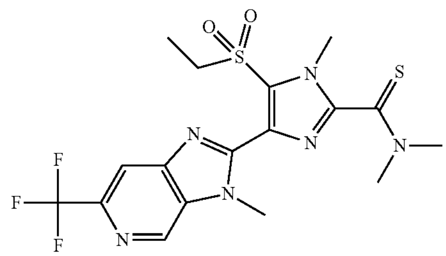 [SMILES: CCS(=O)(=O)c1c(-c2nc3cc(C(F)(F)F)ncc3n2C)nc(C(=S)N(C)C)n1C] | I-048: ¹H-NMR(400.0 MHz, d₆-DMSO): δ = 9.2235 (4.2); 8.2438 (4.5); 8.1331 (0.3); 5.7553 (6.6); 4.1921 (0.4); 3.9849 (16.0); 3.8890 (15.0); 3.8681 (1.1); 3.8496 (3.4); 3.8312 (3.4); 3.8129 (1.0); 3.7263 (0.4); 3.5463 (14.5); 3.3213 (30.4); 3.2712 (15.2); 2.6704 (0.5); 2.5232 (1.1); 2.5055 (67.5); 2.5012 (90.0); 2.4969 (65.2); 2.3279 (0.5); 2.3242 (0.4); 1.3104 (3.7); 1.2920 (8.1); 1.2736 (3.6); 0.0070 (2.4); −0.0007 (64.8); −0.0085 (2.8) |
| I-049 | 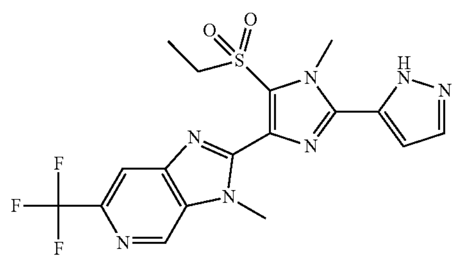 [SMILES: CCS(=O)(=O)c1c(-c2nc3cc(C(F)(F)F)ncc3n2C)nc(-c2ccn[nH]2)n1C] | I-049: ¹H-NMR(400.0 MHz, d₆-DMSO): δ = 9.2258 (3.8); 8.2475 (4.1); 8.1372 (1.0); 7.9785 (3.2); 7.9726 (3.3); 6.8941 (3.7); 6.8883 (3.7); 4.2964 (14.0); 3.9797 (16.0); 3.7548 (1.0); 3.7364 (3.3); 3.7179 (3.4); 3.6994 (1.0); 2.5426 (2.2); 2.5257 (0.6); 2.5208 (0.9); 2.5121 (16.1); 2.5077 (34.6); 2.5033 (47.1); 2.4987 (33.8); 2.4943 (16.0); 2.0865 (7.7); 1.2958 (3.6); 1.2775 (8.1); 1.2590 (3.5); 0.0080 (0.5); −0.0002 (17.2); −0.0084 (0.6) |
| I-050 | 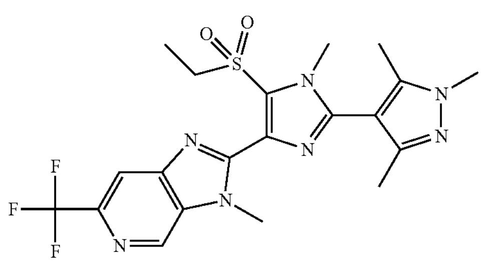 [SMILES: CCS(=O)(=O)c1c(-c2nc3cc(C(F)(F)F)ncc3n2C)nc(-c2c(C)nn(C)c2C)n1C] | I-050: ¹H-NMR(400.0 MHz, d₆-DMSO): δ = 9.2107 (4.1); 8.2314 (4.3); 7.6281 (0.4); 7.5991 (0.3); 5.7574 (8.2); 4.0144 (16.0); 3.8650 (1.0); 3.8466 (3.3); 3.8281 (3.4); 3.8097 (1.0); 3.7642 (15.4); 3.7571 (15.0); 3.3251 (16.3); 2.5421 (0.5); 2.5248 (0.4); 2.5113 (11.9); 2.5072 (24.8); 2.5027 (33.2); 2.4983 (24.0); 2.4941 (11.5); 2.2586 (15.4); 2.1401 (15.7); 1.3247 (3.6); 1.3063 (8.1); 1.2878 (3.6); −0.0002 (8.6); −0.0085 (0.3) |
| I-051 | 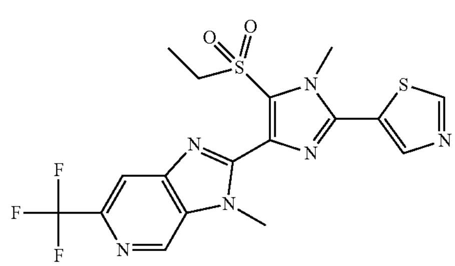 [SMILES: CCS(=O)(=O)c1c(-c2nc3cc(C(F)(F)F)ncc3n2C)nc(-c2cncs2)n1C] | I-051: ¹H-NMR(601.6 MHz, d₆-DMSO): δ = 9.3583 (4.9); 9.2205 (3.4); 8.5626 (4.9); 8.2440 (3.6); 5.7506 (2.1); 4.1175 (15.2); 3.9780 (16.0); 3.9571 (1.3); 3.9232 (1.2); 3.7701 (0.9); 3.7579 (3.3); 3.7456 (3.3); 3.7334 (1.1); 3.3050 (49.6); 2.6125 (0.5); 2.5216 (0.8); 2.5186 (1.0); 2.5155 (0.9); 2.5067 (26.9); 2.5036 (59.9); 2.5006 (85.5); 2.4976 (61.4); 2.4945 (28.7); 2.3849 (0.5); 1.3153 (3.5); 1.3030 (7.9); 1.2907 (3.5); 1.2722 (0.7); 1.2598 (0.4); 0.0053 (2.0); −0.0002 (76.1); −0.0057 (2.5) |

-continued

| Example | Structure | NMR data |
|---|---|---|
| I-052 | 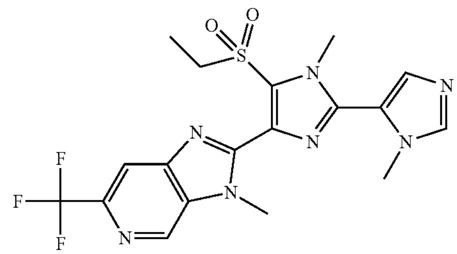 [SMILES: CCS(=O)(=O)c1c(-c2nc3cc(C(F)(F)F)ncc3n2C)nc(-c2cncn2C)n1C] | I-052: ¹H-NMR(400.0 MHz, d₆-DMSO):<br>δ = 9.2296 (3.8); 8.2449 (4.0); 7.9470 (2.5); 7.5840 (2.2); 4.0156 (16.0); 4.0055 (14.7); 3.8302 (15.7); 3.8181 (3.6); 3.7996 (3.4); 3.7812 (1.1); 3.3202 (78.7); 2.6747 (0.5); 2.6705 (0.7); 2.6664 (0.5); 2.5237 (2.0); 2.5102 (42.5); 2.5059 (86.1); 2.5014 (114.9); 2.4970 (86.4); 2.4928 (44.8); 2.3328 (0.5); 2.3282 (0.7); 2.3239 (0.6); 2.0857 (0.4); 1.3390 (3.6); 1.3206 (8.0); 1.3021 (3.5); 1.2338 (0.3); 0.1459 (0.4); 0.0079 (3.0); −0.0002 (90.3); −0.0083 (4.3); −0.1498 (0.4) |
| I-053 | 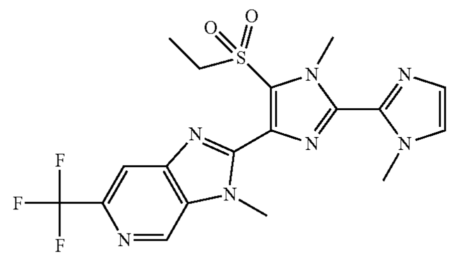 [SMILES: CCS(=O)(=O)c1c(-c2nc3cc(C(F)(F)F)ncc3n2C)nc(-c2nccn2C)n1C] | I-053: ¹H-NMR(400.0 MHz, d₆-DMSO):<br>δ = 9.2294 (3.6); 8.2442 (3.9); 7.9468 (2.3); 7.5837 (2.1); 4.0290 (1.1); 4.0154 (16.0); 4.0052 (14.6); 3.9835 (0.6); 3.8299 (15.4); 3.8178 (3.5); 3.7993 (3.4); 3.7809 (1.0); 3.4329 (0.3); 3.4189 (0.4); 3.3212 (15.2); 3.1685 (0.4); 2.6748 (0.8); 2.6703 (1.1); 2.6657 (0.8); 2.6613 (0.4); 2.5401 (0.5); 2.5236 (3.0); 2.5101 (61.2); 2.5057 (123.4); 2.5012 (163.4); 2.4967 (119.9); 2.4922 (59.1); 2.3370 (0.4); 2.3325 (0.7); 2.3280 (1.0); 2.3234 (0.8); 2.3064 (0.5); 2.0857 (1.1); 1.3481 (0.4); 1.3388 (3.5); 1.3204 (8.0); 1.3019 (3.4); 1.2340 (0.3); 1.1400 (0.4); 0.1458 (0.7); 0.0079 (5.6); −0.0002 (156.9); −0.0085 (6.1); −0.1499 (0.7) |
| I-054 | 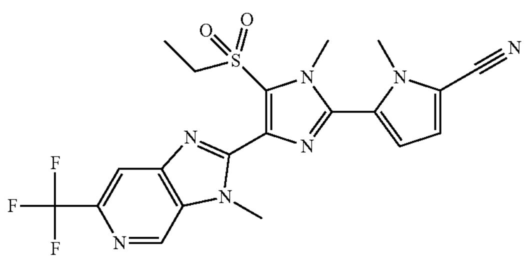 [SMILES: CCS(=O)(=O)c1c(-c2nc3cc(C(F)(F)F)ncc3n2C)nc(-c2ccc(C#N)n2C)n1C] | I-054: ¹H-NMR(400.0 MHz, d₆-DMSO):<br>δ = 9.2351 (3.6); 8.2493 (3.8); 7.2011 (3.1); 7.1906 (3.3); 7.1038 (0.8); 7.0936 (0.8); 6.8742 (3.3); 6.8636 (3.2); 6.5038 (0.8); 6.4935 (0.8); 5.7551 (7.3); 4.0159 (14.7); 3.9954 (0.4); 3.9713 (13.5); 3.8954 (0.7); 3.8828 (16.0); 3.8481 (1.0); 3.8297 (3.2); 3.8111 (3.3); 3.7927 (1.0); 3.6361 (4.7); 3.3196 (130.2); 3.2395 (0.3); 2.6750 (0.7); 2.6705 (1.0); 2.6659 (0.8); 2.5236 (2.9); 2.5102 (63.3); 2.5059 (125.5); 2.5014 (162.8); 2.4969 (117.8); 2.4926 (57.7); 2.3327 (0.8); 2.3281 (1.0); 2.3236 (0.8); 1.3450 (3.4); 1.3265 (7.6); 1.3080 (3.3); 1.2926 (0.6); 1.2749 (0.3); 0.1460 (0.6); 0.0078 (5.4); −0.0002 (142.3); −0.0085 (5.8); −0.1497 (0.6) |
| I-055 | 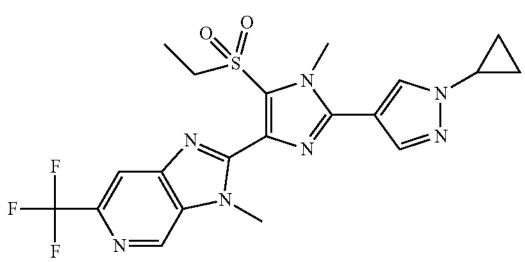 [SMILES: CCS(=O)(=O)c1c(-c2nc3cc(C(F)(F)F)ncc3n2C)nc(-c2cnn(C3CC3)c2)n1C] | I-055: ¹H-NMR(400.0 MHz, d₆-DMSO):<br>δ = 9.2167 (4.3); 8.4783 (5.2); 8.2349 (4.7); 8.0020 (5.1); 5.7551 (11.1); 4.0229 (15.0); 3.9744 (16.0); 3.8973 (0.4); 3.8877 (0.8); 3.8786 (1.1); 3.8695 (1.6); 3.8600 (1.2); 3.8510 (0.8); 3.8414 (0.5); 3.7484 (1.1); 3.7299 (3.6); 3.7115 (3.6); 3.6931 (1.1); 3.3221 (22.9); 2.5069 (21.6); 2.5027 (27.1); 2.4985 (19.5); 1.2986 (3.9); 1.2802 (8.5); 1.2618 (3.8); 1.1703 (0.6); 1.1565 (1.8); 1.1490 (3.0); 1.1407 (2.9); 1.1301 (1.0); 1.1005 (0.5); 1.0618 (1.0); 1.0496 (2.1); 1.0436 (2.5); 1.0311 (2.5); 1.0123 (0.6); 0.0078 (1.5); −0.0002 (28.4) |
| I-056 | 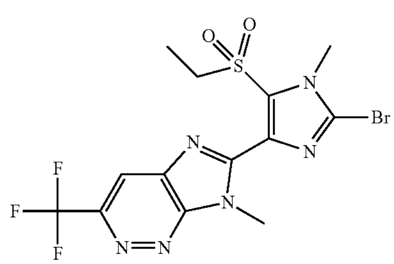 [SMILES: CCS(=O)(=O)c1c(-c2nc3cc(C(F)(F)F)nnc3n2C)nc(Br)n1C] | I-056: ¹H-NMR(400.0 MHz, d₆-DMSO):<br>δ = 8.7026 (5.5); 4.0569 (16.0); 3.9410 (14.5); 3.7958 (1.0); 3.7773 (3.4); 3.7588 (3.5); 3.7404 (1.0); 3.3226 (25.5); 2.5258 (0.4); 2.5123 (9.1); 2.5080 (18.3); 2.5035 (24.1); 2.4989 (17.4); 2.4945 (8.5); 1.3059 (3.6); 1.2970 (0.4); 1.2875 (8.1); 1.2690 (3.6); 0.0078 (0.8); −0.0002 (22.4); −0.0084 (0.9) |
| I-057 | 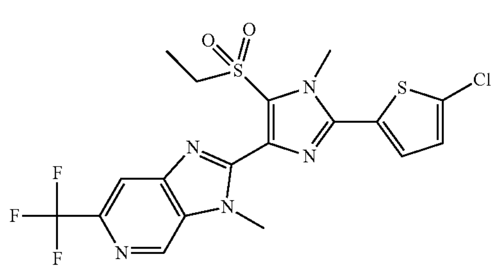 [SMILES: CCS(=O)(=O)c1c(-c2nc3cc(C(F)(F)F)ncc3n2C)nc(-c2ccc(Cl)s2)n1C] | I-057: ¹H-NMR(400.0 MHz, d₆-DMSO):<br>δ = 9.2205 (4.1); 8.2441 (4.5); 7.6744 (3.2); 7.6642 (3.4); 7.3604 (3.4); 7.3502 (3.2); 5.7563 (7.8); 4.1016 (14.6); 4.0341 (0.8); 3.9957 (1.0); 3.9748 (16.0); 3.7732 (1.0); 3.7549 (3.5); 3.7364 (3.5); 3.7179 (1.1); 3.3239 (17.9); 2.5250 (0.4); 2.5115 (9.2); 2.5074 (18.4); 2.5030 (24.3); 2.4985 (17.9); 2.4942 (9.0); 1.3134 (3.8); 1.3061 (1.0); 1.2951 (8.3); 1.2766 (3.7); 0.0077 (1.0); −0.0002 (26.4); −0.0084 (1.2) |

-continued

| Example | Structure | NMR data |
|---|---|---|
| I-058 | 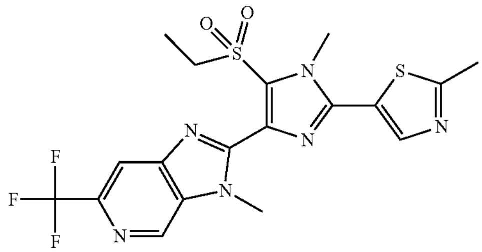 [SMILES: CCS(=O)(=O)c1c(-c2nc3cc(C(F)(F)F)ncc3n2C)nc(-c2cnc(C)s2)n1C] | I-058: $^1$H-NMR(400.0 MHz, d$_6$-DMSO): δ = 9.2192 (4.1); 8.2804 (6.2); 8.2463 (4.4); 5.7561 (0.5); 4.0957 (15.0); 3.9736 (16.0); 3.7800 (1.0); 3.7615 (3.5); 3.7431 (3.5); 3.7247 (1.1); 3.3221 (24.2); 2.7517 (15.7); 2.5246 (0.6); 2.5068 (28.1); 2.5024 (36.2); 2.4979 (26.1); 1.3170 (3.8); 1.2986 (8.4); 1.2801 (3.7); 1.2342 (1.4); 0.0079 (1.1); −0.0002 (32.8); −0.0083 (1.3) |
| I-059 | 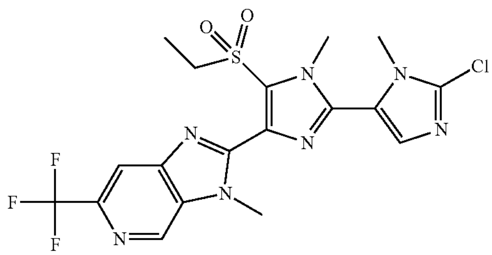 [SMILES: CCS(=O)(=O)c1c(-c2nc3cc(C(F)(F)F)ncc3n2C)nc(-c2cnc(Cl)n2C)n1C] | I-059: $^1$H-NMR(400.0 MHz, d$_6$-DMSO): δ = 9.2335 (3.6); 8.2483 (3.8); 7.5894 (5.8); 5.7559 (4.9); 4.0131 (14.5); 3.9948 (13.4); 3.8403 (0.9); 3.8218 (3.1); 3.8033 (3.2); 3.7848 (1.0); 3.7619 (16.0); 3.3221 (44.8); 2.5064 (38.8); 2.5020 (51.2); 2.4975 (37.6); 1.3404 (3.3); 1.3220 (7.4); 1.3035 (3.2); 0.0079 (2.1); −0.0002 (58.0); −0.0084 (2.8) |
| I-060 | 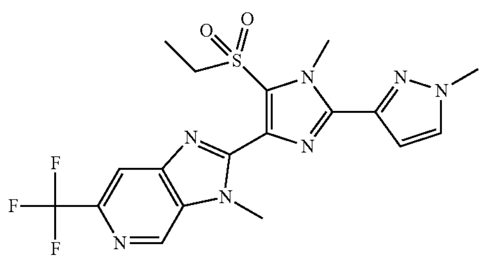 [SMILES: CCS(=O)(=O)c1c(-c2nc3cc(C(F)(F)F)ncc3n2C)nc(-c2ccn(C)n2)n1C] | I-060: $^1$H-NMR(400.0 MHz, d$_6$-DMSO): δ = 9.2198 (3.2); 9.0638 (0.4); 8.2410 (3.4); 8.1023 (0.4); 7.9300 (2.5); 7.9244 (2.5); 6.8591 (2.8); 6.8535 (2.8); 6.7669 (0.4); 6.7612 (0.3); 5.7557 (16.0); 4.3379 (1.7); 4.2776 (12.0); 4.1363 (1.9); 3.9964 (12.7); 3.9701 (13.0); 3.9458 (1.8); 3.8510 (1.6); 3.7494 (0.8); 3.7309 (2.7); 3.7125 (2.8); 3.6941 (0.8); 3.3196 (55.4); 2.6746 (0.4); 2.6703 (0.5); 2.6660 (0.4); 2.5234 (1.3); 2.5100 (30.5); 2.5058 (61.3); 2.5013 (80.5); 2.4968 (58.2); 2.4924 (28.5); 2.3327 (0.4); 2.3280 (0.5); 2.3235 (0.4); 1.2890 (3.0); 1.2706 (6.7), 1.2521 (2.9); 1.2348 (0.7); 0.1456 (0.4); 0.0075 (2.8); −0.0002 (81.9); −0.0085 (3.3); −0.1501 (0.4) |
| I-061 | 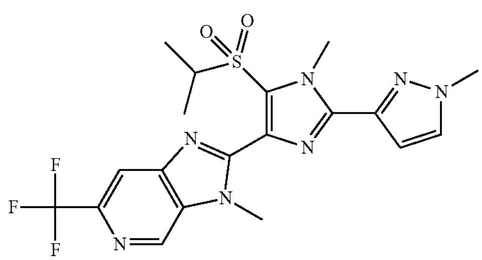 [SMILES: CC(C)S(=O)(=O)c1c(-c2nc3cc(C(F)(F)F)ncc3n2C)nc(-c2ccn(C)n2)n1C] | I-061: $^1$H-NMR(400.0 MHz, d$_6$-DMSO): δ = 9.2196 (4.1); 8.2412 (4.4); 7.9304 (3.0); 7.9247 (3.1); 7.6460 (0.4); 7.6279 (0.8); 7.6160 (0.6); 7.5988 (0.6); 7.5746 (0.4); 7.5669 (0.5); 7.5576 (0.4); 7.5505 (0.5); 6.8646 (3.4); 6.8589 (3.4); 5.7562 (5.6); 4.2717 (14.8); 4.0247 (0.4); 4.0181 (0.3); 4.0077 (1.4); 3.9969 (16.0); 3.9736 (1.4); 3.9468 (15.9); 3.8000 (0.7); 3.3228 (34.1); 2.5249 (0.7); 2.5070 (32.4); 2.5026 (42.0); 2.4982 (30.4); 1.3050 (2.1); 1.2939 (13.8); 1.2768 (13.5); 0.0076 (1.6); −0.0002 (39.5); −0.0085 (1.5) |
| I-062 | 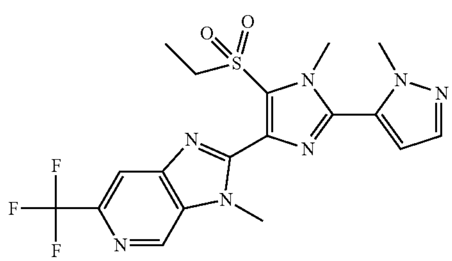 [SMILES: CCS(=O)(=O)c1c(-c2nc3cc(C(F)(F)F)ncc3n2C)nc(-c2ccnn2C)n1C] | I-062: $^1$H-NMR(400.0 MHz, d$_6$-DMSO): δ = 9.2364 (3.6); 8.2523 (3.9); 7.6837 (3.1); 7.6788 (3.2); 6.9157 (3.1); 6.9106 (3.2); 5.7558 (9.5); 4.0287 (14.3); 4.0168 (16.0); 3.9741 (13.1); 3.9587 (0.6); 3.9229 (0.4); 3.8583 (0.9); 3.8398 (3.1); 3.8214 (3.1); 3.8029 (1.0); 3.3208 (25.7); 2.6709 (0.3); 2.5241 (0.9); 2.5063 (43.7); 2.5020 (57.1); 2.4976 (41.8); 2.3289 (0.3); 1.3502 (3.3); 1.3318 (7.2); 1.3133 (3.2); 0.0077 (2.4); −0.0002 (59.3); −0.0082 (2.6) |
| I-063 | 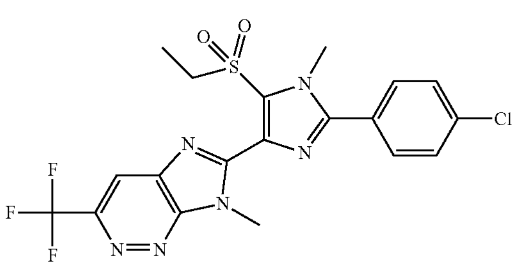 [SMILES: CCS(=O)(=O)c1c(-c2nc3cc(C(F)(F)F)nnc3n2C)nc(-c2ccc(Cl)cc2)n1C] | I-063: $^1$H-NMR(400.0 MHz, d$_6$-DMSO): δ = 8.7040 (5.7); 7.8826 (4.4); 7.8616 (5.1); 7.7027 (5.4); 7.6817 (4.0); 4.1104 (16.0); 4.0561 (0.7); 4.0384 (2.0); 4.0206 (2.1); 4.0026 (1.3); 3.9801 (14.8); 3.8544 (1.4); 3.8359 (3.8); 3.8174 (3.7); 3.7989 (1.2); 3.3251 (34.7); 3.3214 (59.4); 2.6751 (0.5); 2.6712 (0.6); 2.5063 (88.3); 2.5022 (97.5); 2.3330 (0.5); 2.3291 (0.6); 1.9890 (7.0); 1.3977 (5.8); 1.3566 (4.3); 1.3381 (8.4); 1.3197 (3.8); 1.1928 (2.0); 1.1791 (1.8); 1.1751 (3.8); 1.1572 (1.8); 0.1463 (0.3); 0.0038 (36.1); −0.0002 (73.7); −0.1495 (0.4) |

| Example | Structure | NMR data |
|---|---|---|
| I-064 | 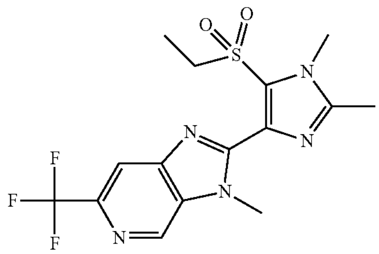 [SMILES: CCS(=O)(=O)c1c(-c2nc3cc(C(F)(F)F)ncc3n2C)nc(C)n1C] | I-064: ¹H-NMR(400.0 MHz, d₆-DMSO): δ = 9.2085 (0.3); 9.1926 (3.9); 8.3148 (0.4); 8.3082 (0.3); 8.2250 (0.4); 8.2111 (4.1); 7.5210 (0.4); 3.9924 (1.1); 3.9635 (1.1); 3.9502 (16.0); 3.8537 (14.3); 3.7152 (1.0); 3.6966 (3.4); 3.6782 (3.5); 3.6597 (1.1); 3.3197 (229.5); 2.6748 (1.4); 2.6704 (2.0); 2.6658 (1.6); 2.5235 (4.6); 2.5057 (258.4); 2.5013 (339.1); 2.4969 (251.2); 2.3324 (1.4); 2.3279 (2.0); 2.3238 (1.6); 1.3978 (12.9); 1.2841 (0.3); 1.2730 (3.7); 1.2654 (1.0); 1.2546 (8.0); 1.2361 (3.7); 1.1399 (0.4); 0.1457 (1.5); 0.0077 (10.8); −0.0004 (318.3); −0.0081 (14.8); −0.1497 (1.5) |
| I-065 | 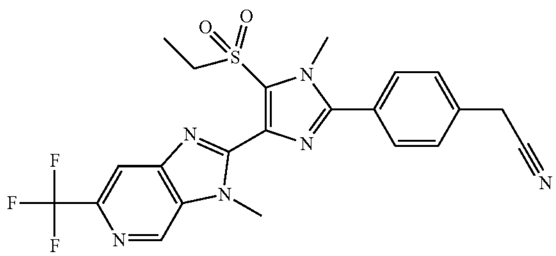 [SMILES: CCS(=O)(=O)c1c(-c2nc3cc(C(F)(F)F)ncc3n2C)nc(-c2ccc(CC#N)cc2)n1C] | I-065: ¹H-NMR(400.0 MHz, d₆-DMSO): δ = 9.2229 (4.0); 8.2479 (4.3); 7.8698 (3.8); 7.8493 (4.5); 7.5941 (3.8); 7.5736 (3.3); 4.1902 (7.9); 4.0118 (16.0); 3.9708 (14.6); 3.8306 (1.1); 3.8121 (3.4); 3.7935 (3.4); 3.7751 (1.0); 3.3236 (123.7); 2.6755 (0.4); 2.6709 (0.5); 2.6662 (0.4); 2.5243 (1.2); 2.5107 (33.2); 2.5064 (69.1); 2.5020 (92.6); 2.4975 (67.5); 2.4932 (33.5); 2.3332 (0.4); 2.3286 (0.6); 2.3244 (0.4); 2.0860 (1.6); 1.3977 (14.8); 1.3427 (3.7); 1.3242 (8.2); 1.3058 (3.6); 0.0078 (0.8); −0.0002 (24.6); −0.0083 (1.2) |
| I-066 | 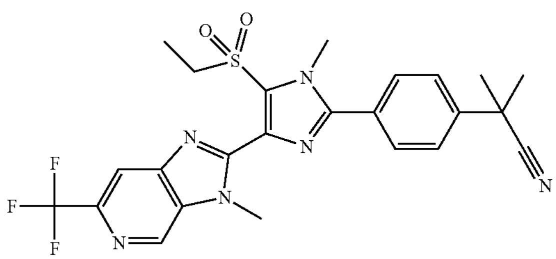 [SMILES: CCS(=O)(=O)c1c(-c2nc3cc(C(F)(F)F)ncc3n2C)nc(-c2ccc(C(C)(C)C#N)cc2)n1C] | I-066: ¹H-NMR(400.0 MHz, d₆-DMSO): δ = 9.2230 (2.3); 8.2483 (2.5); 7.9002 (2.0); 7.8794 (2.8); 7.7640 (2.7); 7.7429 (2.1); 4.0140 (8.9); 3.9759 (8.1); 3.8459 (0.6); 3.8275 (1.9); 3.8090 (2.0); 3.7907 (0.6); 3.3224 (240.3); 2.6747 (0.8); 2.6705 (1.1); 2.6662 (0.8); 2.5059 (137.3); 2.5015 (179.7); 2.4971 (131.4); 2.3326 (0.8); 2.3283 (1.0); 2.3239 (0.8); 1.7628 (16.0); 1.6237 (0.7); 1.3977 (9.7); 1.3472 (2.1); 1.3288 (4.6); 1.3103 (2.0); −0.0002 (42.2); −0.0082 (1.9) |
| I-067 | 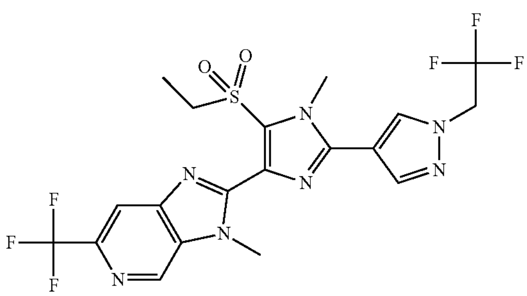 [SMILES: CCS(=O)(=O)c1c(-c2nc3cc(C(F)(F)F)ncc3n2C)nc(-c2cnn(CC(F)(F)F)c2)n1C] | I-067: ¹H-NMR(400.0 MHz, d₆-DMSO): δ = 9.2199 (4.1); 8.5699 (4.8); 8.2407 (4.4); 8.1849 (5.4); 5.7547 (0.6); 5.3234 (0.8); 5.3010 (2.5); 5.2784 (2.6); 5.2558 (0.9); 4.0344 (14.7); 3.9813 (16.0); 3.7511 (1.0); 3.7327 (3.4); 3.7143 (3.4); 3.6959 (1.0); 3.3920 (0.8); 3.3745 (0.8); 3.3568 (0.4); 3.3295 (111.6); 2.5248 (0.7); 2.5110 (18.7); 2.5070 (38.6); 2.5026 (51.7); 2.4982 (37.9); 2.4939 (18.8); 1.3051 (3.7); 1.2868 (8.2); 1.2683 (3.6); 1.1088 (0.8); 1.0913 (1.6); 1.0738 (0.8); 0.0077 (1.2); −0.0002 (35.8); −0.0084 (1.6) |
| I-068 | 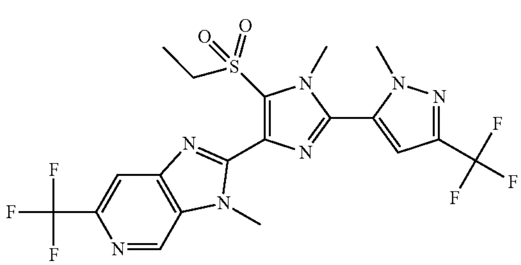 [SMILES: CCS(=O)(=O)c1c(-c2nc3cc(C(F)(F)F)ncc3n2C)nc(-c2cc(C(F)(F)F)nn2C)n1C] | I-068: ¹H-NMR(400.0 MHz, d₆-DMSO): δ = 9.2442 (4.4); 8.2582 (4.8); 7.6273 (0.5); 7.6153 (0.4); 7.5986 (0.4); 7.5664 (0.4); 7.4554 (5.0); 5.7558 (1.6); 4.1092 (14.3); 4.0336 (16.0); 4.0002 (14.9); 3.9656 (0.4); 3.8744 (1.1); 3.8559 (3.6); 3.8375 (3.6); 3.8190 (1.2); 3.3210 (22.8); 2.6712 (0.4); 2.5066 (38.8); 2.5024 (50.9); 2.4986 (38.1); 2.3291 (0.4); 1.3588 (3.8); 1.3403 (8.3); 1.3219 (3.7); 0.0078 (1.4); −0.0002 (37.7) |
| I-069 | 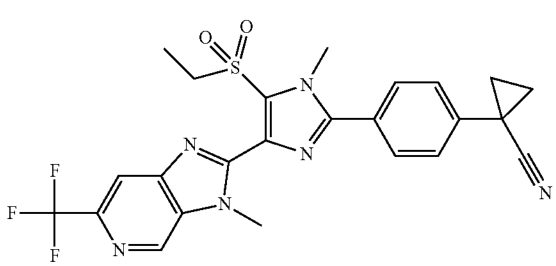 [SMILES: CCS(=O)(=O)c1c(-c2nc3cc(C(F)(F)F)ncc3n2C)nc(-c2ccc(C3(C#N)CC3)cc2)n1C] | I-069: 1H-NMR(400.0 MHz, d₆-DMSO): δ = 9.2195 (4.1); 8.2458 (4.5); 7.8530 (3.9); 7.8322 (4.8); 7.5543 (4.6); 7.5333 (4.1); 5.7550 (5.1); 4.0061 (16.0); 3.9884 (0.4); 3.9618 (14.6); 3.8306 (1.0); 3.8122 (3.4); 3.7936 (3.5); 3.7752 (1.1); 3.3225 (225.3); 2.6748 (0.8); 2.6707 (1.1); 2.6662 (0.8); 2.5238 (2.5); 2.5101 (64.4); 2.5059 (134.6); 2.5015 (181.6); 2.4971 (132.7); 2.4927 (65.6); 2.3326 (0.7); 2.3284 (1.0); 2.3238 (0.8); 2.0860 (0.9); 1.8790 (1.1); 1.8658 (3.4); 1.8586 (3.7); 1.8472 (1.5); 1.6580 (1.4); 1.6457 (3.4); 1.6386 (3.6); 1.6250 (1.1); 1.3975 (4.8); 1.3406 (3.7); 1.3222 (8.3); 1.3037 (3.6); 0.0076 (1.4); 0.0000 (46.2); −0.0083 (2.1) |

-continued

| Example | Structure | NMR data |
|---|---|---|
| I-070 | 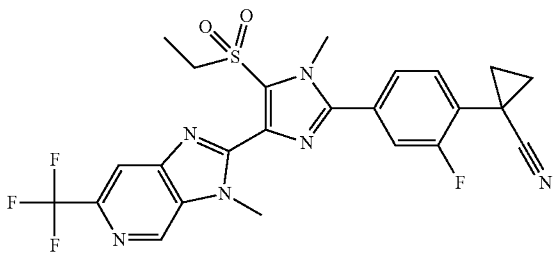 [SMILES: CCS(=O)(=O)c1c(-c2nc3cc(C(F)(F)F)ncc3n2C)nc(-c2ccc(C3(C#N)CC3)c(F)c2)n1C] | I-070: ¹H-NMR(400.0 MHz, d₆-DMSO): δ = 9.2233 (4.4); 8.3139 (0.7); 8.2472 (4.7); 7.8142 (1.7); 7.7884 (1.9); 7.7140 (0.4); 7.6938 (2.2); 7.6818 (4.8); 5.7543 (0.9); 4.0106 (16.0); 3.9814 (14.8); 3.9577 (2.1); 3.9221 (1.9); 3.8467 (1.0); 3.8282 (3.5); 3.8097 (3.5); 3.7909 (1.1); 3.7469 (0.4); 3.7279 (0.4); 3.3217 (397.6); 2.6751 (1.7); 2.6707 (2.4); 2.6664 (1.8); 2.5238 (5.8); 2.5061 (302.8); 2.5017 (403.0); 2.4973 (301.5); 2.3328 (1.7); 2.3284 (2.3); 2.3240 (1.8); 1.7980 (1.2); 1.7848 (3.2); 1.7780 (3.6); 1.7663 (1.5); 1.5838 (1.5); 1.5715 (3.4); 1.5650 (3.6); 1.5514 (1.2); 1.3980(1.9); 1.3487 (3.7); 1.3303 (8.2); 1.3118 (3.6); 1.2899 (0.6); 1.2717 (1.0); 1.2528 (0.5); 0.1459 (0.5); 0.0079 (3.5); −0.0001 (102.8); −0.1496 (0.5) |
| I-071 | 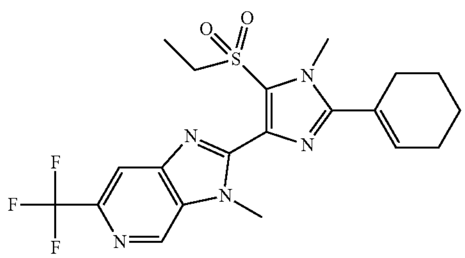 [SMILES: CCS(=O)(=O)c1c(-c2nc3cc(C(F)(F)F)ncc3n2C)nc(C2=CCCCC2)n1C] | I-071: ¹H-NMR(400.0 MHz, d₆-DMSO): δ = 9.1991 (4.1); 8.2161 (4.4); 6.3045 (1.2); 6.3006 (1.6); 3.9526 (16.0); 3.9078 (14.7); 3.7554 (1.0); 3.7370 (3.4); 3.7185 (3.5); 3.7000 (1.1); 3.3227 (110.2); 2.6748 (0.4); 2.6709 (0.6); 2.5239 (1.3); 2.5062 (68.7); 2.5018 (91.9); 2.4975 (67.5); 2.4079 (1.9); 2.4026 (1.9); 2.3284 (0.6); 2.3241 (0.4); 2.2806 (1.3); 2.2742 (1.7); 2.2661 (1.8); 1.7607 (0.4); 1.7454 (0.9); 1.7333 (1.4); 1.7227 (1.5); 1.7190 (1.4); 1.7083 (0.8); 1.7029 (0.8); 1.6867 (0.8); 1.6769 (1.5); 1.6719 (1.5); 1.6627 (1.4); 1.6581 (1.4); 1.6497 (0.9); 1.3977 (13.8); 1.2873 (3.7); 1.2689 (8.1); 1.2504 (3.6); 1.0690 (0.5); 0.0080 (0.9); −0.0002 (26.5); −0.0083 (1.3) |
| I-072 | 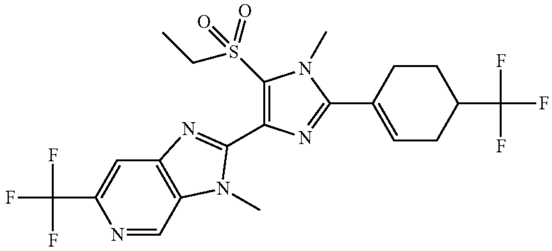 [SMILES: CCS(=O)(=O)c1c(-c2nc3cc(C(F)(F)F)ncc3n2C)nc(C2=CCC(C(F)(F)F)CC2)n1C] | I-072: ¹H-NMR(400.0 MHz, d₆-DMSO): δ = 9.2013 (3.9); 8.2207 (4.2); 6.3180 (1.1); 3.9518 (16.0); 3.9274 (14.7); 3.7604 (1.0); 3.7420 (3.3); 3.7235 (3.3); 3.7050 (1.0); 3.3251 (41.4); 2.7032 (0.4); 2.6954 (0.4); 2.6810 (0.4); 2.6715 (0.5); 2.6665 (0.5); 2.6608 (0.5); 2.6537 (0.5); 2.6001 (0.8); 2.5821 (0.5); 2.5488 (0.7); 2.5367 (1.1); 2.5246 (1.2); 2.5111 (14.2); 2.5068 (29.0); 2.5024 (38.4); 2.4979 (27.5); 2.4935 (13.2); 2.3511 (0.4); 2.3447 (0.4); 2.3336 (0.4); 2.3287 (0.5); 2.3246 (0.5); 2.3096 (0.4); 2.0966 (0.5); 2.0862 (0.6); 2.0777 (0.4); 2.0645 (0.6); 1.6519 (0.6); 1.6383 (0.6); 1.6221 (0.6); 1.6079 (0.5); 1.3975 (0.5); 1.2908 (3.7); 1.2724 (8.2); 1.2540 (3.6); 0.0079 (0.8); −0.0002 (25.1); −0.0085 (0.9) |
| I-073 | 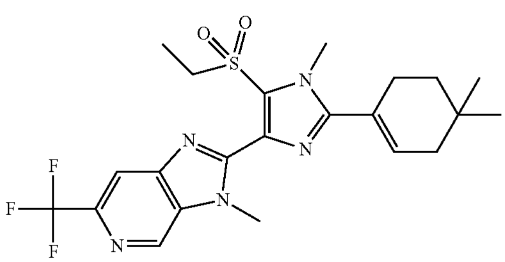 [SMILES: CCS(=O)(=O)c1c(-c2nc3cc(C(F)(F)F)ncc3n2C)nc(C2=CCC(C)(C)CC2)n1C] | I-073: ¹H-NMR(400.0 MHz, d₆-DMSO): δ = 9.1991 (2.5); 8.2176 (2.6); 6.2364 (1.0); 6.2322 (0.8); 3.9516 (9.8); 3.9061 (8.9); 3.7447 (0.6); 3.7264 (2.1); 3.7079 (2.2); 3.6893 (0.6); 3.3190 (20.2); 2.6706 (0.4); 2.5238 (1.4); 2.5103 (26.7); 2.5061 (54.3); 2.5016 (72.4); 2.4972 (53.6); 2.4931 (27.4); 2.4439 (1.2); 2.4389 (1.2); 2.3286 (0.4); 2.0763 (1.6); 2.0677 (1.6); 1.5123 (1.1); 1.4966 (2.3); 1.4803 (1.1); 1.3979 (2.7); 1.2860 (2.2); 1.2675 (5.0); 1.2491 (2.2); 0.9872 (16.0); 0.0078 (1.3); −0.0002 (32.4) |
| I-074 | 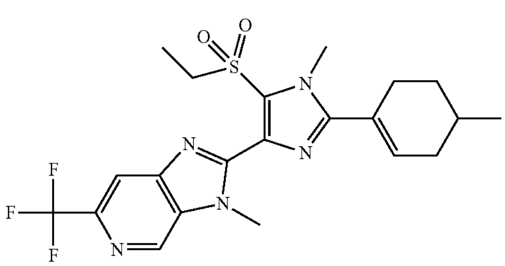 [SMILES: CCS(=O)(=O)c1c(-c2nc3cc(C(F)(F)F)ncc3n2C)nc(C2=CCC(C)CC2)n1C] | I-074: ¹H-NMR(400.0 MHz, d6-DMSO): δ = 9.1987 (4.2); 8.2191 (4.5); 6.2749 (1.8); 3.9481 (16.0); 3.9044 (14.8); 3.7487 (1.2); 3.7301 (3.6); 3.7115 (3.5); 3.6932 (1.1); 3.3291 (47.1); 3.3223 (128.4); 2.6746 (0.7); 2.6706 (0.8); 2.5057 (125.9); 2.5014 (139.4); 2.4971 (96.1); 2.4083 (1.4); 2.3656 (1.1); 2.3328 (0.8); 2.3282 (0.8); 1.9068 (0.6); 1.8843 (0.7); 1.8771 (0.6); 1.8395 (1.2); 1.7976 (1.2); 1.7619 (0.7); 1.3953 (0.4); 1.3683 (0.8); 1.3542 (0.8); 1.3424 (0.7); 1.3376 (0.8); 1.3233 (0.7); 1.3110 (0.6); 1.2835 (4.0); 1.2651 (8.2); 1.2466 (3.6); 1.0215 (6.6); 1.0055 (6.2); −0.0002 (6.4) |

-continued

| Example | Structure | NMR data |
|---|---|---|
| I-075 | 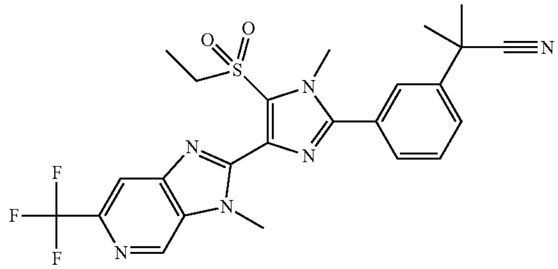 [SMILES: CCS(=O)(=O)c1c(-c2nc3cc(C(F)(F)F)ncc3n2C)nc(-c2cccc(C(C)(C)C#N)c2)n1C] | I-075: $^1$H-NMR(400.0 MHz, d$_6$-DMSO): δ = 9.2243 (2.2); 8.2543 (2.4); 7.9308 (1.5); 7.9270 (1.0); 7.8173 (0.8); 7.7979 (1.0); 7.7835 (0.6); 7.7788 (0.5); 7.7615 (0.9); 7.6946 (1.0); 7.6751 (1.3); 7.6556 (0.5); 4.0059 (8.7); 3.9695 (7.8); 3.8263 (0.6); 3.8080 (1.8); 3.7894 (1.8); 3.7710 (0.6); 3.3204 (14.0); 2.5237 (0.7); 2.5102 (16.1); 2.5059 (34.0); 2.5014 (46.0); 2.4970 (33.4); 2.4926 (16.1); 2.0858 (1.7); 1.7651 (16.0); 1.6392 (0.5); 1.3972 (2.2); 1.3474 (2.0); 1.3290 (4.4); 1.3105 (1.9); −0.0002 (9.0) |
| I-076 | 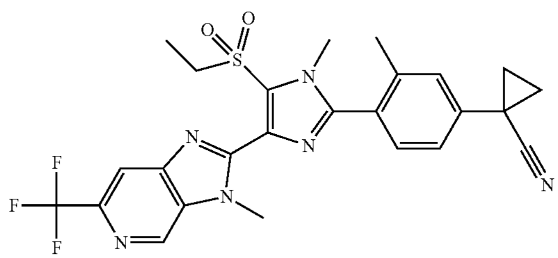 [SMILES: CCS(=O)(=O)c1c(-c2nc3cc(C(F)(F)F)ncc3n2C)nc(-c2ccc(C3(C#N)CC3)cc2C)n1C] | I-076: $^1$H-NMR(400.0 MHz, d$_6$-DMSO): δ = 9.2151 (2.5); 8.2409 (2.6); 7.5986 (1.5); 7.5786 (1.8); 7.3953 (1.6); 7.3706 (0.9); 7.3658 (0.8); 7.3506 (0.8); 7.3458 (0.7); 4.0136 (10.2); 3.8698 (0.6); 3.8512 (2.0); 3.8327 (2.1); 3.8144 (0.6); 3.7292 (9.4); 3.3193 (45.4); 2.6747 (0.6); 2.6702 (0.8); 2.6656 (0.6); 2.5236 (1.8); 2.5187 (2.8); 2.5101 (50.3); 2.5056 (107.4); 2.5011 (144.8); 2.4966 (103.1); 2.4921 (48.7); 2.3325 (0.6); 2.3278 (0.8); 2.3234 (0.6); 2.2684 (7.4); 2.0855 (0.7); 1.8503 (0.7); 1.8374 (2.0); 1.8301 (2.2); 1.8189 (0.9); 1.6437 (0.8); 1.6314 (2.1); 1.6242 (2.2); 1.6106 (0.7); 1.3975 (16.0); 1.3441 (2.3); 1.3257 (5.2); 1.3072 (2.2); 0.0079 (0.9); −0.0003 (30.0); −0.0086 (1.0) |
| I-077 | 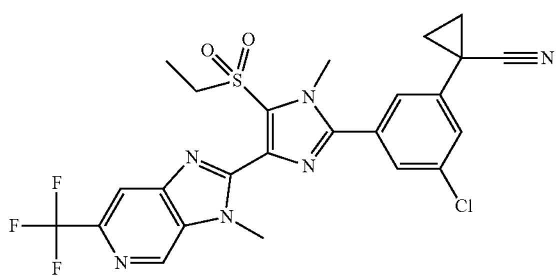 [SMILES: CCS(=O)(=O)c1c(-c2nc3cc(C(F)(F)F)ncc3n2C)nc(-c2cc(Cl)cc(C3(C#N)CC3)c2)n1C] | I-077: $^1$H-NMR(400.0 MHz, d$_6$-DMSO): δ = 9.2241 (3.9); 8.2528 (4.1); 7.8672 (1.9); 7.8630 (3.2); 7.8590 (2.1); 7.7388 (2.0); 7.7349 (3.4); 7.7310 (2.0); 7.6107 (2.0); 7.6061 (3.6); 7.6015 (1.8); 6.7479 (0.4); 6.7437 (0.4); 6.7360 (0.5); 6.7203 (0.4); 4.0202 (0.4); 4.0046 (16.0); 3.9536 (14.2); 3.8202 (0.9); 3.8019 (3.2); 3.7834 (3.2); 3.7649 (1.0); 3.3199 (48.7); 2.6749 (0.6); 2.6705 (0.9); 2.6658 (0.6); 2.5238 (2.0); 2.5189 (3.2); 2.5103 (54.7); 2.5059 (116.3); 2.5014 (156.8); 2.4968 (111.1); 2.4923 (52.2); 2.3326 (0.6); 2.3281 (0.9); 2.3236 (0.6); 2.0857 (1.4); 1.8690 (1.0); 1.8556 (2.9); 1.8481 (3.3); 1.8367 (1.5); 1.7367 (0.6); 1.7295 (0.5); 1.7176 (1.7); 1.7055 (3.2); 1.6982 (3.0); 1.6842 (1.0); 1.5142 (0.5); 1.5071 (0.5); 1.3975 (2.8); 1.3468 (3.5); 1.3284 (8.1); 1.3099 (3.5); 0.0080 (1.0); −0.0001 (33.4); −0.0085 (1.1) |
| I-078 | 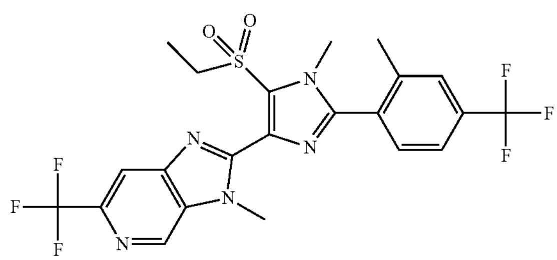 [SMILES: CCS(=O)(=O)c1c(-c2nc3cc(C(F)(F)F)ncc3n2C)nc(-c2ccc(C(F)(F)F)cc2C)n1C] | I-078: $^1$H-NMR(400.0 MHz, d$_6$-DMSO): δ = 9.2218 (2.1); 8.2444 (2.3); 7.8668 (1.4); 7.8514 (0.7); 7.8314 (1.3); 7.7912 (0.9); 7.7708 (0.5); 4.0259 (7.9); 3.8836 (0.5); 3.8652 (1.7); 3.8467 (1.8); 3.8283 (0.5); 3.7553 (7.4); 3.3203 (8.8); 2.5065 (20.4); 2.5022 (27.2); 2.4978 (20.1); 2.3586 (6.2); 1.3974 (16.0); 1.3581 (1.9); 1.3397 (4.1); 1.3212 (1.8); 0.0072 (0.9); −0.0002 (23.2); −0.0083 (1.0) |
| I-079 | 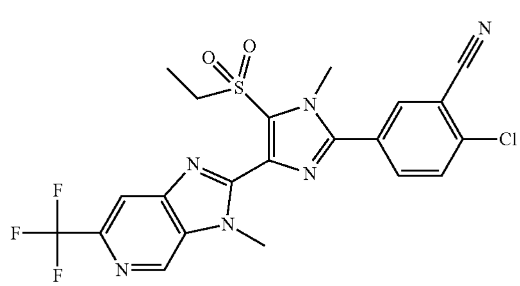 [SMILES: CCS(=O)(=O)c1c(-c2nc3cc(C(F)(F)F)ncc3n2C)nc(-c2ccc(Cl)c(C#N)c2)n1C] | I-079: $^1$H-NMR(400.0 MHz, d$_6$-DMSO): δ = 9.2298 (3.9); 8.4680 (3.1); 8.4627 (3.3); 8.2512 (4.2); 8.1826 (1.6); 8.1772 (1.6); 8.1613 (2.0); 8.1559 (2.0); 8.0072 (3.4); 7.9859 (2.7); 5.7561 (6.5); 4.0208 (16.0); 3.9858 (14.5); 3.9687 (0.5); 3.8405 (1.0); 3.8221 (3.3); 3.8036 (3.4); 3.7851 (1.0); 3.3224 (21.5); 2.5250 (0.5); 2.5115 (13.9); 2.5071 (29.6); 2.5026 (40.3); 2.4981 (29.6); 2.4936 (14.7); 2.0866 (1.5); 1.3527 (3.6); 1.3344 (8.2); 1.3158 (3.5); 0.0079 (0.9); −0.0002 (30.6); −0.0084 (1.4) |

-continued

| Example | Structure | NMR data |
|---|---|---|
| I-080 | 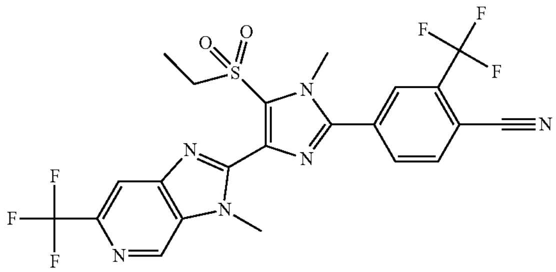 [SMILES: CCS(=O)(=O)c1c(-c2nc3cc(C(F)(F)F)ncc3n2C)nc(-c2ccc(C#N)c(C(F)(F)F)c2)n1C] | I-080: ¹H-NMR(400.0 MHz, d₆-DMSO): δ = 9.2312 (3.5); 8.4459 (1.4); 8.4250 (4.5); 8.3743 (1.7); 8.3705 (1.4); 8.3539 (0.9); 8.3508 (0.9); 8.2557 (3.7); 5.7562 (8.2); 4.3317 (0.5); 4.0394 (0.4); 4.0321 (0.5); 4.0181 (16.0); 4.0135 (14.2); 3.8444 (0.9); 3.8261 (3.0); 3.8076 (3.0); 3.7892 (0.9); 3.7649 (0.4); 3.3287 (16.5); 2.5228 (0.4); 2.5141 (6.7); 2.5097 (14.2); 2.5052 (19.1); 2.5007 (13.8); 2.4962 (6.6); 2.0882 (2.2); 1.3967 (0.5); 1.3623 (3.3); 1.3439 (7.3); 1.3254 (3.1); 0.0079 (0.8); −0.0002 (23.5); −0.0085 (0.9) |
| I-081 | 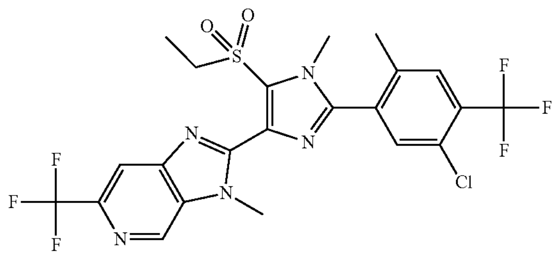 [SMILES: CCS(=O)(=O)c1c(-c2nc3cc(C(F)(F)F)ncc3n2C)nc(-c2cc(Cl)c(C(F)(F)F)cc2C)n1C] | I-081: ¹H-NMR(400.0 MHz, d₆-DMSO): δ = 9.2215 (4.3); 8.2456 (4.4); 8.0725 (4.0); 7.9909 (3.6); 4.0183 (16.0); 3.8687 (1.0); 3.8505 (3.3); 3.8320 (3.4); 3.8135 (1.1); 3.8025 (0.8); 3.7785 (14.4); 3.7538 (0.6); 3.3199 (113.3); 2.6750 (0.8); 2.6705 (1.1); 2.6661 (0.9); 2.5239 (2.8); 2.5191 (4.4); 2.5104 (69.6); 2.5060 (147.5); 2.5016 (199.4); 2.4970 (144.4); 2.4926 (69.9); 2.4616 (0.8); 2.3571 (0.6); 2.3386 (12.2); 2.3286 (1.7); 2.3237 (1.1); 2.1115 (0.5); 1.3977 (1.4); 1.3612 (3.6); 1.3428 (8.0); 1.3243 (3.5); 1.3133 (0.5); 0.1459 (0.4); 0.0078 (3.1); −0.0003 (97.3); −0.0084 (3.9); −0.1497 (0.4) |
| I-082 | 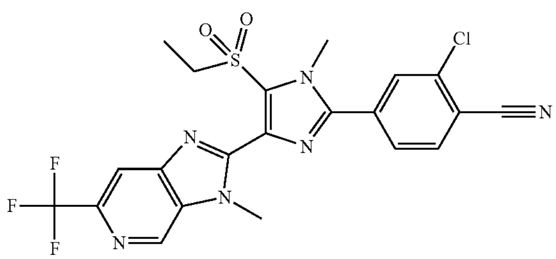 [SMILES: CCS(=O)(=O)c1c(-c2nc3cc(C(F)(F)F)ncc3n2C)nc(-c2ccc(C#N)c(Cl)c2)n1C] | I-082: ¹H-NMR(400.0 MHz, d₆-DMSO): δ = 9.2301 (3.8); 8.2542 (4.1); 8.2360 (2.9); 8.2278 (3.4); 8.2239 (3.5); 8.2159 (3.4); 8.0167 (2.0); 8.0130 (1.9); 7.9964 (1.6); 7.9926 (1.7); 4.0142 (16.0); 3.9967 (14.3); 3.8421 (0.9); 3.8238 (3.2); 3.8053 (3.3); 3.7869 (1.0); 3.3208 (85.1); 2.6753 (0.6); 2.6708 (0.9); 2.6665 (0.7); 2.5241 (2.3); 2.5193 (3.6); 2.5107 (54.0); 2.5063 (114.0); 2.5018 (153.4); 2.4972 (110.0); 2.4928 (52.5); 2.3330 (0.6); 2.3285 (0.9); 2.3240 (0.6); 2.0742 (1.1); 1.3511 (3.5); 1.3326 (8.0); 1.3141 (3.4); −0.0001 (8.1) |
| I-083 | 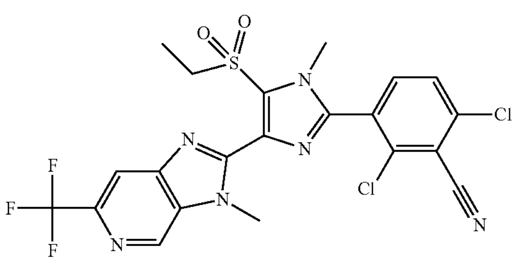 [SMILES: CCS(=O)(=O)c1c(-c2nc3cc(C(F)(F)F)ncc3n2C)nc(-c2ccc(Cl)c(C#N)c2Cl)n1C] | I-083: ¹H-NMR(400.0 MHz, d₆-DMSO): δ = 9.2240 (3.7); 8.2504 (4.0); 8.2486 (4.0); 8.1531 (3.1); 8.1319 (4.4); 8.0292 (4.3); 8.0079 (3.2); 4.0216 (16.0); 3.9029 (0.9); 3.8844 (3.1); 3.8660 (3.2); 3.8475 (0.9); 3.7865 (14.7); 3.3210 (19.9); 2.6756 (0.3); 2.6709 (0.5); 2.6665 (0.4); 2.5244 (1.2); 2.5197 (2.0); 2.5110 (30.0); 2.5065 (64.5); 2.5020 (87.6); 2.4974 (63.4); 2.4929 (30.6); 2.3332 (0.4); 2.3288 (0.5); 2.3243 (0.4); 2.0742 (2.4); 1.3544 (3.4); 1.3360 (8.0); 1.3174 (3.4); −0.0002 (5.1) |
| I-084 | 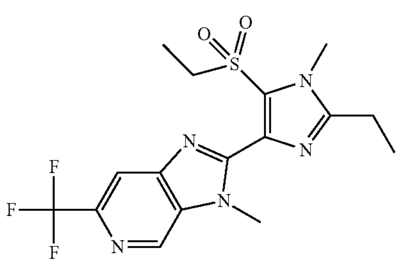 [SMILES: CCc1nc(-c2nc3cc(C(F)(F)F)ncc3n2C)c(S(=O)(=O)CC)n1C] | I-084: ¹H-NMR(400.0 MHz, d₆-DMSO): δ = 9.1935 (4.3); 8.3173 (0.4); 8.2096 (4.6); 5.7570 (1.5); 4.3702 (0.5); 4.0246 (0.5); 3.9591 (16.0); 3.8671 (14.5); 3.7565 (0.4); 3.7196 (1.1); 3.7011 (3.8); 3.6828 (3.6); 3.6644 (1.1); 3.3269 (5.2); 2.8875 (1.2); 2.8687 (3.7); 2.8500 (3.8); 2.8313 (1.3); 2.5083 (13.9); 2.5041 (18.3); 2.5000 (13.9); 1.3298 (4.1); 1.3112 (8.6); 1.2924 (4.0); 1.2736 (3.8); 1.2553 (8.1); 1.2368 (3.8); −0.0002 (0.7) |
| I-085 | 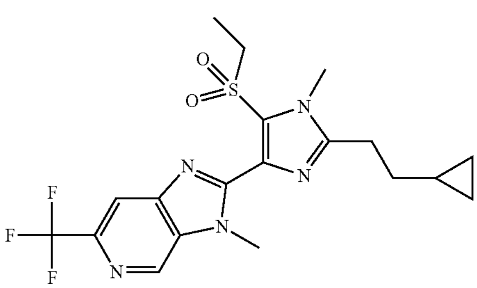 [SMILES: CCS(=O)(=O)c1c(-c2nc3cc(C(F)(F)F)ncc3n2C)nc(CCC2CC2)n1C] | I-085: ¹H-NMR(400.0 MHz, d₆-DMSO): δ = 9.1902 (4.3); 8.2077 (4.6); 5.7571 (7.5); 3.9466 (16.0); 3.8932 (14.3); 3.7211 (1.1); 3.7027 (3.5); 3.6842 (3.6); 3.6658 (1.1); 3.3292 (4.0); 2.9561 (2.0); 2.9376 (3.6); 2.9189 (2.2); 2.5099 (9.9); 2.5057 (12.8); 2.5014 (9.5); 1.6981 (1.1); 1.6800 (2.8); 1.6616 (2.8); 1.6435 (1.1); 1.2741 (3.7); 1.2558 (8.1); 1.2373 (3.6); 0.8499 (0.6); 0.8435 (0.6); 0.8315 (0.9); 0.8191 (0.6); 0.8130 (0.6); 0.8000 (0.3); 0.4441 (0.8); 0.4335 (2.5); 0.4299 (2.6); 0.4245 (1.3); 0.4199 (1.3); 0.4136 (2.4); 0.4100 (2.4); 0.3999 (0.8); 0.0771 (0.9); 0.0641 (3.2); 0.0523 (3.0); 0.0408 (0.7); 0.0078 (0.6); −0.0002 (13.3) |

-continued

| Example | Structure | NMR data |
| --- | --- | --- |
| I-086 | 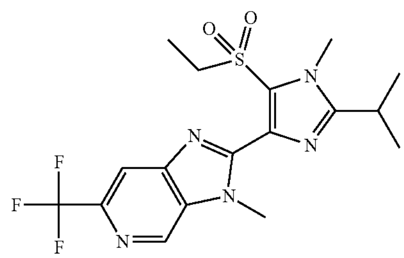 [SMILES: CCS(=O)(=O)c1c(-c2nc3cc(C(F)(F)F)ncc3n2C)nc(C(C)C)n1C] | I-086: ¹H-NMR(400.0 MHz, d₆-DMSO): δ = 9.1930 (3.7); 8.2050 (3.9); 8.2034 (4.0); 5.7583 (12.4); 4.3773 (0.6); 3.9576 (16.0); 3.9141 (14.3); 3.7341 (1.5); 3.7154 (3.4); 3.6969 (3.4); 3.6785 (1.0); 3.3410 (0.5); 3.3334 (6.4); 3.3243 (1.1); 3.3072 (1.4); 3.2903 (1.1); 3.2733 (0.4); 2.5155 (3.5); 2.5111 (7.4); 2.5066 (9.9); 2.5021 (7.1); 2.4976 (3.4); 1.3244 (14.8); 1.3074 (14.3); 1.2978 (1.1); 1.2776 (3.6); 1.2592 (8.0); 1.2407 (3.5); 0.0079 (0.4); −0.0002 (12.2); −0.0085 (0.5) |
| I-087 | 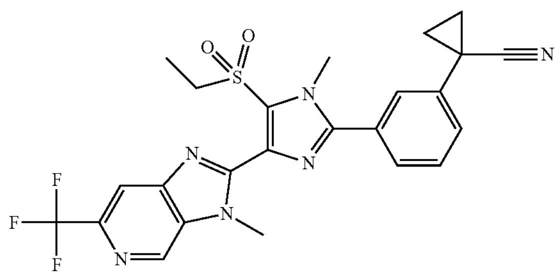 [SMILES: CCS(=O)(=O)c1c(-c2nc3cc(C(F)(F)F)ncc3n2C)nc(-c2cccc(C3(C#N)CC3)c2)n1C] | I-087: ¹H-NMR(400.0 MHz, d₆-DMSO): δ = 9.2227 (3.9); 8.2490 (4.1); 7.7702 (1.4); 7.7669 (1.0); 7.7551 (1.0); 7.7514 (1.9); 7.7482 (1.3); 7.7286 (1.7); 7.7245 (2.7); 7.6510 (1.0); 7.6315 (2.4); 7.6127 (1.7); 7.5958 (1.4); 7.5921 (2.0); 7.5881 (1.4); 7.5760 (0.7); 7.5721 (0.9); 7.5682 (0.7); 5.7552 (3.7); 4.0078 (16.0); 3.9638 (0.6); 3.9524 (14.2); 3.8280 (1.0); 3.8096 (3.2); 3.7911 (3.3); 3.7726 (1.0); 3.3227 (21.7); 2.5249 (0.6); 2.5115 (15.0); 2.5071 (31.5); 2.5026 (42.2); 2.4981 (30.4); 2.4937 (14.7); 2.0864 (7.2); 1.9892 (0.7); 1.8453 (1.1); 1.8323 (3.4); 1.8251 (3.6); 1.8136 (1.4); 1.6454 (1.5); 1.6331 (3.4); 1.6261 (3.5); 1.6125 (1.1); 1.3972 (1.0); 1.3475 (3.6); 1.3290 (8.2); 1.3105 (3.5); 1.1754 (0.4); 0.0079 (0.8); −0.0002 (23.2); −0.0084 (0.9) |
| I-088 | 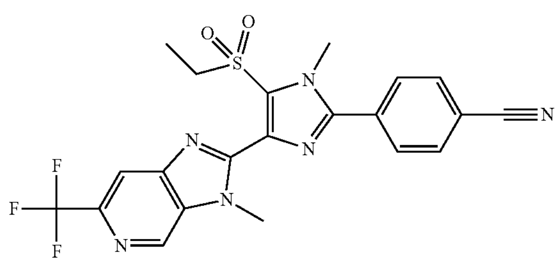 [SMILES: CCS(=O)(=O)c1c(-c2nc3cc(C(F)(F)F)ncc3n2C)nc(-c2ccc(C#N)cc2)n1C] | I-088: ¹H-NMR(400.0 MHz, d₆-DMSO): δ = 9.2274 (2.5); 8.2510 (2.7); 8.1010 (1.5); 8.0847 (1.0); 8.0797 (4.1); 8.0508 (4.0); 8.0459 (1.1); 8.0340 (0.7); 8.0294 (1.6); 4.0154 (10.4); 3.9904 (9.5); 3.8461 (0.6); 3.8276 (2.1); 3.8091 (2.2); 3.7907 (0.6); 3.3213 (15.2); 2.5247 (0.7); 2.5199 (1.2); 2.5112 (15.6); 2.5068 (32.7); 2.5023 (43.7); 2.4978 (31.6); 2.4934 (15.4); 1.3975 (16.0); 1.3509 (2.4); 1.3324 (5.3); 1.3139 (2.3); 0.0079 (1.3); −0.0002 (38.0); −0.0085 (1.6) |
| I-089 | 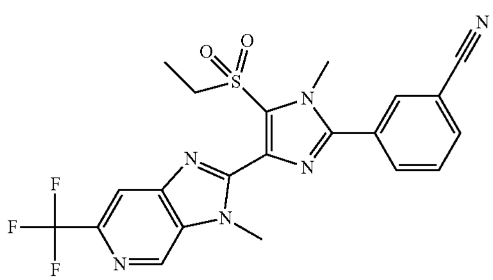 [SMILES: CCS(=O)(=O)c1c(-c2nc3cc(C(F)(F)F)ncc3n2C)nc(-c2cccc(C#N)c2)n1C] | I-089: ¹H-NMR(400.0 MHz, d₆-DMSO): δ = 9.2295 (3.7); 8.3312 (1.6); 8.3273 (2.8); 8.3241 (1.8); 8.2507 (3.9); 8.1761 (0.9); 8.1730 (1.4); 8.1691 (1.0); 8.1563 (1.1); 8.1523 (1.5); 8.1493 (1.2); 8.0995 (1.0); 8.0961 (1.5); 8.0929 (1.0); 8.0799 (1.2); 8.0765 (1.7); 8.0733 (1.1); 7.8406 (1.4); 7.8210 (2.5); 7.8012 (1.1); 4.0229 (16.0); 3.9835 (14.6); 3.8442 (1.0); 3.8259 (3.2); 3.8074 (3.2); 3.7889 (1.0); 3.3200 (42.3); 2.6753 (0.5); 2.6709 (0.7); 2.6663 (0.5); 2.5242 (2.2); 2.5195 (3.4); 2.5108 (41.3); 2.5064 (86.2); 2.5018 (115.2); 2.4973 (82.7); 2.4928 (39.8); 2.3331 (0.5); 2.3286 (0.7); 2.3240 (0.5); 2.0860 (6.7); 1.3977 (9.2); 1.3537 (3.5); 1.3353 (8.1); 1.3167 (3.4); 0.1459 (0.4); 0.0079 (3.7); −0.0002 (108.4); −0.0085 (4.3); −0.1497 (0.4) |
| I-090 | 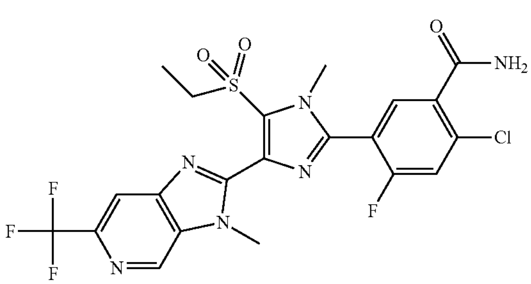 [SMILES: CCS(=O)(=O)c1c(-c2nc3cc(C(F)(F)F)ncc3n2C)nc(-c2cc(C(N)=O)c(Cl)cc2F)n1C] | I-090: ¹H-NMR(400.0 MHz, d₆-DMSO): δ = 9.2242 (4.1); 9.2097 (0.4); 8.3091 (0.4); 8.2522 (4.4); 8.2276 (0.4); 8.0485 (1.7); 7.9009 (2.7); 7.8820 (2.7); 7.8556 (2.7); 7.8313 (2.7); 7.7717 (1.6); 5.7558 (6.9); 4.0580 (0.3); 4.0137 (16.0); 3.9927 (1.6); 3.9638 (1.3); 3.9218 (0.6); 3.8725 (1.1); 3.8542 (11.4); 3.8356 (3.6); 3.8171 (1.1); 3.8090 (0.5); 3.7897 (0.4); 3.3198 (85.4); 2.6751 (0.8); 2.6706 (1.2); 2.6661 (0.9); 2.5238 (2.6); 2.5190 (4.0); 2.5103 (70.7); 2.5060 (151.6); 2.5015 (206.4); 2.4970 (149.0); 2.4926 (71.7); 2.3326 (0.8); 2.3282 (1.2); 2.3238 (0.9); 1.3423 (3.7); 1.3238 (8.3); 1.3054 (3.8); 1.2844 (0.6); 1.2657 (1.0); 1.2589 (0.7); 1.2471 (0.7); 1.2350 (1.6); 1.1773 (0.3); 1.1589 (0.5); 1.1400 (0.3); 0.8551 (0.5); 0.1460 (0.4); 0.0080 (2.8); −0.0001 (88.4); −0.0083 (3.3); −0.1496 (0.4) |

-continued

| Example | Structure | NMR data |
|---|---|---|
| I-091 | 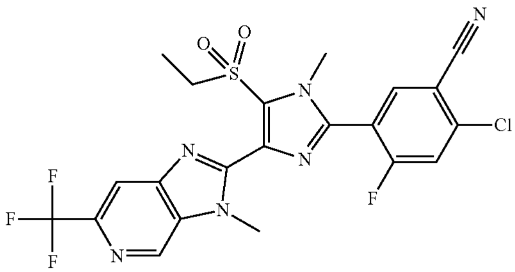 [SMILES: CCS(=O)(=O)c1c(-c2nc3cc(C(F)(F)F)ncc3n2C)nc(-c2cc(C#N)c(Cl)cc2F)n1C] | I-091: ¹H-NMR (400.0 MHz, d₆-DMSO): δ = 10.1979 (1.0); 9.2297 (4.0); 9.2225 (0.5); 9.2077 (0.5); 9.0182 (0.5); 8.5409 (2.7); 8.5229 (2.5); 8.4893 (2.8); 8.3144 (1.9); 8.2545 (4.2); 8.2429 (0.4); 8.2245 (0.4); 8.2012 (2.5); 8.1770 (2.6); 8.1131 (0.7); 7.6740 (0.3); 7.6449 (0.6); 7.6308 (0.7); 7.6262 (0.8); 7.6143 (0.7); 7.6104 (0.7); 7.5962 (0.9); 7.5725 (0.8); 7.5558 (1.4); 7.5213 (3.0); 7.5057 (2.2); 7.4649 (1.7); 7.4437 (1.7); 7.3816 (0.4); 7.3287 (0.6); 7.3097 (0.9); 7.2870 (0.6); 7.2536 (0.7); 7.2413 (0.6); 7.2248 (0.4); 6.7909 (3.6); 5.7546 (2.6); 4.0397 (0.4); 4.0193 (16.0); 3.9929 (1.8); 3.9829 (0.6); 3.9633 (1.4); 3.9578 (1.5); 3.9295 (0.4); 3.9220 (1.5); 3.8910 (1.2); 3.8741 (11.5); 3.8551 (3.3); 3.8373 (1.1); 3.8081 (0.5); 3.7897 (0.5); 3.7470 (0.4); 3.7286 (0.5); 3.5851 (0.4); 3.5759 (0.4); 3.5567 (0.4); 3.5492 (0.4); 3.4381 (0.6); 3.4227 (1.2); 3.4081 (0.7); 3.3927 (1.2); 3.3185 (302.2); 3.2105 (0.4); 3.0637 (0.3); 2.6751 (3.8); 2.6705 (5.3); 2.6660 (4.1); 2.6481 (0.4); 2.6270 (0.3); 2.6210 (0.4); 2.6123 (0.4); 2.5933 (0.4); 2.5748 (0.6); 2.5239 (13.2); 2.5103 (321.8); 2.5060 (681.8); 2.5015 (923.6); 2.4969 (666.6); 2.4925 (320.0); 2.4555 (0.9); 2.3326 (3.8); 2.3282 (5.3); 2.3237 (4.0); 1.3472 (3.6); 1.3287 (8.2); 1.3102 (3.6); 1.2898 (0.5); 1.2839 (0.6); 1.2718 (0.8); 1.2658 (1.1); 1.2548 (0.5); 1.2475 (0.6); 1.2328 (0.9); 1.2137 (0.8); 1.1943 (0.4); 1.0327 (0.4); 1.0205 (0.6); 0.0078 (1.3); −0.0001 (45.6); −0.0083 (1.9) |
| I-092 | 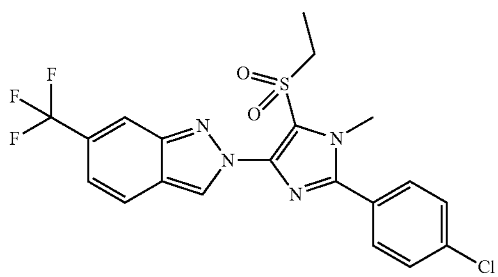 [SMILES: CCS(=O)(=O)c1c(-n2cc3ccc(C(F)(F)F)cc3n2)nc(-c2ccc(Cl)cc2)n1C] | I-092: ¹H-NMR(400.2 MHz, d₆-DMSO): δ = 8.9758 (5.2); 8.1939 (3.2); 8.0633 (2.1); 8.0415 (2.2); 7.8596 (4.4); 7.8384 (5.6); 7.6945 (5.6); 7.6734 (4.4); 7.3719 (2.0); 7.3500 (1.9); 6.5552 (0.6); 3.9526 (16.0); 3.8278 (1.2); 3.8093 (3.9); 3.7910 (3.9); 3.7724 (1.4); 3.3199 (72.8); 2.6699 (1.9); 2.5043 (217.4); 2.5010 (276.8); 2.3279 (1.6); 2.0743 (1.1); 1.3451 (4.1); 1.3266 (8.8); 1.3082 (4.0); 1.2349 (0.4); 0.1459 (0.7); −0.0003 (134.9); −0.1495 (0.6) |
| I-093 | 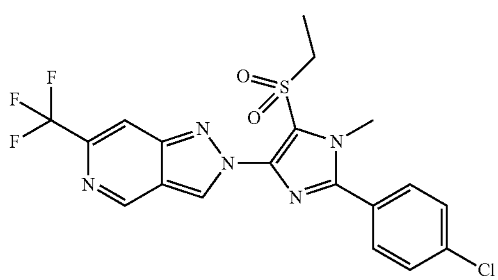 [SMILES: CCS(=O)(=O)c1c(-n2cc3cnc(C(F)(F)F)cc3n2)nc(-c2ccc(Cl)cc2)n1C] | I-093: ¹H-NMR(300.2 MHz, d₆-DMS0): δ = 12.5210 (0.5); 11.5637 (0.4); 9.9892 (0.5); 9.4469 (3.7); 9.3139 (5.1); 8.2806 (3.5); 7.8688 (4.4); 7.8404 (5.9); 7.7026 (6.1); 7.6741 (4.3); 6.5226 (1.0); 3.9658 (16.0); 3.7828 (1.2); 3.7591 (3.7); 3.7342 (3.8); 3.7101 (1.3); 3.3183 (840.6); 3.2498 (0.7); 3.2110 (0.5); 2.9361 (0.5); 2.7328 (2.9); 2.7269 (4.0); 2.7209 (2.8); 2.6131 (0.5); 2.5129 (256.1); 2.5069 (526.6); 2.5009 (718.3); 2.4948 (518.7); 2.4889 (241.9); 2.4235 (0.7); 2.3348 (0.6); 2.3068 (0.6); 2.2768 (2.8); 2.2709 (4.2); 2.2653 (3.0); 1.3326 (3.8); 1.3082 (9.1); 1.2836 (3.8); 1.1485 (0.9); 0.4356 (0.5); 0.1949 (1.5); 0.0107 (17.1); −0.0001 (400.8): −0.0111 (14.1): −0.1988 (1.7) |
| I-094 | 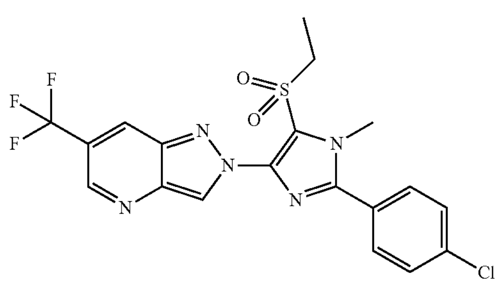 [SMILES: CCS(=O)(=O)c1c(-n2cc3ncc(C(F)(F)F)cc3n2)nc(-c2ccc(Cl)cc2)n1C] | I-094: ¹H-NMR(300.2 MHz, d₆-DMSO): δ = 9.3498 (4.9); 9.3477 (5.0); 8.9284 (3.1); 8.9217 (3.4); 8.8299 (2.5); 8.8268 (2.7); 7.8726 (4.2); 7.8665 (1.6); 7.8441 (6.0); 7.7033 (6.0); 7.6747 (4.3); 3.9692 (16.0); 3.8081 (1.0); 3.7833 (3.6); 3.7587 (3.8); 3.7339 (1.1); 3.4012 (0.3); 3.3855 (0.4); 3.3694 (0.7); 3.3325 (433.4); 3.3019 (1.2); 3.2914 (0.7); 2.5136 (12.1); 2.5078 (24.3); 2.5019 (32.5); 2.4961 (22.8); 2.0739 (0.4); 1.3465 (4.0); 1.3220 (9.1); 1.2974 (3.9); 1.0095 (0.3); −0.0005 (14.4); −0.0114 (0.6) |

| Example | Structure | NMR data |
|---|---|---|
| I-095 | 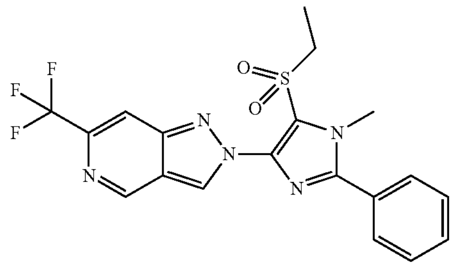 [SMILES: CCS(=O)(=O)c1c(-n2cc3cnc(C(F)(F)F)cc3n2)nc(-c2ccccc2)n1C] | I-095: $^1$H-NMR(300.2 MHz, d$_6$-DMSO):<br>δ = 9.4483 (3.7); 9.3168 (5.0); 8.2814 (3.5); 7.8352 (2.0); 7.8273 (2.4); 7.8154 (3.0); 7.8029 (2.7); 7.6280 (6.2); 7.6196 (5.3); 7.6057 (3.5); 3.9724 (16.0); 3.7887 (1.1); 3.7638 (3.7); 3.7390 (3.9); 3.7149 (1.1); 3.3181 (77.2); 2.7261 (0.6); 2.5127 (45.9); 2.5069 (93.4); 2.5009 (127.1); 2.4949 (92.8); 2.4891 (43.8); 2.2709 (0.8); 2.0741 (0.7); 1.3349 (4.0); 1.3104 (9.1); 1.2857 (3.9); 0.1952 (0.4); 0.0421 (0.4); 0.0107 (3.5); −0.0002 (79.7); −0.0110 (2.8); −0.1989 (0.4) |
| I-096 | 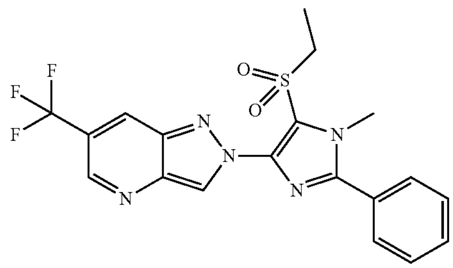 [SMILES: CCS(=O)(=O)c1c(-n2cc3ncc(C(F)(F)F)cc3n2)nc(-c2ccccc2)n1C] | I-096: $^1$H-NMR(300.1 MHz, d$_6$-DMSO):<br>δ = 9.3515 (4.8); 8.9284 (2.9); 8.9218 (3.5); 8.2611 (2.8); 7.8759 (0.7); 7.8305 (2.6); 7.8177 (3.2); 7.8048 (2.6); 7.7859 (0.8); 7.6525 (1.1); 7.6289 (6.0); 7.6205 (5.7); 7.6099 (3.5); 7.5598 (0.7); 7.0080 (0.7); 6.2686 (0.8); 4.7230 (0.7); 4.0114 (0.9); 3.9749 (16.0); 3.8103 (1.2); 3.7858 (4.0); 3.7621 (3.7); 3.7379 (1.6); 3.7162 (0.8); 3.4318 (1.0); 3.4168 (1.9); 3.3238 (1144.8); 3.2267 (3.6); 3.2099 (1.2); 2.7260 (1.2); 2.5068 (138.8); 2.5009 (181.9); 2.4951 (128.0); 2.2715 (1.0); 1.3476 (4.3); 1.3231 (8.8); 1.2991 (3.6); 0.1297 (0.7); 0.0361 (1.0); 0.0103 (5.1); −0.0005 (101.9); −0.0115 (3.1); −3.2022 (0.7) |
| I-097 | 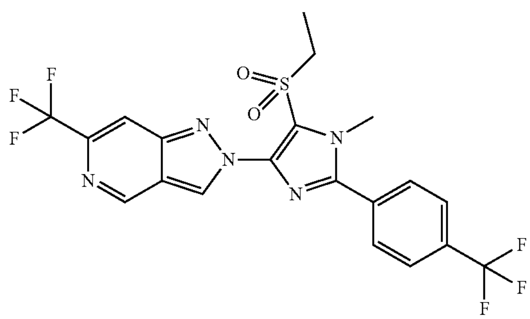 [SMILES: CCS(=O)(=O)c1c(-n2cc3cnc(C(F)(F)F)cc3n2)nc(-c2ccc(C(F)(F)F)cc2)n1C] | I-097: $^1$H-NMR(300.1 MHz, d$_6$-DMSO):<br>δ = 9.4549 (4.0); 9.3257 (5.2); 8.2888 (3.8); 8.0848 (2.4); 8.0574 (4.8); 8.0027 (5.1); 7.9743 (2.6); 4.0001 (16.0); 3.8021 (1.1); 3.7772 (3.8); 3.7527 (3.8); 3.7283 (1.2); 3.3256 (45.6); 2.5075 (34.3); 2.5017 (45.1); 2.4959 (31.4); 1.3445 (4.1); 1.3200 (9.2); 1.2954 (3.9); −0.0004 (2.6) |
| I-098 | 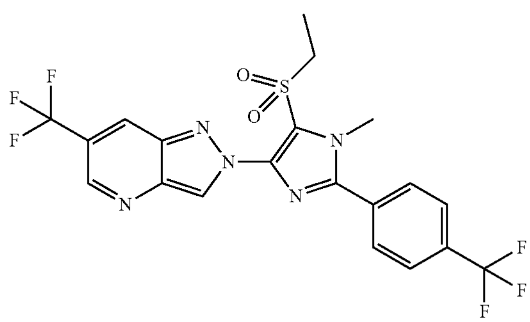 [SMILES: CCS(=O)(=O)c1c(-n2cc3ncc(C(F)(F)F)cc3n2)nc(-c2ccc(C(F)(F)F)cc2)n1C] | I-098: $^1$H-NMR(300.1 MHz, d$_6$-DMSO):<br>δ = 13.0683 (0.8); 10.3906 (0.8); 9.3609 (4.8); 8.9336 (3.1); 8.9273 (3.2); 8.8369 (2.8); 8.0875 (2.5); 8.0603 (4.8); 8.0035 (4.8); 7.9751 (3.1); 7.6151 (0.9); 4.0026 (16.0); 3.8258 (1.3); 3.7984 (4.2); 3.7743 (3.6); 3.4524 (1.0); 3.4283 (1.1); 3.4017 (1.3); 3.3289 (2551.4); 3.2812 (3.0); 3.2607 (1.9); 3.2512 (1.9); 3.2207 (0.9); 3.2113 (0.9); 3.2038 (0.8); 3.1769 (0.9); 2.9440 (0.8); 2.7272 (1.7); 2.5130 (86.8); 2.5072 (170.2); 2.5013 (224.9); 2.4954 (155.3); 2.4386 (0.8); 2.4274 (0.8); 2.2716 (1.4); 2.2648 (1.2); 2.0734 (2.1); 1.3570 (4.2); 1.3324 (9.6); 1.3079 (3.8); 0.0295 (0.8); 0.0103 (5.3); −0.0004 (115.2); −0.0115 (3.1) |

NMR Data of Selected Examples
NMR Peak List Method

The 1H-NMR data of selected examples are noted in the form of 1H-NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore takes the form of: δ$_1$ (intensity$_1$); δ$_2$ (intensity$_2$); ... ; δ$_i$(intensity$_i$); ... ; δ$_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form the subject-matter of the invention, and/or peaks of impurities.

In the reporting of compound signals in the delta range of solvents and/or water, our lists of 1H NMR peaks show the usual solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

Use examples

*Ctenocephalides felis*—In Vitro Contact Tests with Adult Cat Fleas

For the coating of the test tubes, 9 mg of active ingredient are first dissolved in 1 ml of acetone p.a. and then diluted to the desired concentration with acetone p.a. 250 μl of the solution are distributed homogeneously on the inner walls and the base of a 25 ml glass tube by turning and rocking on an orbital shaker (rocking rotation at 30 rpm for 2 h). With 900 ppm of active ingredient solution and internal surface area 44.7 $cm^2$, given homogeneous distribution, an area-based dose of 5 μg/$cm^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 μg/$cm^2$. 100% efficacy means that all the fleas were dead or moribund. 0% efficacy means that no fleas were harmed.

In this test, for example, the following compounds from the preparation examples show an efficacy of 100% at an application rate of 5 μg/$cm^2$ (=500 g/ha): I-003, I-005, I-007, I-009, I-011, I-013, I-014, I-015, I-018, I-019, I-020, I-022, I-023

*Boophilus microplus*—Injection Test

Solvent: dimethyl sulfoxide

To produce a suitable active ingredient formulation, 10 mg of active ingredient are mixed with 0.5 ml of solvent and the concentrate is diluted to the desired concentration with solvent. 1 μl of the active ingredient solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 100% at an application rate of 20 μg/animal: I-041

In this test, for example, the following compounds from the preparation examples show an efficacy of 90% at an application rate of 20 μg/animal: I-016

*Ctenocephalides felis*—Oral Test

Solvent: dimethyl sulfoxide

To produce a suitable active ingredient formulation, 10 mg of active ingredient are mixed with 0.5 ml of dimethyl sulfoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active ingredient formulation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: I-003, I-005, I-011, I-013, I-014, I-015, I-018, I-020, I-023, I-033, I-038, I-039, I-055

In this test, for example, the following compounds from the preparation examples show an efficacy of 95% at an application rate of 100 ppm: I-007, I-009, I-019, I-022, I-029

In this test, for example, the following compounds from the preparation examples show an efficacy of 90% at an application rate of 100 ppm: I-040

In this test, for example, the following compounds from the preparation examples show an efficacy of 80% at an application rate of 100 ppm: I-025, I-049

*Lucilia cuprina* Test

Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

About 20 L1 larvae of the Australian sheep blowfly (*Lucilia cuprina*) are transferred into a test vessel containing minced horsemeat and the active ingredient formulation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: I-001, I-003, I-005, I-007, I-008, I-009, I-011, I-012, I-013, I-014, I-015, I-016, I-018, I-019, I-020, I-022, I-023, I-030, I-033, I-040, I-043, I-049, I-055, I-092

In this test, for example, the following compounds from the preparation examples show an efficacy of 95% at an application rate of 100 ppm: I-029, I-046

In this test, for example, the following compounds from the preparation examples show an efficacy of 80% at an application rate of 100 ppm: I-021

*Musca domestica* Test

Solvent: dimethyl sulfoxide

To produce a suitable active ingredient formulation, 10 mg of active ingredient are mixed with 0.5 ml of dimethyl sulfoxide, and the concentrate is diluted with water to the desired concentration.

Vessels containing a sponge treated with sugar solution and the desired concentration of active ingredient formulation are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 100% at an application rate of 100 ppm: I-005, I-019

In this test, for example, the following compounds from the preparation examples show an efficacy of 90% at an application rate of 100 ppm: I-033

In this test, for example, the following compounds from the preparation examples show an efficacy of 80% at an application rate of 100 ppm: I-009, I-014, I-018, I-049

*Myzus persicae*—Oral Test

| Solvent: | 100 parts by weight of acetone |
| --- | --- |

To produce a suitable active ingredient formulation, 1 part by weight of active ingredient is dissolved with the stated parts by weight of solvent and made up to the desired concentration with water.

50 µl of the active ingredient formulation are transferred into microtitre plates and made up to a final volume of 200 µl with 150 µl of IPL41 insect medium (33%+15% sugar). Subsequently, the plates are sealed with parafilm, which a mixed population of green peach aphids (*Myzus persicae*) within a second microtitre plate is able to puncture and imbibe the solution.

After 5 days, the efficacy in % is determined. 100% means that all the aphids have been killed; 0% means that no aphids have been killed.

In this test, for example, the following compounds from the preparation examples show an efficacy of 100% at an application rate of 4 ppm: I-001, I-002, I-003, I-004, I-005, I-007, I-008, I-009, I-011, I-012, I-013, I-014, I-015, I-016, I-017, I-018, I-019, I-020, I-021, I-022, I-023, I-025, I-026, I-027, I-028, I-029, I-030, I-031, I-032, I-033, I-034, I-036, I-038, I-039, I-040, I-041, I-042, I-043, I-044, I-045, I-046, 1-047, I-048, I-049, I-051, I-052, I-053, I-055, I-056, I-057, I-058, I-059, I-060, I-061, I-062, I-063, I-064, I-065, I-066, I-067, I-068, I-069, I-070, I-072, I-075, I-079, I-080, I-081, I-082, I-084, I-085, I-086, I-087, I-092, I-093, I-094, I-095, I-097, I-098

In this test, for example, the following compounds from the preparation examples show an efficacy of 90% at an application rate of 4 ppm: I-024, I-037, I-050, I-054, I-078, I-096

*Myzus persicae*—Spray Test

| Solvent: | 78 parts by weight of acetone |
| --- | --- |
| Emulsifier: | 1.5 parts by weight of dimethylformamide alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 5 days, the efficacy in % is determined. 100% means that all the aphids have been killed; 0% means that no aphids have been killed.

In this test, for example, the following compounds from the preparation examples show an efficacy of 100% at an application rate of 100 g/ha: I-011, I-014, I-016, I-017, I-018, I-019, I-020, I-021, I-022, I-023, I-030, I-036, I-039, I-040, I-047, I-059, I-060, I-061, I-062, I-063, I-064, I-065, I-067, I-070, I-076

In this test, for example, the following compounds from the preparation examples show an efficacy of 90% at an application rate of 100 g/ha: I-003, I-005, I-007, I-008, I-009, I-012, I-013, I-015, I-026, I-027, I-028, I-033, I-034, I-038, I-041, I-042, I-043, I-048, I-049, I-050, I-051, I-055, I-057, I-058, I-069, I-071, I-074, I-075, I-077, I-079, I-082, I-084, I-085, I-086, I-095, I-096

In this test, for example, the following compounds from the preparation examples show an efficacy of 70% at an application rate of 100 g/ha: I-029, I-066

*Phaedon cochleariae*—Spray Test

| Solvent: | 78.0 parts by weight of acetone |
| --- | --- |
| Emulsifier: | 1.5 parts by weight of dimethylformamide alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) are sprayed with an active ingredient formulation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 83% at an application rate of 500 g/ha: I-066

In this test, for example, the following compounds from the preparation examples show an efficacy of 100% at an application rate of 100 g/ha: I-005, I-007, I-011, I-013, I-014, I-015, I-018, I-019, I-020, I-022, I-023, I-024, I-026, I-027, I-028, I-029, I-036, I-038, I-041, I-042, I-046, I-049, I-055, I-057, I-059, I-060, I-061, I-062, I-063, I-067, I-068, I-069, I-070, I-076, I-077, I-078, I-080, I-081, I-082, I-087, I-093, I-096, I-097, I-098

In this test, for example, the following compounds from the preparation examples show an efficacy of 83% at an application rate of 100 g/ha: I-035, I-064, I-079, I-094

In this test, for example, the following compounds from the preparation examples show an efficacy of 67% at an application rate of 100 g/ha: I-092

*Spodoptera frugiperda*—Spray Test

| Solvent: | 78.0 parts by weight of acetone |
| --- | --- |
| Emulsifier: | 1.5 parts by weight of dimethylformamide alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Leaf discs of maize (*Zea mays*) are sprayed with an active ingredient formulation of the desired concentration and, after drying, populated with caterpillars of the fall armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 100 g/ha: I-005, I-007, I-011, I-014, I-015, I-019, I-024, I-025, I-027, I-033, I-063, I-069, I-076, I-078, I-081, I-087, I-092, I-093, I-094, I-095, I-097, I-098

In this test, for example, the following compounds from the preparation examples show an efficacy of 83% at an application rate of 100 g/ha: I-018, I-020, I-060, I-070, I-082, I-096

In this test, for example, the following compounds from the preparation examples show an efficacy of 67% at an application rate of 100 g/ha: I-057

*Tetranvchus urticae*—Spray Test, OP-Resistant

| Solvent: | 78.0 parts by weight of acetone |
|---|---|
| Emulsifier: | 1.5 parts by weight of dimethylformamide alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active ingredient formulation of the desired concentration.

After 6 days, the efficacy in % is determined. 100% means that all the spider mites have been killed; 0% means that no spider mites have been killed.

In this test, for example, the following compounds from the preparation examples show an efficacy of 100% at an application rate of 100 g/ha: I-054, I-070, I-077, I-082, I-092

In this test, for example, the following compounds from the preparation examples show an efficacy of 90% at an application rate of 100 g/ha: I-049, I-050, I-055, I-066, I-074, I-075, I-076, I-086

In this test, for example, the following compounds from the preparation examples show an efficacy of 100% at an application rate of 20 g/ha: I-082

In this test, for example, the following compounds from the preparation examples show an efficacy of 90% at an application rate of 20 g/ha: I-042, I-049, I-077, I-087.

The invention claimed is:
1. A compound of formula (I)

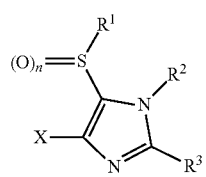

in which:
$R^1$ is $(C_1-C_6)$alkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkyl, $(C_2-C_6)$alkenyl, $(C_2-C_6)$haloalkenyl, $(C_2-C_6)$alkynyl, $(C_2-C_6)$haloalkynyl or $(C_3-C_8)$cycloalkyl,
$R^2$ is hydrogen, $(C_1-C_6)$alkyl, $(C 1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl,
$R^3$ is hydrogen, halogen, cyano, nitro, $(C_1-C_6)$alkyl, $(C_1-C_6)$haloalkyl, $(C_1-C_6)$alkoxy, $(C_1-C_6)$haloalkoxy, $(C_1-C_6)$alkylthio, $(C_1-C_6)$haloalkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, SCN, $(C_1-C_6)$alkylcarbonyl, $(C_1-C_6)$haloalkylcarbonyl, $(C_1-C_6)$alkoxycarbonyl, $(C_1-C_6)$haloalkoxycarbonyl, aminocarbonyl, $(C_1-C_6)$alkylaminocarbonyl, di$(C_1-C_6)$alkylaminocarbonyl, $(C_1-C_6)$haloalkylaminocarbonyl, $(C_3-C_8)$cycloalkylaminocarbonyl, aminothiocarbonyl, $(C_1-C_6)$alkylaminothiocarbonyl, di$(C_1-C_6)$alkylaminothiocarbonyl, $(C_1-C_6)$haloalkylaminothiocarbonyl, $(C_3-C_8)$cycloalkylaminothiocarbonyl, amino, $(C_1-C_6)$alkylamino, $(C_1-C_6)$haloalkylamino, di$(C_1-C_6)$alkylamino, $(C_3-C_8)$cycloalkylamino, $(C_1-C_6)$alkylsulfonylamino, $(C_1-C_6)$alkylcarbonylamino, $(C_1-C_6)$haloalkylcarbonylamino, $(C_1-C_6)$alkylcarbonyl-$(C_1-C_6)$alkylamino, $(C_1-C_6)$haloalkylcarbonyl-$(C_1-C_6)$alkylamino, $(C_3-C_8)$cycloalkylcarbonylamino, $(C_3-C_8)$cycloalkylcarbonyl-$(C_1-C_6)$alkylamino, $(C_1-C_6)$alkylthiocarbonylamino, $(C_1-C_6)$haloalkylthiocarbonylamino, $(C_1-C_6)$alkylthiocarbonyl-$(C_1-C_6)$alkylamino, $(C_1-C_6)$haloalkylthiocarbonyl-$(C_1-C_6)$alkylamino, $(C_3-C_8)$cycloalkylthiocarbonylamino, $(C_3-C_8)$cycloalkylthiocarbonyl-$(C_1-C_6)$alkylamino, $(C_2-C_6)$alkenyl, $(C_2-C_6)$haloalkenyl, $(C_2-C_6)$cyanoalkenyl, $(C_3-C_8)$cycloalkyl-$(C_2)$alkenyl, $(C_2-C_6)$alkynyl, $(C_2-C_6)$haloalkynyl, $(C_3-C_6)$cycloalkyl-$(C_2)$alkynyl, $(C_3-C_6)$cycloalkyl-$(C_1-C_6)$alkyl, $(C_1-C_6)$alkylaminocarbonylamino, di$(C_1-C_6)$alkylaminocarbonylamino, $(C_3-C_6)$cycloalkylaminocarbonylamino, $(C_1-C_6)$haloalkylaminocarbonylamino, $(C_1-C_6)$alkylaminocarbonyl-$(C_1-C_6)$alkylamino, di$(C_1-C_6)$alkylaminocarbonyl-$(C_1-C_6)$alkylamino, $(C_3-C_6)$cycloalkylaminocarbonyl-$(C_1-C_6)$alkylamino or $(C_1-C_6)$haloalkylaminocarbonyl-$(C_1-C_6)$alkylamino,
or is aryl, hetaryl, cyclopentenyl or cyclohexenyl, each of which is optionally mono- or polysubstituted by identical or different substituents, wherein if $R^3$ is hetaryl at least one carbonyl group may optionally be present, and where optional substituents are as follows: cyano, carboxyl, halogen, nitro, acetyl, hydroxyl, amino, SCN, $SF_5$, tri$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, $(C_1-C_6)$haloalkyl-$(C_3-C_8)$cycloalkyl, halo$(C_3-C_8)$cycloalkyl, cyano$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_3-C_8)$cycloalkyl-$(C_2)$alkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkoxyimino, $(C_1-C_6)$haloalkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-

$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)haloalkylsulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di($C_1$-$C_6$)alkylaminocarbonyl, ($C_1$-$C_6$)haloalkylaminocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, ($C_1$-$C_6$)haloalkylamino, ($C_3$-$C_8$)cycloalkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl, ($C_1$-$C_6$)haloalkylaminothiocarbonyl, ($C_3$-$C_8$)cycloalkylaminothiocarbonyl, ($C_1$-$C_6$)alkylcarbonylamino, ($C_1$-$C_6$)haloalkylcarbonylamino, ($C_1$-$C_6$)alkylcarbonyl-($C_1$-$C_6$)alkylamino, ($C_1$-$C_6$)haloalkylcarbonyl-($C_1$-$C_6$)alkylamino, ($C_3$-$C_8$)cycloalkylcarbonylamino, ($C_3$-$C_8$)cycloalkylcarbonyl-($C_1$-$C_6$)alkylamino, ($C_1$-$C_6$)alkylthiocarbonylamino, ($C_1$-$C_6$)haloalkylthiocarbonylamino, ($C_1$-$C_6$)alkylthiocarbonyl-($C_1$-$C_6$)alkylamino, ($C_1$-$C_6$)haloalkylthiocarbonyl-($C_1$-$C_6$)alkylamino, ($C_3$-$C_8$)cycloalkylthiocarbonylamino, ($C_3$-$C_8$)cycloalkylthiocarbonyl-($C_1$-$C_6$)alkylamino, hetaryl, oxohetaryl, halohetaryl, halooxohetaryl, cyanohetaryl, cyanooxohetaryl, ($C_1$-$C_6$)haloalkylhetaryl or ($C_1$-$C_6$)haloalkyloxohetaryl, X is a heteroaromatic 9-membered or 12-membered fused bicyclic or tricyclic ring system from the group of Q1 to Q12

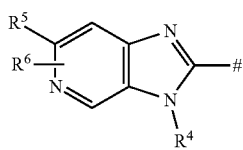
Q1

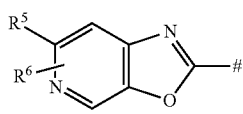
Q2

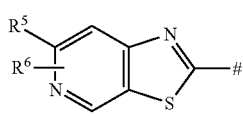
Q3

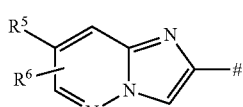
Q4

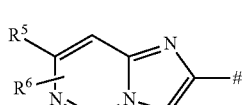
Q5

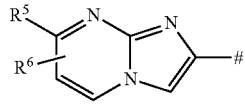
Q6

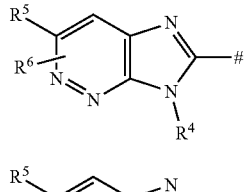
Q7

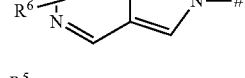
Q8

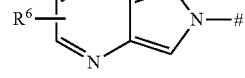
Q9

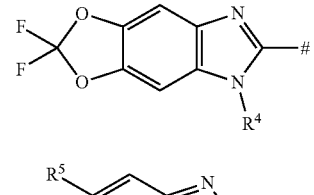
Q10

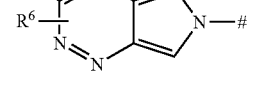
Q11

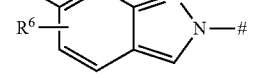
Q12

$R^4$ is hydrogen, ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_2$-$C_6$)alkenyl, or ($C_2$-$C_6$)alkynyl, $R^5$ is hydrogen, ($C_1$-$C_6$)alkyl, or ($C_1$-$C_6$)haloalkyl, $R^6$ is hydrogen, and n is 0, 1 or 2.

2. A compound of formula (I) according to claim 1, in which $R^1$ is ($C_1$-$C_4$)alkyl, ($C_1$-$C_4$)cyanoalkyl, ($C_1$-$C_4$)alkoxy-($C_1$-$C_4$)alkyl, ($C_1$-$C_4$)haloalkyl, ($C_2$-$C_4$)alkenyl, or ($C_2$-$C_4$)alkynyl, $R^2$ is hydrogen, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, or ($C_1$-$C_4$)haloalkoxy-($C_1$-$C_4$)alkyl, $R^3$ is hydrogen, halogen, cyano, nitro, ($C_1$-$C_4$)alkyl, ($C_1$-$C_4$)haloalkyl, ($C_1$-$C_4$)alkoxy, ($C_1$-$C_4$)haloalkoxy, ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, SCN, ($C_1$-$C_4$)alkylcarbonyl, ($C_1$-$C_4$)haloalkylcarbonyl, ($C_1$-$C_4$)alkoxycarbonyl, ($C_1$-$C_4$)haloalkoxycarbonyl, aminocarbonyl, ($C_1$-$C_4$)alkylaminocarbonyl, di($C_1$-$C_4$)alkylaminocarbonyl, ($C_1$-$C_4$)haloalkylaminocarbonyl, ($C_3$-$C_6$)cycloalkylaminocarbonyl, aminothiocarbonyl, ($C_1$-$C_4$)alkylaminothiocarbonyl, di($C_1$-$C_4$)alkylaminothiocarbonyl, ($C_1$-$C_4$)haloalkylaminothiocarbonyl, ($C_3$-$C_6$)cycloalkylaminothiocarbonyl, amino, ($C_1$-$C_4$)alkylamino, ($C_1$-$C_4$)haloalkylamino, di($C_1$-$C_4$)alkylamino, ($C_3$-$C_6$)

cycloalkylamino, ($C_1$-$C_4$)alkylsulfonylamino, ($C_1$-$C_4$)alkylcarbonylamino, ($C_1$-$C_4$)haloalkylcarbonylamino, ($C_1$-$C_4$)alkylcarbonyl-($C_1$-$C_4$)alkylamino, ($C_1$-$C_4$)haloalkylcarbonyl-($C_1$-$C_4$)alkylamino, ($C_3$-$C_6$)cycloalkylcarbonylamino, ($C_3$-$C_6$)cycloalkylcarbonyl-($C_1$-$C_4$) alkylamino, ($C_1$-$C_4$)alkylthiocarbonylamino, ($C_1$-$C_4$) haloalkylthiocarbonylamino, ($C_1$-$C_4$) alkylthiocarbonyl-($C_1$-$C_4$)alkylamino, ($C_1$-$C_4$) haloalkylthiocarbonyl-($C_1$-$C_4$)alkylamino, ($C_3$-$C_6$) cycloalkylthiocarbonylamino, ($C_3$-$C_6$) cycloalkylthiocarbonyl-($C_1$-$C_4$)alkylamino, ($C_2$-$C_4$) alkenyl, ($C_2$-$C_4$)haloalkenyl, ($C_2$-$C_4$)cyanoalkenyl, ($C_3$-$C_6$)cycloalkyl-($C_2$)alkenyl, ($C_2$-$C_4$)alkynyl, ($C_2$-$C_4$)haloalkynyl, ($C_3$-$C_6$)cycloalkyl-($C_2$)alkynyl, ($C_3$-$C_6$)cycloalkyl-($C_1$-$C_4$)alkyl, ($C_1$-$C_4$)alkylaminocarbonylamino, di($C_1$-$C_4$)alkylaminocarbonylamino, ($C_3$-$C_6$)cycloalkylaminocarbonylamino, ($C_1$-$C_4$) haloalkylaminocarbonylamino, ($C_1$-$C_4$) alkylaminocarbonyl-($C_1$-$C_4$)alkylamino, di($C_1$-$C_4$) alkylaminocarbonyl-($C_1$-$C_4$)alkylamino, ($C_3$-$C_6$) cycloalkylaminocarbonyl-($C_1$-$C_4$)alkylamino or ($C_1$-$C_4$)haloalkylaminocarbonyl-($C_1$-$C_4$)alkylamino, or is aryl, hetaryl, cyclopentenyl or cyclohexenyl, each of which is optionally mono- or polysubstituted by identical or different substituents, where if $R^3$ is hetaryl at least one carbonyl group may optionally be present, and where optional substituents are as follows: cyano, carboxyl, halogen, nitro, acetyl, hydroxyl, amino, SCN, $SF_5$, tri($C_1$-$C_4$)alkylsilyl, ($C_3$-$C_6$)cycloalkyl, ($C_3$-$C_6$) cycloalkyl-($C_3$-$C_6$)cycloalkyl, ($C_1$-$C_4$)alkyl-($C_3$-$C_6$) cycloalkyl, ($C_1$-$C_4$)haloalkyl-($C_3$-$C_6$)cycloalkyl, halo ($C_3$-$C_6$)cycloalkyl, cyano($C_3$-$C_6$)cycloalkyl, ($C_1$-$C_4$) alkyl, ($C_1$-$C_4$)haloalkyl, ($C_1$-$C_4$)cyanoalkyl, ($C_1$-$C_4$) hydroxyalkyl, hydroxycarbonyl-($C_1$-$C_4$)alkoxy, ($C_1$-$C_4$)alkoxycarbonyl-($C_1$-$C_4$)alkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$) cyanoalkenyl, ($C_3$-$C_6$)cycloalkyl-($C_2$)alkenyl, ($C_2$-$C_4$) alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxycarbonyl-($C_1$-$C_4$)alkoxy, ($C_1$-$C_4$)alkoxy-($C_1$-$C_4$)alkoxy, ($C_1$-$C_4$)alkoxyimino, ($C_1$-$C_4$)haloalkoxyimino, ($C_1$-$C_4$)alkylthio, ($C_1$-$C_4$) haloalkylthio, ($C_1$-$C_4$)alkoxy-($C_1$-$C_4$)alkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkoxy-($C_1$-$C_4$) alkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$) alkoxy-($C_1$-$C_4$)alkylsulfonyl, ($C_1$-$C_4$)alkylsulfonyl-($C_1$-$C_4$)alkyl, ($C_1$-$C_4$)alkylsulfonyloxy, ($C_1$-$C_4$) haloalkylsulfonyloxy, ($C_1$-$C_4$)alkylcarbonyl, ($C_1$-$C_4$) haloalkylcarbonyl, ($C_1$-$C_4$)alkylcarbonyloxy, ($C_1$-$C_4$) alkoxycarbonyl, ($C_1$-$C_4$)haloalkoxycarbonyl, aminocarbonyl, ($C_1$-$C_4$)alkylaminocarbonyl, ($C_1$-$C_4$) haloalkylaminocarbonyl, di($C_1$-$C_4$)alkylaminocarbonyl, ($C_2$-$C_4$)alkenylaminocarbonyl, di($C_2$-$C_4$)alkenylaminocarbonyl, ($C_3$-$C_6$)cycloalkylaminocarbonyl, ($C_1$-$C_4$)alkylsulfonylamino, ($C_1$-$C_4$)alkylamino, di($C_1$-$C_4$)alkylamino, ($C_1$-$C_4$)haloalkylamino, ($C_3$-$C_6$)cycloalkylamino, aminosulfonyl, ($C_1$-$C_4$)alkylaminosulfonyl, di($C_1$-$C_4$)alkylaminosulfonyl, ($C_1$-$C_4$) alkylsulfoximino, aminothiocarbonyl, ($C_1$-$C_4$) alkylaminothiocarbonyl, di($C_1$-$C_4$) alkylaminothiocarbonyl, ($C_1$-$C_4$) haloalkylaminothiocarbonyl, ($C_3$-$C_6$) cycloalkylaminothiocarbonyl, ($C_1$-$C_4$) alkylcarbonylamino, ($C_1$-$C_4$)haloalkylcarbonylamino, ($C_1$-$C_4$)alkylcarbonyl-($C_1$-$C_4$)alkylamino, ($C_1$-$C_4$)haloalkylcarbonyl-($C_1$-$C_4$)alkylamino, ($C_3$-$C_6$)cycloalkylcarbonylamino, ($C_3$-$C_6$)cycloalkylcarbonyl-($C_1$-$C_4$) alkylamino, ($C_1$-$C_4$)alkylthiocarbonylamino, ($C_1$-$C_4$) haloalkylthiocarbonylamino, ($C_1$-$C_4$) alkylthiocarbonyl-($C_1$-$C_4$)alkylamino, ($C_1$-$C_4$) haloalkylthiocarbonyl-($C_1$-$C_4$)alkylamino, ($C_3$-$C_6$) cycloalkylthiocarbonylamino, ($C_3$-$C_6$) cycloalkylthiocarbonyl-($C_1$-$C_4$)alkylamino, hetaryl, oxohetaryl, halohetaryl, halooxohetaryl, cyanohetaryl, cyanooxohetaryl, ($C_1$-$C_4$)haloalkylhetaryl or ($C_1$-$C_4$) haloalkyloxohetaryl, X is a heteroaromatic 9-membered or 12-membered fused bicyclic or tricyclic ring system from the series Q1 to Q12, $R^4$ is hydrogen, ($C_1$-$C_4$)alkyl, ($C_1$-$C_4$)haloalkyl, ($C_1$-$C_4$) cyanoalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, or ($C_2$-$C_4$) alkynyl, $R^5$ is hydrogen, ($C_1$-$C_4$)alkyl, ($C_1$-$C_4$)haloalkyl, $R^6$ is hydrogen, and n is 0, 1 or 2.

3. A compound of formula (I) according to claim 1, in which $R^1$ is ($C_1$-$C_4$)alkyl, ($C_1$-$C_4$)haloalkyl, ($C_2$-$C_4$)alkenyl, ($C_2$-$C_4$)haloalkenyl or ($C_3$-$C_6$)cycloalkyl, $R^2$ is hydrogen, ($C_1$-$C_4$)alkyl, or ($C_1$-$C_4$)haloalkyl, $R^3$ is hydrogen, halogen, cyano, ($C_1$-$C_4$)alkyl, ($C_1$-$C_4$) haloalkyl, ($C_1$-$C_4$)alkoxy, ($C_1$-$C_4$)haloalkoxy, aminocarbonyl, ($C_1$-$C_4$)alkylaminocarbonyl, di($C_1$-$C_4$)alkylaminocarbonyl, ($C_1$-$C_4$)haloalkylaminocarbonyl, ($C_3$-$C_6$)cycloalkylaminocarbonyl, amino, ($C_1$-$C_4$)alkylamino, ($C_1$-$C_4$)haloalkylamino, di($C_1$-$C_4$)alkylamino, ($C_3$-$C_6$)cycloalkylamino, ($C_1$-$C_4$)alkylsulfonylamino, ($C_1$-$C_4$)alkylcarbonylamino, ($C_1$-$C_4$)haloalkylcarbonylamino, ($C_1$-$C_4$)alkylcarbonyl-($C_1$-$C_2$)alkylamino, ($C_1$-$C_4$)haloalkylcarbonyl-($C_1$-$C_2$)alkylamino, ($C_3$-$C_6$) cycloalkylcarbonylamino, ($C_3$-$C_6$)cycloalkylcarbonyl-($C_1$-$C_2$)alkylamino, ($C_2$-$C_4$)alkenyl, ($C_2$-$C_4$)haloalkenyl, ($C_2$-$C_4$)cyanoalkenyl, ($C_3$-$C_6$)cycloalkyl-($C_2$) alkenyl, ($C_2$-$C_4$)alkynyl, ($C_3$-$C_6$)cycloalkyl-($C_2$) alkynyl, ($C_3$-$C_6$)cycloalkyl-($C_1$-$C_4$)alkyl, ($C_1$-$C_4$) alkoxycarbonyl, aminothiocarbonyl, ($C_1$-$C_4$) alkylaminothiocarbonyl, di($C_1$-$C_4$) alkylaminothiocarbonyl, ($C_1$-$C_4$) haloalkylaminothiocarbonyl, or is phenyl, pyridyl, pyrimidyl, pyridazinyl, thiophenyl, furanyl, pyrazolyl, thiazolyl, oxazolyl, imidazolyl, pyrrolyl, cyclopentenyl or cyclohexenyl, each of which is optionally mono- or polysubstituted by identical or different substituents, where if $R^3$ is hetaryl at least one carbonyl group may optionally be present, and where optional substituents are as follows: cyano, halogen, ($C_3$-$C_6$)cycloalkyl, ($C_1$-$C_4$)alkyl-($C_3$-$C_6$)cycloalkyl, halo($C_3$-$C_6$)cycloalkyl, cyano($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_2$)alkyl, ($C_2$-$C_4$)alkenyl, ($C_2$-$C_4$)haloalkenyl, ($C_2$-$C_4$)cyanoalkenyl, ($C_3$-$C_6$)cycloalkyl-($C_2$)alkenyl, ($C_2$-$C_4$)alkynyl, ($C_2$-$C_4$)haloalkynyl, ($C_2$-$C_4$)cyanoalkynyl, ($C_1$-$C_4$)alkylcarbonyl, ($C_1$-$C_4$)haloalkylcarbonyl, aminocarbonyl, ($C_1$-$C_4$)alkylaminocarbonyl, ($C_1$-$C_4$)haloalkylaminocarbonyl, di($C_1$-$C_4$)alkylaminocarbonyl, ($C_3$-$C_6$)cycloalkylaminocarbonyl, aminothiocarbonyl, ($C_1$-$C_4$)alkylaminothiocarbonyl, di($C_1$-$C_4$) alkylaminothiocarbonyl, ($C_1$-$C_4$) haloalkylaminothiocarbonyl, ($C_3$-$C_6$) cycloalkylaminothiocarbonyl, ($C_1$-$C_4$)

alkylsulfonylamino, $(C_1-C_4)$alkylamino, di$(C_1-C_4)$ alkylamino, $(C_1-C_4)$haloalkylamino, $(C_3-C_6)$cycloalkylamino, aminosulfonyl, $(C_1-C_4)$alkylaminosulfonyl, di$(C_1-C_4)$alkylaminosulfonyl, $(C_1-C_4)$alkylcarbonylamino, $(C_1-C_4)$haloalkylcarbonylamino, $(C_1-C_4)$alkylcarbonyl-$(C_1-C_2)$alkylamino, $(C_1-C_2)$haloalkylcarbonyl-$(C_1-C_2)$alkylamino, $(C_3-C_6)$cycloalkylcarbonylamino, $(C_3-C_6)$cycloalkylcarbonyl-$(C_1-C_2)$alkylamino, $(C_1-C_4)$alkylthiocarbonylamino, $(C_1-C_4)$haloalkylthiocarbonylamino, $(C_1-C_4)$alkylthiocarbonyl-$(C_1-C_2)$alkylamino, $(C_1-C_4)$haloalkylthiocarbonyl-$(C_1-C_2)$alkylamino, $(C_3-C_6)$cycloalkylthiocarbonylamino or $(C_3-C_6)$cycloalkylthiocarbonyl-$(C_1-C_2)$alkylamino, X is a heteroaromatic 9-membered or 12-membered fused bicyclic or tricyclic ring system from the series Q1, Q2, Q4, Q5, Q6, Q7, Q8, Q9, Q10, Q11 or Q12, $R^4$ is hydrogen, $(C_1-C_4)$alkyl, $(C_1-C_4)$haloalkyl, $(C_2-C_4)$alkenyl, or $(C_2-C_4)$alkynyl, $R^5$ is $(C_1-C_4)$haloalkyl, $R^6$ is hydrogen, and n is 0, 1 or 2.

4. A compound of formula (I) according to claim 1, in which $R^1$ is methyl, ethyl, n-propyl, isopropyl, cyclopropyl, fluoromethyl, difluoromethyl, trifluoromethyl, fluoroethyl, difluoroethyl, trifluoroethyl, tetrafluoroethyl or pentafluoroethyl, $R^2$ is hydrogen, methyl, ethyl, n-propyl, isopropyl, n-butyl, isobutyl, tert-butyl, fluoromethyl, difluoromethyl, trifluoromethyl, fluoroethyl, difluoroethyl, trifluoroethyl, tetrafluoroethyl or pentafluoroethyl, $R^3$ is hydrogen, $(C_1-C_4)$alkyl, $(C_1-C_4)$haloalkyl, $(C_2-C_4)$alkenyl, $(C_2-C_4)$haloalkenyl, $(C_2-C_4)$cyanoalkenyl, $(C_3-C_6)$cycloalkyl-$(C_2)$alkenyl, halogen, cyano, $(C_2-C_4)$alkynyl, $(C_3-C_6)$cycloalkyl-$(C_2)$alkynyl, $(C_3-C_6)$cycloalkyl-$(C_1-C_4)$alkyl, $(C_1-C_4)$alkoxycarbonyl, aminocarbonyl, $(C_1-C_4)$alkylaminocarbonyl, di$(C_1-C_4)$alkylaminocarbonyl, $(C_1-C_4)$haloalkylaminocarbonyl, aminothiocarbonyl, $(C_1-C_4)$alkylaminothiocarbonyl, di$(C_1-C_4)$alkylaminothiocarbonyl, $(C_1-C_4)$haloalkylaminothiocarbonyl, or is phenyl, pyridyl, pyrimidyl, pyridazinyl, thiophenyl, thiazolyl, oxazolyl, imidazolyl, pyrazolyl, pyrrolyl, cyclopentenyl or cyclohexenyl, each of which is optionally mono- or polysubstituted by identical or different substituents—bridged via a carbon atom to the rest of the molecule—where optional substituents are as follows: cyano, halogen, nitro, acetyl, hydroxyl, amino, $(C_3-C_6)$cycloalkyl, $(C_1-C_4)$alkyl-$(C_3-C_6)$cycloalkyl, halo$(C_3-C_6)$cycloalkyl, cyano$(C_3-C_6)$cycloalkyl, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_2)$alkyl, $(C_1-C_4)$alkoxy, $(C_1-C_4)$haloalkoxy, $(C_1-C_4)$alkoxy-$(C_1-C_2)$alkoxy, $(C_1-C_4)$alkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylcarbonyl, aminocarbonyl, $(C_1-C_4)$alkylaminocarbonyl, di$(C_1-C_4)$alkylaminocarbonyl, $(C_1-C_4)$haloalkylaminocarbonyl, $(C_3-C_6)$cycloalkylaminocarbonyl, $(C_1-C_4)$alkylsulfonylamino, $(C_1-C_4)$alkylamino, di$(C_1-C_4)$alkylamino, $(C_1-C_4)$haloalkylamino, $(C_3-C_6)$cycloalkylamino, $(C_1-C_4)$alkylcarbonylamino, $(C_1-C_4)$haloalkylcarbonylamino, $(C_1-C_4)$alkylcarbonyl-$(C_1-C_2)$alkylamino, $(C_1-C_4)$haloalkylcarbonyl-$(C_1-C_2)$alkylamino, $(C_3-C_6)$cycloalkylcarbonylamino, $(C_3-C_6)$cycloalkylcarbonyl-$(C_1-C_2)$alkylamino, or is pyrazolyl or imidazolyl, each of which is optionally mono- or polysubstituted by identical or different substituents—bridged via a nitrogen atom to the rest of the molecule—where optional substituents are as follows: cyano, halogen, nitro, hydroxyl, amino, $(C_3-C_6)$cycloalkyl, $(C_1-C_4)$alkyl, $(C_1-C_4)$haloalkyl, $(C_1-C_4)$alkoxy, $(C_1-C_4)$haloalkoxy, aminocarbonyl, X is Q1, Q4, Q5, Q7, Q8, Q9, Q11 or Q12, $R^4$ is methyl, ethyl, n-propyl, isopropyl, n-butyl, isobutyl, tert-butyl, methoxymethyl or methoxyethyl, $R^5$ is fluoromethyl, difluoromethyl, trifluoromethyl, fluoroethyl, difluoroethyl, trifluoroethyl, tetrafluoroethyl, or pentafluoroethyl, $R^6$ is hydrogen, and n is 0, 1 or 2.

5. A compound of formula (I) according to claim 1, in which $R^1$ is ethyl or isopropyl, $R^2$ is methyl, ethyl or isopropyl, $R^3$ is hydrogen, bromine, cyano, ethenyl, cyclopropylethenyl, isopropenyl, cyclopropylethynyl, methyl, ethyl, isopropyl, cyclopropylethyl, methoxycarbonyl, trifluoroethylaminocarbonyl, aminocarbonyl, methylaminocarbonyl, dimethylaminocarbonyl, ethylaminocarbonyl, aminothiocarbonyl, methylaminothiocarbonyl, dimethylaminothiocarbonyl, or is phenyl, pyridyl, pyrimidyl, pyridazinyl, thiophenyl (thienyl), thiazolyl, imidazolyl, pyrazolyl, pyrrolyl or cyclohexenyl, each of which is optionally mono-, di- or trisubstituted by identical or different substituents—bridged via a carbon atom to the rest of the molecule—where optional substituents are as follows: cyano, fluorine, chlorine, methyl, cyclopropyl, cyanomethyl, cyanoisopropyl, cyanocylopropyl, trifluoromethyl, trifluoroethyl, aminocarbonyl, or is pyrazolyl or imidazolyl, each of which is optionally monosubstituted by chlorine—bridged via a nitrogen atom to the rest of the molecule, X is Q1, Q7, Q8, Q9 or Q12, $R^4$ is methyl, $R^5$ is trifluoromethyl, $R^6$ is hydrogen, and n is 0 or 2.

6. A compound of formula (I) according to claim 1, having the structures according to Examples I-001 to I-098.

7. An agrochemical formulation comprising a compound of formula (I) according to claim 1 and one or more extenders and/or surfactants.

8. An agrochemical formulation according to claim 7, additionally comprising a further agrochemical active ingredient.

9. Method for controlling one or more animal pests, comprising allowing a compound of formula (I) according to claim 1 or an agrochemical formulation thereof to act on the animal pests and/or a habitat thereof.

10. A product comprising a compound of formula (I) according to claim 1 or of agrochemical formulation thereof for controlling one or more animal pests.

11. The compound of formula (I) according to claim 5, wherein X is Q1.

12. The compound of formula (I) according to claim 5, wherein X is Q7.

13. The compound of formula (I) according to claim 5, wherein X is Q8.

14. The compound of formula (I) according to claim 5, wherein X is Q9.

15. The compound of formula (I) according to claim 5, wherein X is Q12.

\* \* \* \* \*

UNITED STATES PATENT AND TRADEMARK OFFICE
CERTIFICATE OF CORRECTION

PATENT NO. : 11,083,199 B2
APPLICATION NO. : 16/476393
DATED : August 10, 2021
INVENTOR(S) : David Wilcke et al.

It is certified that error appears in the above-identified patent and that said Letters Patent is hereby corrected as shown below:

In the Claims

In Column 126, Lines 6-9, in Claim 1:
Delete "$R^2$ is hydrogen, $(C_1-C_6)$alkyl, $(C 1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl,"
And insert --$R^2$ is hydrogen, $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, or $(C_2-C_6)$alkynyl,-- therefor.

Signed and Sealed this
Twenty-eighth Day of June, 2022

Katherine Kelly Vidal
*Director of the United States Patent and Trademark Office*